US010858688B2

(12) United States Patent
Kiuchi et al.

(10) Patent No.: US 10,858,688 B2
(45) Date of Patent: Dec. 8, 2020

(54) OBSERVATION METHOD USING BINDING AND DISSOCIATION PROBE

(71) Applicant: KYOTO UNIVERSITY, Kyoto (JP)

(72) Inventors: Tai Kiuchi, Kyoto (JP); Naoki Watanabe, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 507 days.

(21) Appl. No.: 15/696,089

(22) Filed: Sep. 5, 2017

(65) Prior Publication Data

US 2017/0362630 A1  Dec. 21, 2017

Related U.S. Application Data

(63) Continuation of application No. PCT/JP2016/057817, filed on Mar. 11, 2016.

(30) Foreign Application Priority Data

Mar. 11, 2015 (JP) ................. 2015-048692

(51) Int. Cl.
*C12Q 1/02* (2006.01)
*C07K 1/13* (2006.01)
*G01N 33/48* (2006.01)
*G01N 21/64* (2006.01)
*G01N 33/536* (2006.01)
*G01N 33/53* (2006.01)

(52) U.S. Cl.
CPC ................. *C12Q 1/02* (2013.01); *C07K 1/13* (2013.01); *G01N 21/64* (2013.01); *G01N 33/48* (2013.01); *G01N 33/53* (2013.01); *G01N 33/536* (2013.01)

(58) Field of Classification Search
None
See application file for complete search history.

(56) References Cited

U.S. PATENT DOCUMENTS

| | | | |
|---|---|---|---|
| 2002/0168657 A1* | 11/2002 | Chen .................. | G01N 21/6456 435/6.16 |
| 2008/0032414 A1* | 2/2008 | Zhuang .............. | G01N 21/6428 436/172 |
| 2008/0068588 A1 | 3/2008 | Hess et al. | |
| 2008/0068589 A1 | 3/2008 | Hess et al. | |
| 2008/0070322 A1 | 3/2008 | Hess et al. | |
| 2008/0070323 A1 | 3/2008 | Hess et al. | |
| 2008/0111086 A1 | 5/2008 | Betzig et al. | |
| 2008/0312540 A1* | 12/2008 | Ntziachristos ......... | A61B 5/415 600/478 |
| 2009/0206251 A1 | 8/2009 | Hess et al. | |
| 2009/0274360 A1* | 11/2009 | Suzuki .............. | G01N 21/6428 382/133 |
| 2010/0181497 A1 | 7/2010 | Hess et al. | |
| 2011/0064296 A1* | 3/2011 | Dixon .................... | G02B 21/16 382/133 |
| 2011/0102787 A1 | 5/2011 | Hess et al. | |
| 2012/0062722 A1* | 3/2012 | Sase .................. | G01N 21/6458 348/79 |
| 2012/0265014 A1* | 10/2012 | Matsubara ........... | A61B 1/0638 600/118 |
| 2013/0126759 A1 | 5/2013 | Betzig et al. | |
| 2014/0024948 A1* | 1/2014 | Shida ................. | G02B 23/2469 600/476 |
| 2014/0287941 A1 | 9/2014 | Betzig et al. | |
| 2015/0286887 A1* | 10/2015 | Dave .................. | G02B 27/0025 382/275 |
| 2017/0115221 A1 | 4/2017 | Betzig et al. | |

FOREIGN PATENT DOCUMENTS

| | | | |
|---|---|---|---|
| JP | 2008542826 A | 11/2008 | |
| JP | 2014048082 A | 3/2014 | |
| WO | 2006127692 A2 | 11/2006 | |
| WO | 2015160690 A1 | 10/2015 | |

OTHER PUBLICATIONS

Japanese Office Action dated Mar. 13, 2018 issued in counterpart Japanese Application No. 2017-505424.
International Search Report (ISR) and Written Opinion dated Jun. 7, 2016 issued in International Application No. PCT/JP2016/057817.
Kiuchi, et al, "Multitarget super-resolution microscopy with high-density labeling by exchanageable probes," Nature Methods, vol. 12, No. 8, Aug. 2015, pp. 743-746.
Fernandez-Suarez, et al, "Fluorescent probes for superresolution imaging in living cells," Nat. Rev. Mol. Cell Biol. vol. 9, 2008, pp. 929-943.
Stefan W. Hell, "Far-Field Optical Nanoscopy," Science, vol. 316, 2007, pp. 1153-1158.
Huang, et al, "Breaking the Diffraction Barrier: Super-Resolution Imaging of Cells," Cell, 143, 2010, pp. 1047-1058.
Huang, et al, "Super-Resolution Fluorescence Microscopy," Annu. Rev. Biochem., 2009, pp. 993-1016.
Markus Sauer, "Localization microscopy coming of age: from concepts to biological impact," Journal of Cell Science, 126 (16), pp. 3505-3513.
Shroff, et al, "Live-cell photoactivated localization microscopy of nanoscale adhesion dynamics," Nature Methods, vol. 5, No. 5, May 2008, pp. 417-423.

(Continued)

*Primary Examiner* — Ann Y Lam
(74) *Attorney, Agent, or Firm* — Holtz, Holtz & Volek PC

(57) ABSTRACT

An observation method of a sample containing a target substance, the observation method including an imaging step in which a step of obtaining a speckle image including, as a speckle, light emitted from a luminescent substance in which a medium is brought into contact with the sample is performed a plurality of times so as to obtain a plurality of speckle images, the medium containing a probe that contains the luminescent substance emitting light and that repeatedly binds to and dissociates from the target substance directly and specifically, and an observation image generation step of generating an observation image of the target substance in the sample from the plurality of speckle images, wherein a half-life of a probe-target complex formed by binding between the probe and the target substance is equal to or more than 10 milliseconds and equal to or less than 3 seconds.

8 Claims, 19 Drawing Sheets

Specification includes a Sequence Listing.

(56) References Cited

OTHER PUBLICATIONS

Kanchanawong, et al, "Localization-Based Super-Resolution Imaging of Cellular Structures," Adhesion Protein Protocols, Methods in Molecular Biology, vol. 1046, pp. 59-84.
Betzig, et al, "Imaging Intracellular Fluorescent Proteins at Nanometer Resolution," Science, vol. 313, Sep. 2006, pp. 1642-1645.
Rust, et al, "Stochastic optical reconstruction microscopy (STORM) provides sub-diffraction-limit image resolution," Nat. Methods, Oct. 2006, vol. 3, No. 10, pp. 793-795.
Riedl, et al, "Lifeact: a versatile marker to visualize F-actin," Nat. Methods, Jul. 2008, vol. 5, No. 7, pp. 605-607.
Watanabe, et al, "Single-Molecule Speckle Analysis of Actin Filament Turnover in Lamellipodia," Science, vol. 295, Feb. 2002, pp. 1083-1086.
Higashida, et al, "Actin Polymerization—Driven Molecular Movement of mDia1 in Living Cells," Science, vol. 303, Mar. 2004, pp. 2007-2010.
Ronald D. Vale, "Microscopes for Fluorimeters: The Era of Single Molecule Measurements," Cell, 135, Nov. 2008, pp. 779-785.
Holden, et al, "DAOSTORM: an algorithm for high-density super-resolution microscopy," Nat. Methods, Apr. 2011, vol. 8, No. 4, pp. 279-280.
Perez, et al, "CLIP-170 Highlights Growing Microtubule Ends in Vivo," Cell, vol. 96, Feb. 1999, pp. 517-525.
Nikolic, et al, "Basic Amino Acid Residue Cluster within Nuclear Targeting Sequence Motif Is Essential for Cytoplasmic Plectin-Vimentin Network Junctions," The Journal of Cell Biology, vol. 134, No. 6, Sep. 1996, pp. 1455-1467.
Di Paolo, et al, "Recruitment and regulation of phosphatidylinositol phosphate kinase type 1g by the FERM domain of talin," Nature, vol. 420, Nov. 2002, pp. 85-89.
Gell et al, "TIRF microscopy evanescent field calibration using tilted fluorescent microtubules," Journal of Microscopy, vol. 234, Pt 1, 2009, pp. 38-46.
Kanchanawong, et al, "Nanoscale architecture of integrin-based cell adhesions," Nature, vol. 468, Nov. 2010, pp. 580-586.
Sharonov, et al, "Wide-field subdiffraction imaging by accumulated binding of diffusing probes," PNAS, vol. 103, No. 50, Dec. 2006, pp. 18911-18916.
Bates, et al, "Multicolor Super-Resolution Imaging with Photo-Switchable Fluorescent Probes," Science, vol. 317, Sep. 2007, pp. 1749-1753.
Huang, et al, "Whole-cell 3D STORM reveals interactions between cellular structures with nanometer-scale resolution," Nat. Methods, Dec. 2008, vol. 5, No. 12, pp. 1047-1052.
Jungmann, et al, "Multiplexed 3D cellular super-resolution imaging with DNA-PAINT and Exchange-PAINT," Nat. Methods, Mar. 2014, vol. 11, No. 3, pp. 313-320.
Shroff, et al, "Dual-color superresolution imaging of genetically expressed probes within individual adhesion complexes," PNAS, Dec. 2007, vol. 104, No. 51, pp. 20308-20313.
Liu, et al, "RIM-Binding Protein, a Central Part of the Active Zone, Is Essential for Neurotransmitter Release," Science, vol. 334, Dec. 2011, pp. 1565-1569.
Bieling et al, "CLIP-170 tracks growing microtubule ends by dynamically recognizing composite EB1/tubulin-binding sites," The Journal of Cell Biology, vol. 183, No. 7, Dec. 2008, pp. 1223-1233.
Kaverina, et al, "Microtubule Targeting of Substrate Contacts Promotes Their Relaxation and Dissociation," The Journal of Cell Biology, vol. 146, No. 5, Sep. 1999, pp. 1033-1043.
Salmon, et al, "Dual-wavelength fluorescent speckle microscopy reveals coupling of microtubule and actin movements in migrating cells," The Journal of Cell Biology, vol. 158, No. 1, Jul. 2002, pp. 31-37.
Small, et al, "Microtubules meet substrate adhesions to arrange cell polarity," Curr. Opin. Cell Biol., vol. 15, pp. 40-47.
Huda, et al, "Microtubule guidance tested through controlled cell geometry," Journal of Cell Science, vol. 125, pp. 5790-5799.

Yamana, et al, "The Rho-mDia1 Pathway Regulates Cell Polarity and Focal Adhesion Turnover in Migrating Cells through Mobilizing Apc and c-Src," Molecular and Cellular Biology, vol. 26, No. 18, Sep. 2006, pp. 6844-6858.
Tanji, et al, "mDia1 Targets v-Src to the Cell Periphery and Facilitates Cell Transformation, Tumorigenesis, and Invasion," Molecular and Cellular Biology, vol. 30, No. 19, Oct. 2010, pp. 4604-4615.
Yamashiro, et al, "New single-molecule speckle microscopy reveals modification of the retrograde actin flow by focal adhesions at nanometer scales," Molecular Biology of the Cell, 25, pp. 1010-1024.
Desai, et al, "Kin I Kinesins Are Microtubule-Destabilizing Enzymes," Cell, vol. 96, Jan. 1999, pp. 69-78.
Mizuno, et al, "Rotational Movement of the Formin mDia1 Along the Double Helical Strand of an Actin Filament," Science, vol. 331, Jan. 2011, pp. 80-83.
Mizuno, et al, "Rotational Movement of Formins Evaluated by Using Single-Molecule Fluorescence Polarization," Methods in Enzymology, vol. 540, pp. 73-94.
Smith, et al, "Interactive, Computer-Assisted Tracking of Speckle Trajectories in Fluorescence Microscopy: Application to Actin Polymerization and Membrane Fusion," Biophysical Journal, vol. 101, Oct. 2011, pp. 1794-1804.
Mimori-Kiyosue, et al, "CLASP1 and CLASP2 bind to EB1 and regulate microtubule plus-end dynamics at the cell cortex," The Journal of Cell Biology, vol. 168, No. 1, Jan. 2005, pp. 141-153.
Askham, et al, "Regulation and function of the interaction between the APC tumour suppressor protein and EB1," Oncogene, 2000, vol. 19, pp. 1950-1958.
Honnappa, et al, "An EB1-Binding Motif Acts as a Microtubule Tip Localization Signal," Cell, 138, Jul. 2009, pp. 366-376.
Okada, et al, "Processivity of the single-headed kinesin KIF1A through biased binding to tubulin," Nature, vol. 424, Jul. 2003, pp. 574-577.
Cai, et al, "Single Molecule Imaging Reveals Differences in Microtubule Track Selection Between Kinesin Motors," PLoS Biology, vol. 7, Issue 10, Oct. 2009, pp. 1-14.
Olson et al, "Analysis of MAP 4 Function in Living Cells Using Green Fluorescent Protein (GFP) Chimeras," The Journal of Cell Biology, vol. 130, No. 3, Aug. 1995, pp. 639-650.
Lee et al, "Expression of tau protein in non-neuronal cells: microtubule binding and stabilization," Journal of Cell Science, vol. 102, 1992, pp. 227-237.
Yu, et al, "Transient Expression of Fluorescent Tau Proteins Promotes Process Formation in PC12 Cells: Contributions of the Tau C-Terminus to This Process," Journal of Neuroscience Research, vol. 67, 2002, pp. 625-633.
Brown, et al, "Identification of LIM3 as the Principal Determinant of Paxillin Focal Adhesion Localization and Characterization of a Novel Motif on Paxillin Directing Vinculin and Focal Adhesion Kinase Binding," The Journal of Cell Biology, vol. 135, No. 4, Nov. 1996, pp. 1109-1123.
Wood, et al, "Characterisation of the paxillin-binding site and the C-terminal focal adhesion targeting sequence in vinculin," Journal of Cell Science, vol. 107, 1994, pp. 709-717.
Humphries, et al, "Vinculin controls focal adhesion formation by direct interactions with talin and actin," The Journal of Cell Biology, vol. 179, No. 5, Dec. 2007, pp. 1043-1057.
Nuckolls, et al, "Functional Studies of the Domains of Talin," The Journal of Cell Biology, vol. 110, May 1990, pp. 1635-1644.
Calderwood et al, "The Phosphotyrosine Binding-like Domain of Talin Activates Integrins," The Journal of Biological Chemistry, vol. 277, No. 24, Jun. 2002, pp. 21749-21758.
Tremuth et al, "A Fluorescence Cell Biology Approach to Map the Second Integrin-binding Site of Talin to a 130-Amino Acid Sequence within the Rod Domain," The Journal of Biological Chemistry, vol. 279, No. 21, May 2004, pp. 22258-22266.
Patel, et al, "The Activity of the Vinculin Binding Sites in Talin Is Influenced by the Stability of the Helical Bundles That Make Up The Talin Rod," The Journal of Biological Chemistry, vol. 281, No. 11, Mar. 2006, pp. 7458-7467.

(56) References Cited

OTHER PUBLICATIONS

Moes, et al, "The Integrin Binding Site 2 (IBS2) in the Talin Rod Domain Is Essential for Linking Integrin Beta Subunits to the Cytoskeleton," The Journal of Biological Chemistry, vol. 282, No. 23, Jun. 2007, pp. 17280-17288.

Himmel, et al, "Control of High Affinity Interactions in the Talin C Terminus, How Talin Domains Coordinate Protein Dynamics in Cell Adhesions," The Journal of Biological Chemistry, vol. 284, No. 20, May 2009, pp. 13832-13842.

Kaplan, et al, "Association of the amino-terminal half of c-Src with focal adhesions alters their properties and is regulated by phosphorylation of tyrosine 527," The EMBO Journal, vol. 13, No. 20, 1994, pp. 4745-4756.

Hildebrand, et al, "Identification of Sequences Required for the Efficient Localization of the Focal Adhesion Kinase, pp125FAK, to Cellular Focal Adhesions," The Journal of Cell Biology, vol. 123, No. 4, Nov. 1993, pp. 993-1005.

Cooley, et al, "Paxillin Binding Is Not the Sole Determinant of Focal Adhesion Localization or Dominant-Negative Activity of Focal Adhesion Kinase/Focal Adhesion Kinase-related Nonkinase," Molecular Biology of the Cell, vol. 11, Sep. 2000, pp. 3247-3263.

Lietha et al, "Structural Basis for the Autoinhibition of Focal Adhesion Kinase," Cell, vol. 129, Jun. 2007, pp. 1177-1187.

Extended European Search Report (EESR) dated Jul. 9, 2018 issued in counterpart European Application No. 16761865.1.

Ashdown, et al., "Live-Cell-Super-resolution Reveals F-Action and Plasma Membrane Dynamics at the T Cell Synapse", Biophysical Journal, vol. 112, No. 8, Apr. 2017, pp. 1703-1713.

\* cited by examiner (a)

(b)

(c)

(d)

(A)  (B)

SEQUENCE LISTING

<160> NUMBER OF SEQ ID NOS: 20

<210> SEQ ID NO 1
<211> LENGTH: 239
<212> TYPE: PRT
<213> ORGANISM: Artificial
<220> FEATURE:
<223> OTHER INFORMATION: EGFP

<400> SEQUENCE: 1

Met Val Ser Lys Gly Glu Glu Leu Phe Thr Gly Val Val Pro Ile Leu
1               5                   10                  15

```
Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 2
<211> LENGTH: 8
<212> TYPE: PRT
<213> ORGANISM: Artificial
<220> FEATURE:
<223> OTHER INFORMATION: FLAG

<400> SEQUENCE: 2

Asp Tyr Lys Asp Asp Asp Asp Lys
1               5

<210> SEQ ID NO 3
<211> LENGTH: 22
<212> TYPE: PRT
<213> ORGANISM: Artificial
<220> FEATURE:
<223> OTHER INFORMATION: 3xFLAG

<400> SEQUENCE: 3

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 4
<211> LENGTH: 1125
<212> TYPE: PRT
<213> ORGANISM: Mus musculus

<400> SEQUENCE: 4
```

```
Met Ala Asp Leu Ser Leu Val Asp Ala Leu Thr Glu Pro Pro Glu
1               5                   10                  15

Ile Glu Gly Glu Ile Lys Arg Asp Phe Met Ala Leu Glu Ala Glu
            20                  25                  30

Pro Tyr Asp Asp Ile Val Gly Glu Thr Val Glu Lys Thr Glu Phe Ile
        35                  40                  45

Pro Leu Leu Asp Gly Asp Glu Lys Thr Gly Asn Ser Glu Ser Lys Lys
    50                  55                  60

Lys Pro Cys Leu Asp Thr Ser Gln Val Glu Gly Ile Pro Ser Ser Lys
65                  70                  75                  80

Pro Thr Leu Leu Ala Asn Gly Asp His Gly Met Glu Gly Asn Asn Thr
                85                  90                  95

Ala Gly Ser Pro Thr Asp Phe Leu Glu Glu Arg Val Asp Tyr Pro Asp
            100                 105                 110

Tyr Gln Ser Ser Gln Asn Trp Pro Glu Asp Ala Ser Phe Cys Phe Gln
            115                 120                 125

Pro Gln Gln Val Leu Asp Thr Asp Gln Ala Glu Pro Phe Asn Glu His
    130                 135                 140

Arg Asp Asp Gly Leu Ala Asp Leu Leu Phe Val Ser Ser Gly Pro Thr
145                 150                 155                 160

Asn Ala Ser Ala Phe Thr Glu Arg Asp Asn Pro Ser Glu Asp Ser Tyr
                165                 170                 175

Gly Met Leu Pro Cys Asp Ser Phe Ala Ser Thr Ala Val Val Ser Gln
            180                 185                 190

Glu Trp Ser Val Gly Ala Pro Asn Ser Pro Cys Ser Glu Ser Cys Val
            195                 200                 205

Ser Pro Glu Val Thr Ile Glu Thr Leu Gln Pro Ala Thr Glu Leu Ser
    210                 215                 220

Lys Ala Ala Glu Val Glu Ser Val Lys Glu Gln Leu Pro Ala Lys Ala
225                 230                 235                 240

Leu Glu Thr Met Ala Glu Gln Thr Thr Asp Val Val His Ser Pro Ser
                245                 250                 255

Thr Asp Thr Thr Pro Gly Pro Asp Thr Glu Ala Ala Leu Ala Lys Asp
            260                 265                 270

Ile Glu Glu Ile Thr Lys Pro Asp Val Ile Leu Ala Asn Val Thr Gln
            275                 280                 285

Pro Ser Thr Glu Ser Asp Met Phe Leu Ala Gln Asp Met Glu Leu Leu
    290                 295                 300

Thr Gly Thr Glu Ala Ala His Ala Asn Asn Ile Ile Leu Pro Thr Glu
305                 310                 315                 320

Pro Asp Glu Ser Ser Thr Lys Asp Val Ala Pro Pro Met Glu Glu Glu
                325                 330                 335

Ile Val Pro Gly Asn Asp Thr Thr Ser Pro Lys Glu Thr Glu Thr Thr
            340                 345                 350

Leu Pro Ile Lys Met Asp Leu Ala Pro Pro Glu Asp Val Leu Leu Thr
            355                 360                 365

Lys Glu Thr Glu Leu Ala Pro Ala Lys Gly Met Val Ser Leu Ser Glu
    370                 375                 380

Ile Glu Glu Ala Leu Ala Lys Asn Asp Glu Ser Ser Ala Glu Ile Pro
385                 390                 395                 400

Val Ala Gln Glu Thr Val Val Ser Glu Thr Glu Val Val Leu Ala Ile
                405                 410                 415

Glu Val Val Leu Pro Ser Asp Pro Ile Thr Thr Leu Thr Lys Asp Val
```

```
                420             425             430
Thr Leu Pro Leu Glu Ala Glu Arg Pro Leu Val Thr Asp Met Thr Pro
            435             440             445
Ser Leu Glu Thr Glu Met Thr Leu Gly Lys Glu Thr Ala Pro Pro Thr
            450             455             460
Glu Thr Asn Leu Gly Met Ala Lys Asp Met Ser Pro Leu Pro Glu Ser
465             470             475             480
Glu Val Thr Leu Gly Lys Asp Val Val Ile Leu Pro Glu Thr Lys Val
            485             490             495
Ala Glu Phe Asn Asn Val Thr Pro Leu Ser Glu Glu Val Thr Ser
            500             505             510
Val Lys Asp Met Ser Pro Ser Ala Glu Thr Glu Ala Pro Leu Ala Lys
            515             520             525
Asn Ala Asp Leu His Ser Gly Thr Glu Leu Ile Val Asp Asn Ser Met
            530             535             540
Ala Pro Ala Ser Asp Leu Ala Leu Pro Leu Glu Thr Lys Val Ala Thr
545             550             555             560
Val Pro Ile Lys Asp Lys Gly Thr Val Gln Thr Glu Glu Lys Pro Arg
            565             570             575
Glu Asp Ser Gln Leu Ala Ser Met Gln His Lys Gly Gln Ser Thr Val
            580             585             590
Pro Pro Cys Thr Ala Ser Pro Glu Pro Val Lys Ala Ala Glu Gln Met
            595             600             605
Ser Thr Leu Pro Ile Asp Ala Pro Ser Pro Leu Glu Asn Leu Glu Gln
            610             615             620
Lys Glu Thr Pro Gly Ser Gln Pro Ser Glu Pro Cys Ser Gly Val Ser
625             630             635             640
Arg Gln Glu Glu Ala Lys Ala Ala Val Gly Val Thr Gly Asn Asp Ile
            645             650             655
Thr Thr Pro Pro Asn Lys Glu Pro Pro Pro Ser Pro Glu Lys Lys Ala
            660             665             670
Lys Pro Leu Ala Thr Thr Gln Pro Ala Lys Thr Ser Thr Ser Lys Ala
            675             680             685
Lys Thr Gln Pro Thr Ser Leu Pro Lys Gln Pro Ala Pro Thr Thr Ser
            690             695             700
Gly Gly Leu Asn Lys Lys Pro Met Ser Leu Ala Ser Gly Ser Val Pro
705             710             715             720
Ala Ala Pro His Lys Arg Pro Ala Ala Thr Ala Thr Ala Arg Pro
            725             730             735
Ser Thr Leu Pro Ala Arg Asp Val Lys Pro Lys Pro Ile Thr Glu Ala
            740             745             750
Lys Val Ala Glu Lys Arg Thr Ser Pro Ser Lys Pro Ser Ser Ala Pro
            755             760             765
Ala Leu Lys Pro Gly Pro Lys Thr Thr Pro Thr Val Ser Lys Ala Thr
            770             775             780
Ser Pro Ser Thr Leu Val Ser Thr Gly Pro Ser Ser Arg Ser Pro Ala
785             790             795             800
Thr Thr Leu Pro Lys Arg Pro Thr Ser Ile Lys Thr Glu Gly Lys Pro
            805             810             815
Ala Asp Val Lys Arg Met Thr Ala Lys Ser Ala Ser Ala Asp Leu Ser
            820             825             830
Arg Ser Lys Thr Thr Ser Ala Ser Ser Val Lys Arg Asn Thr Thr Pro
            835             840             845
```

Thr Gly Ala Ala Pro Pro Ala Gly Met Thr Ser Thr Arg Val Lys Pro
850                 855                 860

Met Ser Ala Pro Ser Arg Ser Ser Gly Ala Leu Ser Val Asp Lys Lys
865                 870                 875                 880

Pro Thr Ser Thr Lys Pro Ser Ser Ala Pro Arg Val Ser Arg Leu
            885                 890                 895

Ala Thr Thr Val Ser Ala Pro Asp Leu Lys Ser Val Arg Ser Lys Val
            900                 905                 910

Gly Ser Thr Glu Asn Ile Lys His Gln Pro Gly Gly Arg Ala Lys
            915                 920                 925

Val Glu Lys Lys Thr Glu Ala Ala Thr Ala Gly Lys Pro Glu Pro
930                 935                 940

Asn Ala Val Thr Lys Ala Ala Gly Ser Ile Ala Ser Ala Gln Lys Pro
945                 950                 955                 960

Pro Ala Gly Lys Val Gln Ile Val Ser Lys Lys Val Ser Tyr Ser His
            965                 970                 975

Ile Gln Ser Lys Cys Gly Ser Lys Asp Asn Ile Lys His Val Pro Gly
            980                 985                 990

Gly Gly Asn Val Gln Ile Gln Asn Lys Lys Val Asp Ile Ser Lys Val
            995                 1000                1005

Ser Ser Lys Cys Gly Ser Lys Ala Asn Ile Lys His Lys Pro Gly
    1010                1015                1020

Gly Gly Asp Val Lys Ile Glu Ser Gln Lys Leu Asn Phe Lys Glu
    1025                1030                1035

Lys Ala Gln Ala Lys Val Gly Ser Leu Asp Asn Val Gly His Leu
    1040                1045                1050

Pro Ala Gly Gly Ala Val Lys Thr Glu Gly Gly Gly Ser Glu Ala
    1055                1060                1065

Leu Pro Cys Pro Gly Pro Pro Ala Gly Glu Glu Pro Val Ile Pro
    1070                1075                1080

Glu Ala Ala Pro Asp Ala Gly Ala Pro Thr Ser Ala Ser Gly Leu
    1085                1090                1095

Ser Gly His Thr Thr Leu Ser Gly Gly Gly Asp Gln Arg Glu Pro
    1100                1105                1110

Gln Thr Leu Asp Ser Gln Ile Gln Glu Thr Ser Ile
    1115                1120                1125

<210> SEQ ID NO 5
<211> LENGTH: 383
<212> TYPE: PRT
<213> ORGANISM: Homo sapiens

<400> SEQUENCE: 5

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro

```
                    85                  90                  95
Arg Gly Ala Ala Pro Gly Gln Lys Gly Gln Ala Asn Ala Thr Arg
            100                 105                 110
Ile Pro Ala Lys Thr Pro Pro Ala Pro Lys Thr Pro Ser Ser Gly
            115                 120                 125
Glu Pro Pro Lys Ser Gly Asp Arg Ser Gly Tyr Ser Ser Pro Gly
            130                 135                 140
Pro Gly Thr Pro Gly Ser Arg Ser Arg Thr Pro Ser Leu Pro Thr Pro
145                 150                 155                 160
Pro Thr Arg Glu Pro Lys Lys Val Ala Val Arg Thr Pro Pro Lys
                165                 170                 175
Ser Pro Ser Ser Ala Lys Ser Arg Leu Gln Thr Ala Pro Val Pro Met
                180                 185                 190
Pro Asp Leu Lys Asn Val Lys Ser Lys Ile Gly Ser Thr Glu Asn Leu
                195                 200                 205
Lys His Gln Pro Gly Gly Gly Lys Val Gln Ile Ile Asn Lys Lys Leu
                210                 215                 220
Asp Leu Ser Asn Val Gln Ser Lys Cys Gly Ser Lys Asp Asn Ile Lys
225                 230                 235                 240
His Val Pro Gly Gly Gly Ser Val Gln Ile Val Tyr Lys Pro Val Asp
                245                 250                 255
Leu Ser Lys Val Thr Ser Lys Cys Gly Ser Leu Gly Asn Ile His His
                260                 265                 270
Lys Pro Gly Gly Gly Gln Val Glu Val Lys Ser Glu Lys Leu Asp Phe
                275                 280                 285
Lys Asp Arg Val Gln Ser Lys Ile Gly Ser Leu Asp Asn Ile Thr His
                290                 295                 300
Val Pro Gly Gly Gly Asn Lys Lys Ile Glu Thr His Lys Leu Thr Phe
305                 310                 315                 320
Arg Glu Asn Ala Lys Ala Lys Thr Asp His Gly Ala Glu Ile Val Tyr
                325                 330                 335
Lys Ser Pro Val Val Ser Gly Asp Thr Ser Pro Arg His Leu Ser Asn
                340                 345                 350
Val Ser Ser Thr Gly Ser Ile Asp Met Val Asp Ser Pro Gln Leu Ala
                355                 360                 365
Thr Leu Ala Asp Glu Val Ser Ala Ser Leu Ala Lys Gln Gly Leu
                370                 375                 380

<210> SEQ ID NO 6
<211> LENGTH: 352
<212> TYPE: PRT
<213> ORGANISM: Homo sapiens

<400> SEQUENCE: 6

Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
                20                  25                  30
Gln Asp Gln Glu Gly Asp Thr Asp Ala Gly Leu Lys Ala Glu Glu Ala
            35                  40                  45
Gly Ile Gly Asp Thr Pro Ser Leu Glu Asp Glu Ala Ala Gly His Val
        50                  55                  60
Thr Gln Ala Arg Met Val Ser Lys Ser Lys Asp Gly Thr Gly Ser Asp
65                  70                  75                  80
```

```
Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
            115                 120                 125

Glu Pro Pro Lys Ser Gly Asp Arg Ser Gly Tyr Ser Ser Pro Gly Ser
130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
            195                 200                 205

Lys His Gln Pro Gly Gly Gly Lys Val Gln Ile Val Tyr Lys Pro Val
210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Glu Thr His Lys Leu Thr
            275                 280                 285

Phe Arg Glu Asn Ala Lys Ala Lys Thr Asp His Gly Ala Glu Ile Val
290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350

<210> SEQ ID NO 7
<211> LENGTH: 1689
<212> TYPE: PRT
<213> ORGANISM: Mus musculus

<400> SEQUENCE: 7

Met Ala Gly Ala Ser Val Lys Val Ala Val Arg Val Arg Pro Phe Asn
1               5                   10                  15

Ser Arg Glu Met Ser Arg Asp Ser Lys Cys Ile Ile Gln Met Ser Gly
                20                  25                  30

Ser Thr Thr Thr Ile Val Asn Pro Lys Gln Pro Lys Glu Thr Pro Lys
            35                  40                  45

Ser Phe Ser Phe Asp Tyr Ser Tyr Trp Ser His Thr Ser Pro Glu Asp
        50                  55                  60

Ile Asn Tyr Ala Ser Gln Lys Gln Val Tyr Arg Asp Ile Gly Glu Glu
65                  70                  75                  80

Met Leu Gln His Ala Phe Glu Gly Tyr Asn Val Cys Ile Phe Ala Tyr
                85                  90                  95

Gly Gln Thr Gly Ala Gly Lys Ser Tyr Thr Met Met Gly Lys Gln Glu
            100                 105                 110
```

```
Lys Asp Gln Gln Gly Ile Ile Pro Gln Leu Cys Glu Asp Leu Phe Ser
            115                 120                 125

Arg Ile Asn Asp Thr Thr Asn Asp Asn Met Ser Tyr Ser Val Glu Val
        130                 135                 140

Ser Tyr Met Glu Ile Tyr Cys Glu Arg Val Arg Asp Leu Leu Asn Pro
145                 150                 155                 160

Lys Asn Lys Gly Asn Leu Arg Val Arg Glu His Pro Leu Leu Gly Pro
                165                 170                 175

Tyr Val Glu Asp Leu Ser Lys Leu Ala Val Thr Ser Tyr Asn Asp Ile
            180                 185                 190

Gln Asp Leu Met Asp Ser Gly Asn Lys Ala Arg Thr Val Ala Ala Thr
        195                 200                 205

Asn Met Asn Glu Thr Ser Ser Arg Ser His Ala Val Phe Asn Ile Ile
210                 215                 220

Phe Thr Gln Lys Arg His Asp Ala Glu Thr Asn Ile Thr Thr Glu Lys
225                 230                 235                 240

Val Ser Lys Ile Ser Leu Val Asp Leu Ala Gly Ser Glu Arg Ala Asp
                245                 250                 255

Ser Thr Gly Ala Lys Gly Thr Arg Leu Lys Glu Gly Ala Asn Ile Asn
            260                 265                 270

Lys Ser Leu Thr Thr Leu Gly Lys Val Ile Ser Ala Leu Ala Glu Met
        275                 280                 285

Asp Ser Gly Pro Asn Lys Asn Lys Lys Lys Lys Thr Asp Phe Ile
290                 295                 300

Pro Tyr Arg Asp Ser Val Leu Thr Trp Leu Leu Arg Glu Asn Leu Gly
305                 310                 315                 320

Gly Asn Ser Arg Thr Ala Met Val Ala Ala Leu Ser Pro Ala Asp Ile
                325                 330                 335

Asn Tyr Asp Glu Thr Leu Ser Thr Leu Arg Tyr Ala Asp Arg Ala Lys
            340                 345                 350

Gln Ile Arg Cys Asn Ala Ile Ile Asn Glu Asp Pro Asn Asn Lys Leu
        355                 360                 365

Ile Arg Glu Leu Lys Asp Glu Val Thr Arg Leu Arg Asp Leu Leu Tyr
370                 375                 380

Ala Gln Gly Leu Gly Asp Ile Thr Asp Met Thr Asn Ala Leu Val Gly
385                 390                 395                 400

Met Ser Pro Ser Ser Ser Leu Ser Ala Leu Ser Ser Arg Ala Ala Ser
                405                 410                 415

Val Ser Ser Leu His Glu Arg Ile Leu Phe Ala Pro Gly Ser Glu Glu
            420                 425                 430

Ala Ile Glu Arg Leu Lys Glu Thr Glu Lys Ile Ile Ala Glu Leu Asn
        435                 440                 445

Glu Thr Trp Glu Glu Lys Leu Arg Arg Thr Glu Ala Ile Arg Met Glu
450                 455                 460

Arg Glu Ala Leu Leu Ala Glu Met Gly Val Ala Met Arg Glu Asp Gly
465                 470                 475                 480

Gly Thr Leu Gly Val Phe Ser Pro Lys Lys Thr Pro His Leu Val Asn
                485                 490                 495

Leu Asn Glu Asp Pro Leu Met Ser Glu Cys Leu Leu Tyr Tyr Ile Lys
            500                 505                 510

Asp Gly Val Thr Arg Val Gly Arg Glu Asp Ala Glu Arg Arg Gln Asp
        515                 520                 525
```

```
Ile Val Leu Ser Gly His Phe Ile Lys Glu Glu His Cys Ile Phe Arg
            530                 535                 540

Ser Asp Ser Arg Gly Gly Gly Glu Ala Val Val Thr Leu Glu Pro Cys
545                 550                 555                 560

Glu Gly Ala Asp Thr Tyr Val Asn Gly Lys Lys Val Thr Glu Pro Ser
                565                 570                 575

Ile Leu Arg Ser Gly Asn Arg Ile Ile Met Gly Lys Ser His Val Phe
            580                 585                 590

Arg Phe Asn His Pro Glu Gln Ala Arg Gln Glu Arg Glu Arg Thr Pro
            595                 600                 605

Cys Ala Glu Thr Pro Ala Glu Pro Val Asp Trp Ala Phe Ala Gln Arg
610                 615                 620

Glu Leu Leu Glu Lys Gln Gly Ile Asp Met Lys Gln Glu Met Glu Gln
625                 630                 635                 640

Arg Leu Gln Glu Leu Glu Asp Gln Tyr Arg Arg Glu Arg Glu Glu Ala
                645                 650                 655

Thr Tyr Leu Leu Glu Gln Gln Arg Leu Asp Tyr Glu Ser Lys Leu Glu
                660                 665                 670

Ala Leu Gln Lys Gln Met Asp Ser Arg Tyr Tyr Pro Glu Val Asn Glu
            675                 680                 685

Glu Glu Glu Glu Pro Glu Asp Glu Val Gln Trp Thr Glu Arg Glu Cys
690                 695                 700

Glu Leu Ala Leu Trp Ala Phe Arg Lys Trp Lys Trp Tyr Gln Phe Thr
705                 710                 715                 720

Ser Leu Arg Asp Leu Leu Trp Gly Asn Ala Ile Phe Leu Lys Glu Ala
                725                 730                 735

Asn Ala Ile Ser Val Glu Leu Lys Lys Lys Val Gln Phe Gln Phe Val
            740                 745                 750

Leu Leu Thr Asp Thr Leu Tyr Ser Pro Leu Pro Pro Asp Leu Leu Pro
            755                 760                 765

Pro Glu Ala Ala Lys Asp Arg Glu Thr Arg Pro Phe Pro Arg Thr Ile
770                 775                 780

Val Ala Val Glu Val Gln Asp Gln Lys Asn Gly Ala Thr His Tyr Trp
785                 790                 795                 800

Thr Leu Glu Lys Leu Arg Gln Arg Leu Asp Leu Met Arg Glu Met Tyr
                805                 810                 815

Asp Arg Ala Ala Glu Val Pro Ser Ser Val Val Glu Asp Cys Asp Asn
            820                 825                 830

Val Val Thr Gly Gly Asp Pro Phe Tyr Asp Arg Phe Pro Trp Phe Arg
            835                 840                 845

Leu Val Gly Arg Ala Phe Val Tyr Leu Ser Asn Leu Leu Tyr Pro Val
850                 855                 860

Pro Leu Val His Arg Val Ala Ile Val Ser Glu Lys Gly Glu Val Lys
865                 870                 875                 880

Gly Phe Leu Arg Val Ala Val Gln Ala Ile Ser Ala Asp Glu Glu Ala
                885                 890                 895

Pro Asp Tyr Gly Ser Gly Val Arg Gln Ser Gly Thr Ala Lys Ile Ser
            900                 905                 910

Phe Asp Asp Gln His Phe Glu Lys Phe Gln Ser Glu Ser Cys Pro Val
            915                 920                 925

Val Gly Met Ser Arg Ser Gly Thr Ser Gln Glu Glu Leu Arg Ile Val
            930                 935                 940

Glu Gly Gln Gly Gln Gly Ala Asp Ala Gly Pro Ser Ala Asp Glu Val
```

-continued

```
945                 950                 955                 960
Asn Asn Asn Thr Cys Ser Ala Val Pro Pro Glu Gly Leu Met Asp Ser
                965                 970                 975
Pro Glu Lys Ala Ala Leu Asp Gly Pro Leu Asp Thr Ala Leu Asp His
                980                 985                 990
Leu Arg Leu Gly Ser Thr Phe Thr Phe Arg Val Thr Val Leu Gln Ala
                995                1000                1005
Ser Ser Ile Ser Ala Glu Tyr Ala Asp Ile Phe Cys Gln Phe Asn
       1010                1015                1020
Phe Ile His Arg His Asp Glu Ala Phe Ser Thr Glu Pro Leu Lys
       1025                1030                1035
Asn Thr Gly Arg Gly Pro Pro Leu Gly Phe Tyr His Val Gln Asn
       1040                1045                1050
Ile Ala Val Glu Val Thr Lys Ser Phe Ile Glu Tyr Ile Lys Ser
       1055                1060                1065
Gln Pro Ile Val Phe Glu Val Phe Gly His Tyr Gln Gln His Pro
       1070                1075                1080
Phe Pro Pro Leu Cys Lys Asp Val Leu Ser Pro Leu Arg Pro Ser
       1085                1090                1095
Arg Arg His Phe Pro Arg Val Met Pro Leu Ser Lys Pro Val Pro
       1100                1105                1110
Ala Thr Lys Leu Ser Thr Met Thr Arg Pro Ser Pro Gly Pro Cys
       1115                1120                1125
His Cys Lys Tyr Asp Leu Leu Val Tyr Phe Glu Ile Cys Glu Leu
       1130                1135                1140
Glu Ala Asn Gly Asp Tyr Ile Pro Ala Val Val Asp His Arg Gly
       1145                1150                1155
Gly Met Pro Cys Met Gly Thr Phe Leu Leu His Gln Gly Ile Gln
       1160                1165                1170
Arg Arg Ile Thr Val Thr Leu Leu His Glu Thr Gly Ser His Ile
       1175                1180                1185
Arg Trp Lys Glu Val Arg Glu Leu Val Val Gly Arg Ile Arg Asn
       1190                1195                1200
Thr Pro Glu Thr Asp Glu Ala Leu Ile Asp Pro Asn Ile Leu Ser
       1205                1210                1215
Leu Asn Ile Leu Ser Ser Gly Tyr Val His Pro Ala Gln Asp Asp
       1220                1225                1230
Arg Thr Phe Tyr Gln Phe Ala Ala Trp Asp Ser Ser Met His
       1235                1240                1245
Asn Ser Leu Leu Leu Asn Arg Val Thr Pro Tyr Arg Glu Lys Ile
       1250                1255                1260
Tyr Met Thr Leu Ser Ala Tyr Ile Glu Met Glu Asn Cys Thr Gln
       1265                1270                1275
Pro Ala Val Ile Thr Lys Asp Phe Cys Met Val Phe Tyr Ser Arg
       1280                1285                1290
Asp Ala Lys Leu Pro Ala Ser Arg Ser Ile Arg Asn Leu Phe Gly
       1295                1300                1305
Ser Gly Ser Leu Arg Ala Thr Glu Gly Asn Arg Val Thr Gly Val
       1310                1315                1320
Tyr Glu Leu Ser Leu Cys His Val Ala Asp Ala Gly Ser Pro Gly
       1325                1330                1335
Met Gln Arg Arg Arg Arg Val Leu Asp Thr Ser Val Ala Tyr
       1340                1345                1350
```

Val Arg Gly Glu Glu Asn Leu Ala Gly Trp Arg Pro Arg Ser Asp
1355                1360                1365

Ser Leu Ile Leu Asp His Gln Trp Glu Leu Glu Lys Leu Ser Leu
1370                1375                1380

Leu Gln Glu Val Glu Lys Thr Arg His Tyr Leu Leu Arg Glu
1385                1390                1395

Lys Leu Glu Thr Thr Gln Arg Pro Gly Pro Glu Val Leu Ser Pro
1400                1405                1410

Ala Ser Ser Glu Asp Ser Glu Ser Arg Ser Ser Gly Ala Ser
1415                1420                1425

Ser Pro Leu Ser Ala Glu Gly Gln Pro Ser Pro Leu Glu Ala Pro
1430                1435                1440

Asn Glu Arg Gln Arg Glu Leu Ala Val Lys Cys Leu Arg Leu Leu
1445                1450                1455

Met His Thr Phe Asn Arg Glu Tyr Thr His Ser His Val Cys Ile
1460                1465                1470

Ser Ala Ser Glu Ser Lys Leu Ser Glu Met Ser Val Thr Leu Met
1475                1480                1485

Arg Asp Pro Ser Met Ser Pro Leu Gly Ala Ala Thr Leu Thr Pro
1490                1495                1500

Ser Ser Thr Cys Pro Ser Leu Ile Glu Gly Arg Tyr Gly Ala Thr
1505                1510                1515

Asp Val Arg Thr Pro Gln Pro Cys Ser Arg Pro Ala Ser Pro Glu
1520                1525                1530

Pro Glu Leu Leu Pro Glu Leu Asp Ser Lys Lys Thr Pro Ser Pro
1535                1540                1545

Val Arg Ala Thr Glu Thr Glu Lys Glu Pro Gln Arg Leu Leu Val
1550                1555                1560

Pro Asp Ile Gln Glu Ile Arg Val Ser Pro Ile Val Ser Lys Lys
1565                1570                1575

Gly Tyr Leu His Phe Leu Glu Pro His Thr Ala Gly Trp Ala Lys
1580                1585                1590

Arg Phe Val Val Val Arg Arg Pro Tyr Ala Tyr Met Tyr Asn Ser
1595                1600                1605

Asp Lys Asp Thr Val Glu Arg Phe Val Leu Asn Leu Ser Thr Ala
1610                1615                1620

Gln Val Glu Tyr Ser Glu Asp Gln Gln Ala Met Leu Lys Thr Pro
1625                1630                1635

Asn Thr Phe Ala Val Cys Thr Glu His Arg Gly Ile Leu Leu Gln
1640                1645                1650

Ala Asn Ser Asp Lys Asp Met His Asp Trp Leu Tyr Ala Phe Asn
1655                1660                1665

Pro Leu Leu Ala Gly Thr Ile Arg Ser Lys Leu Ser Arg Arg Arg
1670                1675                1680

Ser Ala Gln Met Arg Val
1685

<210> SEQ ID NO 8
<211> LENGTH: 4684
<212> TYPE: PRT
<213> ORGANISM: Homo sapiens

<400> SEQUENCE: 8

Met Val Ala Gly Met Leu Met Pro Arg Asp Gln Leu Arg Ala Ile Tyr

-continued

```
1               5                   10                  15
Glu Val Leu Phe Arg Glu Gly Val Met Val Ala Lys Lys Asp Arg Arg
                20                  25                  30

Pro Arg Ser Leu His Pro His Val Pro Gly Val Thr Asn Leu Gln Val
                35                  40                  45

Met Arg Ala Met Ala Ser Leu Arg Ala Arg Gly Leu Val Arg Glu Thr
            50                  55                  60

Phe Ala Trp Cys His Phe Tyr Trp Tyr Leu Thr Asn Glu Gly Ile Ala
65                  70                  75                  80

His Leu Arg Gln Tyr Leu His Leu Pro Pro Glu Ile Val Pro Ala Ser
                85                  90                  95

Leu Gln Arg Val Arg Arg Pro Val Ala Met Val Met Pro Ala Arg Arg
                100                 105                 110

Thr Pro His Val Gln Ala Val Gln Gly Pro Leu Gly Ser Pro Pro Lys
            115                 120                 125

Arg Gly Pro Leu Pro Thr Glu Glu Gln Arg Val Tyr Arg Arg Lys Glu
        130                 135                 140

Leu Glu Glu Val Ser Pro Glu Thr Pro Val Val Pro Ala Thr Thr Gln
145                 150                 155                 160

Arg Thr Leu Ala Arg Pro Gly Pro Glu Pro Ala Pro Ala Thr Asp Glu
                165                 170                 175

Arg Asp Arg Val Gln Lys Lys Thr Phe Thr Lys Trp Val Asn Lys His
            180                 185                 190

Leu Ile Lys Ala Gln Arg His Ile Ser Asp Leu Tyr Glu Asp Leu Arg
        195                 200                 205

Asp Gly His Asn Leu Ile Ser Leu Leu Glu Val Leu Ser Gly Asp Ser
    210                 215                 220

Leu Pro Arg Glu Lys Gly Arg Met Arg Phe His Lys Leu Gln Asn Val
225                 230                 235                 240

Gln Ile Ala Leu Asp Tyr Leu Arg His Arg Gln Val Lys Leu Val Asn
                245                 250                 255

Ile Arg Asn Asp Asp Ile Ala Asp Gly Asn Pro Lys Leu Thr Leu Gly
            260                 265                 270

Leu Ile Trp Thr Ile Ile Leu His Phe Gln Ile Ser Asp Ile Gln Val
        275                 280                 285

Ser Gly Gln Ser Glu Asp Met Thr Ala Lys Glu Lys Leu Leu Leu Trp
    290                 295                 300

Ser Gln Arg Met Val Glu Gly Tyr Gln Gly Leu Arg Cys Asp Asn Phe
305                 310                 315                 320

Thr Ser Ser Trp Arg Asp Gly Arg Leu Phe Asn Ala Ile Ile His Arg
                325                 330                 335

His Lys Pro Leu Leu Ile Asp Met Asn Lys Val Tyr Arg Gln Thr Asn
            340                 345                 350

Leu Glu Asn Leu Asp Gln Ala Phe Ser Val Ala Glu Arg Asp Leu Gly
        355                 360                 365

Val Thr Arg Leu Leu Asp Pro Glu Asp Val Asp Val Pro Gln Pro Asp
    370                 375                 380

Glu Lys Ser Ile Ile Thr Tyr Val Ser Ser Leu Tyr Asp Ala Met Pro
385                 390                 395                 400

Arg Val Pro Asp Val Gln Asp Gly Val Arg Ala Asn Glu Leu Gln Leu
                405                 410                 415

Arg Trp Gln Glu Tyr Arg Glu Leu Val Leu Leu Leu Leu Gln Trp Met
            420                 425                 430
```

Arg His His Thr Ala Ala Phe Glu Glu Arg Arg Phe Pro Ser Ser Phe
          435                 440                 445

Glu Glu Ile Glu Ile Leu Trp Ser Gln Phe Leu Lys Phe Lys Glu Met
450                 455                 460

Glu Leu Pro Ala Lys Glu Ala Asp Lys Asn Arg Ser Lys Gly Ile Tyr
465                 470                 475                 480

Gln Ser Leu Glu Gly Ala Val Gln Ala Gly Gln Leu Lys Val Pro Pro
              485                 490                 495

Gly Tyr His Pro Leu Asp Val Glu Lys Glu Trp Gly Lys Leu His Val
          500                 505                 510

Ala Ile Leu Glu Arg Glu Lys Gln Leu Arg Ser Glu Phe Glu Arg Leu
          515                 520                 525

Glu Cys Leu Gln Arg Ile Val Thr Lys Leu Gln Met Glu Ala Gly Leu
          530                 535                 540

Cys Glu Glu Gln Leu Asn Gln Ala Asp Ala Leu Leu Gln Ser Asp Val
545                 550                 555                 560

Arg Leu Leu Ala Ala Gly Lys Val Pro Gln Arg Ala Gly Glu Val Glu
              565                 570                 575

Arg Asp Leu Asp Lys Ala Asp Ser Met Ile Arg Leu Leu Phe Asn Asp
          580                 585                 590

Val Gln Thr Leu Lys Asp Gly Arg His Pro Gln Gly Glu Gln Met Tyr
          595                 600                 605

Arg Arg Val Tyr Arg Leu His Glu Arg Leu Val Ala Ile Arg Thr Glu
610                 615                 620

Tyr Asn Leu Arg Leu Lys Ala Gly Val Ala Ala Pro Ala Thr Gln Val
625                 630                 635                 640

Ala Gln Val Thr Leu Gln Ser Val Gln Arg Arg Pro Glu Leu Glu Asp
              645                 650                 655

Ser Thr Leu Arg Tyr Leu Gln Asp Leu Leu Ala Trp Val Glu Glu Asn
          660                 665                 670

Gln His Arg Val Asp Gly Ala Glu Trp Gly Val Asp Leu Pro Ser Val
          675                 680                 685

Glu Ala Gln Leu Gly Ser His Arg Gly Leu His Gln Ser Ile Glu Glu
          690                 695                 700

Phe Arg Ala Lys Ile Glu Arg Ala Arg Ser Asp Glu Gly Gln Leu Ser
705                 710                 715                 720

Pro Ala Thr Arg Gly Ala Tyr Arg Asp Cys Leu Gly Arg Leu Asp Leu
              725                 730                 735

Gln Tyr Ala Lys Leu Leu Asn Ser Ser Lys Ala Arg Leu Arg Ser Leu
              740                 745                 750

Glu Ser Leu His Ser Phe Val Ala Ala Thr Lys Glu Leu Met Trp
          755                 760                 765

Leu Asn Glu Lys Glu Glu Glu Val Gly Phe Asp Trp Ser Asp Arg
770                 775                 780

Asn Thr Asn Met Thr Ala Lys Lys Glu Ser Tyr Ser Ala Leu Met Arg
785                 790                 795                 800

Glu Leu Glu Leu Lys Glu Lys Lys Ile Lys Glu Leu Gln Asn Ala Gly
              805                 810                 815

Asp Arg Leu Leu Arg Glu Asp His Pro Ala Arg Pro Thr Val Glu Ser
          820                 825                 830

Phe Gln Ala Ala Leu Gln Thr Gln Trp Ser Trp Met Leu Gln Leu Cys
          835                 840                 845

```
Cys Cys Ile Glu Ala His Leu Lys Glu Asn Ala Ala Tyr Phe Gln Phe
850                 855                 860

Phe Ser Asp Val Arg Glu Ala Glu Gly Gln Leu Gln Lys Leu Gln Glu
865                 870                 875                 880

Ala Leu Arg Arg Lys Tyr Ser Cys Asp Arg Ser Ala Thr Val Thr Arg
                    885                 890                 895

Leu Glu Asp Leu Leu Gln Asp Ala Gln Asp Glu Lys Glu Gln Leu Asn
                900                 905                 910

Glu Tyr Lys Gly His Leu Ser Gly Leu Ala Lys Arg Ala Lys Ala Val
            915                 920                 925

Val Gln Leu Lys Pro Arg His Pro Ala His Pro Met Arg Gly Arg Leu
930                 935                 940

Pro Leu Leu Ala Val Cys Asp Tyr Lys Gln Val Glu Val Thr Val His
945                 950                 955                 960

Lys Gly Asp Glu Cys Gln Leu Val Gly Pro Ala Gln Pro Ser His Trp
                965                 970                 975

Lys Val Leu Ser Ser Ser Gly Ser Glu Ala Ala Val Pro Ser Val Cys
                980                 985                 990

Phe Leu Val Pro Pro Pro Asn Gln Glu Ala Gln Glu Ala Val Thr Arg
                995                 1000                1005

Leu Glu Ala Gln His Gln Ala Leu Val Thr Leu Trp His Gln Leu
    1010                1015                1020

His Val Asp Met Lys Ser Leu Leu Ala Trp Gln Ser Leu Arg Arg
    1025                1030                1035

Asp Val Gln Leu Ile Arg Ser Trp Ser Leu Ala Thr Phe Arg Thr
    1040                1045                1050

Leu Lys Pro Glu Glu Gln Arg Gln Ala Leu His Ser Leu Glu Leu
    1055                1060                1065

His Tyr Gln Ala Phe Leu Arg Asp Ser Gln Asp Ala Gly Gly Phe
    1070                1075                1080

Gly Pro Glu Asp Arg Leu Met Ala Glu Arg Glu Tyr Gly Ser Cys
    1085                1090                1095

Ser His His Tyr Gln Gln Leu Leu Gln Ser Leu Glu Gln Gly Ala
    1100                1105                1110

Gln Glu Glu Ser Arg Cys Gln Arg Cys Ile Ser Glu Leu Lys Asp
    1115                1120                1125

Ile Arg Leu Gln Leu Glu Ala Cys Glu Thr Arg Thr Val His Arg
    1130                1135                1140

Leu Arg Leu Pro Leu Asp Lys Glu Pro Ala Arg Glu Cys Ala Gln
    1145                1150                1155

Arg Ile Ala Glu Gln Gln Lys Ala Gln Ala Glu Val Glu Gly Leu
    1160                1165                1170

Gly Lys Gly Val Ala Arg Leu Ser Ala Glu Ala Glu Lys Val Leu
    1175                1180                1185

Ala Leu Pro Glu Pro Ser Pro Ala Ala Pro Thr Leu Arg Ser Glu
    1190                1195                1200

Leu Glu Leu Thr Leu Gly Lys Leu Glu Gln Val Arg Ser Leu Ser
    1205                1210                1215

Ala Ile Tyr Leu Glu Lys Leu Lys Thr Ile Ser Leu Val Ile Arg
    1220                1225                1230

Gly Thr Gln Gly Ala Glu Glu Val Leu Arg Ala His Glu Glu Gln
    1235                1240                1245

Leu Lys Glu Ala Gln Ala Val Pro Ala Thr Leu Pro Glu Leu Glu
```

-continued

```
            1250                1255                1260
Ala Thr Lys Ala Ser Leu Lys Lys Leu Arg Ala Gln Ala Glu Ala
            1265                1270                1275
Gln Gln Pro Thr Phe Asp Ala Leu Arg Asp Glu Leu Arg Gly Ala
            1280                1285                1290
Gln Glu Val Gly Glu Arg Leu Gln Gln Arg His Gly Glu Arg Asp
            1295                1300                1305
Val Glu Val Glu Arg Trp Arg Glu Arg Val Ala Gln Leu Leu Glu
            1310                1315                1320
Arg Trp Gln Ala Val Leu Ala Gln Thr Asp Val Arg Gln Arg Glu
            1325                1330                1335
Leu Glu Gln Leu Gly Arg Gln Leu Arg Tyr Tyr Arg Glu Ser Ala
            1340                1345                1350
Asp Pro Leu Gly Ala Trp Leu Gln Asp Ala Arg Arg Arg Gln Glu
            1355                1360                1365
Gln Ile Gln Ala Met Pro Leu Ala Asp Ser Gln Ala Val Arg Glu
            1370                1375                1380
Gln Leu Arg Gln Glu Gln Ala Leu Leu Glu Glu Ile Glu Arg His
            1385                1390                1395
Gly Glu Lys Val Glu Glu Cys Gln Arg Phe Ala Lys Gln Tyr Ile
            1400                1405                1410
Asn Ala Ile Lys Asp Tyr Glu Leu Gln Leu Val Thr Tyr Lys Ala
            1415                1420                1425
Gln Leu Glu Pro Val Ala Ser Pro Ala Lys Lys Pro Lys Val Gln
            1430                1435                1440
Ser Gly Ser Glu Ser Val Ile Gln Glu Tyr Val Asp Leu Arg Thr
            1445                1450                1455
His Tyr Ser Glu Leu Thr Thr Leu Thr Ser Gln Tyr Ile Lys Phe
            1460                1465                1470
Ile Ser Glu Thr Leu Arg Arg Met Glu Glu Glu Arg Leu Ala
            1475                1480                1485
Glu Gln Gln Arg Ala Glu Glu Arg Glu Arg Leu Ala Glu Val Glu
            1490                1495                1500
Ala Ala Leu Glu Lys Gln Arg Gln Leu Ala Glu Ala His Ala Gln
            1505                1510                1515
Ala Lys Ala Gln Ala Glu Arg Glu Ala Lys Glu Leu Gln Gln Arg
            1520                1525                1530
Met Gln Glu Glu Val Val Arg Glu Glu Ala Ala Val Asp Ala
            1535                1540                1545
Gln Gln Gln Lys Arg Ser Ile Gln Glu Glu Leu Gln Gln Leu Arg
            1550                1555                1560
Gln Ser Ser Glu Ala Glu Ile Gln Ala Lys Ala Arg Gln Ala Glu
            1565                1570                1575
Ala Ala Glu Arg Ser Arg Leu Arg Ile Glu Glu Glu Ile Arg Val
            1580                1585                1590
Val Arg Leu Gln Leu Glu Ala Thr Glu Arg Gln Arg Gly Gly Ala
            1595                1600                1605
Glu Gly Glu Leu Gln Ala Leu Arg Ala Arg Ala Glu Glu Ala Glu
            1610                1615                1620
Ala Gln Lys Arg Gln Ala Gln Glu Glu Ala Glu Arg Leu Arg Arg
            1625                1630                1635
Gln Val Gln Asp Glu Ser Gln Arg Lys Arg Gln Ala Glu Val Glu
            1640                1645                1650
```

```
Leu Ala Ser Arg Val Lys Ala Glu Ala Glu Ala Arg Glu Lys
1655                1660                1665

Gln Arg Ala Leu Gln Ala Leu Glu Glu Leu Arg Leu Gln Ala Glu
1670                1675                1680

Glu Ala Glu Arg Arg Leu Arg Gln Ala Glu Val Glu Arg Ala Arg
1685                1690                1695

Gln Val Gln Val Ala Leu Glu Thr Ala Gln Arg Ser Ala Glu Ala
1700                1705                1710

Glu Leu Gln Ser Lys Arg Ala Ser Phe Ala Glu Lys Thr Ala Gln
1715                1720                1725

Leu Glu Arg Ser Leu Gln Glu His Val Ala Val Ala Gln Leu
1730                1735                1740

Arg Glu Glu Ala Glu Arg Arg Ala Gln Gln Gln Ala Glu Ala Glu
1745                1750                1755

Arg Ala Arg Glu Glu Ala Glu Arg Glu Leu Glu Arg Trp Gln Leu
1760                1765                1770

Lys Ala Asn Glu Ala Leu Arg Leu Arg Leu Gln Ala Glu Glu Val
1775                1780                1785

Ala Gln Gln Lys Ser Leu Ala Gln Ala Glu Ala Glu Lys Gln Lys
1790                1795                1800

Glu Glu Ala Glu Arg Glu Ala Arg Arg Arg Gly Lys Ala Glu Glu
1805                1810                1815

Gln Ala Val Arg Gln Arg Glu Leu Ala Glu Gln Glu Leu Glu Lys
1820                1825                1830

Gln Arg Gln Leu Ala Glu Gly Thr Ala Gln Gln Arg Leu Ala Ala
1835                1840                1845

Glu Gln Glu Leu Ile Arg Leu Arg Ala Glu Thr Glu Gln Gly Glu
1850                1855                1860

Gln Gln Arg Gln Leu Leu Glu Glu Glu Leu Ala Arg Leu Gln Arg
1865                1870                1875

Glu Ala Ala Ala Ala Thr Gln Lys Arg Gln Glu Leu Glu Ala Glu
1880                1885                1890

Leu Ala Lys Val Arg Ala Glu Met Glu Val Leu Leu Ala Ser Lys
1895                1900                1905

Ala Arg Ala Glu Glu Glu Ser Arg Ser Thr Ser Glu Lys Ser Lys
1910                1915                1920

Gln Arg Leu Glu Ala Glu Ala Gly Arg Phe Arg Glu Leu Ala Glu
1925                1930                1935

Glu Ala Ala Arg Leu Arg Ala Leu Ala Glu Glu Ala Lys Arg Gln
1940                1945                1950

Arg Gln Leu Ala Glu Glu Asp Ala Ala Arg Gln Arg Ala Glu Ala
1955                1960                1965

Glu Arg Val Leu Ala Glu Lys Leu Ala Ala Ile Gly Glu Ala Thr
1970                1975                1980

Arg Leu Lys Thr Glu Ala Glu Ile Ala Leu Lys Glu Lys Glu Ala
1985                1990                1995

Glu Asn Glu Arg Leu Arg Arg Leu Ala Glu Asp Glu Ala Phe Gln
2000                2005                2010

Arg Arg Arg Leu Glu Glu Gln Ala Ala Gln His Lys Ala Asp Ile
2015                2020                2025

Glu Glu Arg Leu Ala Gln Leu Arg Lys Ala Ser Asp Ser Glu Leu
2030                2035                2040
```

```
Glu Arg Gln Lys Gly Leu Val Glu Asp Thr Leu Arg Gln Arg Arg
    2045                2050                2055

Gln Val Glu Glu Glu Ile Leu Ala Leu Lys Ala Ser Phe Glu Lys
    2060                2065                2070

Ala Ala Ala Gly Lys Ala Glu Leu Glu Leu Glu Leu Gly Arg Ile
    2075                2080                2085

Arg Ser Asn Ala Glu Asp Thr Leu Arg Ser Lys Glu Gln Ala Glu
    2090                2095                2100

Leu Glu Ala Ala Arg Gln Arg Gln Leu Ala Ala Glu Glu Glu Arg
    2105                2110                2115

Arg Arg Arg Glu Ala Glu Glu Arg Val Gln Lys Ser Leu Ala Ala
    2120                2125                2130

Glu Glu Glu Ala Ala Arg Gln Arg Lys Ala Ala Leu Glu Glu Val
    2135                2140                2145

Glu Arg Leu Lys Ala Lys Val Glu Glu Ala Arg Arg Leu Arg Glu
    2150                2155                2160

Arg Ala Glu Gln Glu Ser Ala Arg Gln Leu Gln Leu Ala Gln Glu
    2165                2170                2175

Ala Ala Gln Lys Arg Leu Gln Ala Glu Glu Lys Ala His Ala Phe
    2180                2185                2190

Ala Val Gln Gln Lys Glu Gln Glu Leu Gln Gln Thr Leu Gln Gln
    2195                2200                2205

Glu Gln Ser Val Leu Asp Gln Leu Arg Gly Glu Ala Glu Ala Ala
    2210                2215                2220

Arg Arg Ala Ala Glu Glu Ala Glu Glu Ala Arg Val Gln Ala Glu
    2225                2230                2235

Arg Glu Ala Ala Gln Ser Arg Arg Gln Val Glu Glu Ala Glu Arg
    2240                2245                2250

Leu Lys Gln Ser Ala Glu Glu Gln Ala Gln Ala Arg Ala Gln Ala
    2255                2260                2265

Gln Ala Ala Ala Glu Lys Leu Arg Lys Glu Ala Glu Gln Glu Ala
    2270                2275                2280

Ala Arg Arg Ala Gln Ala Glu Gln Ala Ala Leu Arg Gln Lys Gln
    2285                2290                2295

Ala Ala Asp Ala Glu Met Glu Lys His Lys Lys Phe Ala Glu Gln
    2300                2305                2310

Thr Leu Arg Gln Lys Ala Gln Val Glu Gln Glu Leu Thr Thr Leu
    2315                2320                2325

Arg Leu Gln Leu Glu Glu Thr Asp His Gln Lys Asn Leu Leu Asp
    2330                2335                2340

Glu Glu Leu Gln Arg Leu Lys Ala Glu Ala Thr Glu Ala Ala Arg
    2345                2350                2355

Gln Arg Ser Gln Val Glu Glu Glu Leu Phe Ser Val Arg Val Gln
    2360                2365                2370

Met Glu Glu Leu Ser Lys Leu Lys Ala Arg Ile Glu Ala Glu Asn
    2375                2380                2385

Arg Ala Leu Ile Leu Arg Asp Lys Asp Asn Thr Gln Arg Phe Leu
    2390                2395                2400

Gln Glu Glu Ala Glu Lys Met Lys Gln Val Ala Glu Glu Ala Ala
    2405                2410                2415

Arg Leu Ser Val Ala Ala Gln Glu Ala Ala Arg Leu Arg Gln Leu
    2420                2425                2430

Ala Glu Glu Asp Leu Ala Gln Gln Arg Ala Leu Ala Glu Lys Met
```

```
              2435                2440                2445
Leu Lys  Glu Lys Met Gln Ala  Val Gln Glu Ala Thr  Arg Leu Lys
     2450                2455                2460

Ala Glu  Ala Glu Leu Leu Gln  Gln Gln Lys Glu Leu  Ala Gln Glu
     2465                2470                2475

Gln Ala  Arg Arg Leu Gln Glu  Asp Lys Glu Gln Met  Ala Gln Gln
     2480                2485                2490

Leu Ala  Glu Glu Thr Gln Gly  Phe Gln Arg Thr Leu  Glu Ala Glu
     2495                2500                2505

Arg Gln  Arg Gln Leu Glu Met  Ser Ala Glu Ala Glu  Arg Leu Lys
     2510                2515                2520

Leu Arg  Val Ala Glu Met Ser  Arg Ala Gln Ala Arg  Ala Glu Glu
     2525                2530                2535

Asp Ala  Gln Arg Phe Arg Lys  Gln Ala Glu Glu Ile  Gly Glu Lys
     2540                2545                2550

Leu His  Arg Thr Glu Leu Ala  Thr Gln Glu Lys Val  Thr Leu Val
     2555                2560                2565

Gln Thr  Leu Glu Ile Gln Arg  Gln Gln Ser Asp His  Asp Ala Glu
     2570                2575                2580

Arg Leu  Arg Glu Ala Ile Ala  Glu Leu Glu Arg Glu  Lys Glu Lys
     2585                2590                2595

Leu Gln  Gln Glu Ala Lys Leu  Leu Gln Leu Lys Ser  Glu Glu Met
     2600                2605                2610

Gln Thr  Val Gln Gln Glu Gln  Leu Leu Gln Glu Thr  Gln Ala Leu
     2615                2620                2625

Gln Gln  Ser Phe Leu Ser Glu  Lys Asp Ser Leu Leu  Gln Arg Glu
     2630                2635                2640

Arg Phe  Ile Glu Gln Glu Lys  Ala Lys Leu Glu Gln  Leu Phe Gln
     2645                2650                2655

Asp Glu  Val Ala Lys Ala Gln  Gln Leu Arg Glu Glu  Gln Gln Arg
     2660                2665                2670

Gln Gln  Gln Gln Met Glu Gln  Glu Arg Gln Arg Leu  Val Ala Ser
     2675                2680                2685

Met Glu  Glu Ala Arg Arg Arg  Gln His Glu Ala Glu  Glu Gly Val
     2690                2695                2700

Arg Arg  Lys Gln Glu Glu Leu  Gln Gln Leu Glu Gln  Gln Arg Arg
     2705                2710                2715

Gln Gln  Glu Glu Leu Leu Ala  Glu Glu Asn Gln Arg  Leu Arg Glu
     2720                2725                2730

Gln Leu  Gln Leu Leu Glu Glu  Gln His Arg Ala Ala  Leu Ala His
     2735                2740                2745

Ser Glu  Glu Val Thr Ala Ser  Gln Val Ala Ala Thr  Lys Thr Leu
     2750                2755                2760

Pro Asn  Gly Arg Asp Ala Leu  Asp Gly Pro Ala Ala  Glu Ala Glu
     2765                2770                2775

Pro Glu  His Ser Phe Asp Gly  Leu Arg Arg Lys Val  Ser Ala Gln
     2780                2785                2790

Arg Leu  Gln Glu Ala Gly Ile  Leu Ser Ala Glu Glu  Leu Gln Arg
     2795                2800                2805

Leu Ala  Gln Gly His Thr Thr  Val Asp Glu Leu Ala  Arg Arg Glu
     2810                2815                2820

Asp Val  Arg His Tyr Leu Gln  Gly Arg Ser Ser Ile  Ala Gly Leu
     2825                2830                2835
```

```
Leu Leu Lys Ala Thr Asn Glu Lys Leu Ser Val Tyr Ala Ala Leu
            2840                2845                2850

Gln Arg Gln Leu Leu Ser Pro Gly Thr Ala Leu Ile Leu Leu Glu
            2855                2860                2865

Ala Gln Ala Ala Ser Gly Phe Leu Leu Asp Pro Val Arg Asn Arg
            2870                2875                2880

Arg Leu Thr Val Asn Glu Ala Val Lys Glu Gly Val Val Gly Pro
            2885                2890                2895

Glu Leu His His Lys Leu Leu Ser Ala Glu Arg Ala Val Thr Gly
            2900                2905                2910

Tyr Lys Asp Pro Tyr Thr Gly Gln Gln Ile Ser Leu Phe Gln Ala
            2915                2920                2925

Met Gln Lys Gly Leu Ile Val Arg Glu His Gly Ile Arg Leu Leu
            2930                2935                2940

Glu Ala Gln Ile Ala Thr Gly Gly Val Ile Asp Pro Val His Ser
            2945                2950                2955

His Arg Val Pro Val Asp Val Ala Tyr Arg Arg Gly Tyr Phe Asp
            2960                2965                2970

Glu Glu Met Asn Arg Val Leu Ala Asp Pro Ser Asp Asp Thr Lys
            2975                2980                2985

Gly Phe Phe Asp Pro Asn Thr His Glu Asn Leu Thr Tyr Leu Gln
            2990                2995                3000

Leu Leu Glu Arg Cys Val Glu Asp Pro Glu Thr Gly Leu Cys Leu
            3005                3010                3015

Leu Pro Leu Thr Asp Lys Ala Ala Lys Gly Gly Glu Leu Val Tyr
            3020                3025                3030

Thr Asp Ser Glu Ala Arg Asp Val Phe Glu Lys Ala Thr Val Ser
            3035                3040                3045

Ala Pro Phe Gly Lys Phe Gln Gly Lys Thr Val Thr Ile Trp Glu
            3050                3055                3060

Ile Ile Asn Ser Glu Tyr Phe Thr Ala Glu Gln Arg Arg Asp Leu
            3065                3070                3075

Leu Arg Gln Phe Arg Thr Gly Arg Ile Thr Val Glu Lys Ile Ile
            3080                3085                3090

Lys Ile Ile Ile Thr Val Val Glu Glu Gln Glu Gln Lys Gly Arg
            3095                3100                3105

Leu Cys Phe Glu Gly Leu Arg Ser Leu Val Pro Ala Ala Glu Leu
            3110                3115                3120

Leu Glu Ser Arg Val Ile Asp Arg Glu Leu Tyr Gln Gln Leu Gln
            3125                3130                3135

Arg Gly Glu Arg Ser Val Arg Asp Val Ala Glu Val Asp Thr Val
            3140                3145                3150

Arg Arg Ala Leu Arg Gly Ala Asn Val Ile Ala Gly Val Trp Leu
            3155                3160                3165

Glu Glu Ala Gly Gln Lys Leu Ser Ile Tyr Asn Ala Leu Lys Lys
            3170                3175                3180

Asp Leu Leu Pro Ser Asp Met Ala Val Ala Leu Leu Glu Ala Gln
            3185                3190                3195

Ala Gly Thr Gly His Ile Ile Asp Pro Ala Thr Ser Ala Arg Leu
            3200                3205                3210

Thr Val Asp Glu Ala Val Arg Ala Gly Leu Val Gly Pro Glu Phe
            3215                3220                3225
```

```
His Glu Lys Leu Leu Ser Ala Glu Lys Ala Val Thr Gly Tyr Arg
3230                3235                3240

Asp Pro Tyr Thr Gly Gln Ser Val Ser Leu Phe Gln Ala Leu Lys
    3245                3250                3255

Lys Gly Leu Ile Pro Arg Glu Gln Gly Leu Arg Leu Leu Asp Ala
        3260                3265                3270

Gln Leu Ser Thr Gly Gly Ile Val Asp Pro Ser Lys Ser His Arg
    3275                3280                3285

Val Pro Leu Asp Val Ala Cys Ala Arg Gly Cys Leu Asp Glu Glu
    3290                3295                3300

Thr Ser Arg Ala Leu Ser Ala Pro Arg Ala Asp Ala Lys Ala Tyr
    3305                3310                3315

Ser Asp Pro Ser Thr Gly Glu Pro Ala Thr Tyr Gly Glu Leu Gln
    3320                3325                3330

Gln Arg Cys Arg Pro Asp Gln Leu Thr Gly Leu Ser Leu Leu Pro
    3335                3340                3345

Leu Ser Glu Lys Ala Ala Arg Ala Arg Gln Glu Glu Leu Tyr Ser
    3350                3355                3360

Glu Leu Gln Ala Arg Glu Thr Phe Glu Lys Thr Pro Val Glu Val
    3365                3370                3375

Pro Val Gly Gly Phe Lys Gly Arg Thr Val Thr Val Trp Glu Leu
    3380                3385                3390

Ile Ser Ser Glu Tyr Phe Thr Ala Glu Gln Arg Gln Glu Leu Leu
    3395                3400                3405

Arg Gln Phe Arg Thr Gly Lys Val Thr Val Glu Lys Val Ile Lys
    3410                3415                3420

Ile Leu Ile Thr Ile Val Glu Glu Val Glu Thr Leu Arg Gln Glu
    3425                3430                3435

Arg Leu Ser Phe Ser Gly Leu Arg Ala Pro Val Pro Ala Ser Glu
    3440                3445                3450

Leu Leu Ala Ser Gly Val Leu Ser Arg Ala Gln Phe Glu Gln Leu
    3455                3460                3465

Lys Asp Gly Lys Thr Thr Val Lys Asp Leu Ser Glu Leu Gly Ser
    3470                3475                3480

Val Arg Thr Leu Leu Gln Gly Ser Gly Cys Leu Ala Gly Ile Tyr
    3485                3490                3495

Leu Glu Asp Thr Lys Glu Lys Val Ser Ile Tyr Glu Ala Met Arg
    3500                3505                3510

Arg Gly Leu Leu Arg Ala Thr Ala Ala Leu Leu Leu Glu Ala
    3515                3520                3525

Gln Ala Ala Thr Gly Phe Leu Val Asp Pro Val Arg Asn Gln Arg
    3530                3535                3540

Leu Tyr Val His Glu Ala Val Lys Ala Gly Val Val Gly Pro Glu
    3545                3550                3555

Leu His Glu Gln Leu Leu Ser Ala Glu Lys Ala Val Thr Gly Tyr
    3560                3565                3570

Arg Asp Pro Tyr Ser Gly Ser Thr Ile Ser Leu Phe Gln Ala Met
    3575                3580                3585

Gln Lys Gly Leu Val Leu Arg Gln His Gly Ile Arg Leu Leu Glu
    3590                3595                3600

Ala Gln Ile Ala Thr Gly Gly Ile Ile Asp Pro Val His Ser His
    3605                3610                3615

Arg Val Pro Val Asp Val Ala Tyr Gln Arg Gly Tyr Phe Ser Glu
```

```
              3620                3625                3630

Glu Met Asn Arg Val Leu Ala Asp Pro Ser Asp Thr Lys Gly
    3635                3640                3645

Phe Phe Asp Pro Asn Thr His Glu Asn Leu Thr Tyr Arg Gln Leu
    3650                3655                3660

Leu Glu Arg Cys Val Glu Asp Pro Glu Thr Gly Leu Arg Leu Leu
    3665                3670                3675

Pro Leu Lys Gly Ala Glu Lys Ala Glu Val Val Glu Thr Thr Gln
    3680                3685                3690

Val Tyr Thr Glu Glu Glu Thr Arg Arg Ala Phe Glu Glu Thr Gln
    3695                3700                3705

Ile Asp Ile Pro Gly Gly Gly Ser His Gly Gly Ser Thr Met Ser
    3710                3715                3720

Leu Trp Glu Val Met Gln Ser Asp Leu Ile Pro Glu Glu Gln Arg
    3725                3730                3735

Ala Gln Leu Met Ala Asp Phe Gln Ala Gly Arg Val Thr Lys Glu
    3740                3745                3750

Arg Met Ile Ile Ile Ile Ile Glu Ile Ile Glu Lys Thr Glu Ile
    3755                3760                3765

Ile Arg Gln Gln Gly Leu Ala Ser Tyr Asp Tyr Val Arg Arg Arg
    3770                3775                3780

Leu Thr Ala Glu Asp Leu Phe Glu Ala Arg Ile Ile Ser Leu Glu
    3785                3790                3795

Thr Tyr Asn Leu Leu Arg Glu Gly Thr Arg Ser Leu Arg Glu Ala
    3800                3805                3810

Leu Glu Ala Glu Ser Ala Trp Cys Tyr Leu Tyr Gly Thr Gly Ser
    3815                3820                3825

Val Ala Gly Val Tyr Leu Pro Gly Ser Arg Gln Thr Leu Ser Ile
    3830                3835                3840

Tyr Gln Ala Leu Lys Lys Gly Leu Leu Ser Ala Glu Val Ala Arg
    3845                3850                3855

Leu Leu Leu Glu Ala Gln Ala Ala Thr Gly Phe Leu Leu Asp Pro
    3860                3865                3870

Val Lys Gly Glu Arg Leu Thr Val Asp Glu Ala Val Arg Lys Gly
    3875                3880                3885

Leu Val Gly Pro Glu Leu His Asp Arg Leu Leu Ser Ala Glu Arg
    3890                3895                3900

Ala Val Thr Gly Tyr Arg Asp Pro Tyr Thr Glu Gln Thr Ile Ser
    3905                3910                3915

Leu Phe Gln Ala Met Lys Lys Glu Leu Ile Pro Thr Glu Glu Ala
    3920                3925                3930

Leu Arg Leu Leu Asp Ala Gln Leu Ala Thr Gly Gly Ile Val Asp
    3935                3940                3945

Pro Arg Leu Gly Phe His Leu Pro Leu Glu Val Ala Tyr Gln Arg
    3950                3955                3960

Gly Tyr Leu Asn Lys Asp Thr His Asp Gln Leu Ser Glu Pro Ser
    3965                3970                3975

Glu Val Arg Ser Tyr Val Asp Pro Ser Thr Asp Glu Arg Leu Ser
    3980                3985                3990

Tyr Thr Gln Leu Leu Arg Arg Cys Arg Arg Asp Asp Gly Thr Gly
    3995                4000                4005

Gln Leu Leu Leu Pro Leu Ser Asp Ala Arg Lys Leu Thr Phe Arg
    4010                4015                4020
```

```
Gly Leu Arg Lys Gln Ile Thr Met Glu Glu Leu Val Arg Ser Gln
            4025                4030                4035
Val Met Asp Glu Ala Thr Ala Leu Gln Leu Arg Glu Gly Leu Thr
            4040                4045                4050
Ser Ile Glu Glu Val Thr Lys Asn Leu Gln Lys Phe Leu Glu Gly
            4055                4060                4065
Thr Ser Cys Ile Ala Gly Val Phe Val Asp Ala Thr Lys Glu Arg
            4070                4075                4080
Leu Ser Val Tyr Gln Ala Met Lys Lys Gly Ile Ile Arg Pro Gly
            4085                4090                4095
Thr Ala Phe Glu Leu Leu Glu Ala Gln Ala Ala Thr Gly Tyr Val
            4100                4105                4110
Ile Asp Pro Ile Lys Gly Leu Lys Leu Thr Val Glu Glu Ala Val
            4115                4120                4125
Arg Met Gly Ile Val Gly Pro Glu Phe Lys Asp Lys Leu Leu Ser
            4130                4135                4140
Ala Glu Arg Ala Val Thr Gly Tyr Lys Asp Pro Tyr Ser Gly Lys
            4145                4150                4155
Leu Ile Ser Leu Phe Gln Ala Met Lys Lys Gly Leu Ile Leu Lys
            4160                4165                4170
Asp His Gly Ile Arg Leu Leu Glu Ala Gln Ile Ala Thr Gly Gly
            4175                4180                4185
Ile Ile Asp Pro Glu Glu Ser His Arg Leu Pro Val Glu Val Ala
            4190                4195                4200
Tyr Lys Arg Gly Leu Phe Asp Glu Glu Met Asn Glu Ile Leu Thr
            4205                4210                4215
Asp Pro Ser Asp Asp Thr Lys Gly Phe Phe Asp Pro Asn Thr Glu
            4220                4225                4230
Glu Asn Leu Thr Tyr Leu Gln Leu Met Glu Arg Cys Ile Thr Asp
            4235                4240                4245
Pro Gln Thr Gly Leu Cys Leu Leu Pro Leu Lys Glu Lys Lys Arg
            4250                4255                4260
Glu Arg Lys Thr Ser Ser Lys Ser Ser Val Arg Lys Arg Arg Val
            4265                4270                4275
Val Ile Val Asp Pro Glu Thr Gly Lys Glu Met Ser Val Tyr Glu
            4280                4285                4290
Ala Tyr Arg Lys Gly Leu Ile Asp His Gln Thr Tyr Leu Glu Leu
            4295                4300                4305
Ser Glu Gln Glu Cys Glu Trp Glu Glu Ile Thr Ile Ser Ser Ser
            4310                4315                4320
Asp Gly Val Val Lys Ser Met Ile Ile Asp Arg Arg Ser Gly Arg
            4325                4330                4335
Gln Tyr Asp Ile Asp Asp Ala Ile Ala Lys Asn Leu Ile Asp Arg
            4340                4345                4350
Ser Ala Leu Asp Gln Tyr Arg Ala Gly Thr Leu Ser Ile Thr Glu
            4355                4360                4365
Phe Ala Asp Met Leu Ser Gly Asn Ala Gly Gly Phe Arg Ser Arg
            4370                4375                4380
Ser Ser Ser Val Gly Ser Ser Ser Ser Tyr Pro Ile Ser Pro Ala
            4385                4390                4395
Val Ser Arg Thr Gln Leu Ala Ser Trp Ser Asp Pro Thr Glu Glu
            4400                4405                4410
```

Thr Gly Pro Val Ala Gly Ile Leu Asp Thr Glu Thr Leu Glu Lys
    4415                4420                4425

Val Ser Ile Thr Glu Ala Met His Arg Asn Leu Val Asp Asn Ile
    4430                4435                4440

Thr Gly Gln Arg Leu Leu Glu Ala Gln Ala Cys Thr Gly Gly Ile
    4445                4450                4455

Ile Asp Pro Ser Thr Gly Glu Arg Phe Pro Val Thr Asp Ala Val
    4460                4465                4470

Asn Lys Gly Leu Val Asp Lys Ile Met Val Asp Arg Ile Asn Leu
    4475                4480                4485

Ala Gln Lys Ala Phe Cys Gly Phe Glu Asp Pro Arg Thr Lys Thr
    4490                4495                4500

Lys Met Ser Ala Ala Gln Ala Leu Lys Lys Gly Trp Leu Tyr Tyr
    4505                4510                4515

Glu Ala Gly Gln Arg Phe Leu Glu Val Gln Tyr Leu Thr Gly Gly
    4520                4525                4530

Leu Ile Glu Pro Asp Thr Pro Gly Arg Val Pro Leu Asp Glu Ala
    4535                4540                4545

Leu Gln Arg Gly Thr Val Asp Ala Arg Thr Ala Gln Lys Leu Arg
    4550                4555                4560

Asp Val Gly Ala Tyr Ser Lys Tyr Leu Thr Cys Pro Lys Thr Lys
    4565                4570                4575

Leu Lys Ile Ser Tyr Lys Asp Ala Leu Asp Arg Ser Met Val Glu
    4580                4585                4590

Glu Gly Thr Gly Leu Arg Leu Leu Glu Ala Ala Ala Gln Ser Thr
    4595                4600                4605

Lys Gly Tyr Tyr Ser Pro Tyr Ser Val Ser Gly Ser Gly Ser Thr
    4610                4615                4620

Ala Gly Ser Arg Thr Gly Ser Arg Thr Gly Ser Arg Ala Gly Ser
    4625                4630                4635

Arg Arg Gly Ser Phe Asp Ala Thr Gly Ser Gly Phe Ser Met Thr
    4640                4645                4650

Phe Ser Ser Ser Ser Tyr Ser Ser Ser Gly Tyr Gly Arg Arg Tyr
    4655                4660                4665

Ala Ser Gly Ser Ser Ala Ser Leu Gly Gly Pro Glu Ser Ala Val
    4670                4675                4680

Ala

<210> SEQ ID NO 9
<211> LENGTH: 2353
<212> TYPE: PRT
<213> ORGANISM: Xenopus laevis

<400> SEQUENCE: 9

Met Val Ala Leu Ser Leu Lys Ile Ser Ile Gly Asn Val Val Lys Thr
1               5                   10                  15

Met Gln Phe Glu Pro Ser Thr Met Ile Tyr Asp Ala Cys Arg Ile Ile
                20                  25                  30

Arg Glu Lys Val Pro Glu Ala Gln Ile Gly Gln Pro Asn Asp Phe Gly
            35                  40                  45

Leu Phe Leu Ser Asp Glu Asp Pro Lys Lys Gly Ile Trp Leu Glu Ala
        50                  55                  60

Gly Lys Ala Leu Asp Tyr Tyr Met Leu Arg Asn Gly Asp Thr Leu Glu
65                  70                  75                  80

```
Tyr Arg Lys Lys Gln Arg Pro Leu Glu Ile Arg Met Leu Asp Gly Thr
                85                  90                  95
Val Lys Thr Val Met Val Asp Asp Ser Asn Thr Met Ser Asp Leu Leu
            100                 105                 110
Met Thr Ile Cys Ala Arg Ile Gly Ile Thr Asn Tyr Asp Glu Tyr Ser
        115                 120                 125
Leu Val Arg Glu Ile Met Glu Glu Lys Lys Glu Val Thr Gly Thr
    130                 135                 140
Leu Lys Arg Asp Lys Thr Leu Leu Arg Asp Asp Lys Lys Met Glu Lys
145                 150                 155                 160
Leu Lys Gln Lys Leu His Thr Asp Asp Glu Leu Asn Trp Leu Asp Pro
                165                 170                 175
Gly Arg Thr Leu Arg Glu Gln Gly Val Asp Glu Asn Glu Thr Leu Leu
            180                 185                 190
Leu Arg Arg Lys Phe Phe Tyr Ser Asp Gln Asn Val Asp Ser Arg Asp
        195                 200                 205
Pro Val Gln Leu Asn Leu Leu Tyr Val Gln Ala Arg Asp Asp Ile Leu
    210                 215                 220
Asn Gly Ser His Pro Val Ser Phe Asp Lys Ala Cys Glu Phe Ala Gly
225                 230                 235                 240
Tyr Gln Cys Gln Val Gln Phe Gly Pro His Asn Glu Val Lys His Lys
                245                 250                 255
Pro Gly Phe Leu Glu Leu Lys Asp Phe Leu Pro Lys Glu Tyr Ile Lys
            260                 265                 270
Gln Lys Gly Glu Arg Lys Ile Phe Leu Ala His Lys Gln Cys Gly Asn
        275                 280                 285
Met Ser Glu Ile Glu Ala Lys Ala Arg Tyr Val Lys Leu Ala Arg Ser
    290                 295                 300
Leu Lys Thr Tyr Gly Val Ser Phe Phe Leu Val Lys Glu Lys Met Lys
305                 310                 315                 320
Gly Lys Asn Lys Leu Val Pro Arg Leu Leu Gly Ile Thr Lys Glu Cys
                325                 330                 335
Val Met Arg Val Asp Glu Lys Thr Lys Glu Val Ile Gln Glu Trp Asn
            340                 345                 350
Leu Thr Asn Ile Lys Arg Trp Ala Ala Ser Pro Lys Ser Phe Thr Leu
        355                 360                 365
Asp Phe Gly Asp Tyr Gln Asp Gly Tyr Tyr Ser Val Gln Thr Thr Glu
    370                 375                 380
Gly Glu Gln Ile Ala Gln Leu Ile Ala Gly Tyr Ile Asp Ile Ile Leu
385                 390                 395                 400
Lys Lys Lys Lys Ser Lys Asp His Phe Gly Leu Glu Gly Asp Glu Glu
                405                 410                 415
Ser Thr Met Leu Glu Asp Ser Val Ser Pro Lys Lys Ser Thr Leu Leu
            420                 425                 430
Gln Gln Gln Phe Asn Gln Val Gly Lys Val Glu His Gly Ser Val Ala
        435                 440                 445
Leu Pro Ala Ile Met Arg Ser Gly Ala Ser Gly Pro Glu Asn Phe Gln
    450                 455                 460
Val Gly Ser Met Pro Gln Ala Gln Gln His Ile Thr Ser Gly Gln Met
465                 470                 475                 480
His Leu Gly His Met Pro Pro Leu Thr Ser Ala Gln Gln Ala Leu Thr
                485                 490                 495
Gly Thr Ile Asn Ser Ser Met Gln Ala Ile Asn Ala Ala Gln Ala Thr
```

-continued

```
               500                 505                 510
Leu Asp Asp Phe Asp Ser Leu Pro Pro Leu Gly Asp Asp Ala Ala Ser
            515                 520                 525

Lys Ala Trp Arg Lys Asn Lys Met Asp Asn Ser Lys His Glu Ile His
            530                 535                 540

Ser Gln Val Asp Ala Ile Thr Ala Gly Thr Ala Ser Val Val Asn Leu
545                 550                 555                 560

Thr Ala Gly Asn Pro Ala Asp Thr Asp Tyr Thr Ala Val Gly Cys Ala
            565                 570                 575

Val Thr Thr Ile Ser Ser Asn Leu Thr Glu Met Ser Arg Gly Val Lys
            580                 585                 590

Leu Leu Ala Ala Leu Met Glu Asp Glu Gly Gly Asn Gly Arg Gln Leu
            595                 600                 605

Leu His Ala Ala Lys Asn Leu Ala Gly Ala Val Ser Asp Leu Leu Lys
            610                 615                 620

Thr Ala Gln Pro Ala Ser Thr Glu Pro Arg Gln Val Leu Met Gln Ala
625                 630                 635                 640

Ala Gly Asn Val Gly Met Thr Ser Gly Glu Leu Leu Lys Gln Ile Gly
            645                 650                 655

Glu Cys Asp Thr Asp Ser Gln Phe Gln Asp Met Leu Val Gln Leu Ala
            660                 665                 670

Lys Ala Val Ala Ser Ala Ala Ala Leu Val Leu Lys Ala Lys Asn
            675                 680                 685

Val Ala Glu Arg Thr Asp Asp Gly Ala Gln Gln Thr Gln Val Ile Ala
            690                 695                 700

Ala Ala Thr Gln Cys Ala Leu Ser Thr Ser Gln Leu Val Ala Cys Thr
705                 710                 715                 720

Lys Val Val Ala Pro Thr Ile Ser Ser Pro Val Cys Gln Glu Gln Leu
            725                 730                 735

Leu Glu Ala Gly Lys Gln Val Ala Lys Ser Val Glu Gly Cys Val Glu
            740                 745                 750

Ala Ser Glu Ala Ala Val Glu Asp Pro Glu Leu Leu Lys Ser Val Gly
            755                 760                 765

Val Ala Ala Ser Gly Val Thr Gln Ala Leu Asn Asn Leu Leu Gln His
            770                 775                 780

Ile Lys Lys His Ala Ser Gly Gly Pro Ser Thr Gly Arg Tyr Asp Gln
785                 790                 795                 800

Ala Thr Asp Thr Ile Leu Asn Val Thr Glu Asn Ile Phe Ser Ser Met
            805                 810                 815

Gly Asp Ala Gly Glu Met Val Arg Gln Ala Arg Ile Leu Ala Gln Ala
            820                 825                 830

Thr Ser Asp Leu Val Gly Ala Ile Lys Ala Asp Ala Glu Arg Glu Ser
            835                 840                 845

Asp Leu Glu Asn Ser Arg Lys Leu Leu Cys Ala Ala Lys Leu Leu Ala
            850                 855                 860

Asp Ala Thr Ala Arg Met Val Glu Ala Ala Lys Gly Ala Ala Ala His
865                 870                 875                 880

Pro Asp Ser Glu Glu Gln Gln Gln Lys Leu Arg Glu Ala Ala Glu Gly
            885                 890                 895

Leu Arg Met Ala Thr Asn Ala Ala Ala Gln Asn Ala Ile Lys Lys Lys
            900                 905                 910

Leu Val His Lys Leu Glu Gln Ala Ala Lys Gln Ala Ala Ala Ser Ala
            915                 920                 925
```

```
Thr Gln Thr Ile Ala Ala Ala Gln Asn Ala Ala Ser Ser Asn Lys Asn
    930                 935                 940

Pro Ala Ala Gln Gln Gln Leu Val Gln Ser Cys Lys Val Val Ala Glu
945                 950                 955                 960

Gln Ile Pro Met Leu Val Gln Gly Val Arg Gly Ser Gln Ser Gln Pro
            965                 970                 975

Asp Ser Pro Ser Ala Gln Leu Ser Leu Ile Ser Ala Ser Gln Asn Phe
            980                 985                 990

Leu Gln Pro Gly Ala Lys Leu Val Thr Ala Gly Lys Ser Ala Val Pro
        995                 1000                1005

Thr Val Ser Asp Pro Ala Ser Ala Met Gln Leu Gly Gln Cys Thr
    1010                1015                1020

Lys Asn Leu Ala Ser Ala Leu Ala Glu Leu Arg Thr Ala Ala Gln
    1025                1030                1035

Lys Ala His Glu Ala Cys Gly Pro Leu Glu Ile Asp Ser Ala Leu
    1040                1045                1050

Asn Val Val Arg Ser Leu Glu Gln Asp Leu Gln Glu Ala Arg Ala
    1055                1060                1065

Ala Ala Arg Glu Gly Lys Leu Gln Pro Leu Pro Gly Glu Thr Met
    1070                1075                1080

Glu Lys Cys Ala Gln Asp Leu Gly Ser Ser Thr Lys Ala Val Ser
    1085                1090                1095

Ser Ser Ile Ala Gln Leu Leu Gly Glu Ile Val His Gly Asn Glu
    1100                1105                1110

Asn Tyr Thr Gly Arg Ala Ala Arg Asp Val Ala Gln Ala Leu Arg
    1115                1120                1125

Ser Leu Ala Gln Ala Ser Arg Gly Val Ala Ala Asn Ser Thr Asp
    1130                1135                1140

Pro Ala Val Gln Asn Ala Met Leu Glu Cys Ala Glu Asp Val Met
    1145                1150                1155

Asp Lys Ala Gly Asn Leu Ile Glu Glu Ala Lys Arg Ala Val Gly
    1160                1165                1170

Lys Pro Thr Asp Pro Glu Gly Gln Gln Arg Leu Val Gln Val Ala
    1175                1180                1185

Lys Ala Val Ser Gln Ala Leu Ser Arg Cys Val Asn Cys Leu Pro
    1190                1195                1200

Gly Gln Arg Asp Val Asp Ala Ala Ile Lys Ser Ile Gly Glu Ala
    1205                1210                1215

Ser Lys Ile Leu Leu Ala Ser Ser Phe Pro Ser Gly Thr Lys Asn
    1220                1225                1230

Phe Gln Glu Ala Gln Ser Gln Leu Asn Gln Ala Ala Ala Gly Leu
    1235                1240                1245

Asn Gln Ser Ala Asn Glu Leu Val Gln Ala Ser Arg Thr Thr Pro
    1250                1255                1260

Gln Glu Leu Ala Lys Ala Ser Gly Lys Tyr Ser Gln Asp Phe Asn
    1265                1270                1275

Glu Phe Leu Gln Ala Gly Val Glu Met Ala Gly Gln Ser Gln Asn
    1280                1285                1290

Lys Glu Asp Gln Ala Gln Val Val Ser Asn Leu Lys Ser Ile Ser
    1295                1300                1305

Leu Ser Ser Ser Lys Leu Leu Leu Ala Ala Lys Ala Leu Ser Ala
    1310                1315                1320
```

```
Asp Pro Ala Ala Pro Asn Leu Lys Asn Gln Leu Ala Ala Ala Ala
    1325                1330                1335
Arg Ala Val Thr Asp Ser Ile Asn Gln Leu Ile Thr Val Cys Thr
    1340                1345                1350
Gln Gln Ala Pro Gly Gln Lys Glu Cys Asp Asn Ala Leu Arg Glu
    1355                1360                1365
Leu Glu Thr Val Arg Glu Leu Leu Gln Asn Pro Thr Gln Pro Val
    1370                1375                1380
Asn Asp Gln Ser Tyr Phe His Cys Leu Asp Ser Val Met Glu Asn
    1385                1390                1395
Ser Lys Val Leu Gly Glu Ser Met Ala Gly Ile Ser Gln Asn Ala
    1400                1405                1410
Lys Thr Ser Asn Leu Pro Glu Phe Gly Glu Ser Val Gly Ala Ala
    1415                1420                1425
Ser Lys Ala Leu Cys Gly Leu Thr Glu Ala Ala Ala Gln Ala Ala
    1430                1435                1440
Tyr Leu Val Gly Val Ser Asp Ala Asn Ser His Ala Gly Met Gln
    1445                1450                1455
Gly Leu Val Asp Pro Thr Gln Phe Ala Arg Ala Asn Gln Ala Ile
    1460                1465                1470
Gln Met Ala Cys Gln Asn Leu Gly Asp Pro Ala Cys Thr Gln Ser
    1475                1480                1485
Gln Val Leu Ser Ala Ala Thr Ile Val Ala Lys His Thr Ser Ala
    1490                1495                1500
Leu Cys Asn Ala Cys Arg Val Ala Ser Thr His Thr Ser Asn Pro
    1505                1510                1515
Val Ala Lys Arg Gln Phe Val Gln Ser Ala Lys Glu Val Ala Asn
    1520                1525                1530
Ser Thr Ala Asn Leu Val Lys Thr Ile Lys Ala Leu Asp Gly Thr
    1535                1540                1545
Phe Asn Asp Glu Asn Arg Val Lys Cys Arg Asn Ala Thr Val Pro
    1550                1555                1560
Leu Ile Gln Ala Val Glu Asn Leu Thr Ala Phe Ala Ser Asn Pro
    1565                1570                1575
Glu Phe Ala Ser Val Pro Ala Gln Ile Ser Pro Glu Gly Leu Arg
    1580                1585                1590
Ala Met Glu Pro Ile Val Thr Ala Ala Lys Leu Met Leu Glu Ser
    1595                1600                1605
Ser Ser Gly Leu Ile Gln Thr Ala Arg Ser Leu Ala Ala Asn Pro
    1610                1615                1620
Lys Asp Pro Pro Gln Trp Ser Val Leu Ala Gly His Ser Arg Asn
    1625                1630                1635
Val Ser Asp Ser Ile Lys Lys Leu Ile Thr Asn Met Arg Asp Lys
    1640                1645                1650
Ala Pro Gly Gln Arg Glu Cys Asp Gln Ala Ile Glu Leu Leu Asn
    1655                1660                1665
Gln Ala Val Arg Asp Leu Asp Gln Ala Ser Leu Glu Ala Ile Ser
    1670                1675                1680
Gln Gln Leu Ala Pro Arg Glu Gly Ile Ser Gln Glu Ala Leu His
    1685                1690                1695
Asn Gln Met Gln Thr Ser Val Gln Glu Ile Ser Asn Leu Ile Glu
    1700                1705                1710
Pro Met Ala Ala Ala Ala Arg Ala Asp Ser Ser Gln Leu Gly His
```

-continued

```
        1715                1720                1725

Lys Val Ser Gln Met Ala Gln Tyr Phe Glu Pro Leu Thr His Ala
        1730                1735                1740

Ser Ile Gly Thr Ala Ser Lys Thr Ile Asn His Gln Gln Gln Met
        1745                1750                1755

Asn Leu Leu Asp Gln Thr Lys Thr Leu Ala Glu Ser Ala Leu Gln
        1760                1765                1770

Met Leu Tyr Thr Ala Lys Glu Ala Gly Gly Asn Pro Lys Val Ala
        1775                1780                1785

Ala Gln Thr Gln Glu Ala Leu Asp Glu Ala Ala Gln Met Met His
        1790                1795                1800

Glu Ala Val Gly Asp Leu Thr Val Thr Leu Asn Glu Ala Ala Ser
        1805                1810                1815

Ala Ala Gly Ala Val Gly Gly Met Val Asp Ser Ile Thr Gln Ala
        1820                1825                1830

Ile Asn Lys Leu Asp Glu Glu Pro Thr Gly Glu Pro Glu Gly Ser
        1835                1840                1845

Phe Val Asp Tyr Gln Thr Thr Met Val Lys Thr Ala Lys Ala Ile
        1850                1855                1860

Ala Val Thr Val Gln Glu Met Val Thr Lys Ser Thr Thr Asn Pro
        1865                1870                1875

Asp Glu Leu Gly Thr Leu Ala Asn Gln Leu Thr Asn Glu Tyr Ser
        1880                1885                1890

Gln Leu Ala His Glu Ala Lys Pro Ala Ala Met Thr Ala Glu Asn
        1895                1900                1905

Glu Glu Ile Gly Ser His Ile Lys Gln Arg Val Gln Glu Leu Gly
        1910                1915                1920

His Asn Cys Ser Leu Leu Val Thr Lys Ala Gly Ala Leu Gln Cys
        1925                1930                1935

Ser Pro Asn Asp Ser Tyr Thr Lys Lys Glu Leu Ile Glu Ser Ala
        1940                1945                1950

Arg Arg Val Ser Glu Lys Val Ser His Val Leu Ala Ala Leu Gln
        1955                1960                1965

Ala Gly Asn Arg Gly Thr Gln Ala Cys Ile Thr Ala Ala Ser Ala
        1970                1975                1980

Val Ser Gly Ile Ile Ala Asp Leu Asp Thr Thr Ile Met Phe Ala
        1985                1990                1995

Thr Ala Gly Thr Leu Asn Arg Glu Asn Ala Glu Thr Phe Ala Asp
        2000                2005                2010

His Arg Glu Gly Ile Leu Lys Thr Ala Lys Ala Leu Val Glu Asp
        2015                2020                2025

Thr Lys Val Leu Val Gln Asn Ala Thr Ser Ser Gln Glu Lys Leu
        2030                2035                2040

Ala Gln Ala Ala Gln Ser Ser Val Thr Thr Ile Thr Arg Leu Ala
        2045                2050                2055

Glu Thr Val Lys Leu Gly Ala Ala Ser Leu Gly Ala Glu Asp Pro
        2060                2065                2070

Glu Thr Gln Val Val Leu Ile Asn Ala Val Lys Asp Val Ala Lys
        2075                2080                2085

Ala Leu Gly Asp Leu Ile Ser Ala Thr Lys Ser Ala Ala Gly Lys
        2090                2095                2100

Ser Ser Asp Asp Pro Ser Val Tyr Gln Leu Lys Asn Ser Ala Lys
        2105                2110                2115
```

```
Val Met Val Thr Asn Val Thr Ser Leu Leu Lys Thr Val Lys Ala
    2120                2125                2130

Val Glu Asp Glu Ala Thr Lys Gly Thr Arg Ala Leu Glu Ala Thr
    2135                2140                2145

Ile Glu His Ile Arg Gln Glu Leu Ala Val Phe Ser Ser Pro Glu
    2150                2155                2160

Pro Pro Pro His Thr Ser Thr Pro Glu Asp Phe Ile Arg Met Thr
    2165                2170                2175

Lys Gly Ile Thr Met Ala Thr Ala Lys Ala Val Ala Ala Gly Asn
    2180                2185                2190

Ser Cys Arg Gln Glu Asp Val Ile Ala Thr Ala Asn Leu Ser Arg
    2195                2200                2205

Arg Ala Ile Ala Asp Met Leu Arg Ser Cys Lys Glu Ala Val Tyr
    2210                2215                2220

His Pro Glu Val His Ala Asp Val Arg Met Arg Ala Thr Arg Phe
    2225                2230                2235

Gly Lys Glu Cys Ala Ile Gly Tyr Leu Gln Leu Leu Glu His Val
    2240                2245                2250

Leu Leu Ile Leu Gln Lys Pro Ser Pro Glu Leu Lys Gln Gln Leu
    2255                2260                2265

Ala Ala Tyr Ser Lys Gln Val Ala Gly Ser Val Thr Glu Leu Ile
    2270                2275                2280

Gln Ala Ala Glu Ala Met Lys Gly Thr Glu Trp Val Asp Pro Glu
    2285                2290                2295

Asp Pro Thr Val Ile Ala Glu Asn Glu Leu Leu Gly Ala Ala Ala
    2300                2305                2310

Ala Ile Glu Ala Ala Ala Lys Lys Leu Glu Gln Leu Lys Pro Arg
    2315                2320                2325

Ala Lys Pro Lys Gln Ala Asp Glu Ser Leu Asn Phe Glu Glu Gln
    2330                2335                2340

Ile Leu Glu Ala Ala Lys Ser Ile Ala Ala
    2345                2350
```

<210> SEQ ID NO 10
<211> LENGTH: 1006
<212> TYPE: PRT
<213> ORGANISM: Homo sapiens

<400> SEQUENCE: 10

```
Met Ala Ala Ala Tyr Leu Asp Pro Asn Leu Asn His Thr Pro Asn Ser
1               5                   10                  15

Ser Thr Lys Thr His Leu Gly Thr Gly Met Glu Arg Ser Pro Gly Ala
                20                  25                  30

Met Glu Arg Val Leu Lys Val Phe His Tyr Phe Glu Ser Asn Ser Glu
            35                  40                  45

Pro Thr Thr Trp Ala Ser Ile Ile Arg His Gly Asp Ala Thr Asp Val
        50                  55                  60

Arg Gly Ile Ile Gln Lys Ile Val Asp Ser His Lys Val Lys His Val
65                  70                  75                  80

Ala Cys Tyr Gly Phe Arg Leu Ser His Leu Arg Ser Glu Glu Val His
                85                  90                  95

Trp Leu His Val Asp Met Gly Val Ser Ser Val Arg Glu Lys Tyr Glu
            100                 105                 110

Leu Ala His Pro Pro Glu Glu Trp Lys Tyr Glu Leu Arg Ile Arg Tyr
```

```
            115                 120                 125
Leu Pro Lys Gly Phe Leu Asn Gln Phe Thr Glu Asp Lys Pro Thr Leu
        130                 135                 140
Asn Phe Phe Tyr Gln Gln Val Lys Ser Asp Tyr Met Leu Glu Ile Ala
145                 150                 155                 160
Asp Gln Val Asp Gln Glu Ile Ala Leu Lys Leu Gly Cys Leu Glu Ile
                165                 170                 175
Arg Arg Ser Tyr Trp Glu Met Arg Gly Asn Ala Leu Glu Lys Lys Ser
            180                 185                 190
Asn Tyr Glu Val Leu Glu Lys Asp Val Gly Leu Lys Arg Phe Phe Pro
        195                 200                 205
Lys Ser Leu Leu Asp Ser Val Lys Ala Lys Thr Leu Arg Lys Leu Ile
    210                 215                 220
Gln Gln Thr Phe Arg Gln Phe Ala Asn Leu Asn Arg Glu Glu Ser Ile
225                 230                 235                 240
Leu Lys Phe Phe Glu Ile Leu Ser Pro Val Tyr Arg Phe Asp Lys Glu
                245                 250                 255
Cys Phe Lys Cys Ala Leu Gly Ser Ser Trp Ile Ile Ser Val Glu Leu
            260                 265                 270
Ala Ile Gly Pro Glu Gly Ile Ser Tyr Leu Thr Asp Lys Gly Cys
        275                 280                 285
Asn Pro Thr His Leu Ala Asp Phe Thr Gln Val Gln Thr Ile Gln Tyr
    290                 295                 300
Ser Asn Ser Glu Asp Lys Asp Arg Lys Gly Met Leu Gln Leu Lys Ile
305                 310                 315                 320
Ala Gly Ala Pro Glu Pro Leu Thr Val Thr Ala Pro Ser Leu Thr Ile
                325                 330                 335
Ala Glu Asn Met Ala Asp Leu Ile Asp Gly Tyr Cys Arg Leu Val Asn
            340                 345                 350
Gly Thr Ser Gln Ser Phe Ile Ile Arg Pro Gln Lys Glu Gly Glu Arg
        355                 360                 365
Ala Leu Pro Ser Ile Pro Lys Leu Ala Asn Ser Glu Lys Gln Gly Met
    370                 375                 380
Arg Thr His Ala Val Ser Val Ser Glu Thr Asp Asp Tyr Ala Glu Ile
385                 390                 395                 400
Ile Asp Glu Glu Asp Thr Tyr Thr Met Pro Ser Thr Arg Asp Tyr Glu
                405                 410                 415
Ile Gln Arg Glu Arg Ile Glu Leu Gly Arg Cys Ile Gly Glu Gly Gln
                420                 425                 430
Phe Gly Asp Val His Gln Gly Ile Tyr Met Ser Pro Glu Asn Pro Ala
            435                 440                 445
Leu Ala Val Ala Ile Lys Thr Cys Lys Asn Cys Thr Ser Asp Ser Val
        450                 455                 460
Arg Glu Lys Phe Leu Gln Glu Ala Leu Thr Met Arg Gln Phe Asp His
465                 470                 475                 480
Pro His Ile Val Lys Leu Ile Gly Val Ile Thr Glu Asn Pro Val Trp
                485                 490                 495
Ile Ile Met Glu Leu Cys Thr Leu Gly Glu Leu Arg Ser Phe Leu Gln
                500                 505                 510
Val Arg Lys Tyr Ser Leu Asp Leu Ala Ser Leu Ile Leu Tyr Ala Tyr
            515                 520                 525
Gln Leu Ser Thr Ala Leu Ala Tyr Leu Glu Ser Lys Arg Phe Val His
        530                 535                 540
```

```
Arg Asp Ile Ala Ala Arg Asn Val Leu Val Ser Ser Asn Asp Cys Val
545                 550                 555                 560

Lys Leu Gly Asp Phe Gly Leu Ser Arg Tyr Met Glu Asp Ser Thr Tyr
            565                 570                 575

Tyr Lys Ala Ser Lys Gly Lys Leu Pro Ile Lys Trp Met Ala Pro Glu
        580                 585                 590

Ser Ile Asn Phe Arg Arg Phe Thr Ser Ala Ser Asp Val Trp Met Phe
            595                 600                 605

Gly Val Cys Met Trp Glu Ile Leu Met His Gly Val Lys Pro Phe Gln
        610                 615                 620

Gly Val Lys Asn Asn Asp Val Ile Gly Arg Ile Glu Asn Gly Glu Arg
625                 630                 635                 640

Leu Pro Met Pro Pro Asn Cys Pro Pro Thr Leu Tyr Ser Leu Met Thr
                645                 650                 655

Lys Cys Trp Ala Tyr Asp Pro Ser Arg Arg Pro Arg Phe Thr Glu Leu
                660                 665                 670

Lys Ala Gln Leu Ser Thr Ile Leu Glu Glu Glu Lys Ala Gln Gln Glu
            675                 680                 685

Glu Arg Met Arg Met Glu Ser Arg Arg Gln Ala Thr Val Ser Trp Asp
690                 695                 700

Ser Gly Gly Ser Asp Glu Ala Pro Pro Lys Pro Ser Arg Pro Gly Tyr
705                 710                 715                 720

Pro Ser Pro Arg Ser Ser Glu Gly Phe Tyr Pro Ser Pro Gln His Met
                725                 730                 735

Val Gln Thr Asn His Tyr Gln Asp Ser Thr Val Leu Asp Leu Arg Gly
            740                 745                 750

Ile Gly Gln Val Leu Pro Thr His Leu Met Glu Glu Arg Leu Ile Arg
            755                 760                 765

Gln Gln Gln Glu Met Glu Glu Asp Gln Arg Trp Leu Glu Lys Glu Glu
        770                 775                 780

Arg Phe Leu Lys Pro Asp Val Arg Leu Ser Arg Gly Ser Ile Asp Arg
785                 790                 795                 800

Glu Asp Gly Ser Leu Gln Gly Pro Ile Gly Asn Gln His Ile Tyr Gln
            805                 810                 815

Pro Val Gly Lys Pro Asp Pro Ala Ala Pro Lys Lys Pro Pro Arg
        820                 825                 830

Pro Gly Ala Pro Gly His Leu Gly Ser Leu Ala Ser Leu Ser Ser Pro
        835                 840                 845

Ala Asp Ser Tyr Asn Glu Gly Val Lys Leu Gln Pro Gln Glu Ile Ser
        850                 855                 860

Pro Pro Pro Thr Ala Asn Leu Asp Arg Ser Asn Asp Lys Val Tyr Glu
865                 870                 875                 880

Asn Val Thr Gly Leu Val Lys Ala Val Ile Glu Met Ser Ser Lys Ile
            885                 890                 895

Gln Pro Ala Pro Pro Glu Glu Tyr Val Pro Met Val Lys Glu Val Gly
            900                 905                 910

Leu Ala Leu Arg Thr Leu Leu Ala Thr Val Asp Glu Thr Ile Pro Leu
        915                 920                 925

Leu Pro Ala Ser Thr His Arg Glu Ile Glu Met Ala Gln Lys Leu Leu
        930                 935                 940

Asn Ser Asp Leu Gly Glu Leu Ile Asn Lys Met Lys Leu Ala Gln Gln
945                 950                 955                 960
```

Tyr Val Met Thr Ser Leu Gln Gln Glu Tyr Lys Lys Gln Met Leu Thr
            965                 970                 975

Ala Ala His Ala Leu Ala Val Asp Ala Lys Asn Leu Leu Asp Val Ile
            980                 985                 990

Asp Gln Ala Arg Leu Lys Met Leu Gly Gln Thr Arg Pro His
        995                 1000                1005

<210> SEQ ID NO 11
<211> LENGTH: 268
<212> TYPE: PRT
<213> ORGANISM: Homo sapiens

<400> SEQUENCE: 11

Met Ala Val Asn Val Tyr Ser Thr Ser Val Thr Ser Asp Asn Leu Ser
1               5                   10                  15

Arg His Asp Met Leu Ala Trp Ile Asn Glu Ser Leu Gln Leu Asn Leu
            20                  25                  30

Thr Lys Ile Glu Gln Leu Cys Ser Gly Ala Ala Tyr Cys Gln Phe Met
        35                  40                  45

Asp Met Leu Phe Pro Gly Ser Ile Ala Leu Lys Lys Val Lys Phe Gln
    50                  55                  60

Ala Lys Leu Glu His Glu Tyr Ile Gln Asn Phe Lys Ile Leu Gln Ala
65                  70                  75                  80

Gly Phe Lys Arg Met Gly Val Asp Lys Ile Ile Pro Val Asp Lys Leu
                85                  90                  95

Val Lys Gly Lys Phe Gln Asp Asn Phe Glu Phe Val Gln Trp Phe Lys
            100                 105                 110

Lys Phe Phe Asp Ala Asn Tyr Asp Gly Lys Asp Tyr Asp Pro Val Ala
        115                 120                 125

Ala Arg Gln Gly Gln Glu Thr Ala Val Ala Pro Ser Leu Val Ala Pro
    130                 135                 140

Ala Leu Asn Lys Pro Lys Lys Pro Leu Thr Ser Ser Ser Ala Ala Pro
145                 150                 155                 160

Gln Arg Pro Ile Ser Thr Gln Arg Thr Ala Ala Ala Pro Lys Ala Gly
                165                 170                 175

Pro Gly Val Val Arg Lys Asn Pro Gly Val Gly Asn Gly Asp Asp Glu
            180                 185                 190

Ala Ala Glu Leu Met Gln Gln Val Asn Val Leu Lys Leu Thr Val Glu
        195                 200                 205

Asp Leu Glu Lys Glu Arg Asp Phe Tyr Phe Gly Lys Leu Arg Asn Ile
    210                 215                 220

Glu Leu Ile Cys Gln Glu Asn Glu Gly Glu Asn Asp Pro Val Leu Gln
225                 230                 235                 240

Arg Ile Val Asp Ile Leu Tyr Ala Thr Asp Glu Gly Phe Val Ile Pro
                245                 250                 255

Asp Glu Gly Gly Pro Gln Glu Glu Gln Glu Glu Tyr
            260                 265

<210> SEQ ID NO 12
<211> LENGTH: 1320
<212> TYPE: PRT
<213> ORGANISM: Rattus norvegicus

<400> SEQUENCE: 12

Met Ser Met Leu Lys Pro Ser Gly Leu Lys Ala Pro Thr Lys Ile Leu
1               5                   10                  15

```
Lys Pro Gly Ser Thr Ala Leu Lys Thr Pro Ala Ala Ala Ala Pro
             20                  25                  30

Leu Glu Lys Thr Val Pro Ser Glu Lys Ala Ser Gly Pro Pro Ser Ser
         35                  40                  45

Glu Thr Gln Glu Glu Phe Val Asp Asp Phe Arg Val Gly Glu Arg Val
     50                  55                  60

Trp Val Asn Gly Asn Lys Pro Gly Phe Ile Gln Phe Leu Gly Glu Thr
 65                  70                  75                  80

Gln Phe Ala Pro Gly Gln Trp Ala Gly Ile Val Leu Asp Glu Pro Ile
                 85                  90                  95

Gly Lys Asn Asp Gly Ser Val Ala Gly Val Arg Tyr Phe Gln Cys Glu
                100                 105                 110

Pro Leu Lys Gly Ile Phe Thr Arg Pro Ser Lys Leu Thr Arg Lys Val
            115                 120                 125

Gln Ala Glu Asp Glu Ala Asn Gly Leu Gln Thr Ala His Ala Arg Ala
        130                 135                 140

Ala Ser Pro Leu Ser Thr Ala Ala Thr Met Val Ser Ser Ser Pro
145                 150                 155                 160

Ala Thr Pro Ser Asn Ile Pro Gln Lys Pro Ser Gln Pro Val Ala Lys
                165                 170                 175

Glu Thr Ser Ala Thr Pro Gln Ile Ser Asn Leu Thr Lys Thr Ala Ser
            180                 185                 190

Glu Ser Ile Ser Asn Leu Ser Glu Ala Gly Ser Val Lys Lys Gly Glu
        195                 200                 205

Arg Glu Leu Lys Ile Gly Asp Arg Val Leu Val Gly Gly Thr Lys Ala
210                 215                 220

Gly Val Val Arg Phe Leu Gly Glu Thr Asp Phe Ala Lys Gly Glu Trp
225                 230                 235                 240

Cys Gly Val Glu Leu Asp Glu Pro Leu Gly Lys Asn Asp Gly Ala Val
                245                 250                 255

Ala Gly Thr Arg Tyr Phe Gln Cys Gln Pro Lys Tyr Gly Leu Phe Ala
            260                 265                 270

Pro Val His Lys Val Thr Lys Ile Gly Phe Pro Ser Thr Thr Pro Ala
        275                 280                 285

Lys Ala Lys Ala Ala Ala Val Arg Arg Val Met Ala Thr Thr Pro Ala
290                 295                 300

Ser Leu Lys Arg Ser Pro Ser Ala Ser Ser Leu Ser Ser Met Ser Ser
305                 310                 315                 320

Val Ala Ser Ser Val Ser Ser Lys Pro Ser Arg Thr Gly Leu Leu Thr
                325                 330                 335

Glu Thr Ser Ser Arg Tyr Ala Arg Lys Ile Ser Gly Thr Thr Ala Leu
            340                 345                 350

Gln Glu Ala Leu Lys Glu Lys Gln Gln His Ile Glu Gln Leu Leu Ala
        355                 360                 365

Glu Arg Asp Leu Glu Arg Ala Glu Val Ala Lys Ala Thr Ser His Val
    370                 375                 380

Gly Glu Ile Glu Gln Glu Leu Ala Leu Ala Arg Asp Gly His Asp Gln
385                 390                 395                 400

His Val Leu Glu Leu Glu Ala Lys Met Asp Gln Leu Arg Thr Met Val
                405                 410                 415

Glu Ala Ala Asp Arg Glu Lys Val Glu Leu Leu Asn Gln Leu Glu Glu
            420                 425                 430

Glu Lys Arg Lys Val Glu Asp Leu Gln Phe Arg Val Glu Glu Glu Ser
```

```
                435                 440                 445
Ile Thr Lys Gly Asp Leu Glu Thr Gln Thr Lys Leu Glu His Ala Arg
450                 455                 460

Ile Lys Glu Leu Glu Gln Ser Leu Leu Phe Glu Lys Thr Lys Ala Asp
465                 470                 475                 480

Lys Leu Gln Arg Glu Leu Asp Thr Arg Val Ala Thr Val Ser Glu
                485                 490                 495

Lys Ser Arg Ile Met Glu Leu Glu Lys Asp Leu Ala Leu Arg Val Gln
                500                 505                 510

Glu Val Ala Glu Leu Arg Arg Arg Leu Glu Ser Ser Lys Pro Pro Gly
                515                 520                 525

Asp Val Asp Met Ser Leu Ser Leu Leu Gln Glu Ile Ser Ala Leu Gln
                530                 535                 540

Glu Lys Leu Glu Val Thr His Thr Asp His Gln Asn Glu Val Thr Ser
545                 550                 555                 560

Leu Lys Asp His Phe Gly Thr Arg Glu Glu Met Phe Gln Lys Glu Ile
                565                 570                 575

Lys Ala Leu His Ala Ala Thr Glu Lys Leu Ser Lys Glu Asn Glu Ser
                580                 585                 590

Leu Arg Ser Lys Leu Asp His Ala Asn Lys Glu Asn Ser Asp Val Ile
                595                 600                 605

Ala Leu Trp Lys Ser Lys Leu Glu Thr Ala Ile Ala Ser His Gln Gln
610                 615                 620

Ala Met Glu Glu Leu Lys Val Ser Phe Ser Lys Gly Ile Gly Thr Asp
625                 630                 635                 640

Ser Ala Glu Phe Ala Glu Leu Lys Thr Gln Ile Glu Arg Leu Arg Leu
                645                 650                 655

Asp Tyr Gln His Glu Ile Glu Ser Leu Gln Ser Lys Gln Asp Ser Glu
                660                 665                 670

Arg Ser Ala His Ala Lys Glu Met Glu Ser Met Lys Ala Lys Leu Met
                675                 680                 685

Lys Ile Ile Lys Glu Lys Glu Asp Ser Leu Glu Ala Val Lys Ala Arg
                690                 695                 700

Leu Asp Thr Ala Glu Asp Gln His Leu Val Glu Met Glu Glu Met Leu
705                 710                 715                 720

Ser Lys Leu Gln Glu Ala Glu Ile Lys Lys Glu Lys Phe Ala Ser Ala
                725                 730                 735

Ser Glu Glu Ala Val Ser Thr Gln Thr Ser Met Gln Asp Thr Val Asn
                740                 745                 750

Lys Leu His Gln Lys Glu Gln Phe Asn Met Leu Ser Ser Glu Leu
                755                 760                 765

Glu Lys Leu Arg Glu Asn Leu Thr Asp Met Glu Ala Lys Phe Lys Glu
                770                 775                 780

Lys Asp Glu Arg Glu Asp Gln Leu Val Lys Ala Lys Glu Lys Leu Glu
785                 790                 795                 800

Asn Asp Ile Ala Glu Ile Met Lys Met Ser Gly Asp Asn Ser Ser Gln
                805                 810                 815

Leu Thr Lys Met Asn Asp Glu Leu Arg Leu Lys Glu Arg Ser Val Glu
                820                 825                 830

Glu Leu Gln Leu Lys Leu Thr Lys Ala Asn Glu Asn Ala Ser Leu Leu
                835                 840                 845

Gln Lys Ser Ile Gly Glu Val Thr Leu Lys Ala Glu Gln Ser Gln Gln
850                 855                 860
```

```
Glu Ala Ala Lys Lys His Glu Glu Lys Lys Glu Leu Glu Asn Lys
865                 870                 875                 880

Leu Leu Glu Leu Glu Lys Lys Met Glu Thr Ser His Tyr Gln Cys Gln
            885                 890                 895

Asp Leu Lys Ala Lys Tyr Glu Lys Ala Ser Ser Glu Thr Lys Ile Lys
                900                 905                 910

His Glu Glu Ile Leu Gln Asn Phe Gln Lys Met Leu Val Asp Thr Glu
                915                 920                 925

Asp Lys Leu Lys Ala Ala Gln Glu Ala Asn Arg Asp Leu Met Gln Asp
            930                 935                 940

Met Glu Glu Leu Lys Ser Gln Ala Asp Lys Ala Lys Ala Ala Gln Thr
945                 950                 955                 960

Ala Glu Asp Ala Met Gln Ile Met Glu Gln Met Thr Lys Glu Lys Thr
                965                 970                 975

Glu Thr Leu Ala Ser Leu Glu Asp Thr Lys Gln Thr Asn Ala Lys Leu
            980                 985                 990

Gln Ser Glu Leu Asp Thr Leu Lys  Glu Asn Asn Leu Lys  Thr Val Glu
        995                 1000                1005

Glu Leu  Asn Lys Ser Lys Glu  Leu Leu Asn Glu Glu  Asn Gln Lys
    1010                1015               1020

Met Glu  Glu Phe Lys Lys Glu  Ile Glu Thr Leu Lys  Gln Ala Ala
    1025                1030               1035

Ala Gln  Lys Ser Gln Gln Leu  Ser Ala Leu Gln Glu  Glu Asn Val
    1040                1045               1050

Lys Leu  Ala Glu Glu Leu Gly  Arg Thr Arg Asp Glu  Val Thr Ser
    1055                1060               1065

His Gln  Lys Leu Glu Glu Gly  Arg Ser Val Leu Asn  Asn Gln Leu
    1070                1075               1080

Leu Glu  Met Lys Lys Ser Leu  Pro Ser Asn Thr Leu  Arg Glu Ser
    1085                1090               1095

Glu Tyr  Arg Lys Asp Ala Asp  Glu Glu Lys Ala Ser  Leu Gln Lys
    1100                1105               1110

Ser Ile  Ser Leu Thr Ser Ala  Leu Leu Thr Glu Lys  Asp Ala Glu
    1115                1120               1125

Leu Glu  Lys Leu Arg Asn Glu  Val Thr Val Leu Arg  Gly Glu Asn
    1130                1135               1140

Ala Ser  Ala Lys Ser Leu His  Ser Val Val Gln Thr  Leu Glu Ser
    1145                1150               1155

Asp Lys  Val Lys Leu Glu Leu  Lys Val Lys Asn Leu  Glu Leu Gln
    1160                1165               1170

Leu Lys  Glu Asn Lys Arg Gln  Leu Ser Ser Ser Ser  Gly Asn Thr
    1175                1180               1185

Asp Val  Gln Thr Glu Glu Asp  Glu Arg Ala Gln Glu  Ser Gln Gln
    1190                1195               1200

Met Ile  Asp Phe Leu Asn Ser  Val Ile Val Asp Leu  Gln Arg Lys
    1205                1210               1215

Asn Gln  Asp Leu Lys Met Lys  Val Glu Met Met Ser  Glu Gly Ala
    1220                1225               1230

Leu Asn  Gly Asn Gly Glu Asp  Pro Asn Ser Tyr Asp  Ser Asp Asp
    1235                1240               1245

Gln Glu  Lys Gln Ser Lys Lys  Lys Pro Arg Leu Phe  Cys Asp Ile
    1250                1255               1260
```

```
Cys Asp Cys Phe Asp Leu His Asp Thr Glu Asp Cys Pro Thr Gln
    1265                1270                1275

Ala Gln Met Ser Glu Asp Pro Pro His Ser Thr His His Gly Ser
    1280                1285                1290

Arg Ser Glu Glu Arg Pro Tyr Cys Glu Ile Cys Glu Met Phe Gly
    1295                1300                1305

His Trp Ala Thr Asn Cys Asn Asp Asp Glu Thr Phe
    1310                1315                1320

<210> SEQ ID NO 13
<211> LENGTH: 1294
<212> TYPE: PRT
<213> ORGANISM: Homo sapiens

<400> SEQUENCE: 13

Met Ala Met Gly Asp Asp Lys Ser Phe Asp Glu Glu Ser Val Asp
1               5                   10                  15

Gly Asn Arg Pro Ser Ser Ala Ala Ser Ala Phe Lys Val Pro Ala Pro
            20                  25                  30

Lys Thr Ser Gly Asn Pro Ala Asn Ser Ala Arg Lys Pro Gly Ser Ala
        35                  40                  45

Gly Gly Pro Lys Val Gly Gly Ala Ser Lys Glu Gly Gly Ala Gly Ala
    50                  55                  60

Val Asp Glu Asp Phe Ile Lys Ala Phe Thr Asp Val Pro Ser Ile
65                  70                  75                  80

Gln Ile Tyr Ser Ser Arg Glu Leu Glu Glu Thr Leu Asn Lys Ile Arg
                85                  90                  95

Glu Ile Leu Ser Asp Asp Lys His Asp Trp Asp Gln Arg Ala Asn Ala
            100                 105                 110

Leu Lys Lys Ile Arg Ser Leu Leu Val Ala Gly Ala Ala Gln Tyr Asp
        115                 120                 125

Cys Phe Phe Gln His Leu Arg Leu Leu Asp Gly Ala Leu Lys Leu Ser
    130                 135                 140

Ala Lys Asp Leu Arg Ser Gln Val Val Arg Glu Ala Cys Ile Thr Val
145                 150                 155                 160

Ala His Leu Ser Thr Val Leu Gly Asn Lys Phe Asp His Gly Ala Glu
                165                 170                 175

Ala Ile Val Pro Thr Leu Phe Asn Leu Val Pro Asn Ser Ala Lys Val
            180                 185                 190

Met Ala Thr Ser Gly Cys Ala Ala Ile Arg Phe Ile Ile Arg His Thr
        195                 200                 205

His Val Pro Arg Leu Ile Pro Leu Ile Thr Ser Asn Cys Thr Ser Lys
    210                 215                 220

Ser Val Pro Val Arg Arg Arg Ser Phe Glu Phe Leu Asp Leu Leu Leu
225                 230                 235                 240

Gln Glu Trp Gln Thr His Ser Leu Glu Arg His Ala Ala Val Leu Val
                245                 250                 255

Glu Thr Ile Lys Lys Gly Ile His Asp Ala Asp Ala Glu Ala Arg Val
            260                 265                 270

Glu Ala Arg Lys Thr Tyr Met Gly Leu Arg Asn His Phe Pro Gly Glu
        275                 280                 285

Ala Glu Thr Leu Tyr Asn Ser Leu Glu Pro Ser Tyr Gln Lys Ser Leu
    290                 295                 300

Gln Thr Tyr Leu Lys Ser Ser Gly Ser Val Ala Ser Leu Pro Gln Ser
305                 310                 315                 320
```

```
Asp Arg Ser Ser Ser Ser Gln Glu Ser Leu Asn Arg Pro Phe Ser
                325                 330                 335

Ser Lys Trp Ser Thr Ala Asn Pro Ser Thr Val Ala Gly Arg Val Ser
            340                 345                 350

Ala Gly Ser Ser Lys Ala Ser Ser Leu Pro Gly Ser Leu Gln Arg Ser
                355                 360                 365

Arg Ser Asp Ile Asp Val Asn Ala Ala Gly Ala Lys Ala His His
        370                 375                 380

Ala Ala Gly Gln Ser Val Arg Ser Gly Arg Leu Gly Ala Gly Ala Leu
385                 390                 395                 400

Asn Ala Gly Ser Tyr Ala Ser Leu Glu Asp Thr Ser Asp Lys Leu Asp
                405                 410                 415

Gly Thr Ala Ser Glu Asp Gly Arg Val Arg Ala Lys Leu Ser Ala Pro
                420                 425                 430

Leu Ala Gly Met Gly Asn Ala Lys Ala Asp Ser Arg Gly Arg Ser Arg
                435                 440                 445

Thr Lys Met Val Ser Gln Ser Gln Pro Gly Ser Arg Ser Gly Ser Pro
                450                 455                 460

Gly Arg Val Leu Thr Thr Thr Ala Leu Ser Thr Val Ser Ser Gly Val
465                 470                 475                 480

Gln Arg Val Leu Val Asn Ser Ala Ser Ala Gln Lys Arg Ser Lys Ile
                485                 490                 495

Pro Arg Ser Gln Gly Cys Ser Arg Glu Ala Ser Pro Ser Arg Leu Ser
                500                 505                 510

Val Ala Arg Ser Ser Arg Ile Pro Arg Pro Ser Val Ser Gln Gly Cys
                515                 520                 525

Ser Arg Glu Ala Ser Arg Glu Ser Ser Arg Asp Thr Ser Pro Val Arg
                530                 535                 540

Ser Phe Gln Pro Leu Ala Ser Arg His His Ser Arg Ser Thr Gly Ala
545                 550                 555                 560

Leu Tyr Ala Pro Glu Val Tyr Gly Ala Ser Gly Pro Gly Tyr Gly Ile
                565                 570                 575

Ser Gln Ser Ser Arg Leu Ser Ser Val Ser Ala Met Arg Val Leu
                580                 585                 590

Asn Thr Gly Ser Asp Val Glu Glu Ala Val Ala Asp Ala Leu Lys Lys
                595                 600                 605

Pro Ala Arg Arg Arg Tyr Glu Ser Tyr Gly Met His Ser Asp Asp Asp
                610                 615                 620

Ala Asn Ser Asp Ala Ser Ser Ala Cys Ser Glu Arg Ser Tyr Ser Ser
625                 630                 635                 640

Arg Asn Gly Ser Ile Pro Thr Tyr Met Arg Gln Thr Glu Asp Val Ala
                645                 650                 655

Glu Val Leu Asn Arg Cys Ala Ser Ser Asn Trp Ser Glu Arg Lys Glu
                660                 665                 670

Gly Leu Leu Gly Leu Gln Asn Leu Leu Lys Asn Gln Arg Thr Leu Ser
                675                 680                 685

Arg Val Glu Leu Lys Arg Leu Cys Glu Ile Phe Thr Arg Met Phe Ala
                690                 695                 700

Asp Pro His Gly Lys Arg Val Phe Ser Met Phe Leu Glu Thr Leu Val
705                 710                 715                 720

Asp Phe Ile Gln Val His Lys Asp Asp Leu Gln Asp Trp Leu Phe Val
                725                 730                 735
```

-continued

Leu Leu Thr Gln Leu Leu Lys Lys Met Gly Ala Asp Leu Leu Gly Ser
            740                 745                 750

Val Gln Ala Lys Val Gln Lys Ala Leu Asp Val Thr Arg Glu Ser Phe
        755                 760                 765

Pro Asn Asp Leu Gln Phe Asn Ile Leu Met Arg Phe Thr Val Asp Gln
    770                 775                 780

Thr Gln Thr Pro Ser Leu Lys Val Lys Val Ala Ile Leu Lys Tyr Ile
785                 790                 795                 800

Glu Thr Leu Ala Lys Gln Met Asp Pro Gly Asp Phe Ile Asn Ser Ser
                805                 810                 815

Glu Thr Arg Leu Ala Val Ser Arg Val Ile Thr Trp Thr Thr Glu Pro
            820                 825                 830

Lys Ser Ser Asp Val Arg Lys Ala Ala Gln Ser Val Leu Ile Ser Leu
        835                 840                 845

Phe Glu Leu Asn Thr Pro Glu Phe Thr Met Leu Leu Gly Ala Leu Pro
850                 855                 860

Lys Thr Phe Gln Asp Gly Ala Thr Lys Leu Leu His Asn His Leu Arg
865                 870                 875                 880

Asn Thr Gly Asn Gly Thr Gln Ser Ser Met Gly Ser Pro Leu Thr Arg
                885                 890                 895

Pro Thr Pro Arg Ser Pro Ala Asn Trp Ser Ser Pro Leu Thr Ser Pro
            900                 905                 910

Thr Asn Thr Ser Gln Asn Thr Leu Ser Pro Ser Ala Phe Asp Tyr Asp
        915                 920                 925

Thr Glu Asn Met Asn Ser Glu Asp Ile Tyr Ser Ser Leu Arg Gly Val
930                 935                 940

Thr Glu Ala Ile Gln Asn Phe Ser Phe Arg Ser Gln Glu Asp Met Asn
945                 950                 955                 960

Glu Pro Leu Lys Arg Asp Ser Lys Lys Asp Asp Gly Asp Ser Met Cys
                965                 970                 975

Gly Gly Pro Gly Met Ser Asp Pro Arg Ala Gly Gly Asp Ala Thr Asp
            980                 985                 990

Ser Ser Gln Thr Ala Leu Asp Asn Lys Ala Ser Leu Leu His Ser Met
        995                 1000                1005

Pro Thr His Ser Ser Pro Arg Ser Arg Asp Tyr Asn Pro Tyr Asn
    1010                1015                1020

Tyr Ser Asp Ser Ile Ser Pro Phe Asn Lys Ser Ala Leu Lys Glu
    1025                1030                1035

Ala Met Phe Asp Asp Asp Ala Asp Gln Phe Pro Asp Asp Leu Ser
    1040                1045                1050

Leu Asp His Ser Asp Leu Val Ala Glu Leu Leu Lys Glu Leu Ser
    1055                1060                1065

Asn His Asn Glu Arg Val Glu Glu Arg Lys Ile Ala Leu Tyr Glu
    1070                1075                1080

Leu Met Lys Leu Thr Gln Glu Ser Phe Ser Val Trp Asp Glu
    1085                1090                1095

His Phe Lys Thr Ile Leu Leu Leu Leu Glu Thr Leu Gly Asp
    1100                1105                1110

Lys Glu Pro Thr Ile Arg Ala Leu Ala Leu Lys Val Leu Arg Glu
    1115                1120                1125

Ile Leu Arg His Gln Pro Ala Arg Phe Lys Asn Tyr Ala Glu Leu
    1130                1135                1140

Thr Val Met Lys Thr Leu Glu Ala His Lys Asp Pro His Lys Glu

```
              1145                1150                1155
Val  Val  Arg  Ser  Ala  Glu  Glu  Ala  Ala  Ser  Val  Leu  Ala  Thr  Ser
         1160                1165                1170

Ile  Ser  Pro  Glu  Gln  Cys  Ile  Lys  Val  Leu  Cys  Pro  Ile  Ile  Gln
    1175                1180                1185

Thr  Ala  Asp  Tyr  Pro  Ile  Asn  Leu  Ala  Ala  Ile  Lys  Met  Gln  Thr
    1190                1195                1200

Lys  Val  Ile  Glu  Arg  Val  Ser  Lys  Glu  Thr  Leu  Asn  Leu  Leu  Leu
    1205                1210                1215

Pro  Glu  Ile  Met  Pro  Gly  Leu  Ile  Gln  Gly  Tyr  Asp  Asn  Ser  Glu
    1220                1225                1230

Ser  Ser  Val  Arg  Lys  Ala  Cys  Val  Phe  Cys  Leu  Val  Ala  Val  His
    1235                1240                1245

Ala  Val  Ile  Gly  Asp  Glu  Leu  Lys  Pro  His  Leu  Ser  Gln  Leu  Thr
    1250                1255                1260

Gly  Ser  Lys  Met  Lys  Leu  Leu  Asn  Leu  Tyr  Ile  Lys  Arg  Ala  Gln
    1265                1270                1275

Thr  Gly  Ser  Gly  Gly  Ala  Asp  Pro  Thr  Thr  Asp  Val  Ser  Gly  Gln
    1280                1285                1290

Ser

<210> SEQ ID NO 14
<211> LENGTH: 2843
<212> TYPE: PRT
<213> ORGANISM: Homo sapiens

<400> SEQUENCE: 14

Met  Ala  Ala  Ala  Ser  Tyr  Asp  Gln  Leu  Leu  Lys  Gln  Val  Glu  Ala  Leu
1                   5                   10                  15

Lys  Met  Glu  Asn  Ser  Asn  Leu  Arg  Gln  Glu  Leu  Glu  Asp  Asn  Ser  Asn
            20                  25                  30

His  Leu  Thr  Lys  Leu  Glu  Thr  Glu  Ala  Ser  Asn  Met  Lys  Glu  Val  Leu
        35                  40                  45

Lys  Gln  Leu  Gln  Gly  Ser  Ile  Glu  Asp  Glu  Ala  Met  Ala  Ser  Ser  Gly
    50                  55                  60

Gln  Ile  Asp  Leu  Leu  Glu  Arg  Leu  Lys  Glu  Leu  Asn  Leu  Asp  Ser  Ser
65                  70                  75                  80

Asn  Phe  Pro  Gly  Val  Lys  Leu  Arg  Ser  Lys  Met  Ser  Leu  Arg  Ser  Tyr
                85                  90                  95

Gly  Ser  Arg  Glu  Gly  Ser  Val  Ser  Arg  Ser  Gly  Glu  Cys  Ser  Pro
            100                 105                 110

Val  Pro  Met  Gly  Ser  Phe  Pro  Arg  Arg  Gly  Phe  Val  Asn  Gly  Ser  Arg
        115                 120                 125

Glu  Ser  Thr  Gly  Tyr  Leu  Glu  Glu  Leu  Glu  Lys  Glu  Arg  Ser  Leu  Leu
    130                 135                 140

Leu  Ala  Asp  Leu  Asp  Lys  Glu  Glu  Lys  Glu  Lys  Asp  Trp  Tyr  Tyr  Ala
145                 150                 155                 160

Gln  Leu  Gln  Asn  Leu  Thr  Lys  Arg  Ile  Asp  Ser  Leu  Pro  Leu  Thr  Glu
                165                 170                 175

Asn  Phe  Ser  Leu  Gln  Thr  Asp  Met  Thr  Arg  Arg  Gln  Leu  Glu  Tyr  Glu
            180                 185                 190

Ala  Arg  Gln  Ile  Arg  Val  Ala  Met  Glu  Glu  Gln  Leu  Gly  Thr  Cys  Gln
        195                 200                 205

Asp  Met  Glu  Lys  Arg  Ala  Gln  Arg  Arg  Ile  Ala  Arg  Ile  Gln  Gln  Ile
```

```
            210                 215                 220
Glu Lys Asp Ile Leu Arg Ile Arg Gln Leu Leu Gln Ser Gln Ala Thr
225                 230                 235                 240

Glu Ala Glu Arg Ser Ser Gln Asn Lys His Glu Thr Gly Ser His Asp
                245                 250                 255

Ala Glu Arg Gln Asn Glu Gly Gln Gly Val Gly Glu Ile Asn Met Ala
                260                 265                 270

Thr Ser Gly Asn Gly Gln Gly Ser Thr Thr Arg Met Asp His Glu Thr
            275                 280                 285

Ala Ser Val Leu Ser Ser Ser Thr His Ser Ala Pro Arg Arg Leu
        290                 295                 300

Thr Ser His Leu Gly Thr Lys Val Glu Met Val Tyr Ser Leu Leu Ser
305                 310                 315                 320

Met Leu Gly Thr His Asp Lys Asp Met Ser Arg Thr Leu Leu Ala
                325                 330                 335

Met Ser Ser Ser Gln Asp Ser Cys Ile Ser Met Arg Gln Ser Gly Cys
                340                 345                 350

Leu Pro Leu Leu Ile Gln Leu Leu His Gly Asn Asp Lys Asp Ser Val
                355                 360                 365

Leu Leu Gly Asn Ser Arg Gly Ser Lys Glu Ala Arg Ala Arg Ala Ser
        370                 375                 380

Ala Ala Leu His Asn Ile Ile His Ser Gln Pro Asp Asp Lys Arg Gly
385                 390                 395                 400

Arg Arg Glu Ile Arg Val Leu His Leu Leu Glu Gln Ile Arg Ala Tyr
                405                 410                 415

Cys Glu Thr Cys Trp Glu Trp Gln Glu Ala His Glu Pro Gly Met Asp
                420                 425                 430

Gln Asp Lys Asn Pro Met Pro Ala Pro Val Glu His Gln Ile Cys Pro
                435                 440                 445

Ala Val Cys Val Leu Met Lys Leu Ser Phe Asp Glu Glu His Arg His
        450                 455                 460

Ala Met Asn Glu Leu Gly Gly Leu Gln Ala Ile Ala Glu Leu Leu Gln
465                 470                 475                 480

Val Asp Cys Glu Met Tyr Gly Leu Thr Asn Asp His Tyr Ser Ile Thr
                485                 490                 495

Leu Arg Arg Tyr Ala Gly Met Ala Leu Thr Asn Leu Thr Phe Gly Asp
                500                 505                 510

Val Ala Asn Lys Ala Thr Leu Cys Ser Met Lys Gly Cys Met Arg Ala
            515                 520                 525

Leu Val Ala Gln Leu Lys Ser Glu Ser Glu Asp Leu Gln Gln Val Ile
        530                 535                 540

Ala Ser Val Leu Arg Asn Leu Ser Trp Arg Ala Asp Val Asn Ser Lys
545                 550                 555                 560

Lys Thr Leu Arg Glu Val Gly Ser Val Lys Ala Leu Met Glu Cys Ala
                565                 570                 575

Leu Glu Val Lys Lys Glu Ser Thr Leu Lys Ser Val Leu Ser Ala Leu
                580                 585                 590

Trp Asn Leu Ser Ala His Cys Thr Glu Asn Lys Ala Asp Ile Cys Ala
            595                 600                 605

Val Asp Gly Ala Leu Ala Phe Leu Val Gly Thr Leu Thr Tyr Arg Ser
    610                 615                 620

Gln Thr Asn Thr Leu Ala Ile Ile Glu Ser Gly Gly Gly Ile Leu Arg
625                 630                 635                 640
```

```
Asn Val Ser Ser Leu Ile Ala Thr Asn Glu Asp His Arg Gln Ile Leu
                645                 650                 655

Arg Glu Asn Asn Cys Leu Gln Thr Leu Leu Gln His Leu Lys Ser His
            660                 665                 670

Ser Leu Thr Ile Val Ser Asn Ala Cys Gly Thr Leu Trp Asn Leu Ser
        675                 680                 685

Ala Arg Asn Pro Lys Asp Gln Glu Ala Leu Trp Asp Met Gly Ala Val
    690                 695                 700

Ser Met Leu Lys Asn Leu Ile His Ser Lys His Lys Met Ile Ala Met
705                 710                 715                 720

Gly Ser Ala Ala Ala Leu Arg Asn Leu Met Ala Asn Arg Pro Ala Lys
                725                 730                 735

Tyr Lys Asp Ala Asn Ile Met Ser Pro Gly Ser Ser Leu Pro Ser Leu
            740                 745                 750

His Val Arg Lys Gln Lys Ala Leu Glu Ala Glu Leu Asp Ala Gln His
        755                 760                 765

Leu Ser Glu Thr Phe Asp Asn Ile Asp Asn Leu Ser Pro Lys Ala Ser
    770                 775                 780

His Arg Ser Lys Gln Arg His Lys Gln Ser Leu Tyr Gly Asp Tyr Val
785                 790                 795                 800

Phe Asp Thr Asn Arg His Asp Asp Asn Arg Ser Asp Asn Phe Asn Thr
                805                 810                 815

Gly Asn Met Thr Val Leu Ser Pro Tyr Leu Asn Thr Thr Val Leu Pro
            820                 825                 830

Ser Ser Ser Ser Ser Arg Gly Ser Leu Asp Ser Ser Arg Ser Glu Lys
        835                 840                 845

Asp Arg Ser Leu Glu Arg Glu Arg Gly Ile Gly Leu Gly Asn Tyr His
    850                 855                 860

Pro Ala Thr Glu Asn Pro Gly Thr Ser Ser Lys Arg Gly Leu Gln Ile
865                 870                 875                 880

Ser Thr Thr Ala Ala Gln Ile Ala Lys Val Met Glu Glu Val Ser Ala
                885                 890                 895

Ile His Thr Ser Gln Glu Asp Arg Ser Ser Gly Ser Thr Thr Glu Leu
            900                 905                 910

His Cys Val Thr Asp Glu Arg Asn Ala Leu Arg Arg Ser Ser Ala Ala
        915                 920                 925

His Thr His Ser Asn Thr Tyr Asn Phe Thr Lys Ser Glu Asn Ser Asn
    930                 935                 940

Arg Thr Cys Ser Met Pro Tyr Ala Lys Leu Glu Tyr Lys Arg Ser Ser
945                 950                 955                 960

Asn Asp Ser Leu Asn Ser Val Ser Ser Asp Gly Tyr Gly Lys Arg
                965                 970                 975

Gly Gln Met Lys Pro Ser Ile Glu Ser Tyr Ser Glu Asp Asp Glu Ser
            980                 985                 990

Lys Phe Cys Ser Tyr Gly Gln Tyr Pro Ala Asp Leu Ala His Lys Ile
        995                 1000                1005

His Ser Ala Asn His Met Asp Asp Asn Asp Gly Glu Leu Asp Thr
    1010                1015                1020

Pro Ile Asn Tyr Ser Leu Lys Tyr Ser Asp Glu Gln Leu Asn Ser
        1025                1030                1035

Gly Arg Gln Ser Pro Ser Gln Asn Glu Arg Trp Ala Arg Pro Lys
        1040                1045                1050
```

```
His Ile Ile Glu Asp Glu Ile Lys Gln Ser Glu Gln Arg Gln Ser
    1055                1060                1065

Arg Asn Gln Ser Thr Thr Tyr Pro Val Tyr Thr Glu Ser Thr Asp
    1070                1075                1080

Asp Lys His Leu Lys Phe Gln Pro His Phe Gly Gln Gln Glu Cys
    1085                1090                1095

Val Ser Pro Tyr Arg Ser Arg Gly Ala Asn Gly Ser Glu Thr Asn
    1100                1105                1110

Arg Val Gly Ser Asn His Gly Ile Asn Gln Asn Val Ser Gln Ser
    1115                1120                1125

Leu Cys Gln Glu Asp Asp Tyr Glu Asp Asp Lys Pro Thr Asn Tyr
    1130                1135                1140

Ser Glu Arg Tyr Ser Glu Glu Gln His Glu Glu Glu Glu Glu Arg
    1145                1150                1155

Pro Thr Asn Tyr Ser Ile Lys Tyr Asn Glu Glu Lys Arg His Val
    1160                1165                1170

Asp Gln Pro Ile Asp Tyr Ser Leu Lys Tyr Ala Thr Asp Ile Pro
    1175                1180                1185

Ser Ser Gln Lys Gln Ser Phe Ser Phe Ser Lys Ser Ser Ser Gly
    1190                1195                1200

Gln Ser Ser Lys Thr Glu His Met Ser Ser Ser Glu Asn Thr
    1205                1210                1215

Ser Thr Pro Ser Ser Asn Ala Lys Arg Gln Asn Gln Leu His Pro
    1220                1225                1230

Ser Ser Ala Gln Ser Arg Ser Gly Gln Pro Gln Lys Ala Ala Thr
    1235                1240                1245

Cys Lys Val Ser Ser Ile Asn Gln Glu Thr Ile Gln Thr Tyr Cys
    1250                1255                1260

Val Glu Asp Thr Pro Ile Cys Phe Ser Arg Cys Ser Ser Leu Ser
    1265                1270                1275

Ser Leu Ser Ser Ala Glu Asp Glu Ile Gly Cys Asn Gln Thr Thr
    1280                1285                1290

Gln Glu Ala Asp Ser Ala Asn Thr Leu Gln Ile Ala Glu Ile Lys
    1295                1300                1305

Glu Lys Ile Gly Thr Arg Ser Ala Glu Asp Pro Val Ser Glu Val
    1310                1315                1320

Pro Ala Val Ser Gln His Pro Arg Thr Lys Ser Ser Arg Leu Gln
    1325                1330                1335

Gly Ser Ser Leu Ser Ser Glu Ser Ala Arg His Lys Ala Val Glu
    1340                1345                1350

Phe Ser Ser Gly Ala Lys Ser Pro Ser Lys Ser Gly Ala Gln Thr
    1355                1360                1365

Pro Lys Ser Pro Pro Glu His Tyr Val Gln Glu Thr Pro Leu Met
    1370                1375                1380

Phe Ser Arg Cys Thr Ser Val Ser Ser Leu Asp Ser Phe Glu Ser
    1385                1390                1395

Arg Ser Ile Ala Ser Ser Val Gln Ser Glu Pro Cys Ser Gly Met
    1400                1405                1410

Val Ser Gly Ile Ile Ser Pro Ser Asp Leu Pro Asp Ser Pro Gly
    1415                1420                1425

Gln Thr Met Pro Pro Ser Arg Ser Lys Thr Pro Pro Pro Pro Pro
    1430                1435                1440

Gln Thr Ala Gln Thr Lys Arg Glu Val Pro Lys Asn Lys Ala Pro
```

-continued

```
            1445                1450                1455
Thr Ala Glu Lys Arg Glu Ser Gly Pro Lys Gln Ala Ala Val Asn
            1460                1465                1470
Ala Ala Val Gln Arg Val Gln Val Leu Pro Asp Ala Asp Thr Leu
            1475                1480                1485
Leu His Phe Ala Thr Glu Ser Thr Pro Asp Gly Phe Ser Cys Ser
            1490                1495                1500
Ser Ser Leu Ser Ala Leu Ser Leu Asp Glu Pro Phe Ile Gln Lys
            1505                1510                1515
Asp Val Glu Leu Arg Ile Met Pro Pro Val Gln Glu Asn Asp Asn
            1520                1525                1530
Gly Asn Glu Thr Glu Ser Glu Gln Pro Lys Glu Ser Asn Glu Asn
            1535                1540                1545
Gln Glu Lys Glu Ala Glu Lys Thr Ile Asp Ser Glu Lys Asp Leu
            1550                1555                1560
Leu Asp Asp Ser Asp Asp Asp Asp Ile Glu Ile Leu Glu Glu Cys
            1565                1570                1575
Ile Ile Ser Ala Met Pro Thr Lys Ser Ser Arg Lys Ala Lys Lys
            1580                1585                1590
Pro Ala Gln Thr Ala Ser Lys Leu Pro Pro Val Ala Arg Lys
            1595                1600                1605
Pro Ser Gln Leu Pro Val Tyr Lys Leu Leu Pro Ser Gln Asn Arg
            1610                1615                1620
Leu Gln Pro Gln Lys His Val Ser Phe Thr Pro Gly Asp Asp Met
            1625                1630                1635
Pro Arg Val Tyr Cys Val Glu Gly Thr Pro Ile Asn Phe Ser Thr
            1640                1645                1650
Ala Thr Ser Leu Ser Asp Leu Thr Ile Glu Ser Pro Pro Asn Glu
            1655                1660                1665
Leu Ala Ala Gly Glu Gly Val Arg Gly Gly Ala Gln Ser Gly Glu
            1670                1675                1680
Phe Glu Lys Arg Asp Thr Ile Pro Thr Glu Gly Arg Ser Thr Asp
            1685                1690                1695
Glu Ala Gln Gly Gly Lys Thr Ser Ser Val Thr Ile Pro Glu Leu
            1700                1705                1710
Asp Asp Asn Lys Ala Glu Glu Gly Asp Ile Leu Ala Glu Cys Ile
            1715                1720                1725
Asn Ser Ala Met Pro Lys Gly Lys Ser His Lys Pro Phe Arg Val
            1730                1735                1740
Lys Lys Ile Met Asp Gln Val Gln Gln Ala Ser Ala Ser Ser Ser
            1745                1750                1755
Ala Pro Asn Lys Asn Gln Leu Asp Gly Lys Lys Lys Lys Pro Thr
            1760                1765                1770
Ser Pro Val Lys Pro Ile Pro Gln Asn Thr Glu Tyr Arg Thr Arg
            1775                1780                1785
Val Arg Lys Asn Ala Asp Ser Lys Asn Asn Leu Asn Ala Glu Arg
            1790                1795                1800
Val Phe Ser Asp Asn Lys Asp Ser Lys Lys Gln Asn Leu Lys Asn
            1805                1810                1815
Asn Ser Lys Val Phe Asn Asp Lys Leu Pro Asn Asn Glu Asp Arg
            1820                1825                1830
Val Arg Gly Ser Phe Ala Phe Asp Ser Pro His His Tyr Thr Pro
            1835                1840                1845
```

```
Ile Glu Gly Thr Pro Tyr Cys Phe Ser Arg Asn Asp Ser Leu Ser
1850                1855                1860

Ser Leu Asp Phe Asp Asp Asp Val Asp Leu Ser Arg Glu Lys
1865                1870                1875

Ala Glu Leu Arg Lys Ala Lys Glu Asn Lys Glu Ser Glu Ala Lys
1880                1885                1890

Val Thr Ser His Thr Glu Leu Thr Ser Asn Gln Gln Ser Ala Asn
1895                1900                1905

Lys Thr Gln Ala Ile Ala Lys Gln Pro Ile Asn Arg Gly Gln Pro
1910                1915                1920

Lys Pro Ile Leu Gln Lys Gln Ser Thr Phe Pro Gln Ser Ser Lys
1925                1930                1935

Asp Ile Pro Asp Arg Gly Ala Ala Thr Asp Glu Lys Leu Gln Asn
1940                1945                1950

Phe Ala Ile Glu Asn Thr Pro Val Cys Phe Ser His Asn Ser Ser
1955                1960                1965

Leu Ser Ser Leu Ser Asp Ile Asp Gln Glu Asn Asn Asn Lys Glu
1970                1975                1980

Asn Glu Pro Ile Lys Glu Thr Glu Pro Pro Asp Ser Gln Gly Glu
1985                1990                1995

Pro Ser Lys Pro Gln Ala Ser Gly Tyr Ala Pro Lys Ser Phe His
2000                2005                2010

Val Glu Asp Thr Pro Val Cys Phe Ser Arg Asn Ser Ser Leu Ser
2015                2020                2025

Ser Leu Ser Ile Asp Ser Glu Asp Asp Leu Leu Gln Glu Cys Ile
2030                2035                2040

Ser Ser Ala Met Pro Lys Lys Lys Lys Pro Ser Arg Leu Lys Gly
2045                2050                2055

Asp Asn Glu Lys His Ser Pro Arg Asn Met Gly Gly Ile Leu Gly
2060                2065                2070

Glu Asp Leu Thr Leu Asp Leu Lys Asp Ile Gln Arg Pro Asp Ser
2075                2080                2085

Glu His Gly Leu Ser Pro Asp Ser Glu Asn Phe Asp Trp Lys Ala
2090                2095                2100

Ile Gln Glu Gly Ala Asn Ser Ile Val Ser Ser Leu His Gln Ala
2105                2110                2115

Ala Ala Ala Ala Cys Leu Ser Arg Gln Ala Ser Ser Asp Ser Asp
2120                2125                2130

Ser Ile Leu Ser Leu Lys Ser Gly Ile Ser Leu Gly Ser Pro Phe
2135                2140                2145

His Leu Thr Pro Asp Gln Glu Glu Lys Pro Phe Thr Ser Asn Lys
2150                2155                2160

Gly Pro Arg Ile Leu Lys Pro Gly Glu Lys Ser Thr Leu Glu Thr
2165                2170                2175

Lys Lys Ile Glu Ser Glu Ser Lys Gly Ile Lys Gly Gly Lys Lys
2180                2185                2190

Val Tyr Lys Ser Leu Ile Thr Gly Lys Val Arg Ser Asn Ser Glu
2195                2200                2205

Ile Ser Gly Gln Met Lys Gln Pro Leu Gln Ala Asn Met Pro Ser
2210                2215                2220

Ile Ser Arg Gly Arg Thr Met Ile His Ile Pro Gly Val Arg Asn
2225                2230                2235
```

```
Ser  Ser  Ser  Ser  Thr  Ser  Pro  Val  Ser  Lys  Lys  Gly  Pro  Pro  Leu
2240                2245                               2250

Lys  Thr  Pro  Ala  Ser  Lys  Ser  Pro  Ser  Glu  Gly  Gln  Thr  Ala  Thr
2255                2260                               2265

Thr  Ser  Pro  Arg  Gly  Ala  Lys  Pro  Ser  Val  Lys  Ser  Glu  Leu  Ser
2270                2275                               2280

Pro  Val  Ala  Arg  Gln  Thr  Ser  Gln  Ile  Gly  Gly  Ser  Ser  Lys  Ala
2285                2290                               2295

Pro  Ser  Arg  Ser  Gly  Ser  Arg  Asp  Ser  Thr  Pro  Ser  Arg  Pro  Ala
2300                2305                               2310

Gln  Gln  Pro  Leu  Ser  Arg  Pro  Ile  Gln  Ser  Pro  Gly  Arg  Asn  Ser
2315                2320                               2325

Ile  Ser  Pro  Gly  Arg  Asn  Gly  Ile  Ser  Pro  Pro  Asn  Lys  Leu  Ser
2330                2335                               2340

Gln  Leu  Pro  Arg  Thr  Ser  Ser  Pro  Ser  Thr  Ala  Ser  Thr  Lys  Ser
2345                2350                               2355

Ser  Gly  Ser  Gly  Lys  Met  Ser  Tyr  Thr  Ser  Pro  Gly  Arg  Gln  Met
2360                2365                               2370

Ser  Gln  Gln  Asn  Leu  Thr  Lys  Gln  Thr  Gly  Leu  Ser  Lys  Asn  Ala
2375                2380                               2385

Ser  Ser  Ile  Pro  Arg  Ser  Glu  Ser  Ala  Ser  Lys  Gly  Leu  Asn  Gln
2390                2395                               2400

Met  Asn  Gly  Asn  Gly  Ala  Asn  Lys  Lys  Val  Glu  Leu  Ser  Arg
2405                2410                               2415

Met  Ser  Ser  Thr  Lys  Ser  Ser  Gly  Ser  Glu  Ser  Asp  Arg  Ser  Glu
2420                2425                               2430

Arg  Pro  Val  Leu  Val  Arg  Gln  Ser  Thr  Phe  Ile  Lys  Glu  Ala  Pro
2435                2440                               2445

Ser  Pro  Thr  Leu  Arg  Arg  Lys  Leu  Glu  Glu  Ser  Ala  Ser  Phe  Glu
2450                2455                               2460

Ser  Leu  Ser  Pro  Ser  Ser  Arg  Pro  Ala  Ser  Pro  Thr  Arg  Ser  Gln
2465                2470                               2475

Ala  Gln  Thr  Pro  Val  Leu  Ser  Pro  Ser  Leu  Pro  Asp  Met  Ser  Leu
2480                2485                               2490

Ser  Thr  His  Ser  Ser  Val  Gln  Ala  Gly  Gly  Trp  Arg  Lys  Leu  Pro
2495                2500                               2505

Pro  Asn  Leu  Ser  Pro  Thr  Ile  Glu  Tyr  Asn  Asp  Gly  Arg  Pro  Ala
2510                2515                               2520

Lys  Arg  His  Asp  Ile  Ala  Arg  Ser  His  Ser  Glu  Ser  Pro  Ser  Arg
2525                2530                               2535

Leu  Pro  Ile  Asn  Arg  Ser  Gly  Thr  Trp  Lys  Arg  Glu  His  Ser  Lys
2540                2545                               2550

His  Ser  Ser  Ser  Leu  Pro  Arg  Val  Ser  Thr  Trp  Arg  Arg  Thr  Gly
2555                2560                               2565

Ser  Ser  Ser  Ser  Ile  Leu  Ser  Ala  Ser  Ser  Glu  Ser  Ser  Glu  Lys
2570                2575                               2580

Ala  Lys  Ser  Glu  Asp  Glu  Lys  His  Val  Asn  Ser  Ile  Ser  Gly  Thr
2585                2590                               2595

Lys  Gln  Ser  Lys  Glu  Asn  Gln  Val  Ser  Ala  Lys  Gly  Thr  Trp  Arg
2600                2605                               2610

Lys  Ile  Lys  Glu  Asn  Glu  Phe  Ser  Pro  Thr  Asn  Ser  Thr  Ser  Gln
2615                2620                               2625

Thr  Val  Ser  Ser  Gly  Ala  Thr  Asn  Gly  Ala  Glu  Ser  Lys  Thr  Leu
```

```
                2630                2635                2640

Ile Tyr Gln Met Ala Pro Ala Val Ser Lys Thr Glu Asp Val Trp
    2645                2650                2655

Val Arg Ile Glu Asp Cys Pro Ile Asn Asn Pro Arg Ser Gly Arg
2660                2665                2670

Ser Pro Thr Gly Asn Thr Pro Pro Val Ile Asp Ser Val Ser Glu
    2675                2680                2685

Lys Ala Asn Pro Asn Ile Lys Asp Ser Lys Asp Asn Gln Ala Lys
2690                2695                2700

Gln Asn Val Gly Asn Gly Ser Val Pro Met Arg Thr Val Gly Leu
    2705                2710                2715

Glu Asn Arg Leu Asn Ser Phe Ile Gln Val Asp Ala Pro Asp Gln
2720                2725                2730

Lys Gly Thr Glu Ile Lys Pro Gly Gln Asn Asn Pro Val Pro Val
    2735                2740                2745

Ser Glu Thr Asn Glu Ser Ser Ile Val Glu Arg Thr Pro Phe Ser
2750                2755                2760

Ser Ser Ser Ser Ser Lys His Ser Ser Pro Ser Gly Thr Val Ala
    2765                2770                2775

Ala Arg Val Thr Pro Phe Asn Tyr Asn Pro Ser Pro Arg Lys Ser
2780                2785                2790

Ser Ala Asp Ser Thr Ser Ala Arg Pro Ser Gln Ile Pro Thr Pro
    2795                2800                2805

Val Asn Asn Asn Thr Lys Lys Arg Asp Ser Lys Thr Asp Ser Thr
2810                2815                2820

Glu Ser Ser Gly Thr Gln Ser Pro Lys Arg His Ser Gly Ser Tyr
    2825                2830                2835

Leu Val Thr Ser Val
    2840

<210> SEQ ID NO 15
<211> LENGTH: 557
<212> TYPE: PRT
<213> ORGANISM: Homo sapiens

<400> SEQUENCE: 15

Met Asp Asp Leu Asp Ala Leu Leu Ala Asp Leu Glu Ser Thr Thr Ser
1               5                   10                  15

His Ile Ser Lys Arg Pro Val Phe Leu Ser Glu Glu Thr Pro Tyr Ser
            20                  25                  30

Tyr Pro Thr Gly Asn His Thr Tyr Gln Glu Ile Ala Val Pro Pro Pro
        35                  40                  45

Val Pro Pro Pro Pro Ser Ser Glu Ala Leu Asn Gly Thr Ile Leu Asp
    50                  55                  60

Pro Leu Asp Gln Trp Gln Pro Ser Gly Ser Arg Phe Ile His Gln Gln
65                  70                  75                  80

Pro Gln Ser Ser Ser Pro Val Tyr Gly Ser Ser Ala Lys Thr Ser Ser
                85                  90                  95

Val Ser Asn Pro Gln Asp Ser Val Gly Ser Pro Cys Ser Arg Val Gly
            100                 105                 110

Glu Glu Glu His Val Tyr Ser Phe Pro Asn Lys Gln Lys Ser Ala Glu
        115                 120                 125

Pro Ser Pro Thr Val Met Ser Thr Ser Leu Gly Ser Asn Leu Ser Glu
    130                 135                 140
```

```
Leu Asp Arg Leu Leu Leu Glu Leu Asn Ala Val Gln His Asn Pro Pro
145                 150                 155                 160

Gly Phe Pro Ala Asp Glu Ala Asn Ser Ser Pro Pro Leu Pro Gly Ala
            165                 170                 175

Leu Ser Pro Leu Tyr Gly Val Pro Glu Thr Asn Ser Pro Leu Gly Gly
            180                 185                 190

Lys Ala Gly Pro Leu Thr Lys Glu Lys Pro Lys Arg Asn Gly Gly Arg
            195                 200                 205

Gly Leu Glu Asp Val Arg Pro Ser Val Glu Ser Leu Leu Asp Glu Leu
            210                 215                 220

Glu Ser Ser Val Pro Ser Pro Val Pro Ala Ile Thr Val Asn Gln Gly
225                 230                 235                 240

Glu Met Ser Ser Pro Gln Arg Val Thr Ser Thr Gln Gln Thr Arg
            245                 250                 255

Ile Ser Ala Ser Ser Ala Thr Arg Glu Leu Asp Glu Leu Met Ala Ser
            260                 265                 270

Leu Ser Asp Phe Lys Phe Met Ala Gln Gly Lys Thr Gly Ser Ser Ser
            275                 280                 285

Pro Pro Gly Gly Pro Pro Lys Pro Gly Ser Gln Leu Asp Ser Met Leu
290                 295                 300

Gly Ser Leu Gln Ser Asp Leu Asn Lys Leu Gly Val Ala Thr Val Ala
305                 310                 315                 320

Lys Gly Val Cys Gly Ala Cys Lys Lys Pro Ile Ala Gly Gln Val Val
            325                 330                 335

Thr Ala Met Gly Lys Thr Trp His Pro Glu His Phe Val Cys Thr His
            340                 345                 350

Cys Gln Glu Glu Ile Gly Ser Arg Asn Phe Phe Glu Arg Asp Gly Gln
            355                 360                 365

Pro Tyr Cys Glu Lys Asp Tyr His Asn Leu Phe Ser Pro Arg Cys Tyr
            370                 375                 380

Tyr Cys Asn Gly Pro Ile Leu Asp Lys Val Val Thr Ala Leu Asp Arg
385                 390                 395                 400

Thr Trp His Pro Glu His Phe Phe Cys Ala Gln Cys Gly Ala Phe Phe
            405                 410                 415

Gly Pro Glu Gly Phe His Glu Lys Asp Gly Lys Ala Tyr Cys Arg Lys
            420                 425                 430

Asp Tyr Phe Asp Met Phe Ala Pro Lys Cys Gly Gly Cys Ala Arg Ala
            435                 440                 445

Ile Leu Glu Asn Tyr Ile Ser Ala Leu Asn Thr Leu Trp His Pro Glu
450                 455                 460

Cys Phe Val Cys Arg Glu Cys Phe Thr Pro Phe Val Asn Gly Ser Phe
465                 470                 475                 480

Phe Glu His Asp Gly Gln Pro Tyr Cys Glu Val His Tyr His Glu Arg
            485                 490                 495

Arg Gly Ser Leu Cys Ser Gly Cys Gln Lys Pro Ile Thr Gly Arg Cys
            500                 505                 510

Ile Thr Ala Met Ala Lys Lys Phe His Pro Glu His Phe Val Cys Ala
            515                 520                 525

Phe Cys Leu Lys Gln Leu Asn Lys Gly Thr Phe Lys Glu Gln Asn Asp
            530                 535                 540

Lys Pro Tyr Cys Gln Asn Cys Phe Leu Lys Leu Phe Cys
545                 550                 555
```

```
<210> SEQ ID NO 16
<211> LENGTH: 533
<212> TYPE: PRT
<213> ORGANISM: Gallus gallus domesticus

<400> SEQUENCE: 16

Met Gly Ser Ser Lys Ser Lys Pro Lys Asp Pro Ser Gln Arg Arg Arg
1               5                   10                  15

Ser Leu Glu Pro Pro Asp Ser Thr His His Gly Gly Phe Pro Ala Ser
            20                  25                  30

Gln Thr Pro Asn Lys Thr Ala Ala Pro Asp Thr His Arg Thr Pro Ser
        35                  40                  45

Arg Ser Phe Gly Thr Val Ala Thr Glu Pro Lys Leu Phe Gly Gly Phe
    50                  55                  60

Asn Thr Ser Asp Thr Val Thr Ser Pro Gln Arg Ala Gly Ala Leu Ala
65                  70                  75                  80

Gly Gly Val Thr Thr Phe Val Ala Leu Tyr Asp Tyr Glu Ser Arg Thr
                85                  90                  95

Glu Thr Asp Leu Ser Phe Lys Lys Gly Glu Arg Leu Gln Ile Val Asn
            100                 105                 110

Asn Thr Glu Gly Asp Trp Trp Leu Ala His Ser Leu Thr Thr Gly Gln
        115                 120                 125

Thr Gly Tyr Ile Pro Ser Asn Tyr Val Ala Pro Ser Asp Ser Ile Gln
    130                 135                 140

Ala Glu Glu Trp Tyr Phe Gly Lys Ile Thr Arg Arg Glu Ser Glu Arg
145                 150                 155                 160

Leu Leu Leu Asn Pro Glu Asn Pro Arg Gly Thr Phe Leu Val Arg Glu
                165                 170                 175

Ser Glu Thr Thr Lys Gly Ala Tyr Cys Leu Ser Val Ser Asp Phe Asp
            180                 185                 190

Asn Ala Lys Gly Leu Asn Val Lys His Tyr Lys Ile Arg Lys Leu Asp
        195                 200                 205

Ser Gly Gly Phe Tyr Ile Thr Ser Arg Thr Gln Phe Ser Ser Leu Gln
    210                 215                 220

Gln Leu Val Ala Tyr Tyr Ser Lys His Ala Asp Gly Leu Cys His Arg
225                 230                 235                 240

Leu Thr Asn Val Cys Pro Thr Ser Lys Pro Gln Thr Gln Gly Leu Ala
                245                 250                 255

Lys Asp Ala Trp Glu Ile Pro Arg Glu Ser Leu Arg Leu Glu Val Lys
            260                 265                 270

Leu Gly Gln Gly Cys Phe Gly Glu Val Trp Met Gly Thr Trp Asn Gly
        275                 280                 285

Thr Thr Arg Val Ala Ile Lys Thr Leu Lys Pro Gly Thr Met Ser Pro
    290                 295                 300

Glu Ala Phe Leu Gln Glu Ala Gln Val Met Lys Lys Leu Arg His Glu
305                 310                 315                 320

Lys Leu Val Gln Leu Tyr Ala Val Val Ser Glu Glu Pro Ile Tyr Ile
                325                 330                 335

Val Thr Glu Tyr Met Ser Lys Gly Ser Leu Leu Asp Phe Leu Lys Gly
            340                 345                 350

Glu Met Gly Lys Tyr Leu Arg Leu Pro Gln Leu Val Asp Met Ala Ala
        355                 360                 365

Gln Ile Ala Ser Gly Met Ala Tyr Val Glu Arg Met Asn Tyr Val His
    370                 375                 380
```

```
Arg Asp Leu Arg Ala Ala Asn Ile Leu Val Gly Glu Asn Leu Val Cys
385                 390                 395                 400

Lys Val Ala Asp Phe Gly Leu Ala Arg Leu Ile Glu Asp Asn Glu Tyr
            405                 410                 415

Thr Ala Arg Gln Gly Ala Lys Phe Pro Ile Lys Trp Thr Ala Pro Glu
            420                 425                 430

Ala Ala Leu Tyr Gly Arg Phe Thr Ile Lys Ser Asp Val Trp Ser Phe
            435                 440                 445

Gly Ile Leu Leu Thr Glu Leu Thr Thr Lys Gly Arg Val Pro Tyr Pro
            450                 455                 460

Gly Met Val Asn Arg Glu Val Leu Asp Gln Val Glu Arg Gly Tyr Arg
465                 470                 475                 480

Met Pro Cys Pro Pro Glu Cys Pro Glu Ser Leu His Asp Leu Met Cys
            485                 490                 495

Gln Cys Trp Arg Lys Asp Pro Glu Glu Arg Pro Thr Phe Glu Tyr Leu
            500                 505                 510

Gln Ala Phe Leu Glu Asp Tyr Phe Thr Ser Thr Glu Pro Gln Tyr Gln
            515                 520                 525

Pro Gly Glu Asn Leu
        530

<210> SEQ ID NO 17
<211> LENGTH: 1066
<212> TYPE: PRT
<213> ORGANISM: Homo sapiens

<400> SEQUENCE: 17

Met Pro Val Phe His Thr Arg Thr Ile Glu Ser Ile Leu Glu Pro Val
1               5                   10                  15

Ala Gln Gln Ile Ser His Leu Val Ile Met His Glu Glu Gly Glu Val
            20                  25                  30

Asp Gly Lys Ala Ile Pro Asp Leu Thr Ala Pro Val Ala Ala Val Gln
        35                  40                  45

Ala Ala Val Ser Asn Leu Val Arg Val Gly Lys Glu Thr Val Gln Thr
    50                  55                  60

Thr Glu Asp Gln Ile Leu Lys Arg Asp Met Pro Pro Ala Phe Ile Lys
65                  70                  75                  80

Val Glu Asn Ala Cys Thr Lys Leu Val Gln Ala Ala Gln Met Leu Gln
                85                  90                  95

Ser Asp Pro Tyr Ser Val Pro Ala Arg Asp Tyr Leu Ile Asp Gly Ser
            100                 105                 110

Arg Gly Ile Leu Ser Gly Thr Ser Asp Leu Leu Leu Thr Phe Asp Glu
        115                 120                 125

Ala Glu Val Arg Lys Ile Ile Arg Val Cys Lys Gly Ile Leu Glu Tyr
    130                 135                 140

Leu Thr Val Ala Glu Val Val Glu Thr Met Glu Asp Leu Val Thr Tyr
145                 150                 155                 160

Thr Lys Asn Leu Gly Pro Gly Met Thr Lys Met Ala Lys Met Ile Asp
                165                 170                 175

Glu Arg Gln Gln Glu Leu Thr His Gln Glu His Arg Val Met Leu Val
            180                 185                 190

Asn Ser Met Asn Thr Val Lys Glu Leu Leu Pro Val Leu Ile Ser Ala
        195                 200                 205

Met Lys Ile Phe Val Thr Thr Lys Asn Ser Lys Asn Gln Gly Ile Glu
    210                 215                 220
```

```
Glu Ala Leu Lys Asn Arg Asn Phe Thr Leu Glu Lys Met Ser Ala Glu
225                 230                 235                 240

Ile Asn Glu Ile Ile Arg Val Leu Gln Leu Thr Ser Trp Asp Glu Asp
            245                 250                 255

Ala Trp Ala Ser Lys Asp Thr Glu Ala Met Lys Arg Ala Leu Ala Ser
                260                 265                 270

Ile Asp Ser Lys Leu Asn Gln Ala Lys Gly Trp Leu Arg Asp Pro Ser
            275                 280                 285

Ala Ser Pro Gly Asp Ala Gly Glu Gln Ala Ile Arg Gln Ile Leu Asp
            290                 295                 300

Glu Ala Gly Lys Val Gly Glu Leu Cys Ala Gly Lys Glu Arg Arg Glu
305                 310                 315                 320

Ile Leu Gly Thr Cys Lys Met Leu Gly Gln Met Thr Asp Gln Val Ala
                325                 330                 335

Asp Leu Arg Ala Arg Gly Gln Gly Ser Ser Pro Val Ala Met Gln Lys
            340                 345                 350

Ala Gln Gln Val Ser Gln Gly Leu Asp Val Leu Thr Ala Lys Val Glu
            355                 360                 365

Asn Ala Ala Arg Lys Leu Glu Ala Met Thr Asn Ser Lys Gln Ser Ile
370                 375                 380

Ala Lys Lys Ile Asp Ala Ala Gln Asn Trp Leu Ala Asp Pro Asn Gly
385                 390                 395                 400

Gly Pro Glu Gly Glu Glu Gln Ile Arg Gly Ala Leu Ala Glu Ala Arg
                405                 410                 415

Lys Ile Ala Glu Leu Cys Asp Asp Pro Lys Glu Arg Asp Asp Ile Leu
                420                 425                 430

Arg Ser Leu Gly Glu Ile Ser Ala Leu Thr Ser Lys Leu Ala Asp Leu
            435                 440                 445

Arg Arg Gln Gly Lys Gly Asp Ser Pro Glu Ala Arg Ala Leu Ala Lys
450                 455                 460

Gln Val Ala Thr Ala Leu Gln Asn Leu Gln Thr Lys Thr Asn Arg Ala
465                 470                 475                 480

Val Ala Asn Ser Arg Pro Ala Lys Ala Ala Val His Leu Glu Gly Lys
                485                 490                 495

Ile Glu Gln Ala Gln Arg Trp Ile Asp Asn Pro Thr Val Asp Asp Arg
                500                 505                 510

Gly Val Gly Gln Ala Ala Ile Arg Gly Leu Val Ala Glu Gly His Arg
            515                 520                 525

Leu Ala Asn Val Met Met Gly Pro Tyr Arg Gln Asp Leu Leu Ala Lys
            530                 535                 540

Cys Asp Arg Val Asp Gln Leu Thr Ala Gln Leu Ala Asp Leu Ala Ala
545                 550                 555                 560

Arg Gly Glu Gly Glu Ser Pro Gln Ala Arg Ala Leu Ala Ser Gln Leu
                565                 570                 575

Gln Asp Ser Leu Lys Asp Leu Lys Ala Arg Met Gln Glu Ala Met Thr
            580                 585                 590

Gln Glu Val Ser Asp Val Phe Ser Asp Thr Thr Pro Ile Lys Leu
            595                 600                 605

Leu Ala Val Ala Ala Thr Ala Pro Pro Asp Ala Pro Asn Arg Glu Glu
            610                 615                 620

Val Phe Asp Glu Arg Ala Ala Asn Phe Glu Asn His Ser Gly Lys Leu
625                 630                 635                 640
```

Gly Ala Thr Ala Glu Lys Ala Ala Val Gly Thr Ala Asn Lys Ser
                    645             650             655

Thr Val Glu Gly Ile Gln Ala Ser Val Lys Thr Ala Arg Glu Leu Thr
            660             665             670

Pro Gln Val Val Ser Ala Ala Arg Ile Leu Leu Arg Asn Pro Gly Asn
        675             680             685

Gln Ala Ala Tyr Glu His Phe Glu Thr Met Lys Asn Gln Trp Ile Asp
    690             695             700

Asn Val Glu Lys Met Thr Gly Leu Val Asp Glu Ala Ile Asp Thr Lys
705             710             715             720

Ser Leu Leu Asp Ala Ser Glu Glu Ala Ile Lys Lys Asp Leu Asp Lys
                725             730             735

Cys Lys Val Ala Met Ala Asn Ile Gln Pro Gln Met Leu Val Ala Gly
            740             745             750

Ala Thr Ser Ile Ala Arg Arg Ala Asn Arg Ile Leu Leu Val Ala Lys
        755             760             765

Arg Glu Val Glu Asn Ser Glu Asp Pro Lys Phe Arg Glu Ala Val Lys
    770             775             780

Ala Ala Ser Asp Glu Leu Ser Lys Thr Ile Ser Pro Met Val Met Asp
785             790             795             800

Ala Lys Ala Val Ala Gly Asn Ile Ser Asp Pro Gly Leu Gln Lys Ser
                805             810             815

Phe Leu Asp Ser Gly Tyr Arg Ile Leu Gly Ala Val Ala Lys Val Arg
            820             825             830

Glu Ala Phe Gln Pro Gln Glu Pro Asp Phe Pro Pro Pro Pro Pro Asp
        835             840             845

Leu Glu Gln Leu Arg Leu Thr Asp Glu Leu Ala Pro Pro Lys Pro Pro
    850             855             860

Leu Pro Glu Gly Glu Val Pro Pro Arg Pro Pro Pro Pro Glu Glu
865             870             875             880

Lys Asp Glu Glu Phe Pro Glu Gln Lys Ala Gly Glu Val Ile Asn Gln
                885             890             895

Pro Met Met Met Ala Ala Arg Gln Leu His Asp Glu Ala Arg Lys Trp
            900             905             910

Ser Ser Lys Gly Asn Asp Ile Ile Ala Ala Lys Arg Met Ala Leu
        915             920             925

Leu Met Ala Glu Met Ser Arg Leu Val Arg Gly Gly Ser Gly Thr Lys
    930             935             940

Arg Ala Leu Ile Gln Cys Ala Lys Asp Ile Ala Lys Ala Ser Asp Glu
945             950             955             960

Val Thr Arg Leu Ala Lys Glu Val Ala Lys Gln Cys Thr Asp Lys Arg
                965             970             975

Ile Arg Thr Asn Leu Leu Gln Val Cys Glu Arg Ile Pro Thr Ile Ser
            980             985             990

Thr Gln Leu Lys Ile Leu Ser Thr Val Lys Ala Thr Met Leu Gly Arg
        995             1000            1005

Thr Asn Ile Ser Asp Glu Glu Ser Glu Gln Ala Thr Glu Met Leu
    1010            1015            1020

Val His Asn Ala Gln Asn Leu Met Gln Ser Val Lys Glu Thr Val
    1025            1030            1035

Arg Glu Ala Glu Ala Ala Ser Ile Lys Ile Arg Thr Asp Ala Gly
    1040            1045            1050

Phe Thr Leu Arg Trp Val Arg Lys Thr Pro Trp Tyr Gln

<210> SEQ ID NO 18
<211> LENGTH: 28
<212> TYPE: PRT
<213> ORGANISM: Artificial
<220> FEATURE:
<223> OTHER INFORMATION: PIPKI gamma fragment

<400> SEQUENCE: 18

Pro Thr Asp Glu Arg Ser Trp Val Tyr Ser Pro Leu His Tyr Ser Ala
1               5                   10                  15

Gln Ala Pro Pro Ala Ser Asp Gly Glu Ser Asp Thr
            20                  25

<210> SEQ ID NO 19
<211> LENGTH: 17
<212> TYPE: PRT
<213> ORGANISM: Artificial
<220> FEATURE:
<223> OTHER INFORMATION: Lifeact peptide

<400> SEQUENCE: 19

Met Gly Val Ala Asp Leu Ile Lys Lys Phe Glu Ser Ile Ser Lys Glu
1               5                   10                  15

Glu

<210> SEQ ID NO 20
<211> LENGTH: 1164
<212> TYPE: DNA
<213> ORGANISM: Artificial
<220> FEATURE:
<223> OTHER INFORMATION: FLAG-Actin

<400> SEQUENCE: 20
atggactaca aagacgatga cgacaagaga tctcgagcta tggatgatga tatcgccgcg      60
ctcgtcgtcg acaacggctc cggcatgtgc aaggccggct tcgcgggcga cgatgccccc     120
cgggccgtct cccctccat cgtggggcgc cccaggcacc agggcgtgat ggtgggcatg      180
ggtcagaagg attcctatgt gggcgacgag gcccagagca agagaggcat cctcaccctg     240
aagtacccca tcgagcacgg catcgtcacc aactgggacg acatggagaa atctggcac     300
cacaccttct acaatgagct gcgtgtggct cccgaggagc accccgtgct gctgaccgag     360
gcccccctga ccccaaggc caaccgcgag aagatgaccc agatcatgtt tgagaccttc     420
aacaccccag ccatgtacgt tgctatccag gctgtgctat ccctgtacgc ctctggccgt     480
accactggca tcgtgatgga ctccggtgac ggggtcaccc acactgtgcc catctacgag     540
gggtatgccc tcccccatgc catcctgcgt ctggacctgg ctggccggga cctgactgac     600
tacctcatga agatcctcac cgagcgcggc tacagcttca ccaccacggc cgagcgggaa     660
atcgtgcgtg acattaagga gaagctgtgc tacgtcgccc tggacttcga gcaagagatg     720
gccacggctg cttccagctc ctccctggag aagagctacg agctgcctga cggccaggtc     780
atcaccattg caatgagcg gttccgctgc cctgaggcac tcttccagcc ttccttcctg     840
ggcatggagt cctgtggcat ccacgaaact accttcaact ccatcatgaa gtgtgacgtg     900
gacatccgca agacctgta cgccaacaca gtgctgtctg gcggcaccac catgtaccct     960
ggcattgccg acaggatgca gaaggagatc actgccctgg cacccagcac aatgaagatc    1020
aagatcattg ctcctcctga gcgcaagtac tccgtgtgga tcggcggctc catcctggcc    1080

```
tcgctgtcca ccttccagca gatgtggatc agcaagcagg agtatgacga gtccggcccc    1140
tccatcgtcc accgcaaatg cttc                                           1164
```

OBSERVATION METHOD USING BINDING AND DISSOCIATION PROBE

CROSS REFERENCE TO RELATED APPLICATIONS

This application is based upon and claims the benefit of priority from prior Japanese Patent Application No. 2015-048692, filed Mar. 11, 2015, the entire contents of which are incorporated herein by this reference. This is a Continuation Application of PCT Application No. PCT/JP2016/057817, filed Mar. 11, 2016, which was not published under PCT Article 21 (2) in English.

BACKGROUND OF THE INVENTION

Field of the Invention

The present invention is related to an observation method using a binding and dissociation probe by which a super-resolution image of a sample can be obtained.

Description of the Related Art

In recent years, super-resolution microscopy (STED, SIM, PALM/STORM; resolution capability: 10 nm through 100 nm) with a resolution capability exceeding that of optical microscopes (>200 nm) has been developed (Nat. Rev. Mol. Cell Biol., 9, 929-943, 2008), and major microscope manufacturing companies (Nikon, Carl Zeiss, Leica) are selling their super-resolution microscope apparatuses. In the field of biological science particularly, important discoveries are expected from applications of PALM (photoactivated localization microscopy, Japanese National Publication of International Patent Application No. 2008-542826, Science, 313, 1642-1645, 2006)/STORM (stochastic optical reconstruction microscopy, Nature Methods, 3, 793-795 and United States Patent Application No. US2008/0032414). In each super-resolution microscopy, fluorescent dye is made to bind to a target so as to label the target, and the spatial distribution of the fluorescent dye is observed with a high resolution capability in Stimulated Emission Depletion (STED), structured illumination microscopy (SIM), and localization microscopy (PALM/STORM).

The outline of localization microscopy is as follows. First, a target substance to be observed is labeled with a luminescent substance such as a fluorescent substance. Then, the luminescent substance with which the target substance is labeled is made to emit light at a low density so that speckle images are obtained in which the speckles of emissions of light are separated individually, i.e., in which luminescent substances of single molecules are separated. The central positions of the individual speckles can be obtained in the respective speckle images that have been obtained. The above step of obtaining speckle images including separated speckles so as to obtain information of the positions of speckles is repeated a plurality of times, e.g., hundreds of times through hundreds of thousands of times, and the central positions of roughly all luminescent substances on the target substance are obtained, and thereby an observation image of the target substance is constructed. Explanations will be schematically given for the localization microscopy by referring to FIG. 1. For example, it is assumed as shown in FIG. 1 (a) that five molecules 100 of target substances to be observed are distributed. The five molecules 100 of the target substance are respectively labeled with luminescent substances and are made to emit light separately in such a manner that the speckles of light emission do not overlap each other. For example, as shown in FIG. 1 (b), three speckle images 110, 111 and 112 having separate speckles 101 are obtained at different times t1, t2 and t3. A gauss function is fit to the image of each speckle 101 in each of the speckle images 110, 111 and 112 so as to obtain the central positions of the speckles, and position information 102 which is information of the central positions is recorded (FIG. 1 (c)). Pieces of position information 102 of individual recorded speckles are synthesized so as to draw an observation image 120 as shown in FIG. 1 (d). The above method can be implemented by using for example DAOSTORM, a computer program (Nature methods, 8 279-280, 2011). In localization microscopy, as schematically shown in FIG. (1b), it is necessary that images of the molecules 100, which are labeled target substances, be picked up over time while the molecules 100 are sequentially made to emit light at a relatively low density so as to obtain a plurality of speckle images so that the speckles of luminescent substances of single molecules can be separated.

PALM/STORM use a fluorescent substance that can perform activation or switching through irradiation with light for making a fluorescent substance emit light at a low density so as to adjust a light irradiation condition in order to stochastically perform activation or switching on the state of the fluorescent substance, and thereby obtain speckle images in which speckles are separated individually.

Proceedings of the national Academy of Sciences of the United States of America 103, 18911-18916 (2006) reports a method referred to as PAINT (point accumulation for imaging in nanoscale topography). The document discloses that super-resolution observation of a form of a lipid bilayer was conducted through PAINT by using the fluorescent dye Nile-red that swiftly goes back and forth between an aqueous solution and the lipid bilayer.

Recently, as a multicolor super-resolution microscopy to which PAINT above is applied, a method has been reported in which a target substance is labeled with an antibody that was made to fuse with a DNA oligomer and a fluorescent DNA oligomer which is a complementary base sequence that temporarily binds to and dissociates from the DNA oligomer is used (Exchange-PAINT, Nature methods, 11, 313-318, 2014).

SUMMARY OF THE INVENTION

The present inventors have found that a luminescent probe can be used for labeling different positions on a target substance in respective speckle images so that the labeling density with respect to the target substance can be substantially increased by increasing the number of the speckle images that are picked up and a high resolution observation image exceeding a diffraction limit can be generated by the localization microscopy from respective speckle images when a plurality of images of light emission speckles (speckle images) are picked up at different times and while keeping a contact state between the luminescent probe and a sample, by using the luminescent probe, as a binding and dissociation luminescent probe, that is a luminescent probe which repeatedly binds to and dissociates from a target substance directly and specifically and for which the half-life of a probe-target complex formed by binding between the luminescent probe and the target substance is in a prescribed scope, and the present inventors have completed the present invention. The present invention incorporates the following inventions.

(1) An observation method of a sample containing a target substance, the observation method comprising:
- an imaging step in which a step of obtaining a speckle image including, as a speckle, light emitted from a luminescent substance under a prescribed condition in a state in which a medium is brought into contact with the sample is performed a plurality of times at different times respectively so as to obtain a plurality of speckle images, the medium containing a probe that contains the luminescent substance emitting light under the prescribed condition and that repeatedly binds to and dissociates from the target substance directly and specifically; and
- an observation image generation step of generating an observation image of the target substance in the sample from the plurality of speckle images, wherein
- a half-life of a probe-target complex formed by binding between the probe and the target substance is equal to or more than 10 milliseconds and equal to or less than 3 seconds.

(2) The method according to (1), wherein
- the observation image generation step is a step in which information of a position of a speckle included in each of the plurality of speckle images is obtained for each of the plurality of speckle images and the observation image is generated on the basis of the information from the plurality of speckle images.

(3) The method according to (1), wherein
- the sample includes two or more target substances, the imaging step is sequentially performed on the sample by using the probe that is specific to each of the target substances, and
- the observation image generation step is a step in which observation images of the respective target substances in the sample are respectively generated from the plurality of speckle images obtained from the respective imaging steps.

(4) The method according to (3), further comprising
- a multiple-observation image generation step in which observation images of the respective target substances in the sample generated in the observation image generation step are superposed so as to generate a multiple-observation image, which is an observation image of the two or more target substances in the sample.

(5) The method according to (1), wherein
- the luminescent substance is a fluorescent substance, and the prescribed condition is irradiation with excitation light.

(6) The method according to (1), wherein
- a combination between the probe and the target substance is selected from a group of:
  - a combination wherein the probe is (a1) a polypeptide, linked to the luminescent substance, which consists of an amino acid sequence of sequence number 19, (a2) a polypeptide, linked to the luminescent substance, which consists of the amino acid sequence described in (a1) where one or a plurality of amino acids have been substituted, deleted, inserted or added and for which a half-life of a probe-target complex formed by binding between the probe and the target substance is equal to or more than 10 milliseconds and equal to or less than 3 seconds, or (a3) a polypeptide, linked to the luminescent substance, which consists of an amino acid sequence having at least a 70% identity with the amino acid sequence described in (a1) and for which a half-life of a probe-target complex formed by binding between the probe and the target substance is equal to or more than 10 milliseconds and equal to or less than 3 seconds, and the target substance is an actin polymer;
  - a combination wherein the probe is (b1) a polypeptide, linked to the luminescent substance, which consists of an amino acid sequence that is a partial amino acid sequence of an amino acid sequence of sequence number 12, that at least partially contains an amino acid sequence of 3-309 and that has 407 or fewer amino acids, an amino acid sequence that is a partial amino acid sequence of an amino acid sequence of sequence number 14, that at least partially contains an amino acid sequence of 2536-2843 and that has 408 or fewer amino acids, an amino acid sequence that is a partial amino acid sequence of an amino acid sequence of sequence number 14, that at least partially contains an amino acid sequence of 2781-2819 and that has 138 or fewer amino acids, an amino acid sequence that is a partial amino acid sequence of an amino acid sequence of sequence number 4, that at least partially contains an amino acid sequence of 1-908 and that has 1008 or fewer amino acids, an amino acid sequence that is a partial amino acid sequence of an amino acid sequence of sequence number 4, that at least partially contains an amino acid sequence of 659-908 and that has 394 or fewer amino acids, an amino acid sequence of sequence number 5, or an amino acid sequence of sequence number 6, (b2) a polypeptide, linked to the luminescent substance, which consists of the amino acid sequence described in (b1) where one or a plurality of amino acids have been substituted, deleted, inserted or added and for which a half-life of a probe-target complex formed by binding between the probe and the target substance is equal to or more than 10 milliseconds and equal to or less than 3 seconds, or (b3) a polypeptide, linked to the luminescent substance, which consists of an amino acid sequence having at least a 70% identity with the amino acid sequence described in (b1) and for which a half-life of a probe-target complex formed by binding between the probe and the target substance is equal to or more than 10 milliseconds and equal to or less than 3 seconds, and the target substance is a microtubule;
  - a combination wherein the probe is (c1) a polypeptide, linked to the luminescent substance, which consists of an amino acid sequence that is a partial amino acid sequence of an amino acid sequence of sequence number 8, that at least partially contains an amino acid sequence of 3777-4684 and that has 1008 or fewer amino acids, an amino acid sequence that is a partial amino acid sequence of an amino acid sequence of sequence number 8, that at least partially contains an amino acid sequence of 3777-4364 and that has 688 or fewer amino acids, an amino acid sequence that is a partial amino acid sequence of an amino acid sequence of sequence number 8, that at least partially contains an amino acid sequence of 3777-4313 and that has 637 or fewer amino acids, or an amino acid sequence that is a partial amino acid sequence of an amino acid sequence of sequence number 8, that at least partially contains an amino acid sequence of 4022-4364 and that has 443 or fewer amino acids, (c2) a polypeptide, linked to the luminescent substance, which consists of the amino acid sequence described in (c1) where one or a plurality of amino acids have been substituted, deleted, inserted or added and for which a half-life of a probe-target complex formed by binding between the probe and the target substance is equal to or more than 10 milliseconds and equal to or less than 3 seconds, or (c3) a polypeptide, linked to the luminescent substance, which consists of an amino acid sequence having at least a 70% identity with the amino acid sequence described in (c1) and for which a half-life of a probe-target complex formed by binding between the probe and the target substance is equal to or more than 10 milliseconds and equal to or less than 3 seconds, and the target substance is an intermediate filament; and a combination wherein the probe is (d1) a polypeptide, linked to the luminescent substance, which consists of an amino acid sequence of sequence number 15, an amino acid sequence that is a partial amino acid sequence of an amino acid sequence of sequence number 15, that at least partially contains an amino acid sequence of 54-557 and that has 556 or fewer amino acids, an amino acid sequence that is a partial amino acid sequence of an amino acid sequence of sequence number 15, that at least partially contains an amino acid sequence of 54-498 and that has 545 or fewer amino acids, an amino acid sequence that is a partial amino acid sequence of an amino acid sequence of sequence number 15, that at least partially contains an amino acid sequence of 167-557 and that has 491 or fewer amino acids, an amino acid sequence that is a partial amino acid sequence of an amino acid sequence of sequence number 16, that at least partially contains an amino acid sequence of 1-251 and that has 351 or fewer amino acids, an amino acid sequence that is a partial amino acid sequence of an amino acid sequence of sequence number 16, that at least partially contains an amino acid sequence of 3-251 and that has 349 or fewer amino acids or an amino acid sequence of sequence number 18, (d2) a polypeptide, linked to the luminescent substance, which consists of the amino acid sequence described in (d1) where one or a plurality of amino acids have been substituted, deleted, inserted or added and for which a half-life of a probe-target complex formed by binding between the probe and the target substance is equal to or more than 10 milliseconds and equal to or less than 3 seconds, or (d3) a polypeptide, linked to the luminescent substance, which consists of an amino acid sequence having at least a 70% identity with the amino acid sequence described in (d1) and for which a half-life of a probe-target complex formed by binding between the probe and the target substance is equal to or more than 10 milliseconds and equal to or less than 3 seconds, and the target substance is a focal adhesion.

(7) The method according to (1), wherein
the probe contains an antibody or a fragment of an antibody, the antibody or the fragment being to the target substance and the antibody or the fragment being linked to the luminescent substance.

(8) The method according to (7), wherein the fragment of the antibody is a Fab fragment.

(9) A probe used for labeling a target substance, wherein
the probe contains a luminescent substance that emits light under a prescribed condition,
the probe can repeatedly bind to and dissociate from the target substance directly and specifically, and
a half-life of a probe-target complex formed by binding to the target substance is equal to or more than 10 milliseconds and equal to or less than 3 seconds.

(10) The probe according to (9), wherein
the target substance is an actin polymer and the probe is (a1) a polypeptide, linked to the luminescent substance, which consists of an amino acid sequence of sequence number 19, (a2) a polypeptide, linked to the luminescent substance, which consists of the amino acid sequence described in (a1) where one or a plurality of amino acids have been substituted, deleted, inserted or added and for which a half-life of a probe-target complex formed by binding between the probe and the target substance is equal to or more than 10 milliseconds and equal to or less than 3 seconds, or (a3) a polypeptide, linked to the luminescent substance, which consists of an amino acid sequence having at least a 70% identity with the amino acid sequence described in (a1) and for which a half-life of a probe-target complex formed by binding between the probe and the target substance is equal to or more than 10 milliseconds and equal to or less than 3 seconds, the target substance is a microtubule and the probe is (b1) a polypeptide, linked to the luminescent substance, which consists of an amino acid sequence that is a partial amino acid sequence of an amino acid sequence of sequence number 12, that at least partially contains an amino acid sequence of 3-309 and that has 407 or fewer amino acids, an amino acid sequence that is a partial amino acid sequence of an amino acid sequence of sequence number 14, that at least partially contains an amino acid sequence of 2536-2843 and that has 408 or fewer amino acids, an amino acid sequence that is a partial amino acid sequence of an amino acid sequence of sequence number 14, that at least partially contains an amino acid sequence of 2781-2819 and that has 138 or fewer amino acids, an amino acid sequence that is a partial amino acid sequence of an amino acid sequence of sequence number 4, that at least partially contains an amino acid sequence of 1-908 and that has 1008 or fewer amino acids, an amino acid sequence that is a partial amino acid sequence of an amino acid sequence of sequence number 4, that at least partially contains an amino acid sequence of 659-908 and that has 394 or fewer amino acids, an amino acid sequence of sequence number 5 or an amino acid sequence of sequence number 6, (b2) a polypeptide, linked to the luminescent substance, which consists of the amino acid sequence described in (b1) where one or a plurality of amino acids have been substituted, deleted, inserted or added and for which a half-life of a probe-target complex formed by binding between the probe and the target substance is equal to or more than 10 milliseconds and equal to or less than 3 seconds, or (b3) a polypeptide, linked to the luminescent substance, which consists of an amino acid sequence having at least a 70% identity with the amino acid sequence described in (b1) and for which a half-life of a probe-target complex formed by binding between the probe and the target substance is equal to or more than 10 milliseconds and equal to or less than 3 seconds, the target substance is an intermediate filament and the probe is (c1) a polypeptide, linked to the luminescent substance, which consists of an amino acid sequence that is a partial amino acid sequence of an amino acid sequence of sequence number 8, that at least partially contains an amino acid sequence of 3777-4684 and that has 1008 or fewer amino acids, an amino acid sequence that is a partial amino acid sequence of an amino acid sequence of sequence number 8, that at least partially contains an amino acid sequence of 3777-4364 and that has 688 or fewer amino acids, an amino acid sequence that is a partial amino acid sequence of an amino acid sequence of sequence number 8, that at least partially contains an amino acid sequence of 3777-4313 and that has 637 or fewer amino acids or an amino acid sequence that is a partial amino acid sequence of an amino acid sequence of sequence number 8, that at least partially contains an amino acid sequence of 4022-4364 and that has 443 or fewer amino acids, (c2) a polypeptide, linked to the luminescent substance, which consists of the amino acid sequence described in (c1) where one or a plurality of amino acids have been substituted, deleted, inserted or added and for which a half-life of a probe-target complex formed by binding between the probe and the target substance is equal to or more than 10 milliseconds and equal to or less than 3 seconds, or (c3) a polypeptide, linked to the luminescent substance, which consists of an amino acid sequence having at least a 70% identity with the amino acid sequence described in (c1) and for which a half-life of a probe-target complex formed by binding between the probe and the target substance is equal to or more than 10 milliseconds and equal to or less than 3 seconds, or the target substance is a focal adhesion and the probe is (d1) a polypeptide, linked to the luminescent substance, which consists of an amino acid sequence of sequence number 15, an amino acid sequence that is a partial amino acid sequence of an amino acid sequence of sequence number 15, that at least partially contains an amino acid sequence of 54-557 and that has 556 or fewer amino acids, an amino acid sequence that is a partial amino acid sequence of an amino acid sequence of sequence number 15, that at least partially contains an amino acid sequence of 54-498 and that has 545 or fewer amino acids, an amino acid sequence that is a partial amino acid sequence of an amino acid sequence of sequence number 15, that at least partially contains an amino acid sequence of 167-557 and that has 491 or fewer amino acids, an amino acid sequence that is a partial amino acid sequence of an amino acid sequence of sequence number 16, that at least partially contains an amino acid sequence of 1-251 and that has 351 or fewer amino acids, an amino acid sequence that is a partial amino acid sequence of an amino acid sequence of sequence number 16, that at least partially contains an amino acid sequence of 3-251 and that has 349 or fewer amino acids, or an amino acid sequence of sequence number 18, (d2) a polypeptide, linked to the luminescent substance, which consists of the amino acid sequence described in (d1) where one or a plurality of amino acids have been substituted, deleted, inserted or added and for which a half-life of a probe-target complex formed by binding between the probe and the target substance is equal to or more than 10 milliseconds and equal to or less than 3 seconds or (d3) a polypeptide, linked to the luminescent substance, which consists of an amino acid sequence having at least a 70% identity with the amino acid sequence described in (d1) and for which a half-life of a probe-target complex formed by binding between the probe and the target substance is equal to or more than 10 milliseconds and equal to or less than 3 seconds.

(11) The probe according to (9), wherein
the probe contains an antibody or a fragment of an antibody, the antibody or the fragment being to the target substance and the antibody or the fragment being linked to the luminescent substance.

(12) The probe according to (11), wherein
the fragment of the antibody is a Fab fragment.

(13) A reagent kit for labeling a target substance, wherein
the reagent kit at least includes the probe according to (9).

(14) A screening method of a site in which identifies a target substance in the probe according to (9), the screening method comprising:
an immobilization step in which a candidate substance of the site or a substance partially containing the candidate substance is fixed to a solid support;
an observation step in which a target substance linked to a luminescent substance and a solid support obtained in the immobilization step are observed in a medium while the target substance linked to a luminescent substance and the solid support obtained in the immobilization step are kept in contact, in a condition that allows observation, in units of 1 molecule, of light emission from the luminescent substance in a probe-target complex formed by binding between the target substance and the candidate substance, and
a screening step in which the candidate substance resulting in a half-life of the probe-target complex that is equal to or more than 10 milliseconds and equal to or less than 3 seconds is selected as the site on the basis of observation in the observation step.

(15) The method according to (14) wherein
the candidate substance is an antibody or a fragment of an antibody from a library of hybridoma that produces an antibody to the target substance, and
the antibody is fixed to a solid support in the immobilization step.

The present document incorporates the contents of the disclosure of Japanese patent application No. 2015-048692, on the basis of which the priority is claimed for the present application.

According to the present invention, operations and effects that are remarkably more advantageous than those of existing super-resolution microscopy can be provided because (i) the problem of a labeling density, which has been the cause of reduced reliability of existing super-resolution microscopy, can be resolved and (ii) it is easy to visualize a plurality of target substances by protein-based exchangeable probes and there are no limitations on the number of target substances.

BRIEF DESCRIPTION OF THE DRAWINGS

The present invention will be more apparent from the following detailed description when the accompanying drawings are referenced.

FIG. 1 (*a*) shows the distribution of the actual probe molecules. FIG. 1 (*b*) shows speckle images containing fluorescent speckles picked up at different times. FIG. 1 (*c*) shows position information of speckles in the respective speckle images. FIG. 1 (*d*) shows an observation image reconstructed on the basis of the position information.

FIG. 2 (b) is a schematic view for explaining the principle of STORM.

FIG. 5 (a) shows the outline of IRIS. Transient associations of single-molecule fluorescent probes with their targets are visualized, and central positions of the probes are identified with nanometer accuracy. Integrating the position information from many frames produces a super-resolution image of the target substance. FIG. 5 (b) shows a super-resolution image of a single actin filament in vitro by TIRF (total internal reflection fluorescence) microscopy using Atto 488-Lifeact. An observation image was reconstructed by using high-brightness speckles in order to improve the localization accuracy (see FIG. 9c). FIG. 5 (c) shows the cross-sectional profile of single actin filaments (n=10 filaments, gray bars). The black curve shows the Gaussian fit to the mean profile, with a FWHM of 23 nm. Error bars show S.E.M. FIG. 5 (d) shows dependency of image quality on the labeling density in vitro. The labeling density of Atto 488-Lifeact per unit length is indicated at the top of each view. FIG. 5 (e) shows line profiles of the labeling density of Atto 488-Lifeact along the frame in FIG. 5 (d). The labeling density is shown after being normalized by the mean labeling density of an entire actin filament. FIG. 5 (f) shows an IRIS image of actin filaments in a cell using Atto 488-Lifeact and total internal reflection illumination. The image was reconstructed from $5 \times 10^5$ frames. FIG. 5 (g) shows a comparison between the IRIS super-resolution image (upper left) and the added SiMS image (lower left) of the region in the frame in FIG. 5 (f). The right graph shows cross-sectional profiles of two adjacent filaments between the two arrowheads in the upper left image. Atto 488-Lifeact was excited by the simultaneous irradiation with 473-nm and 488-nm laser beams in the TIRF mode to obtain a strong signal from each speckle. The stage drift of the microscope was corrected with a bright-field image of nonfluorescent beads in observation of an actin filament in vitro and was corrected with a bright-field image of the cell itself in observation of an actin filament in the cell (see "Methods" in the examples).

FIG. 6 (b) shows super-resolution images of microtubules using a CLIP-170 fragment (amino acid residues 3-309 of sequence number 12). FIG. 6 (c) shows super-resolution images of intermediate filaments using a Plecin-1 (PLEC) fragment (amino acid residue 4022-4364 of sequence number 8). FIG. 6 (d) shows a super-resolution image of a focal adhesion using a phosphatidylinositol-(4)-phosphate 5-kinase type Iγ-90 (PIPKIγ) fragment (641-668) (sequence number 18). Except for a case when a PIPKIγ fragment was used as a probe, SiMS images (speckle images) of individual probes were obtained by alternately conducting total internal reflection illumination and epi-illumination. Specifically, imaging (exposure time was 50 ms/frame, 20 Hz) for 250 consecutive frames of speckle images based on the total internal reflection fluorescence in accordance with the condition explained in "procedures for imaging of multicolor super-resolution by IRIS" in "methods" of examples and imaging (exposure time was 50 ms/frame, 20 Hz) for 250 consecutive frames of speckle images based on the epi-fluorescence were repeated for observation of actin filament, microtubule and intermediate filament. For imaging of focal adhesions, speckle images based on epi-illumination were not obtained and imaging (exposure time was 50 ms/frame, 20 Hz) of 500 consecutive frames based on total internal reflection illumination was repeated. Then, the super-resolution images in the cell bottom (TIRF=total internal reflection fluorescence) and the entire cell peripheral regions (Epi=epi-fluorescence) were merged so as to reconstruct a super-resolution image. In FIG. 6 (a) through FIG. 6 (c), images obtained by merging TIRF images and epi-fluorescence images are shown, and the enlarged images of the regions enclosed by the frames are shown as the rightmost images. FIG. 6 (e) shows an image resulting from merging seven super-resolution images. The images were respectively reconstructed from $2 \times 10^5$ frames (Lifeact (TIRF), Lifeact (Epi)), $4 \times 10^4$ frames (CLIP frag. (TIRF), CLIP frag. (Epi)), $1.2 \times 10^5$ frames (PLEC frag. (TIRF), PLEC frag. (Epi)) and $4 \times 10^4$ frames (PIPKIγ frag. (TIRF)). The number of frames of speckle images used for constructing the TIRF image of FIG. 6 (a) is $2 \times 10^5$, the number of frames of speckle images used for constructing the Epi image of FIG. 6 (a) is $2 \times 10^5$, the number of frames of speckle images used for constructing the TIRF image of FIG. 6 (b) is $4 \times 10^4$, the number of frames of speckle images used for constructing the Epi of FIG. 6 (b) is $4 \times 10^4$, the number of frames of speckle images used for constructing the TIRF image of FIG. 6 (c) is $1.2 \times 10^5$, the number of frames of speckle images used for constructing the Epi of FIG. 6 (c) is $1.2 \times 10^5$, and the number of frames of speckle images used for constructing the TIRF image of FIG. 6 (d) is $4 \times 10^4$. Also, the probe concentration in the imaging solution for speckle imaging was 2.4 nM for the imaging in FIG. 6 (a), 8 nM for the imaging in FIG. 6 (b), 9.2 nM for the imaging in FIG. 6 (c) and 84 nM for the imaging in FIG. 6 (d). Note that the above probe concentrations are the actual probe concentration in the case when Atto488-Lifeact was used as the probe and are conversion values based on the fluorescence intensity of labeling fluorescent proteins in the case when other probes were used.

FIG. 7(a) shows an epi-fluorescence super-resolution image of intermediate filaments in the lamella region in ROI1 in FIG. 6 (e). FIG. 7 (b) shows a merged super-resolution image of the intermediate filaments (IF) and actin filaments (Act). FIG. 7 (c) shows a merged super-resolution image of intermediate filaments (IF) and microtubules (MT). FIG. 7 (d) shows a merged super-resolution of intermediate filaments (IF), actin filaments (Act) andmicrotubules (MT) in super-resolution image (a). FIG. 7 (e) shows cross-sectional profiles of three types of cytoskeletons between the arrowheads in FIG. 7 (d). Intermediate filaments are tangled with actin stress fibers (at the positions of arrows) in the lamellar region but are not tangled with microtubules. FIG. 7 (f) shows a TIRF super-resolution image of intermediate filaments in the peripheral region of ROI2 in FIG. 6 (e). FIG. 7 (g) shows a merged TIRF super-resolution image of intermediate filaments (IF) and actin filaments (Act). FIG. 7 (h) shows a merged TIRF super-resolution image of intermediate filaments (IF) and microtubules (MT). FIG. 7 (i) shows a merged TIRF super-resolution image of intermediate filaments (IF), actin filaments (Act), microtubules (MT) and focal adhesions (FA) in the region in the frame in super-resolution image (f). In FIG. 7 (g), which shows a TIRF super-resolution image, the intermediate filaments (IF) are denoted by narrow arrowheads and the actin filaments (Act) are denoted by thick arrowheads. In FIG. 7 (h), which shows a TIRF super-resolution image, the intermediate filaments (IF) are denoted by narrow arrowheads and the microtubules (MT) are denoted by thick arrowheads. FIG. 7 (j) shows cross-sectional profiles of three types of cytoskeletons between the arrowheads in FIG. 7 (i). In this peripheral region, the intermediate filaments overlap a microtubule at the position of the arrow but do not overlap actin filaments.

FIG. 8 (b) shows the line profiles (CLIP frag) of the z position of a microtubule, the intensity (Lifeact) of an actin filament and the intensity (PIPKIγ) of a focal adhesion along the interval between S and E of the microtubules denoted by the thick arrowheads in FIG. 8 (a). The curve of the thick solid line shows a movement average of four data points for the z position of the microtubule. The left image of FIG. 8 (c) is a map of the z positions of microtubules, and the right image of FIG. 8 (c) is an image resulting from merging the TIRF super-resolution images of actin filaments (grey) and focal adhesions (magenta). The focal adhesion was visualized by combining a super-resolution image obtained by using the Src fragment (residues 3-251 of sequence number 15) as a probe and a super-resolution image obtained by using the Paxillin full length as a probe. In FIG. 8 (d), the left panels are live-cell epi-fluorescence observation images (red) and TIRF observation images (green) of EB1-EGFP obtained before IRIS imaging. The middle panels are results of causing overlap between the z position of the tip of the EB1-labeled microtubule, the actin filament and focal adhesion shown in the right image of FIG. 8 (c), and the right panels are results of causing overlap between the speed of the portion of the tip of the EB1-labeled microtubule, the actin filament and focal adhesion shown in the right image of FIG. 8 (c). The microtubule analyzed with the trajectory of EB1 is indicated by an asterisk in FIG. 8 (c).

FIG. 9 (a) shows speckle lifetime distribution of Atto488-Lifeact in fixed XTC cells. The SiMS images (speckle images) were picked up consecutively with an exposure time of 10 ms/frame and at a frame rate of 100 Hz by using a 488 nm laser (with the main body output of 50 mW but reaching the sample after being attenuated by AOTF etc.). The measurement of the speckle lifetime (having obtained 100 pixels×100 pixels) of a narrow scope of the sample was performed using the Speckle TrackerJ plug-in so that 100 Hz is achieved, i.e. so that 1 frame was able to be obtained per 10 ms. The black line shows a half-life of 23 ms fit to the single exponential curve of the lifetime distribution of speckles between 20 ms and 110 ms. The photobleaching rate of Atto488-Lifeact was negligible in the term of 200 ms. FIG. 9b shows analysis of Atto488-Lifeact speckles using DAOSTORM (circles in the image). The SiMS images of Atto488-Lifeact in a cell were obtained with an exposure time of 50 ms. The central position of each speckle was determined with nanometer accuracy. The distribution of speckles changed greatly in the frame next to a frame in which an image was picked up 50 milliseconds later. FIG. 9 (c) shows super-resolved images of a single actin filament in vitro by TIRF microscopy using Atto488-Lifeact. The left image is an image obtained by the reconstruction from only high-brightness speckles (top 12% of all measured speckles) and is the same as that shown in FIG. 5 (b). The right image was reconstructed from all speckles. The labeling density on the actin filament is indicated at the top of each image. FIG. 9 (d) shows the cross-sectional profiles of single actin filaments in vitro (n=10 filaments) in the image reconstructed from high-brightness speckles (black) or in the image reconstructed from all speckles (white). Normalization was conducted so that all counts became 1. The black curve shows a Gaussian fit curve with a FWHM of 23 nm (high-brightness speckles) and the white curve shows a Gaussian fit curve with a FWHM of 38 nm (all speckles). The error bar represents ±S.E.M.

FIG. 10 (a) shows super-resolution images of microtubules by IRIS using CLIP-170 as probes. These images are part of the epi-fluorescence IRIS observation image of FIG. 6 (b). FIG. 10 (b) shows line profiles of labeling intensity along microtubules in the right image of FIG. 10 (a) (assumed to be IRIS (a)), the super-resolution of a microtubule by STORM using the anti-β tubulin described in document 21 (assumed to be STORM (b)), the super-resolution image of a microtubule by STORM using the anti-β tubulin described in document 22 (assumed to be STORM (c)), and the super-resolution image of a microtubule by Exchange-PAINT using the anti-β tubulin described in document 23 (assumed to be PAINT (d)). The labeling density is shown after being normalized by the mean labeling density of an entire actin filament.

FIG. 12 (a) and FIG. 12 (b) show live-cell imaging during the fixation operation. In FIG. 12 (a), the accumulation of EB1-EGFP at the tips of microtubules disappeared in a process by 3.7% PFA and 0.5% Triton-X 100. In FIG. 12 (b), EB1-EGFP was fixed in a state in which it was accumulated at the tips of the microtubules in a process by cold methanol. FIG. 12 (c) shows TIRF IRIS images (observation images) of microtubules using CLIP-170 fragment and Tau isoform 3 in cells processed by PFA and Triton-X 100. With these probes, IRIS images of the entire microtubules were obtained. The image resulting from merging these IRIS images indicates that the entire microtubules visualized by these probes correspond to each other. FIG. 12 (d) shows the TIRF IRIS images of microtubules using a CLIP-170 fragment and an APC fragment in cells preprocessed with cold methanol for 5 seconds and next with PFA and Triton X-100 as a preprocess. These probes resulted in IRIS images of microtubules where the microtubule tips were visualized with much stronger signals than were the entire microtubules. The image resulting from merging these images shows a coincidence of the microtubule tips visualized by these probes. FIG. 12 (e) shows TIRF IRIS images of microtubules using a CLIP-170 fragment, a MAP4 fragment and Tau isoform 3 in cold methanol-preprocessed cells. The microtubule tips were labeled strongly with a CLIP-170 fragment while they were weakly labeled with a MAP4 fragment and Tau isoform 3 (see merged images in the lower tier).

FIG. 13 (a) shows live-cell images in which GFP-Paxillin was used for visualizing focal adhesions for comparison. FIG. 13 (b) shows images of cells obtained by fixing and providing a permeabilization process to the living cells after the imaging of FIG. 13 (a). FIG. 13 (c) shows a state in which a remaining fluorescence of GFP-Paxillin was completely bleached by irradiation with a strong excitation laser. FIG. 13 (d) through FIG. 13 (f) are IRIS images in the order of the Src fragment, Paxillin FL, and a PIPKIγ fragment after the photobleaching of FIG. 13 (c). In an IRIS image view of FIG. 13 (d), generated by using the Src fragment, some dot structures appeared (arrowheads in FIG. 13 (d)) in the focal adhesion. These dot structures were not reconstructed by probes that did not dissolve, but were reconstructed by probes that repeatedly bound. In Paxillin FL, a focal adhesion was labeled partially. The left image of FIG. 13 (g) is a result of merging FIGS. 13 (a) (d) (e) and (f), the center image is a result of merging FIGS. 13 (d) and (e), and the right image is a result of merging FIGS. 13 (d) and (f). In the center image, the dot structures visualized by Src fragments (portions denoted by the arrowheads) have many portions that do not correspond to the focal adhesions visualized by Paxillin FL. FIG. 13 (h) shows the cross-sectional profiles of the focal adhesions in three IRIS images and the living-cell image of GFP-Paxillin. The measured scope is denoted by the line in the left image of FIG. 13 (g). The dot structures visualized by Src fragments are not completely visualized by Paxillin FL (arrow in FIG. 13 (h)). These proteins have different binding partners in focal adhesions (documents 17, 38 and 39). These differences between IRIS images may indicate a distribution of partners that respective proteins can associate with in focal adhesions.

FIG. 14 (a) shows fluorescence images of HyLight488-labeled microtubules obtained by total internal reflection fluorescence (TIRF) and epi fluorescence. The epi fluorescence images were obtained as z-stack images (0.2 μm step size). The z-stack epi-fluorescence images were used to determine the z-directional distance of each point along the tilted microtubule (see "Methods"). The bar represents 5 μm. FIG. 14 (b) shows the Z profile of the TIRF excitation intensity.

FIG. 15 (d) shows a distribution of z positions of actin bundles in lamellipodia (LP), stress fibers (SF) and actin arcs (Arc). In these layered actin structures, a calculated z position represents the height position of the center of gravity in the z axial direction of an actin filament. FIG. 15 (e) shows the z-position profile along the longitudinal direction of a microtubule. The microtubule submerges toward the periphery of a cell (arrowheads in FIG. 15 (b)). S and E in FIG. 15 (b) represent the starting and ending points of the line profile.

FIG. 18 (A) shows a reaction positive example. Speckles representing binding between FLAG-EGFP and antibodies are observed at a high density. An observation result of a great number of speckles indicates that solid-phased antibodies are anti-FLAG antibodies having a binding capacity to FLAG-EGFP. FIG. 18 (B) shows a reaction negative example. Few speckles are observed. This is a similar level to a case where FLAG-EGFP was added to a glass surface that was not solid phased.

DESCRIPTION OF THE EMBODIMENTS

In super-resolution microscopy, an increased resolution capability has brought the new problems of a low labeling density and unevenness thereof. According to a sampling theorem for example, it has been shown that one labeling substance has to be included at 10 nm in a target in order to obtain a spatial resolution capability of 20 nm (J. Cell Sci., 126, 3505-3513, 2013). In conventional super-resolution imaging of proteins in cells, target proteins are labeled by using the expression of target proteins with which fluorescent proteins have been made to fuse or by using a fluorescent antibody. This imposes limitations on a labeling density, depending upon the expression amount ratio to endogenous target proteins and upon the size (about 10 nm) of an antibody itself. Also, because fluorescent dyes that have bound to a target substance are used, the maximum number of types of target substances that can be visualized in one sample is two or three. The limitations on the number of proteins that can be stained have been a long-standing issue in the study of a cell consisting of various types of proteins.

In Exchange-PAINT above as well, target substances have to be labeled with antibodies that were made to fuse with DNA oligomers, and thus it is expected that a plurality of antibodies will interfere with each other spatially in a region at or below the diffraction limit. In principle, the greater the number of types of antibodies there are, the more difficult it is to perform labeling evenly.

Uneven labeling leads to reconstruction of false super-resolution, which is problematic.

Proceedings of the national Academy of Sciences of the United States of America 103, 18911-18916 (2006), which discloses PAINT, does not at all describe increasing of the labeling density of target substances by labeling substances.

Thus, it is an object of the present invention to provide a super-resolution microscope observation method that can obtain position information of luminescent substances at a high density, the luminescent substances being used for labeling.

According to the method of the present invention, it is possible to label target substances at a high density in a sample by using luminescent probes and to generate a highly accurate observation image of a target substance.

1. Principle of IRIS

The present inventors have named the observation method of the present invention IRIS (image reconstruction by integrating exchangeable single-molecule localization).

Figure 1:
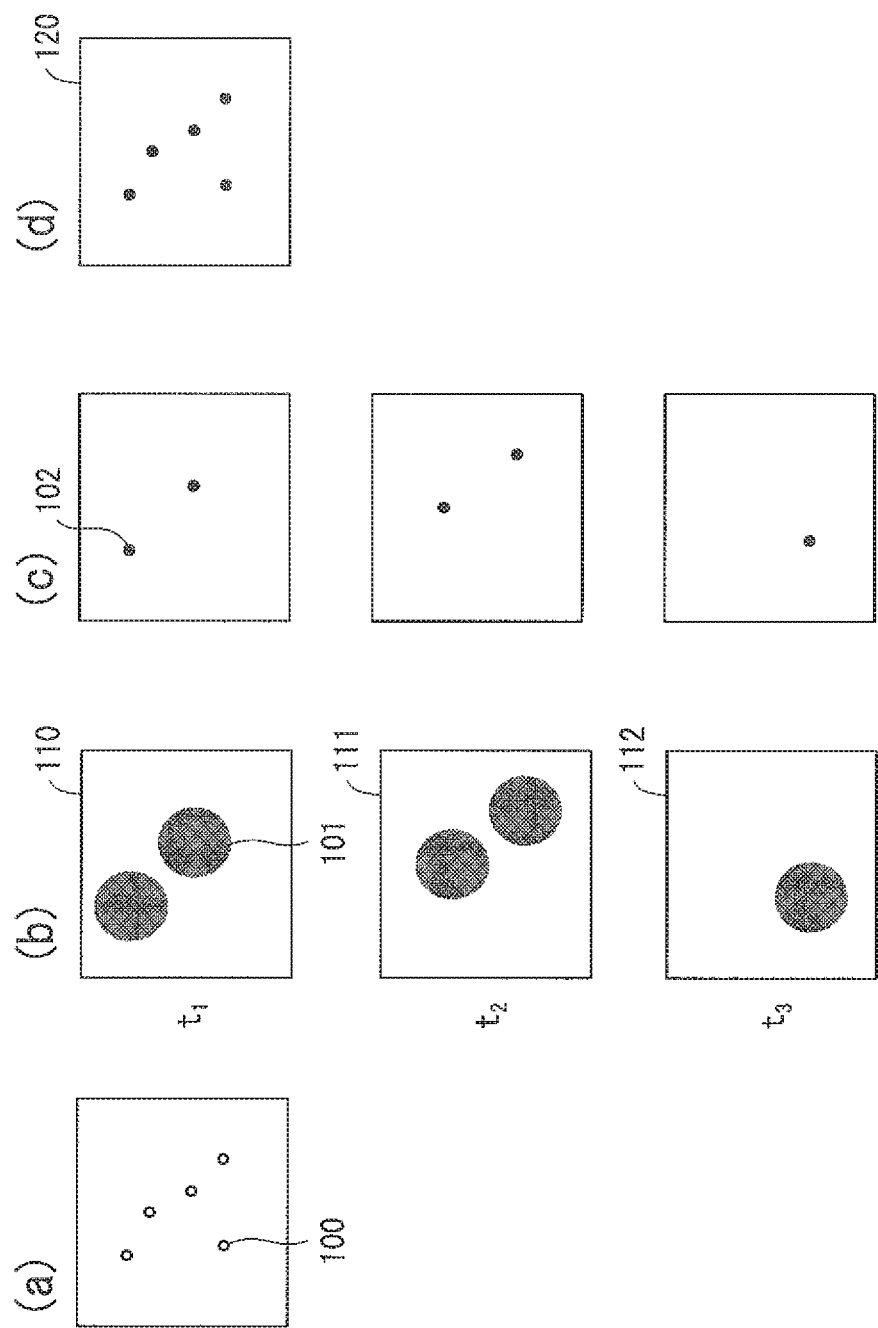
FIG. 1 explains the outline of the localization microscopy.
Figure 2:
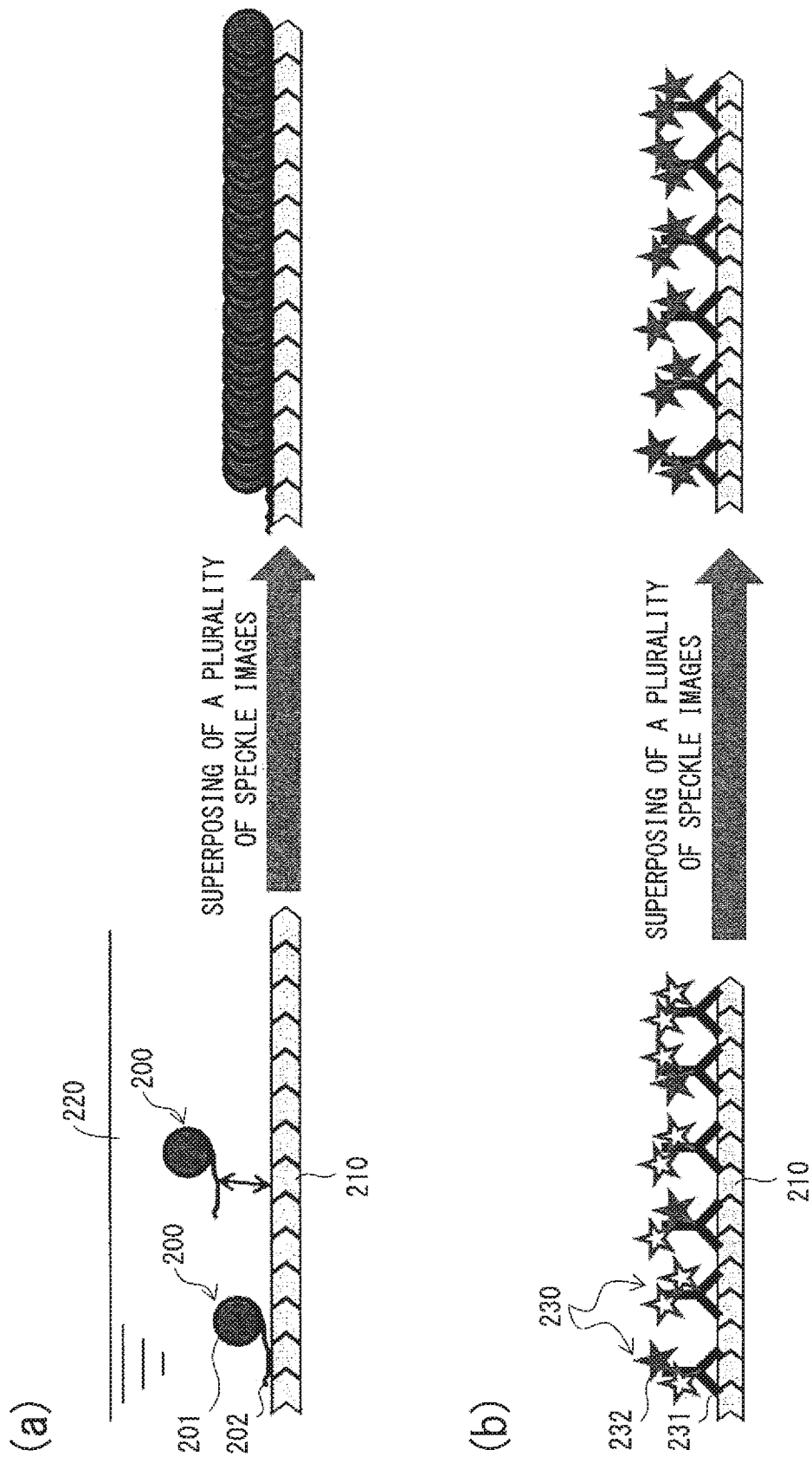
FIG. 2 (a) is a schematic view for explaining the principle by which the labeling density can be increased by using the method of the present invention.

FIG. 2 (a) explains functions of a luminescent probe in the observation method of the present invention. A probe 200 contains a luminescent substance 201 that emits light under a prescribed condition (for example a fluorescent substance that emits fluorescence when irradiated with excitation light), and usually further contains a binding substance 202 that is involved in binding to and dissociation from a target substance that is linked to the luminescent substance 201. The probe 200 can repeatedly bind to and dissociate from a target substance 210 directly and specifically. Characteristics of binding of the probe 200 are as below. When the probe 200 is in a state in which it has bound to the target substance 210, the light emitted by the luminescent substance 201 can be picked up as a speckle in a speckle image, and when the probe 200 has dissociated from the target substance 210, the light emitted by the luminescent substance 201 is not picked up as a speckle in an image because the probe is in a disordered thermal motion in a medium 220. In an imaging step of the present invention, a step is performed a plurality of times (e.g. hundreds of times through hundreds of thousands of times respectively at different times) in which a speckle image including, as a speckle, light emitted from the luminescent substance 201 under a prescribed condition is obtained in a state in which the medium 220 containing the probe 200 is brought into contact with a sample containing the target substance 210. As is shown when superposing the obtained plurality speckle images, an imaging step of the present invention can attain the same effect as that attained by labeling the target substances 210 with probes 200 at a high density and picking up images of them. Theoretically, there is no upper limit on the density of the labeling in the above. Also, when the concentration of the probes 200 in the medium 220 is adjusted appropriately, it is possible to identify a plurality of individual speckles in a separate manner in one speckle image.

Meanwhile, in PALM, STORM and Exchange-PAINT, which have conventionally been known as localization microscopy, an antibody to which a luminescent substance is linked is used for labeling a target substance. In an example of STORM for example, as shown in FIG. 2 (b), luminescent antibodies 230 resulting from linking luminescent substances 232 and antibodies 231 for the target substance 210 are made to bind to the target substance 210 and images are picked up a plurality of times (e.g. hundreds of times through hundreds of thousands of times) at different times while making the luminescent substances 232 emit light discretely at a density that is low enough to prevent the speckles from overlapping. By superposing the obtained plurality of speckle images, an image with all the luminescent substances 232 emitting light can be obtained. However, the labeling density at which the target substance is labeled with the luminescent antibodies 230 is limited by the size (about 10 nm) of the antibodies themselves. In order to achieve a resolution capability of X nm, it is necessary to label a target substance at intervals of X/2 nm (Nyquist Sampling Theorem). The luminescent antibody 230 has a size of at least about 10 nm, so making labeling at a high density is impossible. Also, in Exchange-PAINT, a plurality of target substances in one sample are labeled with a plurality of antibodies that are specific to the respective target substances, which causes interference between the plurality of antibodies, making it further difficult to perform labeling at a high density. The observation method according to the present invention can solve the above problem of labeling density in conventional localization microscopy.

2. Observation of a Plurality of Target Substances

The observation method according to the present invention can preferably be implemented even when a plurality of target substances exist in one sample.

When a plurality of target substances exist in one sample, the observation method according to the present invention are implemented through the following procedures. A medium containing a probe that repeatedly binds to and dissociates from one type from among a plurality of target substances directly and specifically is brought into contact with a sample so that an imaging step of the present invention is conducted and thereby a plurality of speckle images including speckles of light emitted from the probes that have bound to that one type of the target substance are obtained. Next, probes are removed by washing the sample and a medium containing a probe that repeatedly binds to and dissociates from one different type from among a plurality of target substances directly and specifically is brought into contact with the sample so that an imaging step of the present invention is conducted and thereby a plurality of speckle images including speckles of light emitted from the probes that have bound to that one different type of the target substance are obtained. These procedures are performed until a plurality of speckle images are obtained for each of all the target substances that are to be observed. The wash of the sample between the respective imaging steps can be implemented by for example performing at least one time an operation in which an appropriate washing medium such as the above medium etc. not containing the probe is brought into contact with the sample the sample is washed. Observation images of respective target substances can be generated from a plurality of speckle images for respective target substances obtained by using respective probes. Also, by superposing observation images of respective target substances in the same sample, a multiple-observation image including observation images of a plurality of target substances in the sample can also be generated.

A probe used in the present invention is a probe that can repeatedly bind to and dissociate from a target substance directly and specifically. "Bind to a target substance directly" used herein refers to binding between a probe and a target substance that is not through another binding substance such as an antibody etc. When a probe and a target substance are binding through at least one type of binding selected from a group consisting of for example hydrogen binding, hydrophilic and/or hydrophobic binding, electrostatic binding and van der Waals binding, the probe and the target substance can be treated as binding directly.

In the present invention, because a probe and a target substance bind to and dissociate from each other directly, the original state of the sample can be recovered when the sample is washed so as to remove the probe after performing an imaging step in which the sample is processed with the probe so as to make the sample emit light. Even in a case when an operation is repeatedly performed sequentially for each target substance, in which a medium containing a probe is brought into contact with a sample, an imaging step is performed and washing is performed in order to obtain observation images of a plurality of target substances included in one sample, and each imaging step can be performed in a state where only a probe for one type of a target substance that is to be observed exists and probes for other target substances do not exist. This prevents interference from occurring between probes and makes it possible to observe each target substance in a sample that is in a more natural state.

Figure 3:
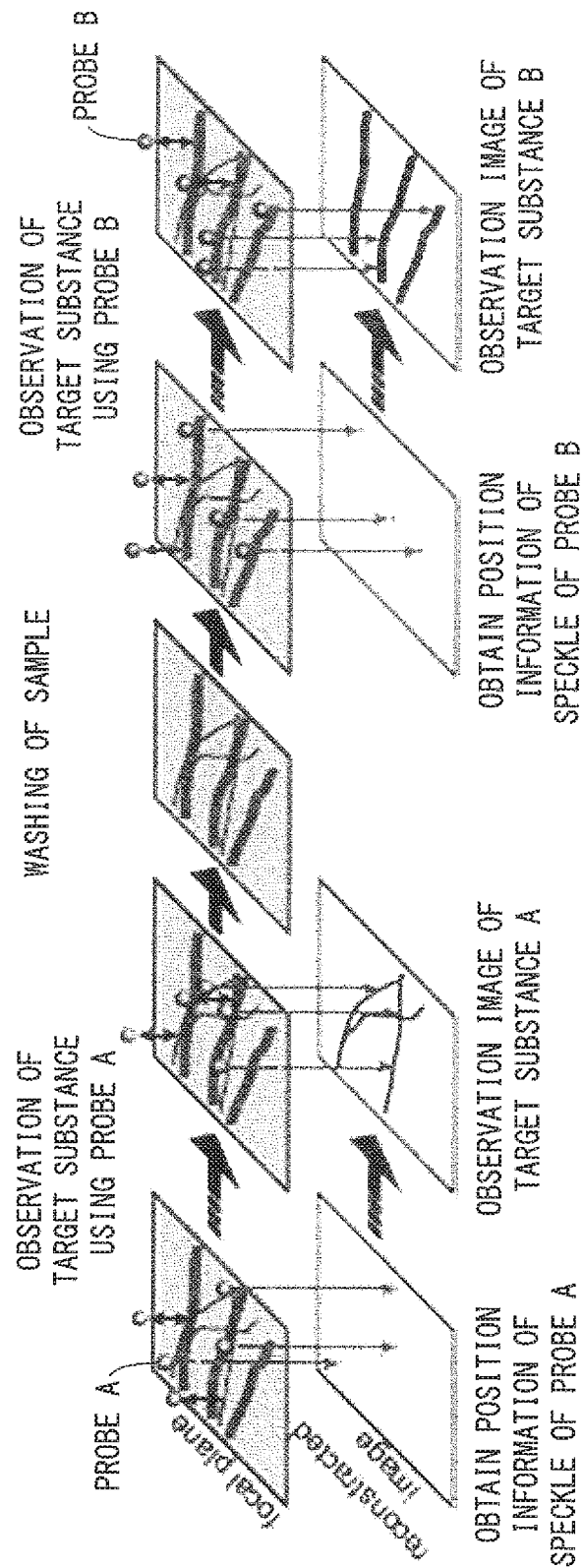
FIG. 3 is a schematic view for explaining procedures for observing a plurality of target substances in one sample by using the method of the present invention.

FIG. 3 schematically shows procedures for obtaining each observation image by using one sample containing target substances A and target substances B. First, an imaging step is performed in a state where a medium containing probes A that are specific to target substances A is brought into contact with a sample so as to obtain a plurality of speckle images. Next, the sample is washed so as to remove the probes A. Thereafter, an imaging step is performed in a state where a medium containing probes B that are specific to target substances B is brought into contact with the sample so as to obtain a plurality of speckle images. An observation image is generated for each of target substance A and target substance B from a plurality of speckle images for the respective target substances. It is also possible to generate a multiple-observation image by superposing an observation image of target substance A and an observation image of target substance B.

3. Explanations for Sample and Probe

A sample used for observation is typically a biological sample such as a cell, a tissue etc. consisting of a plurality of cells. When a sample is a biological sample, it is preferable to use a sample in a fixed state, and it is particularly preferable to use a sample that has further received a permeabilization process as necessary.

A sample contains at least one target substance. "Target substance" used herein refers to an object, as an observation target, that is contained in a sample. Examples of a target substance may include a structure body that constitutes a cytoskeleton preferably such as an actin polymer, a microtubule, an intermediate filament, a focal adhesion, etc. A target substance is preferably a structure that is, like the above structure, formed as a result of many constituents assembling, the constituents having the same structure or having a structure having common characteristics. Origin organisms for a structure body that constitutes a biological sample such as a cell, a tissue, etc. that can be an observation sample and a cytoskeleton that can be a target substance are not particularly limited. For example, a structure originating from vertebrates such as mammals (humans, rabbits, rodents, etc.), amphibians (frogs etc. *Xenopus* for example), fish including bony fish and cartilaginous fish, reptiles, birds, etc., invertebrates such as mollusks, protochordates, echinoderm, cnidarians, arthropods, etc., and unicellular organisms such as eukaryotic unicellular organisms (yeast etc.) can be used. Among them, structure bodies constituting cytoskeletons are held by a wide variety of species, and a method of observing a structure body constituting a cytoskeleton whose effectiveness has been confirmed in the examples can be applied regardless of the type of origin organism. It is preferable that a target substance be an object having a shape that does not substantially change during an imaging step of picking up a plurality of speckle images, and a target substance may receive a fixation process as necessary.

A target substance is preferably a target substance containing a protein, and is more preferably a protein target substance that exits together with one or more different proteins, which are not the target substance, and that are in an observation target sample. In the present embodiment of the present invention, a probe specifically binds to a protein that is a target substance from among a plurality of types of proteins, making it possible to selectively visualize a target substance.

A probe has a property of repeatedly binding to and dissociating from one specific type of target substances in a sample directly and specifically. The meaning of "binding to a target substance directly" is as mentioned previously.

While a probe may be a luminescent substance that by itself has a property of binding to and dissociating from a target substance, it usually contains a luminescent substance and a binding substance that is linked to that luminescent substance and that has a property of repeatedly binding to and dissociating from a target substance directly and specifically.

A probe and a target substance have the following binding characteristics. Specifically, the half-life of a probe-target complex formed by binding between a probe and a target substance is preferably equal to or more than 10 milliseconds and equal to or less than 3 seconds, more preferably equal to or more than 10 milliseconds and equal to or less than 2 seconds, more preferably equal to or more than 10 milliseconds and equal to or less than 1 second, more preferably equal to or more than 10 milliseconds and equal to or less than 900 milliseconds, more preferably equal to or more than 10 milliseconds and equal to or less than 800 milliseconds, more preferably equal to or more than 10 milliseconds and equal to or less than 700 milliseconds, more preferably equal to or more than 10 milliseconds and equal to or less than 600 milliseconds, more preferably equal to or more than 10 milliseconds and equal to or less than 500 milliseconds, more preferably equal to or more than 20 milliseconds, and more preferably equal to or less than 300 milliseconds, particularly preferably equal to or less than 250 milliseconds. The above half-life herein is preferably a half-life of a probe-target complex formed by binding between a probe and a target substance in a case when a medium containing a probe and a sample containing a target substance that is to be observed are brought into contact under a condition for performing an imaging step. The half-life is defined by a period of time before the number of probes that have bound to target substances at a given moment is reduced to half through dissociation. Measurement procedures for the half-life are as below. A medium containing a probe is brought into contact with a sample containing a target substance that is to be observed and a period of time between when light emission speckle based on the probe appears and when it disappears is measured for each light emission speckle while performing observation under a condition that is used for observation. Then, periods of time between the appearance and disappearance of the speckles are plotted in accordance with a complementary cumulative relative frequency function (1-Ndissociation). Ndissociation is a cumulative relative frequency of a probe that dissociated. A cumulative relative frequency is a ratio of the speckles that disappeared within a given period of time to the total number of measured speckles (i.e. probes) (i.e. probes that dissociated within a given period of time), and represents the total number as 1. Then, by fitting the above complementary cumulative relative frequency function with an exponent function, that half-life is calculated.

The period of time between the appearance and disappearance of a light emission speckle based on a probe can be measured by the following procedures. Specifically, while keeping a medium containing a probe in contact with a target substance and providing a prescribed condition necessary for emitting light (for example irradiation with excitation light), speckle images including speckles based on the light emission of luminescent substances of probes are consecutively picked up with an exposure time of X seconds (for example 0.050 seconds, 0.100 seconds, etc.) and at a frame rate of 1/XHz. Then, the period of time is measured between when a probe that has bound to a target appears in a speckle image and when it disappears through dissociation. In the above, when observation is performed for Y consecutive frames, and for a speckle not observed in frames before and after them, the period of time between the appearance and disappearance of that speckle can be treated as YX seconds.

A probe with the above half-life equal to or more than 10 milliseconds provides a period of time between binding to and dissociation from a target substance that is sufficiently long to allow an ordinary highly sensitive imaging device such as an EM-CCD camera etc. to pick up an image of a speckle based on the luminescent substance of the probe that has been bound. When by contrast the half-life is too long, a region including a probe having a long binding time to a target substance represents a signal that is particularly strong in a reconstructed observation image, which can cause uneven labeling. This makes it difficult to obtain an accurate distribution of target substances. From the results obtained thus far, it is possible to obtain a speckle image and an observation image that are relatively even when a probe whose half-life is equal to or less than 3 seconds is used and the shorter the half-life of a probe that is used is, the easier it is to obtain a speckle image and an observation image that are even. This point of view has made obvious that a half-life that is equal to or less than 500 milliseconds is particularly preferable. Also, as a general rule, the longer a half-life is, the longer an exposure time for one frame and imaging intervals have to be, which sometimes requires a long period of time for obtaining speckle images that are needed for generating a reconstruction image. From this point of view, it is preferable that the half-life be equal to or less than 3 seconds or that the half-life be further shorter.

In the present invention, a step of obtaining each speckle image will be referred to as a "frame imaging step". In each frame imaging step, a speckle image including a speckle of light emitted from a luminescent substance under a prescribed condition is picked up by using an imaging device. A term in which one speckle image is picked up will be referred to as a "frame", a term between the starting time of a frame and the starting time of the next frame will be referred to as an "interval", and a term between the ending time of a frame and the starting time of the next frame will be referred to as an "inter-frame term". A period of time for one frame (exposure time) can be determined in accordance with the binding half-life between a probe and a target substance in an appropriate manner. It is preferable that a period of time for one frame (exposure time) be longer than the binding half-life between a probe and a target substance, but the scope of the present embodiment is not limited to this.

Target substances and probes that meet the above requirements can be selected appropriately while a combination between a target substance and a binding substance of a probe is preferably selected from a group of:

a combination wherein the probe is (a1) a polypeptide, linked to the luminescent substance, which consists of an amino acid sequence of sequence number 19, (a2) a polypeptide, linked to the luminescent substance, which consists of the amino acid sequence described in (a1) where one or a plurality of amino acids have been substituted, deleted, inserted or added, and for which a half-life of a probe-target complex formed by binding between the probe and the target substance is equal to or more than 10 milliseconds and equal to or less than 3 seconds, or (a3) a polypeptide, linked to the luminescent substance, which consists of an amino acid sequence having at least a 70% identity with the amino acid sequence described in (a1) and for which a half-life of a probe-target complex formed by binding between the probe and the target substance is equal to or more than 10 milliseconds and equal to or less than 3 seconds, and the target substance is an actin polymer;

a combination wherein the probe is (b1) a polypeptide, linked to the luminescent substance, which consists of an amino acid sequence which is a partial amino acid sequence of an amino acid sequence of sequence number 12, which at least partially contains an amino acid sequence of 3-309 and which has 407 or fewer, preferably 357 or fewer, more preferably 327 or fewer and most preferably 307 amino acids, an amino acid sequence which is a partial amino acid sequence of an amino acid sequence of sequence number 14, which at least partially contains an amino acid sequence of 2536-2843 and which has 408 or fewer, preferably 358 or fewer, more preferably 328 or fewer and most preferably 308 amino acids, an amino acid sequence which is a partial amino acid sequence of an amino acid sequence of sequence number 14, which at least partially contains an amino acid sequence of 2781-2819 and which has 138 or fewer, preferably 88 or fewer, more preferably 58 or fewer and most preferably 38 amino acids, an amino acid sequence which is a partial amino acid sequence of an amino acid sequence of sequence number 4, which at least partially contains an amino acid sequence of 1-908 and which has 1008 or fewer, preferably 958 or fewer, more preferably 928 or fewer and most preferably 908 amino acids, an amino acid sequence which is a partial amino acid sequence of an amino acid sequence of sequence number 4, which at least partially contains an amino acid sequence of 659-908 and which has 394 or fewer, preferably 344 or fewer, more preferably 314 or fewer and most preferably 294 amino acids, an amino acid sequence of sequence number 5 or an amino acid sequence of sequence number 6, (b2) a polypeptide, linked to the luminescent substance, which consists of the amino acid sequence described in (b1) where one or a plurality of amino acids have been substituted, deleted, inserted or added and for which a half-life of a probe-target complex formed by binding between the probe and the target substance is equal to or more than 10 milliseconds and equal to or less than 3 seconds or (b3) a polypeptide, linked to the luminescent substance, which consists of an amino acid sequence having at least a 70% identity with the amino acid sequence described in (b1) and for which a half-life of a probe-target complex formed by binding between the probe and the target substance is equal to or more than 10 milliseconds and equal to or less than 3 seconds, and the target substance is a microtubule;

a combination wherein the probe is (c1) a polypeptide, linked to the luminescent substance, which consists of an amino acid sequence which is a partial amino acid sequence of an amino acid sequence of sequence number 8, which at least partially contains an amino acid sequence of 3777-4684 and which has 1008 or fewer, preferably 958 or fewer, more preferably 928 or fewer and most preferably 908 amino acids, an amino acid sequence which is a partial amino acid sequence of an amino acid sequence of sequence number 8, which at least partially contains an amino acid sequence of 3777-4364 and which has 688 or fewer, preferably 638 or fewer, more preferably 608 or fewer and most preferably 588 amino acids, an amino acid sequence which is a partial amino acid sequence of an amino acid sequence of sequence number 8, which at least partially contains an amino acid sequence of 3777-4313 and which has 637 or fewer, preferably 587 or fewer, more preferably 557 or fewer and most preferably 537 amino acids, or an amino acid sequence which is a partial amino acid sequence of an amino acid sequence of sequence number 8, which at least partially contains an amino acid sequence of 4022-4364 and which has 443 or fewer, preferably 393 or fewer, more preferably 363 or fewer and most preferably 343 amino acids, (c2) a polypeptide, linked to the luminescent substance, which consists of the amino acid sequence described in (c1) where one or a plurality of amino acids have been substituted, deleted, inserted or added and for which a half-life of a probe-target complex formed by binding between the probe and the target substance is equal to or more than 10 milliseconds and equal to or less than 3 seconds, or (c3) a polypeptide, linked to the luminescent substance, which consists of an amino acid sequence having at least a 70% identity with the amino acid sequence described in (c1) and for which a half-life of a probe-target complex formed by binding between the probe and the target substance is equal to or more than 10 milliseconds and equal to or less than 3 seconds, and the target substance is an intermediate filament; and (d1) a polypeptide, linked to the luminescent substance, which consists of an amino acid sequence of sequence number 15, an amino acid sequence which is a partial amino acid sequence of an amino acid sequence of sequence number 15, which at least partially contains an amino acid sequence of 54-557 and which has 556 or fewer, more preferably 524 or fewer and most preferably 504 amino acids, an amino acid sequence which is a partial amino acid sequence of an amino acid sequence of sequence number 15, which at least partially contains an amino acid sequence of 54-498 and which has 545 or fewer, preferably 495 or fewer, more preferably 465 or fewer and most preferably 445 amino acids, an amino acid sequence which is a partial amino acid sequence of an amino acid sequence of sequence number 15, which at least partially contains an amino acid sequence of 167-557 and which has 491 or fewer, preferably 441 or fewer, more preferably 411 or fewer and most preferably 391 amino acids, an amino acid sequence which is a partial amino acid sequence of an amino acid sequence of sequence number 16, which at least partially contains an amino acid sequence of 1-251 and which has 351 or fewer, preferably 301 or fewer, more preferably 271 or fewer and most preferably 251 amino acids, an amino acid sequence which is a partial amino acid sequence of an amino acid sequence of sequence number 16, which at least partially contains an amino acid sequence of 3-251 and which has 349 or fewer, preferably 299 or fewer, more preferably 269 or fewer and most preferably 249 amino acids, or an amino acid sequence of sequence number 18, (d2) a polypeptide, linked to the luminescent substance, which consists of the amino acid sequence described in (d1) where one or a plurality of amino acids have been substituted, deleted, inserted or added and for which a half-life of a probe-target complex formed by binding between the probe and the target substance is equal to or more than 10 milliseconds and equal to or less than 3 seconds or (d3) a polypeptide, linked to the luminescent substance, which consists of an amino acid sequence having at least a 70% identity with the amino acid sequence described in (d1) and for which a half-life of a probe-target complex formed by binding between the probe and the target substance is equal to or more than 10 milliseconds and equal to or less than 3 seconds, and the target substance is a focal adhesion. It is also preferable that a more preferable scope of half-lives of probe-target complexes in the above respective combinations be in accordance with the above and particularly be a period of time that is equal to or more than 10 milliseconds and equal to or less than 500 milliseconds or shorter. In the above combinations, more preferable scopes for a half-life of a probe-target complex are as described above and it is particularly preferable that a half-life of a probe-target complex be equal to or more than 10 milliseconds and equal to or less than 500 milliseconds or that a half-life of a probe-target complex be further shorter.

Origin organisms for an actin polymer, a microtubule, an intermediate filament and/or focal adhesion in the above combinations are not particularly limited, however a substance originating from vertebrates such as mammals (humans, rabbits, rodents, etc.), amphibians (frogs etc. *Xenopus* for example), fish including bony fishes and cartilaginous fishes, reptiles, birds, etc., invertebrates such as mollusks, protochordates, echinoderm, cnidarians, arthropods, etc., a unicellular organism such as eukaryotic unicellular organisms (yeast etc.), and a substance resulting from artificially introducing variation to them can be used.

"Actin polymer" used herein refers to a structure body formed through polymerization of an actin molecule, and typically to an actin filament.

In this document, a "microtubule" refers to for example a structure in which 13 protofilaments where heterodimers of atubulin and (tubulin are connected in a fibrous manner are collected to form a tubular structure body having a diameter of 25 nm.

In this document, intermediate filaments of type I, type II, type III and type IV are known as an "intermediate filament", and all of them may be observation targets of the present invention. Plectin can bind to all types of intermediate filaments.

In this document, "focal adhesion" refers to a structure made by for example a plurality of proteins (integrin, paxillin, vinculin, talin, etc.) being provided at adhesion points between a cell and an extracellular matrix.

"One or a plurality" for substitution, deletion, insertion or addition of an amino acid in the above (a2), (b2), (c2) and (d2) refers to for example 1 to 50, preferably 1 to 25, more preferably 1 to 20, more preferably 1 to 15, more preferably 1 to 10, more preferably 1 to 7, more preferably 1 to 5, more preferably 1 to 4, more preferably 1 to 3, and most preferably 1 or 2. Further preferably, the above expression of "one or a plurality" refers to preferably equal to or less than 20%, more preferably equal to or less than 10% and most preferably equal to or less than 5% of the number of amino acids of the polypeptides in the above (a1), (b1), (c1) and (d1). Substitution of an amino acid is preferably conservative amino acid substitution. "conservative amino acid substitution" refers to substitution between amino acids having similar physicochemical functions such as an electric charge, a side chain, a polarity, an aromatic property, etc. Amino acids having similar physicochemical functions can be categorized into for example a basic amino acid (arginine, lysine, histidine), an acidic amino acid (aspartic acid, glutamic acid), a non-charged polar amino acid (asparagine, glutamine, serine, threonine, cysteine, tyrosine), a non-polar amino acid (glycine, leucine, isoleucine, alanine, valine, proline, phenylalanine, tryptophan, methionine), a branched-chain amino acid (leucine, valine, isoleucine), an aromatic amino acid (phenylalanine, tyrosine, tryptophan, histidine), etc. Addition of one or a plurality of amino acids in each amino acid sequence is preferably addition of a total of one or a plurality of amino acids to at least one of the N-terminus and the C-terminus of that amino acid sequence. Also, deletion of one or a plurality of amino acids in each amino acid sequence is preferably deletion of a total of one or a plurality of amino acids from at least one of the N-terminus and the C-terminus of that amino acid sequence.

Identity with the amino acid sequences respectively described in the above (a1), (b1), (c1) and (d1) in the above (a3), (b3), (c3), and (d3) is preferably equal to or more than 80%, more preferably equal to or more than 85%, more preferably equal to or more than 90%, more preferably equal to or more than 95%, more preferably equal to or more than 97%, more preferably equal to or more than 98%, and most preferably equal to or more than 99%. In the present invention, the value of identity of amino acid sequences is calculated in a default setting by using software that computes identity between a plurality of amino acid sequences (for example FASTA, DANASYS and BLAST). The value of identity of amino acid sequences is calculated by calculating the number of amino acid residues that match when a pair of amino acid sequences is aligned in such a manner that the matching degree becomes the maximum and is calculated as a ratio of the number of the matching amino acid residues to the total number of the amino acid residues of the amino acid sequences that were compared. In this example, when there are gaps, the above total number of the amino acid residues is the number of amino acid residues obtained by counting one gap as one amino acid residue. When thus calculated, the total numbers of all the amino acid residues are different between the amino acid sequences that are compared, and the identity is calculated on the basis of the greater total number of the amino acid residues. For a detailed method of determining identity, reference is to be made to for example Altschul et al, Nuc. Acids. Res. 25, 3389-3402, 1977 and Altschul et al, J. Mol. Biol. 215, 403-410, 1990.

Also, more preferably, polypeptides in the above (a3), (b3), (c3) and (d3) are polypeptides having preferably equal to or more than 75%, more preferably equal to or more than 80%, more preferably equal to or more than 85%, more preferably equal to or more than 90%, more preferably equal to or more than 95%, more preferably equal to or more than 97%, more preferably equal to or more than 98%, and most preferably equal to or more than 99%, of similarly to the amino acid sequences respectively described in the above (a1), (b1), (c1) and (d1). The value of similarity of amino acid sequences is calculated by calculating the total of the number of amino acid residues that match when a pair of amino acid sequences is aligned in such a manner that the matching degree becomes the maximum and the amino acid residues have similar physicochemical functions, and is calculated as a ratio of the total number to the total number of the amino acid residues of the amino acid sequences that were compared. In this example, similarity of amino acid sequences can be calculated by a computer by using software similar to that described for the identity of amino acid sequences. A method of calculating the total number of amino acid residues is as described above for amino acid identity. The meaning of amino acid residues having similar physicochemical functions is as described above.

In a preferable embodiment of the present invention, a binding substance contained in a probe (a site for identification of a target substance) is an antibody or a fragment of an antibody, to a target substance, and particularly preferably a fragment of an antibody.

A technique for producing an antibody to an arbitrary target substance has already been established. Thus, using an antibody or a fragment of an antibody produced in accordance with a target substance as a binding substance of a probe makes it possible to use the technique of the present invention for observation of a target substance ranging in a wide scope.

It is sufficient if a target substance in this embodiment is a target substance presenting antigenicity, and it is typically a protein.

An antibody that an antibody or a fragment of an antibody contained in a probe is from is typically immunoglobulin G (IgG), however a different isotype is possible, and it may be for example immunoglobulin M (IgM), immunoglobulin D (IgD), immunoglobulinA (IgA), immunoglobulin E (IgE), etc. When these types of immunoglobulin contain a plurality of subclasses, one belonging to an arbitrary subclass is possible. Examples of another type of antibody may include a single domain antibody. These antibodies may be a variation or may be in a form in which it is made to fuse with a different polypeptide.

Although origins of an antibody are not particularly limited, for example, an antibody originating from for example nonhuman animals such as mice, rats, llamas, camels, etc. and from humans etc. can be used. Also, an antibody may be a chimeric antibody formed by causing a fusion of domains of antibodies of a plurality of origins.

An antibody may be a polyclonal antibody or may be a monoclonal antibody.

"Fragment" of an antibody in the present embodiment refers to a "functional fragment" having avidity to a target substance (antigen). A fragment of an antibody may be a variant or may be in a form in which it is made to fuse with a different polypeptide.

Examples of a fragment of an antibody may include a Fab fragment, a Fab' fragment, a F (ab')2 fragment, an scFv (single-strand Fv) fragment, a VHH fragment of a single domain antibody (for example a commercial name of a nanobody), etc. A Fab fragment can be obtained by cutting an antibody with papain, a protein breakdown enzyme. A F (ab')2 fragment can be obtained by cutting an antibody with pepsin. A Fab' fragment can be obtained by further processing a F (ab')2 fragment under a reduction condition. An scFv fragment is a result of linking a heavy-chain variable region and a light-chain variable region of an antibody with a linker of a polypeptide so as to make them single-stranded and can be produced by a gene engineering method that utilizes a polynucleotide having a base sequence that encodes the heavy-chain variable region, the linker and a light-chain variable region.

In the present embodiment, the half-life of a probe-target complex formed by binding of a probe containing an antibody or a fragment of an antibody to a target substance is equal to or more than 10 milliseconds and equal to or less than 3 seconds. Generally, because an antibody has a bivalent binding capacity to an antigen (i.e., an antibody of 1 molecule has two antigen binding sites), the binding tendency to an antigen is strong and the half-life of a probe-target complex between an antibody and an antigen far exceeds the upper limit of the above scope. Thus, it is preferable that a fragment of an antibody that can repeatedly bind to and dissociate from a target substance be used and that a fragment of an antibody have a univalent binding capacity to a target substance, which is an antigen (i.e., 1 molecule has 1 antigen binding site). Examples of an antibody fragment having a univalent binding capacity to a target substance may include a Fab fragment, a Fab' fragment, an scFv fragment, a VHH fragment of a single domain antibody (for example a commercial name of nanobody), etc.

Methods of producing the above antibody and fragment of an antibody are not particularly limited. A preferable embodiment for a method of screening for an antibody presenting the above prescribed half-life from candidates for antibodies adjusted by an arbitrary method such as a hybridoma method etc. will be explained later.

Luminescent substances contained in probes are not particularly limited as long as they are substances emitting light that makes observation possible under a prescribed condition. As a luminescent substance, a fluorescent substance that can emit fluorescence when irradiated with excitation light is particularly preferable. Examples of fluorescent substances may include a fluorescent protein such as a green fluorescent protein (GFP), an enhanced green fluorescent protein (EGFP), a red fluorescent protein (RFP), TagRFP, etc.; fluorescent dye such as Atto (trademark) 488, Atto (trademark) 550, Dylight (trademark) 488, Dylight (trademark) 550, CF (trademark) dye (CF680R, CF488A, CF543, etc.), etc.; and a quantum dot.

In an imaging step of the present invention, a mixture of a medium, a probe and an observation target sample is preferably exposed at intervals that are sufficiently shorter than a period of time between when the luminescent substance starts to be exposed to the prescribed condition and when it photobleaches the light (photobleaching period of time) or may be exposed consecutively, in the prescribed condition (irradiation with excitation light for example) for making a luminescent substance included in the probe emit light. For example, in an embodiment in which a luminescent substance is a fluorescent substance, a mixture of a medium, a probe and an observation target sample may be irradiated with excitation light at intervals that are sufficiently shorter than a photobleaching period of time or may be irradiated consecutively.

A luminescent substance in a probe and a binding substance can be linked through chemical binding via an appropriate linker component as necessary. Examples of chemical binding may include covalent binding, coordinate binding, etc., and covalent binding is preferable in view of stability. When a luminescent substance and a binding substance are both polypeptides, a probe can be formed as a fused polypeptide resulting from the luminescent substance and the binding substance linking to each other through normal peptide binding.

An imaging step of the present invention is performed in a state in which a medium containing a probe and a sample are in contact with each other. Media are not particularly limited as long as they allow a probe and a target substance to maintain the above binding characteristics, however they are usually liquid, and the liquid is preferably an aqueous solution, is more preferably an aqueous buffer solution adjusted to an appropriate pH, is more preferably an aqueous buffer solution adjusted to a pH of 6.1 to pH 7.5, and more preferably contains active oxygen remover. As an active oxygen remover, at least one type or two or more types selected from glucose oxidase, catalase, 2-mercaptoethanol, glucose, etc. can be used. An example of a proper amount of glucose oxidase may be 200 µg/ml, an example of a proper amount of catalase may be 35 µg/ml, an example of a proper amount of 2-mercaptoethanol may be 0.5%, and an example of a proper amount of glucose may be 4.5 mg/ml. As a buffer component for preparing an aqueous buffer solution, HEPES, Tris, etc. can be used.

It is preferable that the concentration of probes in a medium have appropriately been adjusted to a concentration that allows identification of emission of light of a luminescent substance as a separate speckle for each molecule in one speckle image.

Temperature conditions in a case when a medium containing a probe is brought into contact with a sample are not particularly limited, and for example 20 degrees Celsius through 30 degrees, and more preferably an ambient temperature, specifically 25 degrees Celsius, can be adopted.

4. Embodiment of Observation Method of Present Invention that Uses Microscope

Devices used for an observation method of the present invention are not particularly limited.

Figure 4:
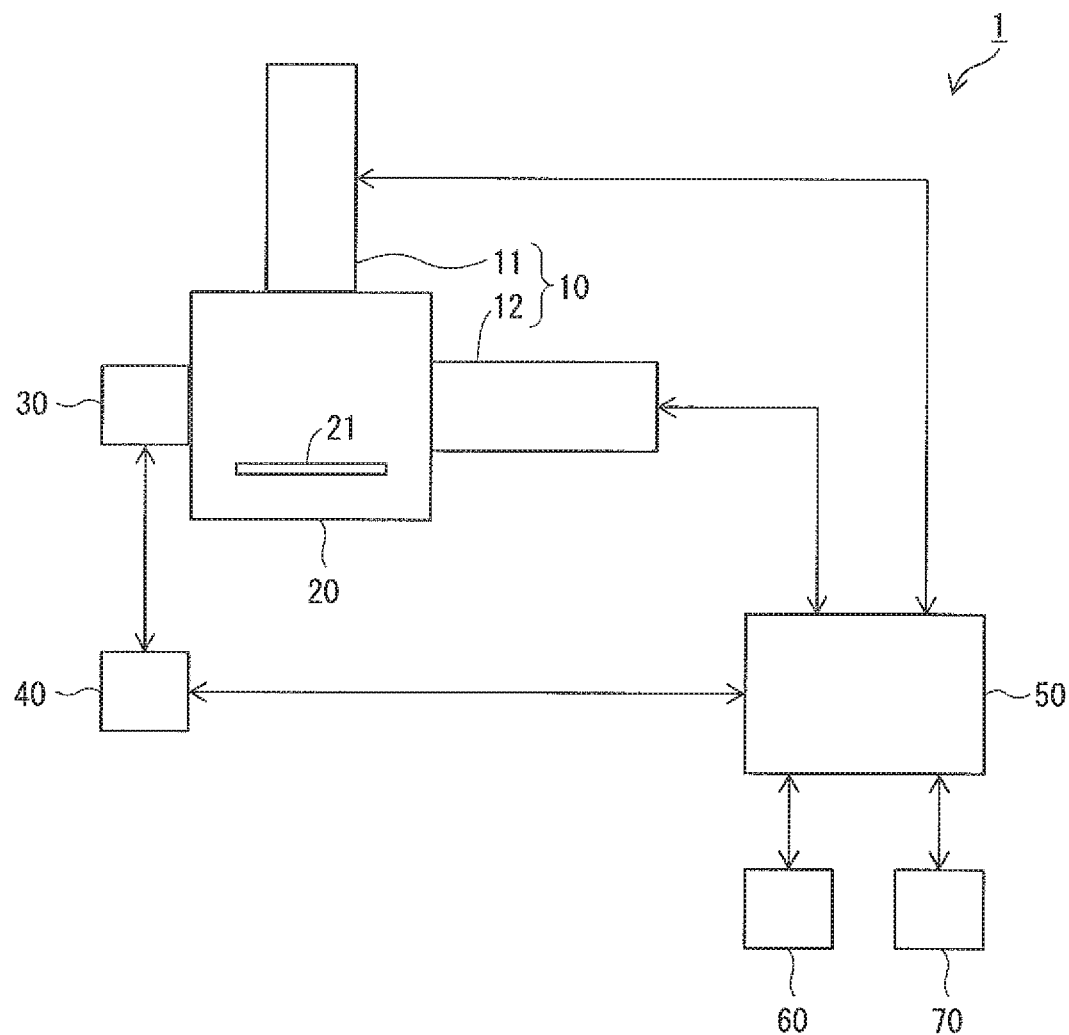
FIG. 4 is a functional block diagram of a microscope apparatus used for implementing the method of the present invention.

FIG. 4 shows an example of a device that can be used for an embodiment of the present invention in which a luminescent substance contained in a probe is a fluorescent substance that emits fluorescence when irradiated with excitation light.

A microscope apparatus 1 shown in FIG. 4 includes excitation illumination devices 10 (including a first excitation illumination device 11 and a second excitation illumination device 12), a microscope body 20, a camera 30, a camera controller 40, a control unit 50, a display device 60 and a storage unit 70.

The excitation illumination devices 10 (including the first excitation illumination device 11 and the second excitation illumination device 12) are devices that provide the microscope body 20 with excitation light for making a fluorescent substance emit light. Any device can be used as the excitation illumination devices 10 (including the first excitation illumination device 11 and the second excitation illumination device 12) as long as it can provide excitation light of a wavelength in accordance with the fluorescent substance. Although they are not shown, each of the first excitation illumination device 11 and the second excitation illumination device 12 may be a system combining a plurality of devices and usually includes a laser beam source, a shutter, and a total reflection mirror. The laser beam source is a light source that emits excitation light. The shutter is a device that switches between supply and suspend of excitation light to the microscope body 20. The total reflection mirror is a mechanism for totally reflecting excitation light emitted from the laser beam source toward a stage 21 of the microscope body 20.

The microscope body 20 may be an inverted microscope for example. The microscope body 20 includes the stage 21 for mounting thereon a sample that is to be observed. To the microscope body 20, the camera 30 for picking up a fluorescence image of the sample mounted on the stage 21 is connected. As the camera 30, for example a CCD camera having a plurality of pixels can be used.

The microscope body 20 is provided with a an objective lens for issuing excitation light toward the stage 21, an imaging lens for condensing, on the light receiving plane of the camera 30, fluorescence radiated from a fluorescent substance in the sample, etc. The above objective lens and the imaging lens constitute an imaging optical system.

The microscope body 20 including the stage 21 and the imaging optical system is configured to be able to provide total internal reflection illumination by which excitation light is totally reflected on the interface between the glass in contact with the sample and the sample. The total internal reflection illumination makes it possible to illuminate the sample with evanescent light that leaks to the sample side from the glass when the excitation light is totally reflected. In the shown embodiment, the second excitation illumination device 12 is equivalent to a device for providing excitation light through total internal reflection illumination.

The microscope body 20 is further configured to be able to switch between the above total internal reflection illumination and epi-illumination to use them. In the shown embodiment, the first excitation illumination device 11 is equivalent to a device for providing excitation light based on epi-illumination. Using a speckle image of fluorescence based on the total internal reflection illumination of excitation light and a speckle image of fluorescence based on epi-illumination makes it possible to calculate the position in the depth direction (z direction) in an observation image. Alternatively, it is also possible to make a probe emit intensive fluorescence by issuing excitation light based on epi-illumination and excitation light based on total internal reflection illumination simultaneously.

The excitation illumination devices 10 do not always have to include the first excitation illumination device 11 and the second excitation illumination device 12 and may have only one of the first and second excitation illumination devices 11 and 12.

The control unit 50 is a computer that totally controls the microscope apparatus 1, and is connected to the excitation illumination devices 10 (first excitation illumination device 11 and second excitation illumination device 12), the display unit 60, the storage unit 70, and the camera controller 40. The control unit 50 has at least a control signal generation function of generating a control signal for controlling these devices, a speckle image obtainment function of obtaining a speckle image via the camera controller 40, an image analysis function of analyzing an obtained speckle image, a light source control function of controlling driving of a light source included in the excitation illumination devices 10, and an image forming function of generating an observation image from a plurality of speckle images. The control unit 50 constitutes an image generation unit that generates an observation image as the overall function.

The camera controller 40 performs driving control of the camera 30. The camera controller 40 operates the camera 30 on the basis of a control signal input from the control unit 50 so as to obtain a speckle image of fluorescence, and outputs the obtained speckle image to the control unit 50.

The display unit 60 is a display (display device), a printer (printing device), etc., and provides a function of displaying and printing an image based on image data output from the control unit 50 (data of a speckle image, data of an observation image, etc.).

The storage unit 70 can be configured by a storage device such as a semiconductor memory, a hard disk etc. A program used in the control unit 50 and data provided from the control unit 50 (such as a speckle image etc.) are stored in a state in which they can be read by the control unit 50.

Hereinafter, explanations will be given for the observation method of the present invention, by the microscope apparatus 1, that uses a fluorescent substance emitting fluorescence when irradiated with excitation light as a luminescent substance contained in a probe.

An imaging step using the microscope apparatus 1 is a step in which a step is performed a plurality of times at different times respectively, where a sample that has been brought into contact with a medium containing a probe on the stage 21 is irradiated with excitation light by using the excitation light illumination devices 10 (one or both of the first excitation illumination device 11 and the second excitation illumination device 12) and a speckle image including, as a speckle of fluorescence, fluorescence emitted from a substance contained in a probe that has bound to a target substance in the sample is obtained by the camera 30, and thereby a plurality of speckle images are obtained. A step of obtaining each speckle image will be referred to as a "frame imaging step". In each frame imaging step, the camera 30 picks up a speckle image of fluorescence emitted from a fluorescent substance each time excitation light is issued. A speckle image has a different pattern for each frame.

In each frame imaging step, the control unit 50 operates the camera 30 via the camera controller 40 so as to pick up an image of fluorescence emitted from a fluorescent substance, and thereby obtains a speckle image. An obtained speckle image is output to the control unit 50 from the camera controller 40. The control unit 50 also stores a thus-obtained speckle image in the storage unit 70.

In an imaging step, the control unit 50 repeatedly performs the above frame imaging step at appropriate intervals. Examples of the number of times of the frame imaging step may include hundreds of times through hundreds of thousands of times including for example 1,000 to 999,000 times.

An observation image generation step in the present invention is a step in which an observation image of a target substance that binds to the probe in the sample is generated from a plurality of speckle images obtained in the above imaging step. Specifically, the control unit 50 executes an appropriate computer program so as to obtain, for each of the plurality of speckle images recorded in the storage unit 70, information of position of a speckle included in a speckle image so as to generate an observation image by integrating the pieces of information from the plurality of speckle images. In this example, information of the position of each speckle is typically information of the central position (position of the center of gravity) of each speckle, and can be obtained by using for example DAOSTORM, a computer program (Nature methods, 8 279-280, 2011). In the above, in order to increase the accuracy, only a speckle of luminance that is equal to or higher than a prescribed threshold may be used for generating an observation image in each of the speckle images. When generating an observation image, an observation image can be generated by drawing, at the central position of each speckle of a blank image, a point having an appropriate size. Specifically, by turning the size of pixels of a blank image into an appropriate size (for example a square pixel with the length of each side being 5 nm through 20 nm) and by plotting the central position of each speckle to each pixel, an observation image can be generated. The control unit 50 records the data of the generated observation image in the storage unit 70 and also displays it in the display unit 60.

When a plurality of target substances exist in one sample, it is sufficient to perform the above imaging step sequentially by using probes that are specific to the respective target substances. "Probes that are specific to respective target substances" refer to probes that repeatedly bind to and dissociate from the respective target substances directly and specifically. It is preferable that the sample be washed sufficiently between the respective imaging steps. Then, the control unit 50 can generate an observation image of each target substance in the sample from a plurality of speckle images, stored in the storage unit 70, obtained in the respective imaging steps. The control unit 50 can also synthesize pieces of data of observation images of a plurality of target substances in the same sample so as to output the result to the display unit 60 and display a multiple-observation image resulting from superposing observation images of a plurality of target substances.

The above is an embodiment of the observation method of the present invention that uses a probe containing a fluorescent substance as a luminescent substance. When a luminescent substance is a luminescent substance that is not a fluorescent substance, the method of the present invention can be implemented through the same procedures as that described above if means for providing a condition in a sample mounted on the stage 21 for that luminescent substance to radiate light instead of the excitation illumination devices 10 in the microscope apparatus 1 are arranged and the camera 30 that can pick up an image of light emitted by the luminescent substance in the probe that has bound to a target substance in the sample as a speckle is used.

5. Probe and Kit

The present invention also provides the above probe itself and a kit including at least the above probe.

The above probe may be provided solely in solid form such as powder, may be provided in liquid form that has dispersed or has been dissolved in an appropriate liquid medium or may be provided in solid form such as powder together with an appropriate solid component (such as a diluting agent etc.). In other words, a probe of the present invention may be provided solely by itself or may be provided as a probe-containing composition that includes at least a probe and may include a different complementary component.

Any kit may be used as the above kit as long as it includes at least a probe of the above various forms and it may further include a different element used for observing a target substance. Examples of a different element for the above kit may include a medium such as a liquid medium for dissolving or dispersing the probe etc., and a reagent to be used for a process of observing a sample etc. The above medium may be a medium that includes a probe and that is used for bringing it into contact with a sample for performing observation. The probe and a different element in the above kit are usually wrapped separately so that they will not be mixed physically.

6. Screening Method

The present invention also provides a screening method of a site (also referred to as a target substance identification site or a binding substance) in which a target substance is identified in the probe accordingly, the screening method including:

an immobilization step in which a candidate substance of the site or a substance partially containing the candidate substance is fixed to a solid support;

an observation step in which a target substance linked to a luminescent substance and a solid support obtained in the immobilization step are observed in a medium while the target substance linked to a luminescent substance and the solid support obtained in the immobilization step are kept in contact, in a condition that allows observation, in units of 1 molecule, of light emission from the luminescent substance in a probe-target complex formed by binding between the target substance and the candidate substance, and a screening step in which the candidate substance resulting in a half-life of the probe-target complex that is equal to or more than 10 milliseconds and equal to or less than 3 seconds is selected as the site on the basis of observation in the observation step.

According to this embodiment of the present invention, it is possible to efficiently perform screening for a substance that presents a desired binding tendency to a target substance from a library of candidate substances.

Examples of a solid support used for an immobilization step may include an inner wall surface of each well of for example a multiwell plate.

Means for fixing a candidate substance to a solid support in an immobilization step are not particularly limited, and when for example a candidate substance is an antibody or an antibody fragment, it is preferable that a Fab domain of an antibody or an antibody fragment be immobilized to the solid support in a state in which it can bind to the target substance. For example, by fixing to a solid support a protein having a binding capability to an Fc domain of an antibody (for example, Protein G) and then immobilizing the antibody to the solid support to which the protein has been immobilized, it is possible to immobilize the antibody to the solid support in a state in which the Fab domain can bind to the target substance. Methods of immobilizing the protein to a solid support are not particularly limited, however it is possible to immobilize the protein via a functional group introduced to a surface of a solid support.

As a medium used in an observation step, the same medium as that used in an imaging step of the present invention can be used.

Types of luminescent substances are not particularly limited in a target substance linked to the luminescent substance used in an observation step, however a fluorescent substance that can emit fluorescence when irradiated with excitation light is particularly preferable. Specific examples of a fluorescent substance are the same as those of the fluorescent substance described above for a probe.

In an observation step, in a medium, a target substance linked to a luminescent substance and a solid support to which a candidate substance is fixed are observed in a state in which they are in contact with each other, in a condition that allows observation, in units of 1 molecule, of emission of light by the luminescent substance in a probe-target complex of the target substance and the candidate substance. In this step, the fact that light emission of a target substance that has not bound cannot be detected because it causes thermal motions randomly in the medium, whereas emission of light from the target substance that has bound to the candidate substance can be detected and is utilized. In order to observe emission of light by the luminescent substance in units of 1 molecule, it is effective to reduce the concentration of the target substance in the medium. Even when a candidate substance is a bivalent antibody or antibody fragment having two antigen binding sites, reducing the concentration of the target substance in the medium makes it possible to observe binding of the target substance individually in each antigen binding site.

Observation means in an observation step may appropriately be selected in accordance with the luminescent substance. When the luminescent substance is a fluorescent substance, observation is possible by using a fluorescence microscope (for example, a TIRF fluorescence microscope).

In a screening step, on the basis of observation in the observation step, the candidate substance leading to the half-life of the probe-target complex that is equal to or more than 10 milliseconds and equal to or less than 3 seconds is selected as a target substance identification site. The half-life is more preferably equal to or more than 10 milliseconds and equal to or less than 2 seconds, more preferably equal to or more than 10 milliseconds and equal to or less than 1 second, more preferably equal to or more than 10 milliseconds and equal to or less than 900 milliseconds, more preferably equal to or more than 10 milliseconds and equal to or less than 800 milliseconds, more preferably equal to or more than 10 milliseconds and equal to or less than 700 milliseconds, more preferably equal to or more than 10 milliseconds and equal to or less than 600 milliseconds, more preferably equal to or more than 10 milliseconds and equal to or less than 500 milliseconds, more preferably equal to or more than 20 milliseconds and equal to or less than 300 milliseconds, and particularly preferably equal to or less than 250 milliseconds. The half-life is defined by a period of time before the number of target substances that have bound to candidate substances on solid supports at a given moment is reduced to half through dissociation. Measurement procedures for the half-life are as below. A medium containing a target substance labeled with a luminescent substance is brought into contact with a solid support to which the candidate substance has been fixed, and a period of time between when a light emission speckle appears and when it disappears is measured, for each light emission speckle, while performing observation under a condition used for observation. Then, periods of time between the appearance and disappearance of the speckles are plotted in accordance with a complementary cumulative relative frequency function (1-Ndissociation). Then, by fitting the above complementary cumulative relative frequency with an exponent function, that half-life is calculated.

A period of time between appearance and disappearance of a light emission speckle based on a labeled target substance is measured by the following procedures. Specifically, while keeping a medium containing a labeled target substance in contact with a solid support to which the candidate substance has been immobilized and providing a prescribed condition necessary for emitting light (for example irradiation with excitation light), speckle images including speckles based on the light emission of the labeled target substance are consecutively picked up with an exposure time of X seconds (for example 0.050 seconds, 0.100 seconds, etc.) and at a frame rate of 1/XHz. Then, a period of time is measured between when a target substance that has bound to a candidate substance appears in a speckle image and when it disappears through dissociation. In the above, observation is performed for Y consecutive frames, and for a speckle not observed in frames before and after them, the period of time between the appearance and disappearance of that speckle can be treated as YX seconds.

In a screening method of the present invention, the candidate substance is more preferably an antibody or a fragment of an antibody that binds to a prescribed target substance and fixes the antibody to a solid support in the immobilization step. When screening is performed for antibodies binding to prescribed target substances, ELISA is generally used in which target substances are immobilized to solid supports and candidate antibodies are brought into contact with the solid supports. In a screening method according to the present embodiment, contrary to ELISA, an antibody (the candidate substance) is solid phased. Then, in the medium, an antigen (target substance) linked to a luminescent substance and the solid support are observed in a state in which they are in contact with each other, in a condition that allows observation, in units of 1 molecule, of emission of light by the luminescent substance in a probe-target complex formed by binding of the target substance and the candidate substance. This method has advantages as described below.

1) It is possible to measure the half-life of binding of an antibody and an antigen. Because binding/dissociation between an antibody and an antigen is visualized through the appearance and disappearance of a fluorescent single molecule, the half-life of that binding can be measured directly for each single molecule of an antigen.

2) It is possible to measure univalent binding/dissociation of an antigen and an antibody. Epitope that allows identification of a monoclonal antibody is at one location in an antigen. Accordingly, an antigen that has bound to 1 antigen binding site of a solid-phased antibody cannot bind to a different antigen binding site existing nearby, and an antigen inevitably binds with the antibody molecule in a univalent state. When an antigen has been solid phased, an antibody can bind to one or two antigens, making it impossible to measure univalent binding/dissociation of an antigen and an antibody. A method in which this antibody is solid phased makes it possible to estimate the half-life of binding of an antibody fragment such as a Fab fragment that binds in a univalent manner without producing it.

3) It is possible to perform screening for an antibody fragment from a library of hybridoma in an inexpensive and simple manner. In one embodiment of this screening method, main structure factors are a solid support resulting from immobilizing an antibody contained in each supernatant of a hybridoma library and a labeling body of antigen epitope. The half-life of binding of an antibody fragment and an antigen can be estimated even without producing a light-emission-labeled antibody fragment from an antibody of each supernatant of a library, making it possible to perform screening on candidate substances at a very low cost. Also, visualization is performed in units of molecules, measurement is possible even when the amount of antibodies that have been solid phased is small. Thereby, immense amounts of labor and time taken for cultivation of a hybridoma library can be saved.

The present screening method has solved a major problem in evaluation of the affinity of an antibody by ELISA. 1) In ELISA, an antigen is solid phased, and accordingly an antibody may bind to an antigen regardless of whether the binding is univalent or bivalent. Further, by a secondary antibody used for measuring a binding amount of primary antibodies, a primary antibody is crosslinked. This prevents measurement of the half-life of univalent binding of an antibody and an antigen. 2) The binding amount of antibodies obtained in ELISA is influenced not only by the affinity of antibodies but also by the amount of antibodies produced by hybridoma. This makes it difficult to evaluate the property of binding of one antibody in ELISA. 3) In addition, because washing is conducted a plurality of times in a reaction step in ELISA, there is a risk that an antibody that has bound with a short half-life that is equal to or less than 3 seconds, which is needed in the present invention, may be lost before being visualized. The method of the present embodiment has solved these problems by solid phasing an antibody instead of an antigen and visualizing binding/dissociation of an antigen and an antibody in actual time. The method of the present embodiment is more suitable for selecting an antibody having a short binding half-life, which is the aim of the present invention, than ELISA in principle in that it can evaluate univalent binding/dissociation, it is not influenced by the production amount of antibodies, and it can also measure a short binding half-life.

According to a screening method of the present invention, a library of polypeptides and a library of phage display can be solid phased as candidate substances for a target substance identification site of a probe in addition to a antibody or an antibody fragment. A screening method of the present invention can also be applied to solid-phasing of these for performing screening for a polypeptide that binds to and dissociates from a target substance.

The present invention will be explained in more detail by the following examples, however they are just exemplary and do not limit the present invention. All the experiments below were conducted at an ambient temperature, i.e., 25 degrees Celsius, unless limitations are particularly given.

1. Experiment 1

Methods
Plasmid and Reagent

Expression plasmid (pFLAG-EGFP-C1) encoding EGFP (sequence number 1) having an N terminus tagged with FLAG (sequence number 2) and an expression plasmid (p3×FLAG-EGFP-N3) encoding EGFP having a C terminus tagged with 3×FLAG (sequence number 3) were constructed respectively by using a pEGFP-C1 vector and a pEGFP-N3 vector (Clontech Laboratories, Inc).

EST clones encoding mouse MAP4, human Tau isoforms 3 and 4, mouse KIF1A, human plectin-1 and *Xenopus laevis* talin-1 were purchased from OpenBiosystems.

cDNA encoding human FAK was purchased from the DNASU Plasmid Repository.

The GenBank/EMBL/DDBJ accession numbers for each sequence are as follows:

BC055332 (MAP4), BC114948 (Tau isoform 3), BC101936 (Tau isoform 4), BC062891 (KIF1A), BM559026 (Plectin-1), CF282569 (Talin1) and BC035404 (FAK).

cDNAs encoding human EB1, rat CLIP-170, human CLASP2γ and human APC were provided by Y. Mimori-Kiyosue (RIKEN).

As plasmids encoding human paxillin, chicken Src and human vinculin, those described in documents 31 to 33 were used.

Each cDNA was inserted into a pFLAG-EGFP-C1 vector or a p3×FLAG-EGFP-N3 vector by using a PCR. For a probe having an N terminus at the fusion position of GFP in table 1 below, a pFLAG-EGFP-C1 vector was used. For a probe having a C terminus at the fusion position of GFP in table 1 below, a p3×FLAG-EGFP-N3 vector was used.

An expression plasmid encoding PIPKIγ fragment (amino acid residues 641-668) having an N terminus tagged with FLAG-EGFP was constructed by inserting a synthetic cDNA encoding PTDERSWVYSPLHYSAQAPPASDG-ESDT (sequence number 18) into a pFLAG-EGFP-C1 vector.

Lifeact peptide (MGVADLIKKFESISKEE (sequence number 19)) with an Atto 488 fluorescent body linked to an N terminus was purchased from Sigma-Aldrich.

The amino acid sequence of EGFP is denoted by sequence number 1.

The amino acid sequence of FLAG is denoted by sequence number 2.

The amino acid sequence of 3×FLAG is denoted by sequence number 3.

The amino acid sequence of mouse MAP4 is denoted by sequence number 4.

The amino acid sequence of human Tau isoform 3 is denoted by sequence number 5.

The amino acid sequence of human Tau isoform 4 is denoted by sequence number 6.

The amino acid sequence of mouse KIF1A is denoted by sequence number 7.

The amino acid sequence of human Plectin-1 is denoted by sequence number 8.

The amino acid sequence of *Xenopus laevis* Talin1 (amino acid residues 1-2353) is denoted by sequence number 9.

The amino acid sequence of human FAK is denoted by sequence number 10.

The amino acid sequence of human EB1 is denoted by sequence number 11.

The amino acid sequence of rat CLIP-170 is denoted by sequence number 12.

The amino acid sequence of human CLASP2γ is denoted by sequence number 13.

The amino acid sequence of human APC is denoted by sequence number 14.

The amino acid sequence of human Paxillin is denoted by sequence number 15.

The amino acid sequence of chicken Src is denoted by sequence number 16.

The amino acid sequence of human Vinculin is denoted by sequence number 17.

The amino acid sequence of human PIPKIγ-90 fragment (amino acid residues 641-668) is denoted by sequence number 18.

The amino acid sequence of Lifeact peptide is denoted by sequence number 19.

Production and Screening of Exchangeable Protein Probes

In order to find exchangeable probes for super-resolution images of microtubules, intermediate filaments and focal adhesions, a test was conducted by using, as candidate molecules for probes, a protein (polypeptide) and a protein fragment that are known to be able to localize in each target structure. "Exchangeable" used herein refers to being able to repeatedly bind to and dissociate from a target structure.

Table 1 shows the tested probe candidates. The test was conducted a plurality of times by using, as a probe candidate, a protein or a fragment of a protein mentioned in the section of "plasmid and reagent".

An expression plasmid for expression as a molecule made to fuse with EGFP was constructed for each probe candidate in accordance with the documents described in table 1.

HEK (Human embryonic kidney)-293F cells were transfected with a plasmid encoding a probe candidate protein tagged with FLAG-EGFP or 3×FLAG-EGFP. 3 to 4 days later, the cells were dissolved in a cell lysis buffer (10 mM HEPES, pH 7.2, 90 mM KCl, 3 mM MgCl2, 0.2% Triton X-100, 100 µM DTT) containing a protease inhibitor cocktail (Nacalai Tesque). Centrifugal separation was performed on the lysate and the supernatant liquid was collected. In order to perform screening for a probe for IRIS, the binding capacity of a probe candidate in the supernatant liquid with respect to the structure of an XCT cell that was fixed with paraformaldehyde (PFA) and that received a permeabilization process was tested. The appearance and disappearance of single molecule speckles (Single-molecule speckles, SiMS) in the structure was tested. Screening was performed for a probe for IRIS in accordance with the following criteria:

(1) It is possible to confirm a distribution of target substances in the structure in an image resulting from adding SiMS images;
(2) It is possible to wash and remove a probe after SiMS imaging (imaging step);
(3) A probe that has bound can dissociate from the target substance swiftly (half-life is equal to or less than 500 ms); and
(4) It is possible to reconstruct an image of a target substance by integrating the central positions of the respective speckles.

Table 1 describes that "localization" is positive (P) when above criterion (1) is met, that "washability" is positive (P) when above criterion (2) is met, and that "IRIS image" is positive (P) when above criterion (3) is met.

Probes used for an IRIS experiment were purified in the following procedures. Specifically, each probe was overexpressed in HEK-293F cells and collected with anti-DYKDDDDK (Flag) antibody beads (Wako). The beads were washed four times with an excess amount of HEPES-buffered solution (10 mM Hepes pH 7.2, 90 mM KCl, 3 mM MgCl2, 100 µM DTT). Proteins that had bound to beads after the washing were processed with the HEPES-buffered solution containing 0.5 mg/ml DYKDDDDK (Flag) peptide (Wako) or 3×FLAG peptide (Sigma-Aldrich) for 30 minutes and were eluted.

The localization test of the above (1), whose result is shown in table 1, was performed in the following procedures. First, the supernatant liquid of lysate of a cell that expressed each probe candidate was brought into contact with an XCT cell that was fixed on a coverglass and that received a permeabilization process. A coverglass on which the sample was mounted was arranged in the observation chamber of a fluorescence microscope apparatus, which will be described in detail in the section of "procedures for imaging of multicolor super-resolution by IRIS" below, and speckle images of 10000 frames were obtained with an exposure time of 50 ms or 100 ms for one frame and at a frame rate of 20 Hz (20 frames per second) or with an exposure time of 100 ms and at a frame rate of 10 Hz (10 frames per second) while irradiating the sample with a 488 nm-laser beam line (with a main body output of 50 mW but reaching the sample after being attenuated by AOTF etc.) for total internal reflection fluorescence observation. The obtained speckle images of 10000 frames were integrated so as to confirm whether or not a distribution of target substances in the cell (microtubule, intermediate filament, focal adhesion or actin filament) was able to be confirmed. When a distribution of a target substances was able to be confirmed, the result of the localization test was treated as P (positive).

The localization test of the above (2), whose result is shown in table 1, was performed in the following procedures. After the picking up of speckle images explained in the previous paragraph, 1 ml of the supernatant liquid containing respective probe candidates in the observation chamber was aspirated by using an aspirator and 1 ml of an imaging solution (however, it was not supplemented with active oxygen-scavenging mix) that does not contain a probe and that will be described below was added. This switching of imaging solution was conducted slowly so that the observation position would not shift. Next, an imaging solution not containing a probe and not containing the active oxygen-scavenging mix was switched 10 to 20 times. After the switching, for confirmation, for an XCT cell sample in the observation chamber, speckle images of 10 frames were picked up under a similar condition to that of the localization test described in the previous paragraph, and when the number of speckles confirmed in the speckle images (i.e., the number of probes that had bound) became sufficiently smaller (equal to or less than about 10%) than the number of the speckles in the speckle images before the washing operation, washing was determined to be possible and the result was treated as P (positive).

The measurement of binding half-life, whose result is shown in table 1, was performed in the following procedures. Speckle images of 10000 frames picked up in the localization test were used in order to measure a period of time between the appearance of a probe that has bound to a target in a speckle image and disappearance through dissociation in a semi-manual mode by using Speckle TrackerJ, an ImageJ plug-in. In case of for example picking up of images with an exposure time of 50 ms and at a frame rate of 20 Hz, it is assumed that a period of time between the appearance and disappearance of a speckle that is observed in only one of consecutive frames is 50 ms and a period of time between the appearance and disappearance of a speckle observed in only two consecutive frames is 100 ms. Then, the number of binding probes with respect to periods of time between the appearance and disappearance was plotted in accordance with a complementary cumulative relative frequency function (1-Ndissociation). Ndissociation is a cumulative relative frequency of probes that dissociated. Then, by fitting the complementary cumulative relative frequency function with an exponent function, the half-life was calculated. However, the binding half-life with respect to an actin filament of Atto488-Lifeact was measured by using a method that is described in detail in the section for FIG. 9 in the Brief Description of the Drawings.

The IRIS image test of the above (3) whose result is described in table 1 was performed in the following procedures. By using all the speckle images of 10000 frames picked up in the localization test, the central point of a probe that has bound to a target in each frame of the speckle images was determined with nanometer accuracy by using DAOSTORM. By adding a large number of pieces of central point information in the fluorescence images of 10000 frames, a reconstruction image (observation image) was generated. Whether or not a distribution of a target molecule was able to be observed in that reconstruction image was determined, and when a distribution of a target molecule was observed, the result was treated as P (positive).

Procedures for Imaging of Multicolor Super-Resolution by IRIS

*Xenopus laevis* XTC cells were cultured in 70% Leibovitz's L15 medium supplemented with 10% fetal bovine serum. A multicolor super-resolution image was produced from a large number of fluorescence single molecule speckle (SiMS) images that were sequentially obtained from a fixed and XTC cell (20,000 to 500,000 frames per probe) with various exchangeable probes. The cells were allowed to spread on a 0.1 mg/ml poly (L-lysine) and 10 g/ml fibronectin-coated coverglass in 70% Leibovitz's L15 medium without serum and distinct stress fibers and focal adhesions were formed (document 33). 2 hours later, the cells were fixed and received a permeabilization process with a cytoskeleton buffer containing 3.7% PFA and 0.5% Triton X-100 in (10 mM Mes pH6.1, 90 mM KCl, 3 mM MgCl2, 2 mM glycol ether diamine tetraacetic acid (EGTA)). After performing blocking with 4% bovine serum albumin for 30 minutes, the purified IRIS probes were brought into contact with the cells in an imaging solution including the HEPES-buffered solution (10 mM Hepes pH 7.2, 90 mM KCl, 3 mM MgCl2, 100 µM DTT) with an oxygen-scavenging mix (200 µg/ml glucose oxidase, 35 µg/ml catalase, 4.5 mg/ml glucose, 0.5% 2-mercaptoethanol) (document 34). The concentration of the probe was 1 nM through 100 nM. When the oxygen-scavenging mix was not used, laser-induced photodamage was apparent after obtaining SiMS images several tens of thousands of times.

For the imaging of actin filaments in vitro, monomeric actin was prepared from rabbit skeletal muscle in a method described in documents 33, 35 and 36. Phalloidin-stabilized F-actin was observed on a 1 mg/ml poly (L-lysine)-coated coverglass in the imaging solution.

SiMS images were obtained by using an inverted microscope (Olympus IX83-ZDC) equipped with an Olympus PlanApo 1.45×100 through a numerical aperture (NA) objective lens, a 2×intermediate lens and an EM-CCD camera (Evolve 512, Roper), and controlled by MetaMorph software (Molecular Device). The focus was automatically maintained at the bottom of the cell by a z drift compensation system during the long-term imaging. The IRIS probe was alternately excited with a 473-nm laser beam (50 mW) for epi-illumination microscopy and a 488-nm laser beam (50 mW) for epi-fluorescence observation in the following procedures. In the epi-illumination mode, the incidence angle of the 473-nm laser beam was tilted so as to reduce background fluorescence from out-of-focus probes that have not bound. The epi-fluorescence image and TIRF image were used to estimate the z position of the target object (see below). Specifically, images were picked up by repeating the following procedures:

(a) imaging in bright field;
(b) imaging of a SiMS image (speckle image) with epi-fluorescence (exposure time for one frame: 50 ms, frame rate: 20 Hz (20 frames per second), number of frames picked up consecutively: 250 frames); and
(c) imaging of SiMS image (speckle image) with TIRF (exposure time for one frame: 50 ms, frame rate: 20 Hz (20 frames per second, number of frames picked up consecutively: 250 frames).

An image obtained in a bright field was used to correct a drift of the microscope stage in a lateral direction (see below) In case of observation of focal adhesions, epi-fluorescence observation was not performed and TIRF observation was performed (frame rate: 20 Hz, 500 frames). Each one of the procedures required 27 seconds and was repeated 160 to 240 times (probe/target substance=CLIP-170 fragment) (amino acid residues 3-309 of sequence number 12)/microtubule, 40 times (probe/target substance=PIPKIγ fragment (641-668) (sequence number 18), Paxillin (overall length of sequence number 15) and the Src fragment (amino acid residues 3-251 of sequence number 16)/focal adhesion), 800 times (probe/target substance=Lifeact (sequence number 19)/actin filament), and 400 to 480 times (probe/target substance=Plectin-1 fragment (amino acid residues 4022-4364 of sequence number 8/intermediate filament). In order to maintain the oxygen-scavenging capacity in the imaging solution, an imaging solution containing the probe was replaced with a fresh imaging solution every 40 sets when the CLIP-170 fragment, the PIPKIγ fragment, paxillin and the Src fragment were used and every 80 sets when Lifeact and the plectin-1 fragment were used. For multicolor imaging of three types of cytoskeletons and focal adhesions, a pick up of SiMS images was conducted in the order of the CLIP-170 fragment, the PIPKIγ fragment (or the Src fragment and paxillin), Lifeact and the plectin-1 fragment. After obtaining SiMS images on the basis of each probe, washing was conducted 10 times by using the HEPES-buffered solution. The remaining fluorescence of a probe was completely photobleached in the HEPES-buffered solution supplemented with an oxygen-scavenging mix, and the next probe was made to react.

In the present example, imaging steps of obtaining observation images were conducted under the above conditions unless otherwise described.

Procedures for Image Reconstruction in IRIS

A super-resolution image was reconstructed by plotting the central points of each fluorescent speckle on a blank image with subpixel accuracy. The number of plotted points was typically $10^6$ to $10^8$. A central point was estimated with subpixel accuracy by fitting of a point-spread function (PSF) of this microscope using a computer program known as DAOSTORM (document 14). In order to correct a stage drift of the microscope, the drift distance was calculated by an autocorrelation function, i.e., $A_N(x_{drift}, y_{drift})$ of the bright-field images obtained at each set of imaging procedures.

$$A_N(x_{drift}, y_{drift}) = \sum_{y=y_0}^{y_m} \sum_{x=x_0}^{x_m} [I_0(x, y) \times I_N(x + x_{drift}, y + y_{drift})]$$
[Numerical expression 1]

where $x_{drift}$ and $y_{drift}$ are drift distances in the directions of the x axis and y axis, respectively. $I_0(x, y)$ and IN $(x+x_{drift}, y+y_{drift})$ are intensities at the pixel positions (x, y) and $(x+x_{drift}, y+y_{drift})$ in the bright field images obtained in the 1st and Nth sets, respectively.

The product of $I_0(x, y)$ and IN $(x+x_{drift}, y+y_{drift})$ is integrated within a prescribed region in the bright-field image. $A_N(x_{drift}, y_{drift})$, which is a function of variables $x_{drift}$ and $y_{drift}$, becomes the maximum when the two bright-field images coincide. The $x_{drift}$ and $y_{drift}$ values leading to a maximum value as $A_N(x_{drift}, y_{drift})$ were calculated by using a customized plug-in in ImageJ software (http://rsb.info.nih.gov/ij/). First, the drift of the bright-field image in the Nth set was corrected using the $x_{drift}$ and $y_{drift}$ values with pixel accuracy. To further determine the drift distance with sub-pixel accuracy, the bright-field image and the corrected image in the first and Nth sets were enlarged by using a bicubic method. Using the $A_N$ ($x_{drift}$, $y_{drift}$) of the enlarged images, the drift distances were determined with subpixel accuracy. The central positions of speckles in the SiMS images in the Nth set were corrected with the drift distances. By plotting the corrected central positions, a super-resolution image was produced. The positions of speckles consecutively observed in 10 or more frames or in 20 or more frames were not used when generating a reconstruction image (observation image) based on Lifeact or generating a reconstruction image (observation image) based on the plectin-1 fragment. These two probes in some cases bound to a target substance when strong excitation laser output was employed.

Image Process for Mapping z Position of Observation Target Object

Figure 14:
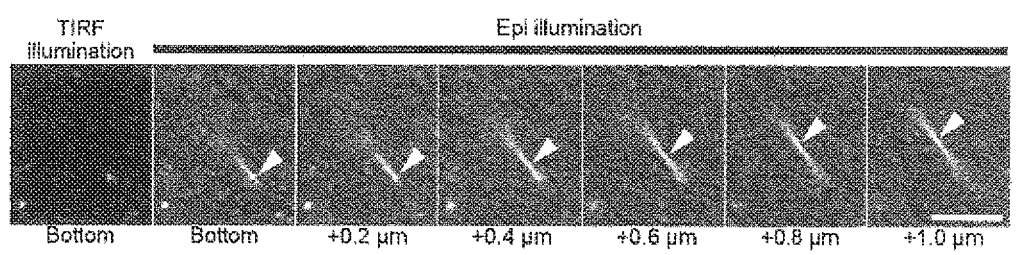
FIG. 14 show the z profile of the TIRF excitation intensity.
Figure 14:
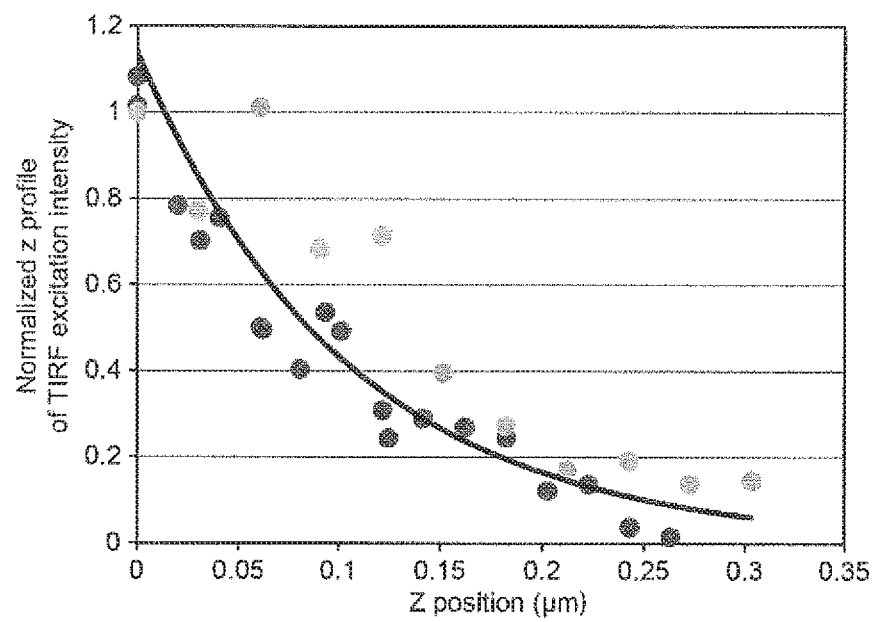

Because a TIRF excitation light intensity exponentially decreases with increasing distance from the coverglass, the height of the observation target object was estimated from the ratio of a TIRF image and an epi-fluorescence image. The z position from the coverglass surface was measured by the method, described in document 18, using fluorescent microtubules that were tilted with respect to the coverglass in a low-melting-point agarose gel. HyLight 488-labeled tubulin was purchased from Cytoskeleton. The labeled microtubules were prepared according to the method described in document 18. Images of the tilted microtubules each having one end touching the coverglass were picked up by TIRF and epi-fluorescence. Epi-fluorescence images were obtained as z stack images (0.2-μm step size) (FIG. 14 (a)). In the intensity line profile along the microtubules of epi-fluorescence images, the x-y position of the highest intensity was used to determine the intersection of the tilted microtubule and the focal plane (FIG. 14 (a) arrows). By connecting the intersections among the z-stacked images, the z-directional distance of each point along the tilted microtubule was obtained. The z profile of the excitation light intensity based on a TIRF method was determined by associating the z-directional distance of each point with the ratio of the intensity of the microtubule in a TIRF image and the intensity of the microtubule in an epi-fluorescence image (FIG. 14 (b)). This z profile was fitted with a single exponential decay function (FIG. 14 (b)). The scale of the z positions were again adjusted by a factor of 0.82, taking into consideration the difference in the refractive index between the immersion oil and the imaging solution (document 18). The inverse function of the exponential function was used to determine the z position of the observation target object by the following numerical expression.

$$z = -\alpha_z \ln\left(\beta \frac{F^{TIRF}}{F^{Epi}}\right)$$ [Numerical expression 2]

(where $\alpha_z$ is the z position at which the intensity of TIRF illumination is 1/e, $\beta$ is a parameter for calibrating the difference in the laser output between TIRF observation and epi-fluorescence observation, and $F^{TIRF}$ and $F^{Epi}$ are the fluorescence intensities of the target object in a TIRF image and an epi-fluorescence image, respectively)

The z-position maps of three types of cytoskeletons were converted from the image of a ratio of the IRIS image (observation image) based on TIRF to the IRIS image (observation image) based on an epi-fluorescence image. For this purpose, the peak intensity of the fluorescent speckle was also fitted by using DAOSTORM. The IRIS images were reconstructed by plotting the peak intensity at the central position of the speckle. In the obtained z-position map, the fluorescence intensity in an image resulting from adding the IRIS image based on TIRF and the IRIS image based on epi-fluorescence was masked by a threshold and noise in a region having no cytoskeletons was removed. In a layered structure such as an actin stress fiber, etc., the calculated z position represents the height of the center of gravity of the structure in the z axial direction.

The z position of the microtubule plus end traced by live-cell imaging of EB1-EGFP was obtained by converting a ratio of an average intensity in a 0.4-μm-diameter region of the microtubule plus end in the TIRF image to that in a corresponding region in the epi-fluorescence image.

Live-Cell Imaging of the Movement of Microtubule Plus End

XTC cells were transfected with an expression plasmid of EGFP fused EB1. 3 to 4 days later, live-cell imaging of EB1-EGFP was conducted on the cells at one-second intervals. In each interval term, an imaging with an exposure time of 100 ms of fluorescence by excitation light for epi-fluorescence observation and imaging with an exposure time of 100 ms of fluorescence by excitation light for total reflection fluorescence observation were conducted. In the above, each excitation light was emitted under the above conditions for IRIS super-resolution except that the excitation light was emitted after having its laser power reduced to about 20% of that used for an IRIS super-resolution imaging in order to avoid damaging live cells. At each imaging time point, two fluorescence images were obtained by alternately using total internal reflection illumination and epi-illumination with an exposure time of 100 milliseconds. An EB1-labeled microtubule plus end was traced by using Speckle TrackerJ, an ImageJ plug-in (documents 33 and 37). The z position of the traced microtubule plus end was calculated by the above method. The speed of the site of the microtubule plus end was calculated with a linear approximation of its x-y positions at five consecutive imaging time points.

Results

The results of screening tests on probe candidates were as below.

TABLE 1

| TARGET SUBSTANCE | PROBE | SEQUENCE NUMBER | AMINO ACID NUMBER | EGFP FUSION POSITION | LOCALIZATION | WASHABILITY | HALF-LIFE | IRIS IMAGE | DOCUMENT |
|---|---|---|---|---|---|---|---|---|---|
| MICROTUBULE | CLIP-170 | 12 | 3-309 | N TERMINUS | P | P | 44 ms | P | 41 |
| | APC | 14 | 2536-2843 | C TERMINUS | P | P | 100 ms | P | 43.44 |
| | APC | 14 | 2781-2819 | N TERMINUS | P | P | 27 ms | P | 43.44 |
| | MAP4 | 4 | 1-908 | N TERMINUS | P | P | 109 ms | P | 47 |
| | MAP4 | 4 | 659-908 | N TERMINUS | P | P | 106 ms | P | 47 |
| | TAU ISOFORM 3 | 5 | 1-383 | N TERMINUS | P | P | 110 ms | P | 48.49 |
| | TAU ISOFORM 4 | 6 | 1-352 | N TERMINUS | P | P | 60 ms | P | 48.49 |

TABLE 1-continued

| TARGET SUBSTANCE | PROBE | SEQUENCE NUMBER | AMINO ACID NUMBER | EGFP FUSION POSITION | LOCALI-ZATION | WASH-ABILITY | HALF-LIFE | IRIS IMAGE | DOCUMENT |
|---|---|---|---|---|---|---|---|---|---|
| INTERMEDIATE FILAMENT | Plectin-1 | 8 | 3777-4684 | N TERMINUS | P | P | 457 ms | P | 16 |
| | Plectin-1 | 8 | 3777-4364 | N TERMINUS | P | P | 59 ms | P | 16 |
| | Plectin-1 | 8 | 3777-4313 | N TERMINUS | P | P | 52 ms | P | 16 |
| | Plectin-1 | 8 | 4022-4364 | N TERMINUS | P | P | 103 ms | P | 16 |
| | Plectin-1 | 8 | 4066-4364 | N TERMINUS | P | P | 7.7 s | NA | 16 |
| FOCAL ADHESION | Paxillin | 15 | 1-557 | N TERMINUS | P | P | 196 ms | P | 50 |
| | Paxillin | 15 | 54-557 | N TERMINUS | P | P | 246 ms | P | 50 |
| | Paxillin | 15 | 54-498 | N TERMINUS | P | P | 91 ms | P | 50 |
| | Paxillin | 15 | 167-557 | N TERMINUS | P | P | 138 ms | P | 50 |
| | Src | 16 | 1-251 | C TERMINUS | P | P | 161 ms | P | 59 |
| | Src | 16 | 3-251 | C TERMINUS | P | P | 141 ms | P | 59 |
| | PIPKIγ90 | 18 | 641-668 | N TERMINUS | P | P | 496 ms | P | 17 |
| ACTIN FILAMENT | Atto488-Lifeact | 19 | — | — | — | — | 23 ms | — | — |

In the table, P represents positive while NA indicates that measurement was not conducted (not accessed).

In the sequence table, sequence number 18 represents an amino acid sequence of fragments 641-668 of PIPKIγ90.

A probe candidate that had not passed either a localization test or a washing test received neither a test of an IRIS image nor half-life measurement, and thus is not described in the above table 1. A probe candidate that did not pass a test is estimated to have a very long or very short binding half-life to a target substance or to not bind to a target substance.

Figure 9:
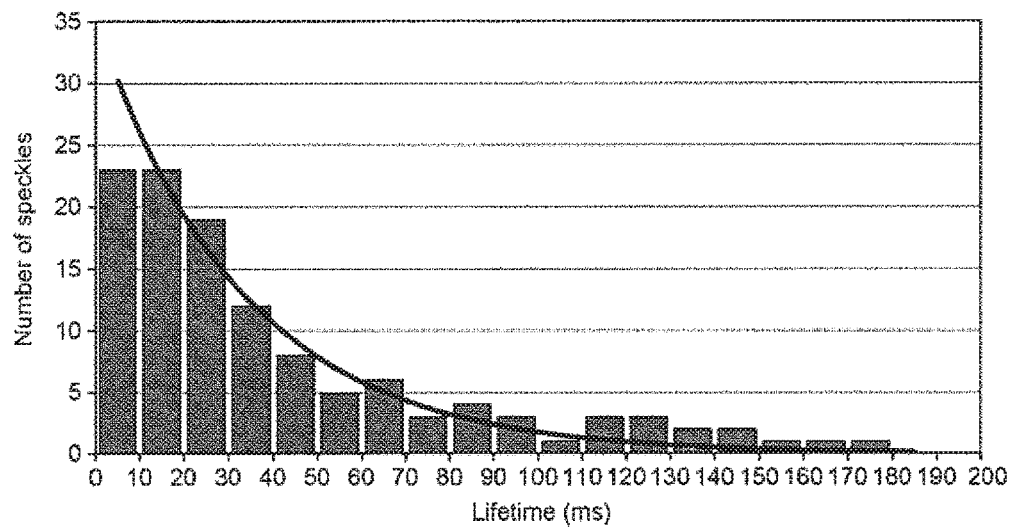
FIG. 9 show characteristic evaluation of Atto 488-Lifeact.
Figure 9:
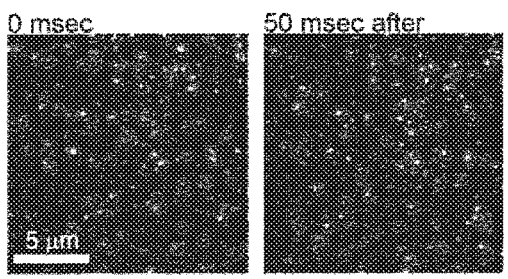
Figure 9:
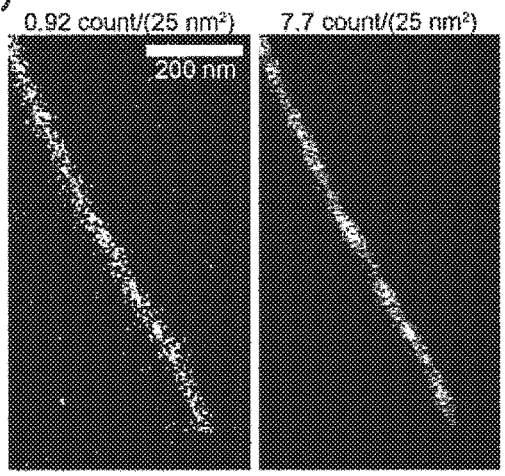
Figure 9:
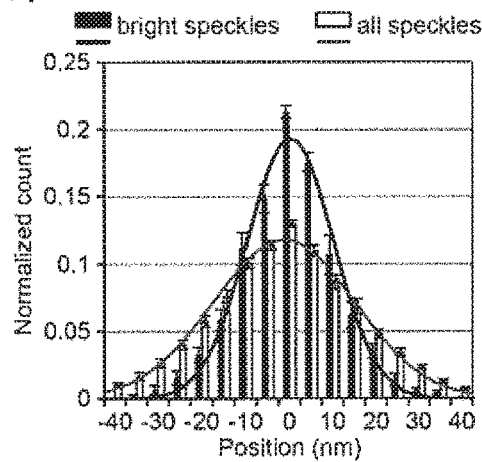

Because the test described in detail in FIG. 9 and the explanations for the figure have independently confirmed that Atto488-Lifeact is effective for an actin filament and that the half-life thereof is 23 nm, these facts are described in the above table as reference results.

Super-Resolution of Actin Filament in High Labeling Density by IRIS

The present inventors confirmed whether or not a super-resolution image can be generated through the IRIS method by using Lifeact, which is a widely used actin marker. Lifeact is a short peptide that stains an actin filament in a live cell or a fixed cell (document 10). Lifeact has a property of being exchanged within 0.4 seconds on an actin filament (document 10). The high-speed exchangeability of Lifeact is confirmed through single-molecule speckle (SiMS) microscopy (documents 11 to 13). The dwell time of Atto488-labeled Lifeact showed a single exponential decay of a half-life of 23 milliseconds (FIG. 9 (a)) The present inventors selected a concentration of 2.4 nM as the Atto488-labeled Lifeact concentration in the imaging solution and obtained $2 \times 10^5$ SiMS images of Lifeact on an actin filament in vitro through consecutive imaging using a total internal reflection illumination of 488 nm with an exposure time of 50 ms/frame and at a frame rate of 20 Hz. The central position of each fluorescent speckle was determined by using a computer program named DAOSTORM (document 14) (FIG. 9 (b)). Pieces of position information from a great number of Lifeact speckles in the above speckle images of $2 \times 10^5$ frames were integrated so as to reconstruct an image of actin filaments (FIG. 5 (b) and FIG. 9 (c)). The average width of single actin filaments was 23 nm as the full-width at half-maximum (FWHM) in an image reconstructed by using only high-brightness speckles (highest 12% approximately) in order to guarantee a high accuracy of localization (FIG. 5 (c) and FIG. 9 (d)).

A major problem in conventional super-resolution microscopy is that using an antibody and a photoactivatable fluorescent protein makes it difficult to label an observation target structure in a sufficient density. The actin subunit and the antibody have the widths of 6 nm and 12 nm, respectively, and accordingly a single actin filament having 360 subunits per 1 μm can only be used for labeling up to a density of at most 180 subunits per 1 μm in the labeling of antibodies. This labeling density is equivalent to the labeling density in an observation image reconstructed from speckle images of $2 \times 10^3$ frames in the IRIS method of the present inventors. As shown in the left view of FIG. 5 (d) and in FIG. 5 (e), actin filaments show a pattern that is not continuous in the longitudinal direction in an observation image reconstructed from speckle images of $2 \times 10^3$ in the IRIS method. Even a labeling density that was 6.5 times its original was not sufficient for continuous staining of actin filaments (FIG. 5 (d)), however it was possible to achieve a labeling density of $1.2 \times 10^4$ for an observation image reconstructed from speckle images of $2 \times 10^5$ frames and to obtain consecutive super-resolution images of actin filaments (FIG. 5 (d) and FIG. 5 (e)). As described above, it was made obvious that the IRIS method of the present invention can eliminate the problem of a labeling density that had conventionally been an obstacle to dissolving two or three types of target substances coexisting close to each other.

Figure 5:
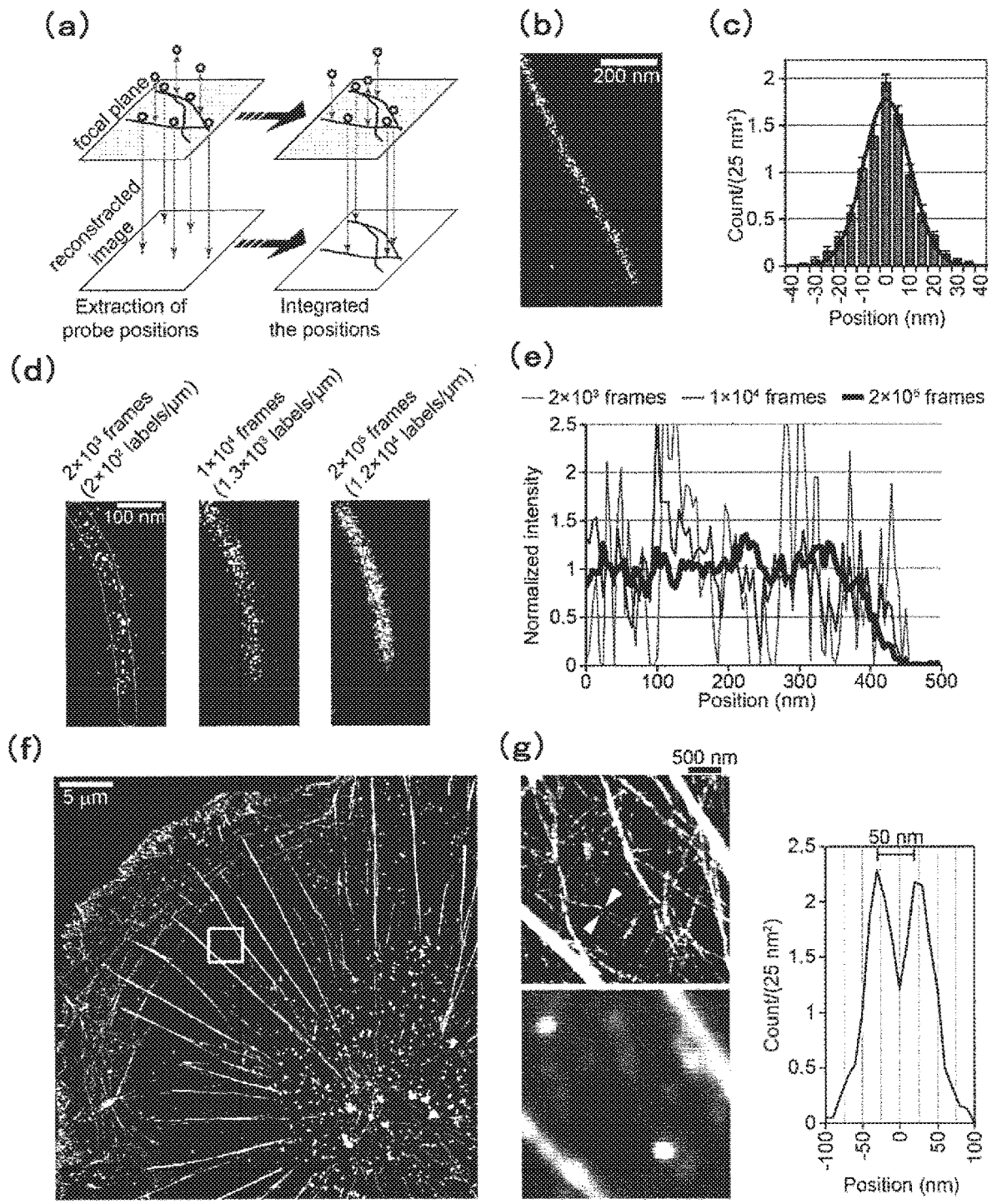
FIG. 5 are related to super-resolution microscopy according to the present invention. Super-resolution microscopy according to the present invention will be referred to as IRIS (image reconstruction by integrating exchangeable single-molecule localization).
Figure 10:
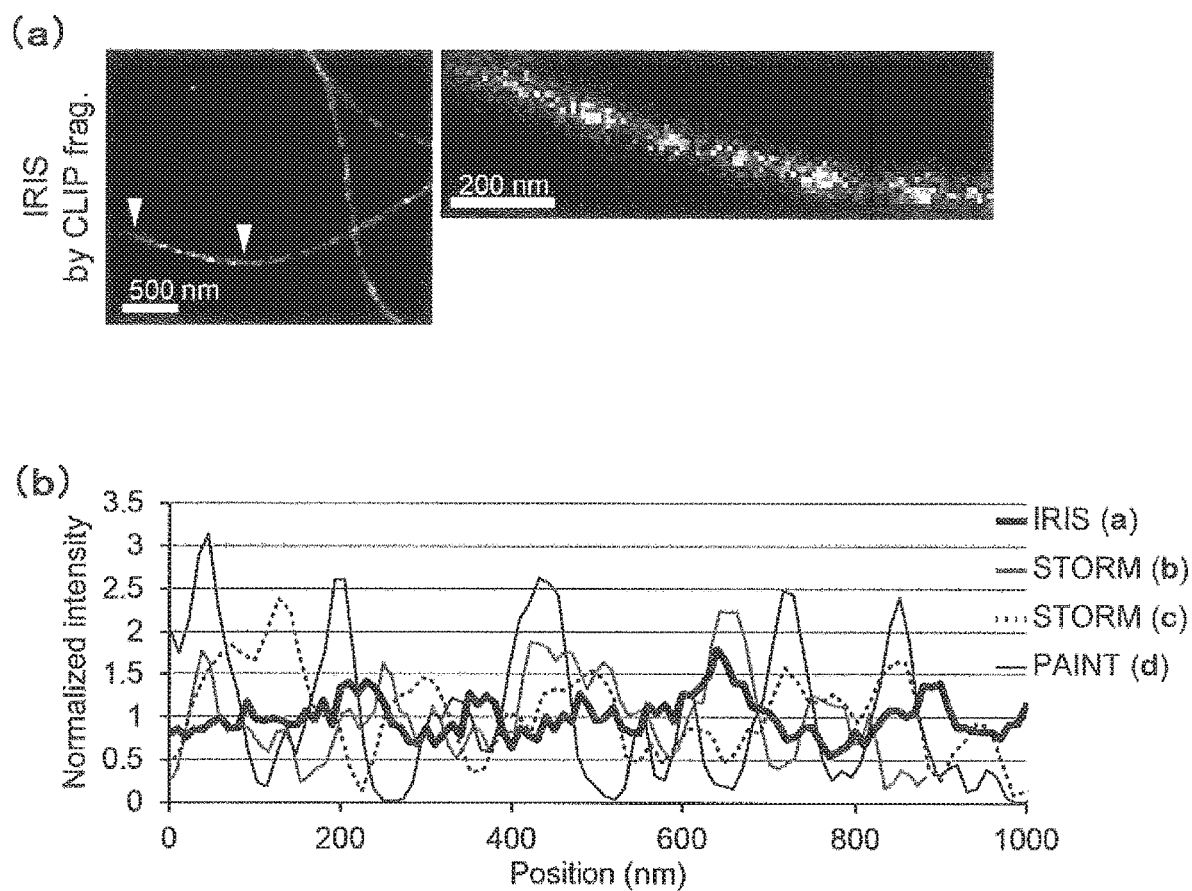
FIG. 10 show a comparison of labeling patterns along the longitudinal direction of microtubules between IRIS and other super-resolution techniques.

For a cell that was fixed and had received a permeabilization process, in an observation image generated by using the IRIS method that utilizes a Lifeact probe of an actin filament, it was possible to dissolve two parallel actin bundles that were apart by 50 nm (FIG. 5 (d) through FIG. 5 (f)). By contrast, in an image resulting from adding SiMS images (speckle images) (which is equivalent to an image that can be obtained by a conventional immunofluorescence method), it was not possible to dissolve two such actin bundles (lower left view of FIG. 5 (g)). According to the IRIS method, it is possible to obtain consecutive observation images of an actin filament or a microtubule (below). This is remarkable progress from the conventional super-resolution microscopy (FIG. 10).

Establishment of Screening Method of IRIS Probe

The present inventors established an effective method for swiftly determining an IRIS probe for a different cell structure while taking into consideration a necessary molecular characteristic determined by data using a Lifeact probe. A probe candidate was generated by making a protein and EGFP fuse with each other, the protein and the EGFP being known to bind to a target substance. Live-cell fluorescence single molecule speckle (SiMS) microscopy (documents 11 and 12) is also effective for testing a probe candidate.

Figure 11:
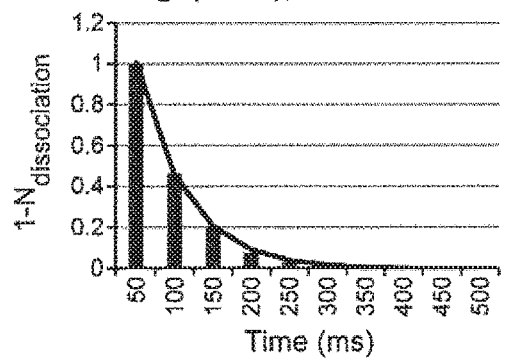
FIG. 11 shows the lifetime distribution data of the selected IRIS probes on the targets. 100 to 112 lifetimes were plotted in accordance with a complementary cumulative distribution function (1-Ndissociation) for each probe. Ndissociation is the cumulative relative frequency of dissociated probes. The half-life of probes on the targets was determined by fitting the life time distribution data by a single exponential function. Part of the measurement results shown on table 1 is shown here.
Figure 11:
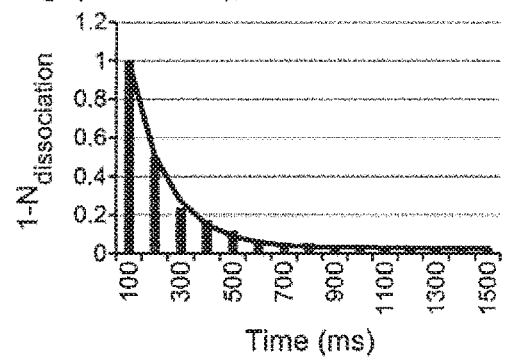
Figure 11:
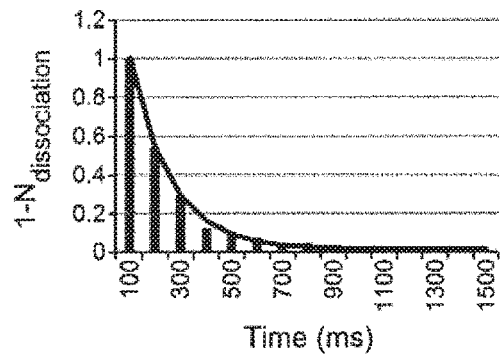
Figure 11:
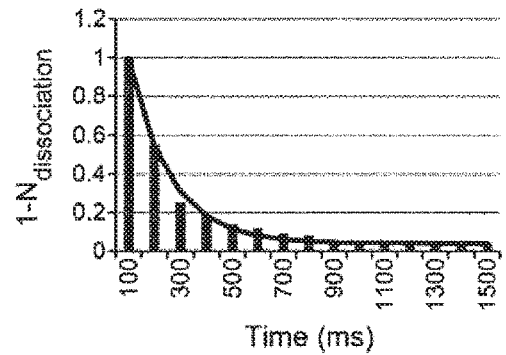
Figure 11:
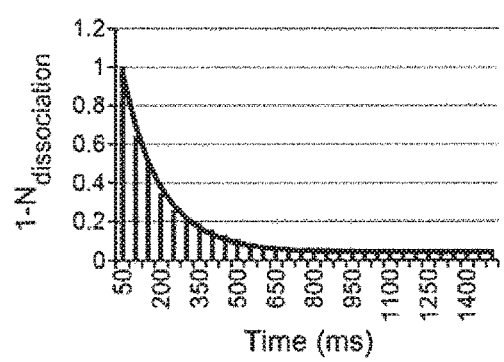
Figure 11:
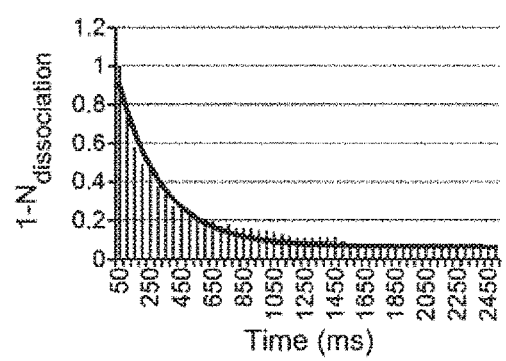
Figure 11:
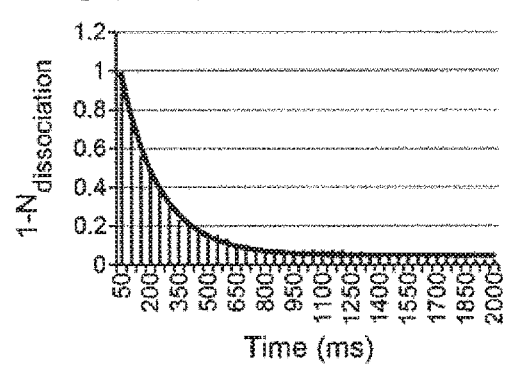
Figure 11:
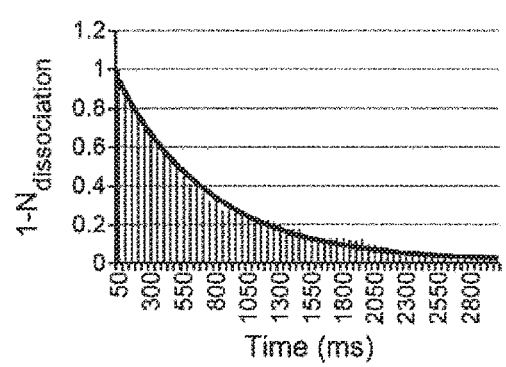

However, the present inventors discovered that the binding specificity and dissociation dynamics of a probe candidate can easily be clarified by bringing crude lysate of a cell that expresses EGFP fused probe candidate into contact with a fixed cell. The inventors selected an IRIS probe in the following four steps:

(i) SiMS images (speckle images) of 10,000 frames were picked up at intervals of 50 ms or 100 ms, and probe candidates that were not able to localize in targets in an integrated SiMS image were excluded;
(ii) probe candidates that were not able to be easily removed through washing were excluded;
(iii) probe candidates having high dissociation speeds (with a half-life of 10 ms through 500 ms, see FIG. 11) were selected; and
(iv) it was confirmed, in a reconstruction IRIS image (observation image), that probe candidates were able to localize in targets.

Figure 12:
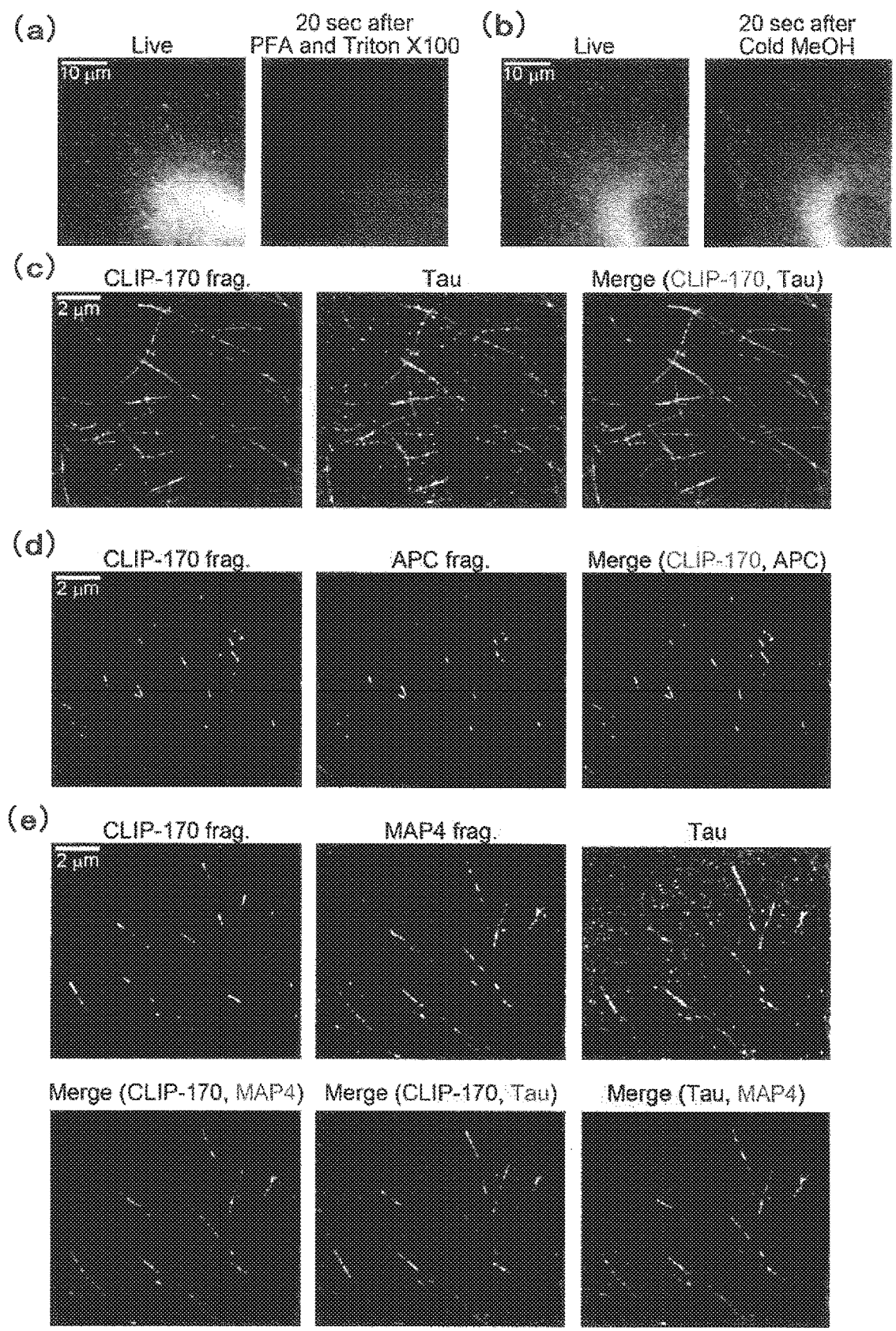
FIG. 12 show labeling patterns of microtubules by a CLIP-170 fragment (amino acid residues 3-309 of sequence number 12), an APC fragment (amino acid residues 2536-2843 of sequence number 14), a MAP4 fragment (amino acid residues 1-908 of sequence number 4) and Tau isoform 3 (full length of sequence number 5). The patterns are different depending upon procedures for fixing cells.
Figure 13:
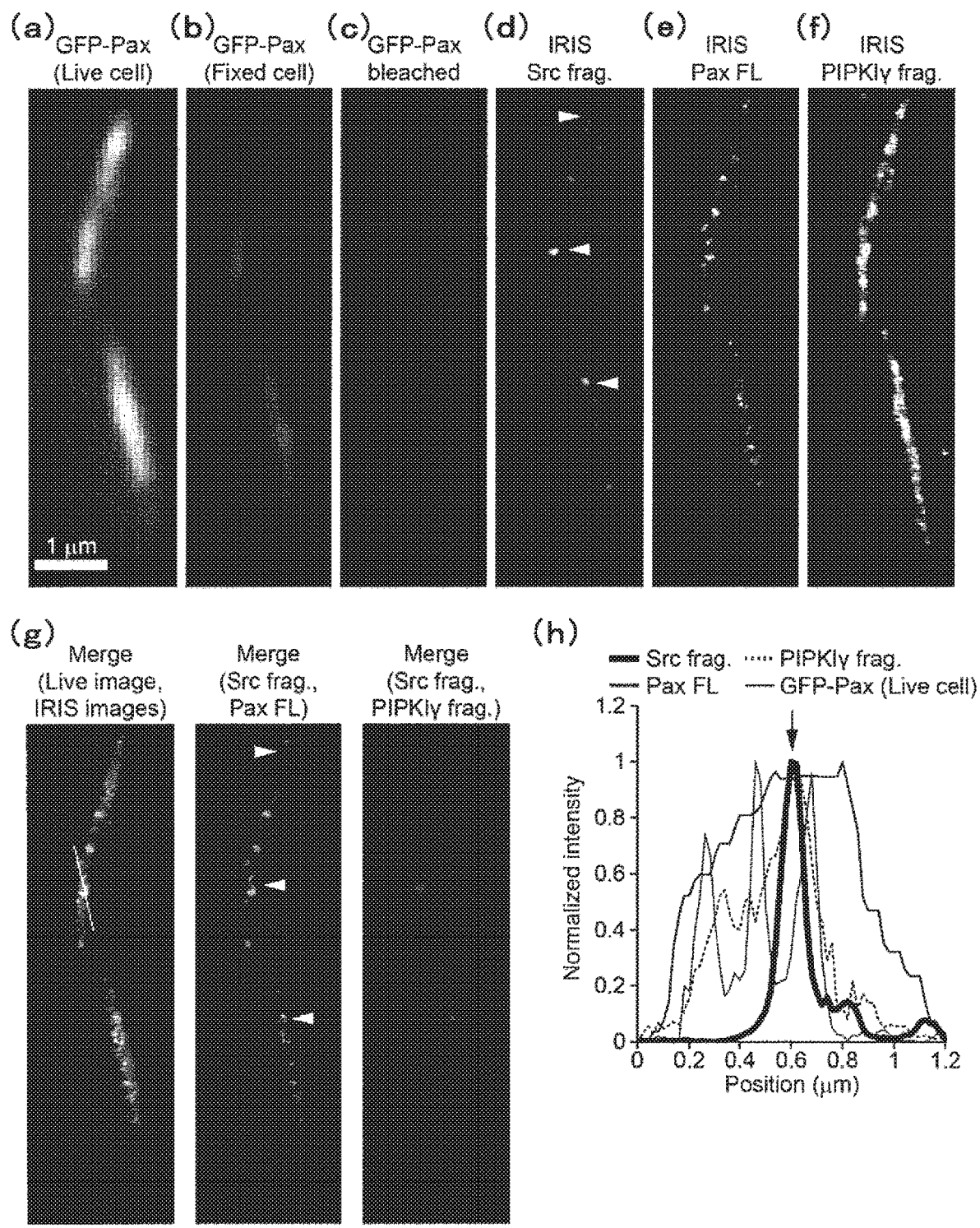
FIG. 13 show labeling patterns of focal adhesions by Paxillin full length (FL) (full length of sequence number 15), the Src fragment (amino acid residues 3-251 of sequence number 16) and a PIPKIγ fragment (residues 641-668) (sequence number 18).

As shown in table 1, 18 types were selected by the above screening method from among the probe candidates. By a plurality of probes for microtubule and focal adhesion, different sites of their structure bodies were able to be visualized (FIG. 12 and FIG. 13). Also, independently from the above, it has been confirmed that Atto488-Lifeact is effective as a probe for an actin filament and is effective for the visualization of an actin filament (FIG. 9 etc.). This suggests that IRIS is effective for mapping a distribution of probe identification sites in one structure body.

Super-Resolution Image of a Plurality of Target Substances by IRIS

It was discovered that Lifeact, a CLIP-170 fragment (residues 3-309), a Plecin-1 fragment (residues 4022-4364) and a phosphatidyl inositol-(4)-phosphate 5-kinase type Iγ-90 (PIPKIγ) fragment (residues 641-668) are preferable respectively for observation of actin, microtubules, intermediate filaments and focal adhesion. By utilizing the exchangeability of IRIS probes, images in which the IRIS probes bound to 4 different types of cytoskeleton structures were obtained sequentially.

Figure 6:
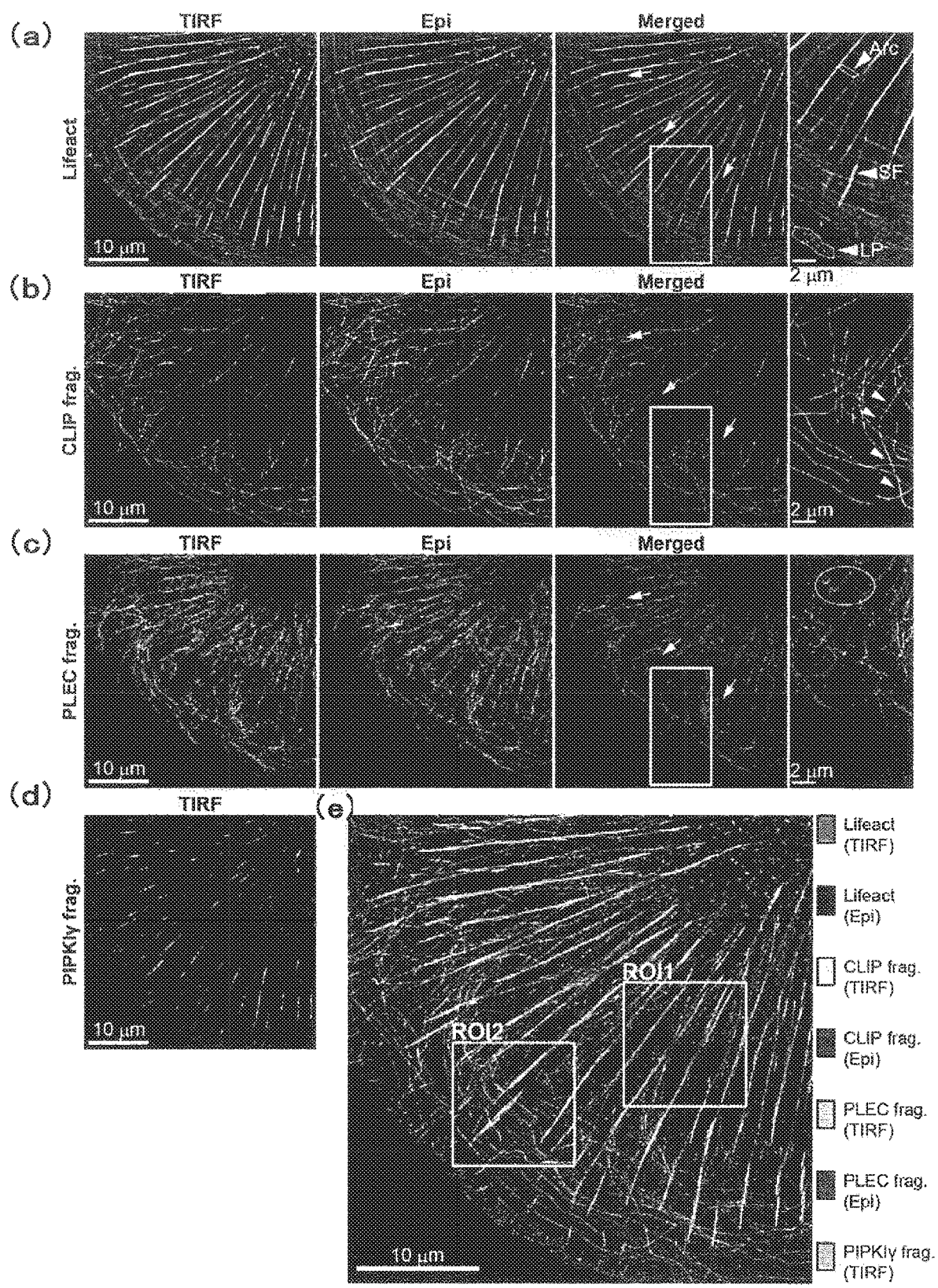
FIG. 6 (a) shows super-resolution images of actin filaments using Lifeact.

Further, the present inventors investigated a three-dimensional (3D) network of an actin filament, a microtubule and an intermediate filament. An image based on each IRIS probe was obtained by alternately using total internal reflection illumination and epi-illumination, and super-resolution images at the bottom and in the entire peripheral region of the cell were reconstructed respectively by using the obtained images. These images show that actin arcs running parallel to the cell contour gradually rise as if they were climbing on the radial actin bundles localizing at the bottom (arrows in FIG. 6 (a)) with decreasing distance to the center. It was confirmed that microtubules and intermediate filaments behind the lamellipodium (lobopodium) base were eliminated from the cell bottom at several locations (arrows in FIG. 6 (b) and FIG. 6 (c)).

Figure 15:
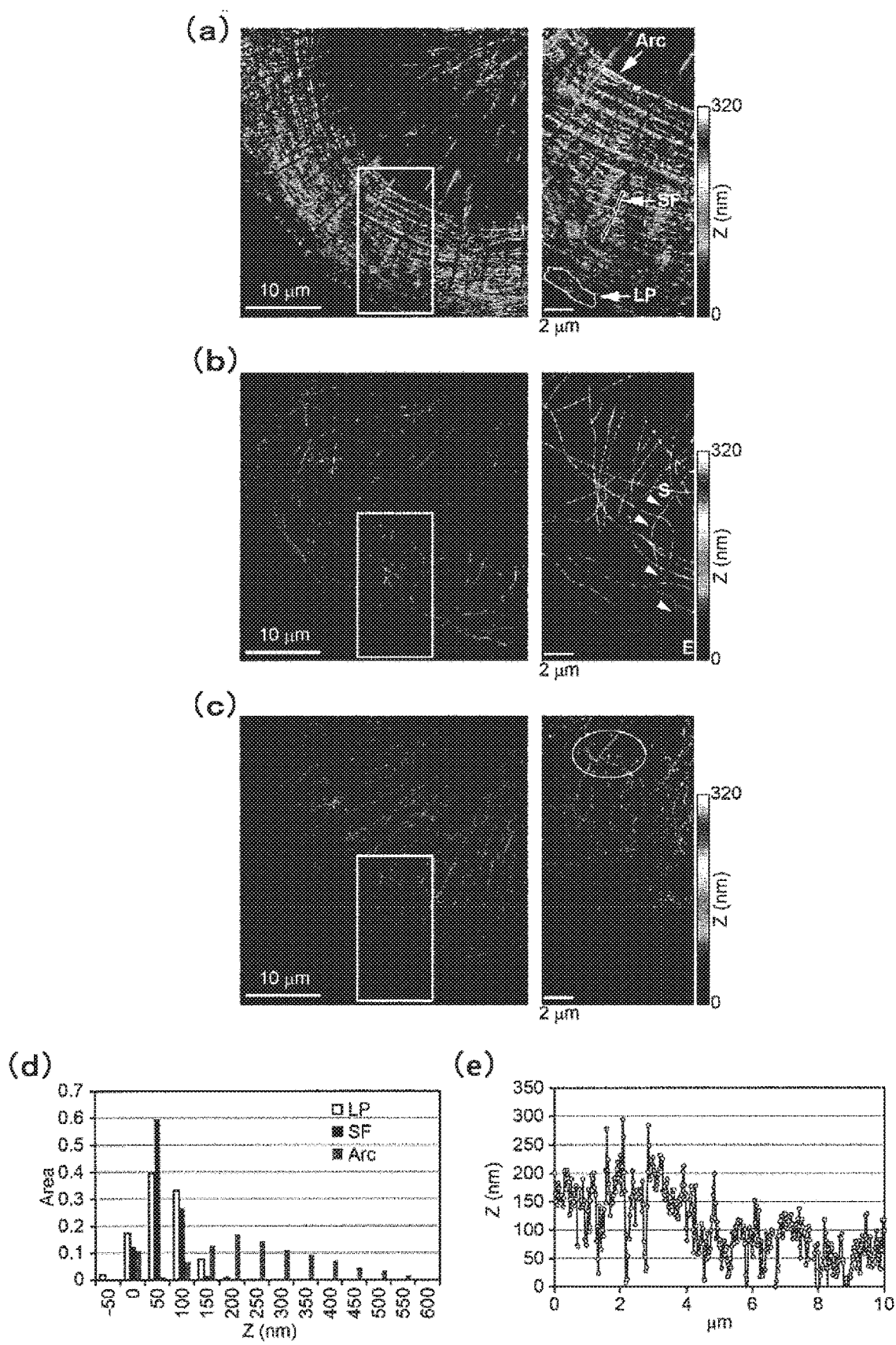
FIG. 15 (a) shows z-position mapping of actin bundles, FIG. 15 (b) shows z-position mapping of microtubules, and FIG. 15 (c) shows z-position mapping of intermediate filaments. The respective images of FIGS. 15 (a), (b) and (c) were calculated and generated from the total internal reflection fluorescence (TIRF) IRIS image and the epi-fluorescence IRIS image shown in FIGS. 6 (a), (b) and (c) (see "Methods"). The right image is an enlarged image of the region in the frame shown in the left image.

The z position of each observation target object was estimated by using a signal ratio between an IRIS image based on TIRF and an IRIS image based on epi-fluorescence on the basis of measurements that used images of tilted fluorescent microtubules described in an above method (document 18). The 3D images as shown in FIG. 15 clarified the structure of the target substance. Lamellipodia (LP), stress fibers (SF) and actin arcs (Arc) were distributed with height positions of their centers of gravity (average ±S.D.) of 42±43 nm, 34±30 nm and 217±132 nm, respectively (arrows in FIG. 15 (a) and FIG. 15 (d)). The z positions of the microtubules became lower from 150 nm through 200 nm to 50 nm through 100 nm in the vicinity of the cell perimeters (arrowheads in FIG. 15 (b) and FIG. 15 (e)). Intermediate filaments formed mesh-shaped structures throughout the cell body, and some of the filaments were located at a height of approximately 200 nm behind the lamellipodium (ellipse in FIG. 15 (c)).

Figure 7:
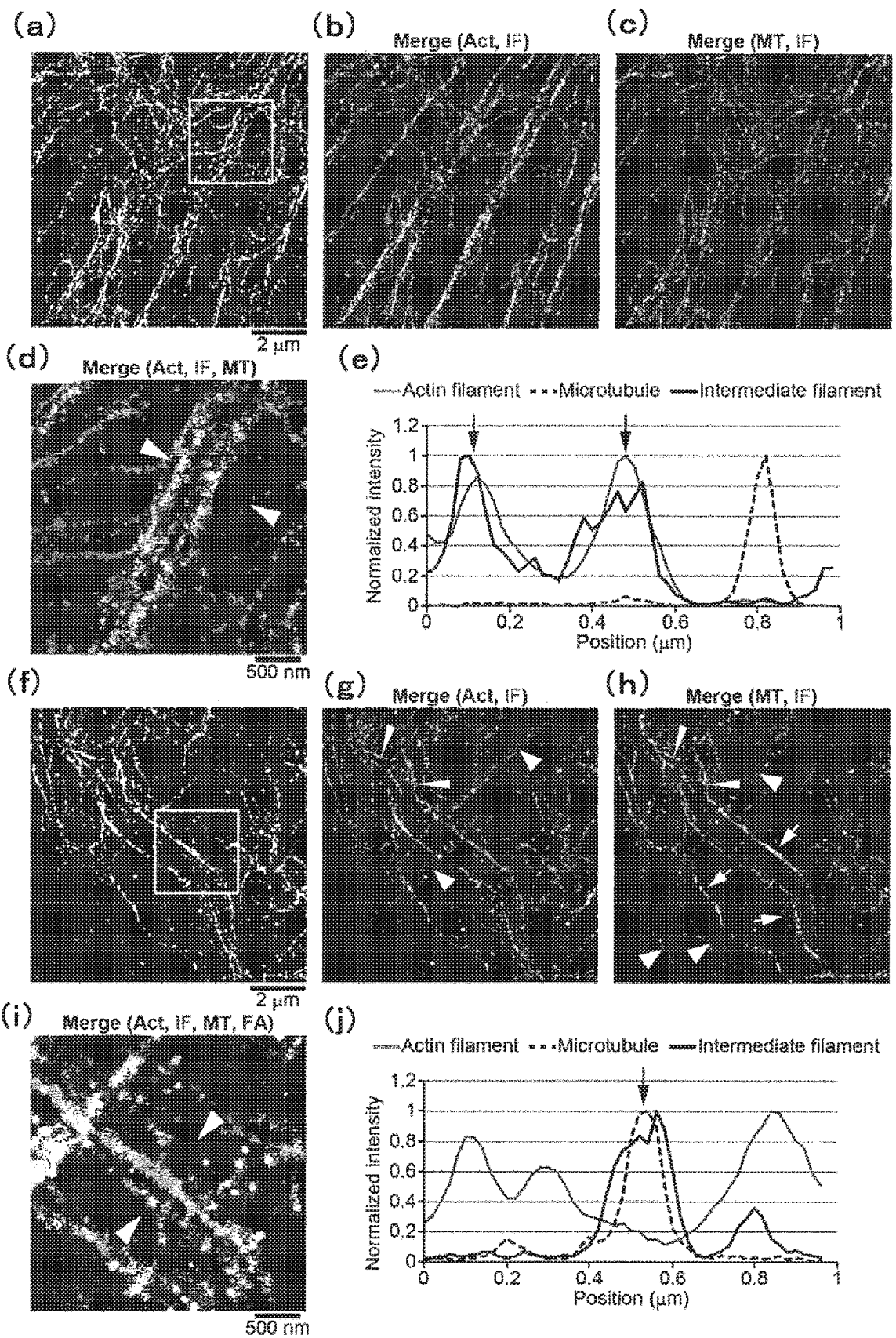
FIG. 7 show region-specific proximity between cytoskeletons and focal adhesions.

An IRIS image makes it possible to observe a spatial relationship between a plurality of cytoskeletal structures in a single cell at a resolution capability exceeding the diffraction limit. In a lamellar region, intermediate filaments were tangled with actin stress fibers in many cases, but they are not tangled with microtubules (FIG. 7 (a) through FIG. 7 (c)). The tangled actins and intermediate filaments appear to be linked to each other. Their cross-sectional profiles show that actin stress fibers overlapped intermediate filaments (arrows in FIG. 7 (e)). In peripheral regions, intermediate filaments did not tangle with actin stress fibers (FIG. 7 (g) and FIG. 7 (i)), whereas some intermediate filaments ran along microtubules (arrows in FIG. 7 (h)). The cross-sectional profiles show that intermediate filaments overlapped microtubules but did not overlap actin filaments (arrows in FIG. 3 (i), and FIG. 3 (j)). Thus, IRIS can reveal a region-specific proximity between 4 cytoskeletal components.

Figure 8:
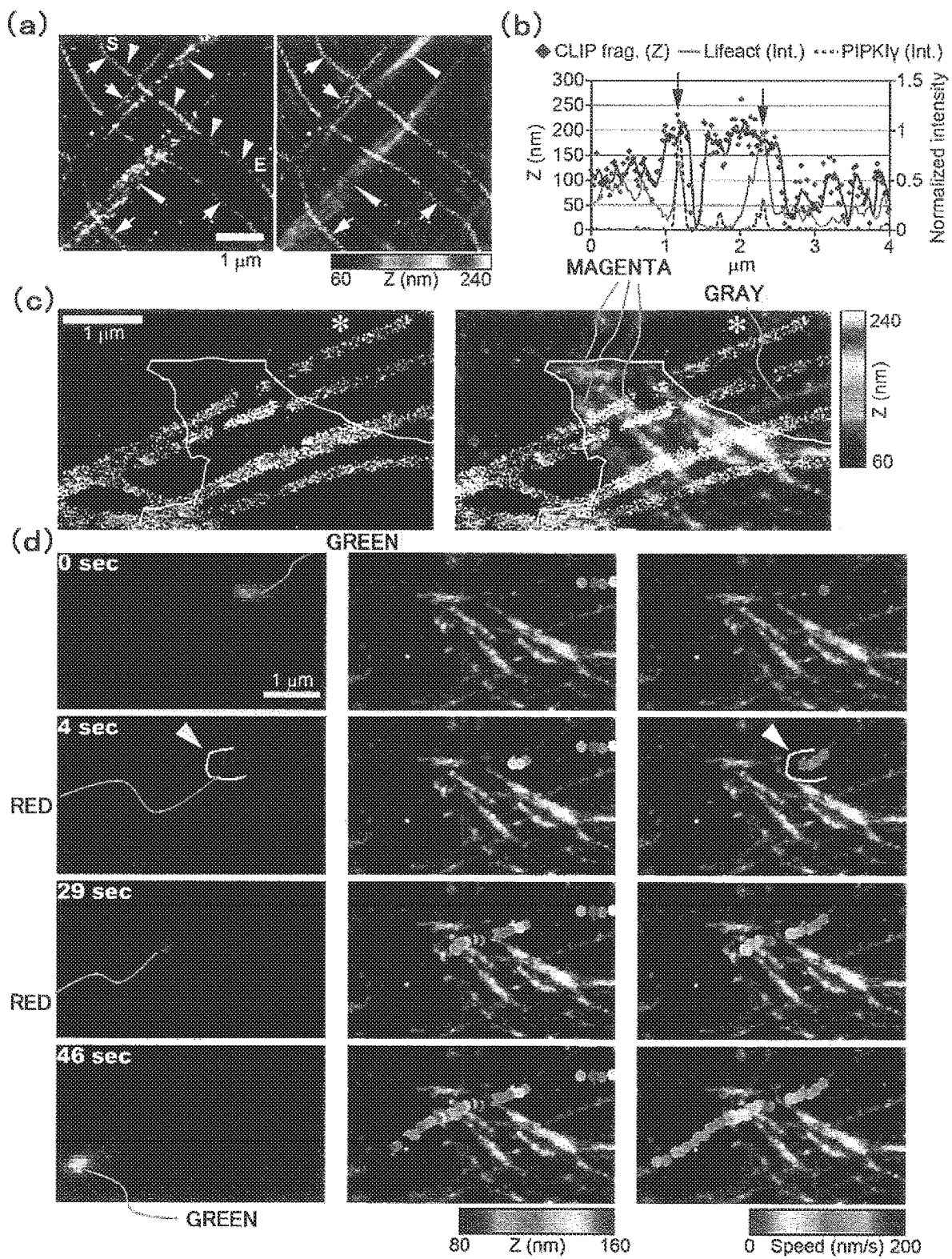
FIG. 8 show movements of microtubule tips in the vicinity of actin stress fibers and focal adhesions. The left image of FIG. 8 (a) is an image resulting from merging a z position map (FIG. 16) of microtubules (MT) and a TIRF super-resolution image of a focal adhesion (FA) in the central region in FIG. 7 (i). The right image of FIG. 8 (a) is an image resulting from merging a z position map (FIG. 16) of microtubules (MT) and a TIRF super-resolution image of actin filaments (Act) in the central region in FIG. 7 (i). The z positions of microtubules were calculated from the signal intensity ratio between an epi-fluorescence super-resolution image and a TIRF super-resolution image (see "Methods" in the examples). In the left image of FIG. 8 (a), the microtubules (MT) are denoted by arrows and the focal adhesions (FA) are denoted by narrow arrowheads. In the right image of FIG. 8 (a), the microtubules (MT) are denoted by arrows and the actin filaments (Act) are denoted by narrow arrowheads.
Figure 16:
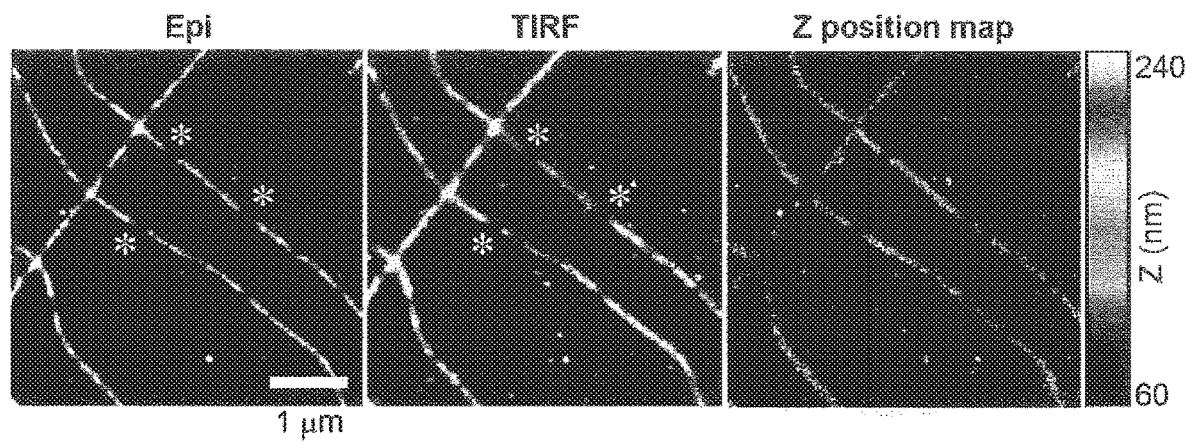
FIG. 16 shows an epi-fluorescence super-resolution image of microtubules (left), a TIRF image (center) and the z-position mapping shown in FIG. 8 (a) (right). In CLIP-170 fragment-visualized microtubules, signals were partially lost (asterisks in the left and center images).

Behavior of Plus End of Microtubule in Live Cell and Comparison with Super-Resolution of Cytoskeleton Network The present inventors discovered that the heights of microtubules locally change in the vicinity of focal adhesions and stress fibers. When microtubules crossed focal adhesions and stress fibers, they were lifted to positions at 200 nm from positions at 100 nm from the glass surface (arrowheads in FIG. 8 (a), FIG. 8 (b) and FIG. 16). Components of focal adhesions are located at a height of 30 nm through 80 nm from the glass surface (document 19). It appears that the lifted microtubules climbed on actin stress fibers without touching focal adhesions.

The present inventors further investigated a relationship between a microtubule plus end and a cytoskeleton network in that portion by observing the behavior of EB1-EGFP in a live cell and then reconstructing a super-resolution image of a 3D cytoskeleton network after fixation. The imaging system of the present inventors makes it possible to perform live-cell 3D imaging with acousto-optic tunable filters for swiftly switching between total internal reflection illumination and epi-illumination. The trajectory of the tip of the EB1-labeled microtubule was compared with focal adhesions and stress fibers in a super-resolution image (asterisk in FIG. 8 (c)). When the tip of the microtubule glowing was brought into contact with a stress fiber, the tip moved upward so as to move away from a focal adhesion existing below (FIG. 8 (d)). When the tip of the EB1-labeled microtubule was brought into contact with a stress fiber, the growth slowed down and the moving direction changed (arrow in FIG. 8 (d)). These pieces of data suggest that the speed and the direction of growth of a microtubule are greatly influenced by the collision and subsequent interaction with an actin stress fiber. As described above, a combination between IRIS and live-cell imaging makes it possible to clarify formation processes of a plurality of cytoskeletal structures that dynamically interact with each other.

Consideration

Consideration 1: Comparison with PAINT

Document 20 (Proceedings of the national Academy of Sciences of the United States of America 103, 18911-18916 (2006)) has reported a method called PAINT (point accumulation for imaging in nanoscale topography). This document has reported that super-resolution observation based on PAINT was conducted on lipid bilayer morphology by using Nile-red, which is a fluorescent dye that rapidly shuttles between an aqueous solution and the lipid bilayer. However, Nile-red is not a probe that binds to and dissociates from a specific bilayer molecule type. This prevents highly accurate determination of the position of a specific lipid molecule type that constitutes a lipid layer. By contrast, a probe of IRIS can bind to and dissociate from a specific target protein from among various types of proteins existing in a cell so as to make it possible to determine the position of the molecule thereof highly accurately. In addition, the concept of PAINT does not include a concept of obtaining a distribution of a plurality of target substances through probe exchange of IRIS. High resolution-capability imaging of various target substances by IRIS cannot be realized by the concept of PAINT. Also, this document has does not disclose improving of resolution by increasing the number of times of observation in PAINT. The reason appears to be that even an increased number of times of observation does not fix a lipid layer, which is a target substance, and thus the resolution does not improve through a change in the shape. In addition, the reason also seems to be that the problem of labeling density first became widely recognized a few years later than the document as an unsolved problem among those skilled in the art (documents 4 through 7).

The problem of labeling density was proposed in 2008 (document 6), whereas it had long been an unsolved problem in super-resolution microscope observation (documents 4, 5 and 7). As a method of increasing a target density, the review of 2013 (document 5) introduced an attempt to make fluorescent dye, which is an organic compound that is smaller than an antibody and a fluorescent protein, stably bind to a target substance and to make a single domain antibody such as Nanobody etc., which stably binds, stably bind to a target substance. This means that PAINT had not been recognized as a method of increasing a target density. Also, even the method introduced in the above review did not achieve a labeling density equivalent to that realized by the present invention, and the problem of a labeling density had remained unsolved. From these points, it can be said that there had not been an idea of using a binding and dissociation probe for solving the problem of a labeling density. In FIG. 10, an observation image of a microtubule based on IRIS and those based on STORM and Exchange-PAINT, which are conventionally known super-resolution microscopy, are compared (documents 21 to 23). According to the line profiles of label intensities along the longitudinal direction of microtubules, the observation image based on IRIS shows a more continuous pattern than those of observation images based on STORM and Exchange-PAINT (FIG. 10 (b)). Also, it is easy for the labeling density of actin filaments based on IRIS to become 60 times the maximum density of antibodies that bind to actin filaments. From these results, it is obvious that IRIS according to the present invention can solve the problem of labeling density that has caused a deterioration in reliability of the conventional super-resolution microscopy.

In addition to the ability to overcome the problem of labeling density, according to IRIS of the present invention, it is easy to visualize a plurality of target substances by protein-based exchangeable probes and there are no limitations on the number of target substances. In super-resolution microscopy that has conventionally been known and available, only up to 2 target substances can be observed (documents 21, 22, 24 and 25). Recently, Exchange-PAINT, which makes it possible to conduct super-resolution observation of a plurality of target substances, was announced (document 23 (Nature methods, 11, 313-318, 2014)). Exchange-PAINT uses characteristic labeling means of hybridizing short and fluorescence-labeled DNA with complementary DNA conjugated to antibody molecules. Exchange-PAINT is similar to IRIS in that it sequentially visualizes a plurality of target substances one by one by sequentially hybridizing pairs of various types of oligonucleotides. However, in Exchange-PAINT, uneven labeling and/or interference between antibodies sometimes lead to inaccurate analysis of the distribution of labeling substance (FIG. 10 (b)). By contrast, an IRIS probe is washed and removed and thereafter the next IRIS probe is brought into contact with the sample, resulting in no interference between a plurality of probes that are respectively for a plurality of target substances. The data of the present inventors shows the region-specific proximity of three types of cytoskeleton structures and focal adhesions with an accuracy exceeding the diffraction limit. In principle, the number of target substances that can be observed by IRIS is not limited even when they coalesce in a narrow region. This effect is remarkably advantageous in comparison with existing super-resolution microscopy.

Consideration 2: Probe

As shown in the above table, the present inventors have confirmed that probes of Document 19 are actually effective for the IRIS method. The above probes have been probes that use a binding partner known to associate with a target substance material, however the scope of the invention is not limited to this example. Using a phage display or an assay that confirms interactions between proteins of yeast-two hybrid system etc. makes it possible to perform screening for useful IRIS probes.

A plurality of IRIS probes for a microtubule and a focal adhesion visualized different sites of their structure bodies. A MAP4 fragment and a tau protein weakly visualized a microtubule plus end when EB1 existed (FIG. 12 (e)). A CLIP-170 fragment strongly labeled a microtubule tip when EB1 existed and continuously labeled the entire microtubule when EB1 did not exist (FIG. 12 (c) and FIG. 12 (e)). The result corresponds to in-vitro data (document 26). Further, Paxillin and the Src fragment visualized different portions of focal adhesion (FIG. 13). Thus, IRIS can also be applied to mapping analysis of a site in which a plurality of protein fragments bind. Development of an IRIS probe that binds to a molecule in a specific state also makes it is possible to perform super-resolution mapping on the molecule in the specific state.

2. Experiment 2

2.1. Method of Producing a Fab Probe from a Polyclonal Antibody

An anti-p40 antibody including antiserum was produced from a rabbit by using an antigen *Xenopus laevis* derived p40 produced in the present inventors' laboratory. Rabbit antiserum was put into an affinity column filled with antigens and polyclonal antibodies were made to adsorb on the column. pH in the column was reduced in a stepwise manner (pH5 to pH2) and the antibodies made to adsorb were eluted. 2 ml of fraction eluted at a high pH (pH2 through pH3.5) was added to 1.4 ml of a 50% slurry solution of Protein A Protein beads (Protein A Sepharose CL-4B, GE) and the antibodies were made to adsorb on the beads over 1 night at 4 degrees Celsius. After using PBS to wash and remove antibodies that had not been made to adsorb, the beads were suspended in 1 ml of PBS. To this suspension of beads, 50 µl of 1 µg/µl DyLight 488 NHS Ester (ThermoScientific) in which DMSO was dissolved was added, and antibodies were fluorescence-labeled at an ambient temperature over one hour. DyLight 488 NHS Ester that had made no reactions was washed and removed by using PBS and only beads were collected through centrifugation. In order to produce a Fab fragment from an antibody that was made to adsorb on beads, 1 ml of 7 µg/ml papain dissolved in a Digestion Buffer (50 mM Tris-HCl pH8.0, 10 mM Cysteine-HCl, 2 mM EDTA) was added and reactions were caused for 1 hour at 37 degrees Celsius. After the centrifugation, supernatant containing a Fab fragment was collected and 1 µl of 1 mg/ml leupeptin was added in order to inhibit the activity of papain. The obtained Fab fragment was put into an affinity column filled with antigens, and the Fab fragment was made to adsorb. pH in the column was reduced in a stepwise manner and a Fab fragment of a fraction eluted at a high pH (pH 5 to pH 4) was obtained. As described above, in the production of a Fab fragment from a polyclonal antibody, column purification was conducted twice. By using the affinity column of the first time, an antibody having a weak antigen-binding force was purified. From that antibody, a Fab fragment having a further weak antigen-binding force was produced. By using the affinity column of the second time, a Fab fragment in which an antigen-binding force still remained was purified. A Fab fragment prepared in this method was derived from IgG.

2.2. Iris Super-Resolution Imaging of Actin

Preparation of Arp2/3 complex observation cell sample
By following the procedures described in detail in "procedures for imaging of multicolor super-resolution by IRIS" of experiment 1, a *Xenopus laevis* XTC cell was fixed and received a permeabilization process. After a blocking step with 4% bovine serum albumin for 30 minutes, the Fab probes were brought into contact with the cells in an imaging solution comprising the HEPES-buffered solution (10 mM Hepes pH 7.2, 90 mM KCl, 3 mM MgCl2, 100 µM DTT, 0.1% Triton X-100) supplemented with an oxygen-scavenging mix (200 µg/ml glucose oxidase, 35 µg/ml catalase, 4.5 mg/ml glucose, 0.5% 2-mercaptoethanol). The Fab probe concentration was 100 nM in the imaging solution.

Imaging and Image Reconstruction
Similarly to "procedures for imaging of multicolor super-resolution by IRIS" of experiment 1, SiMS images (speckle images) were obtained by using an inverted microscope (Olympus IX83-ZDC) equipped with an Olympus PlanApo 100×/1.45-numerical aperture (NA) objective lens, a 2×intermediate lens and an EM-CCD camera (Evolve 512, Roper) and controlled by MetaMorph software (Molecular Device). The Fab probe fluorescence-labeled by being irradiated with a 488 nm laser beam (50 mW) was excited for TIRF observation. SiMS images (speckle images) of a total of 33,750 frames were picked up by conducting consecutive imaging of 250 frames for each under a condition that the exposure time was 100 milliseconds for 1 frame and the frame rate (imaging speed) was 10 Hz (10 frames per second).

The procedures for image reconstruction from the above SiMS images of 33,750 frames are as described in detail in "procedures for image reconstruction in IRIS" of experiment 1.

The half-life of a probe-target complex formed between a purified Fab probe and a target antigen was obtained in a similar method to that in Experiment 1. In other words, by using the SiMS images picked up in the above, a period of time between when the Fab probe that had bound to the target appeared in a speckle image and it disappeared through dissociation was measured in a semi-manual mode by using Speckle TrackerJ, a plug-in of ImageJ. Then, the number of binding probes with respect to the period of time between the appearance and disappearance was plotted in accordance with a complementary cumulative relative frequency function (1-Ndissociation). Then, by fitting the complementary cumulative relative frequency function with an exponent function, the half-life was calculated. The result showed that the half-life of a probe-target complex formed between the Fab probe and a target antigen was 216 milliseconds.

2.3. Results

Figure 17:
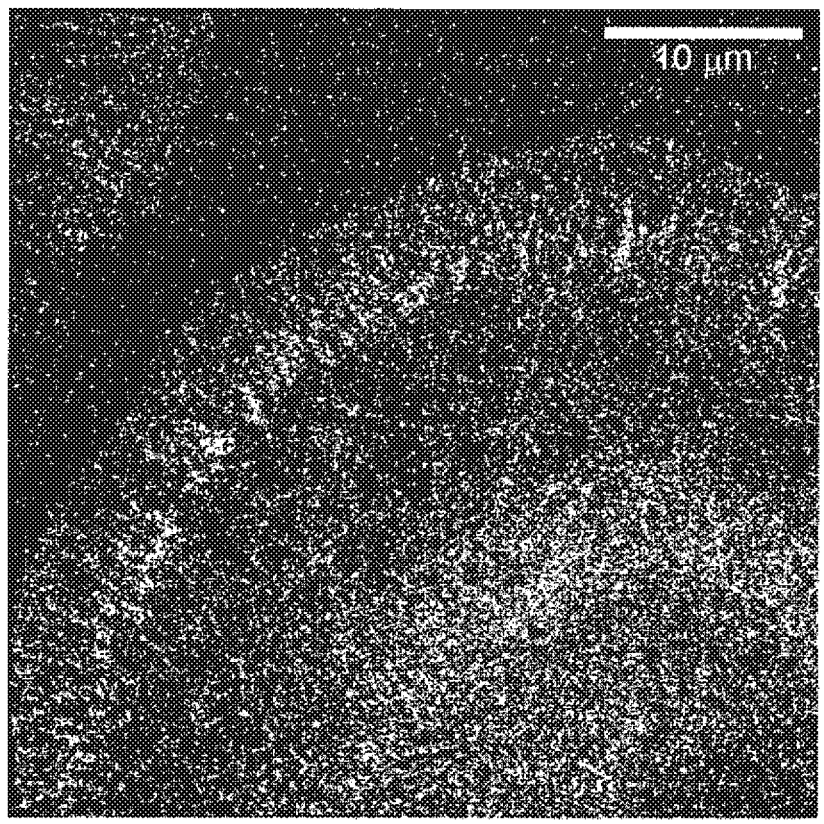
FIG. 17 shows a result of IRIS super-resolution imaging using a probe containing a Fab fragment (Fab probe). It is a result of imaging a distribution of p40, which is a subunit of an Arp2/3 complex, by using a Fab probe that is produced from anti-p40 polyclonal antibody.

FIG. 17 shows a reconstruction image based on the Fab probe generated from a polyclonal antibody derived from a rabbit with respect to a p40 subunit of an Arp2/3 complex, which is an actin polymerization promotion factor. It is known that much p40 is distributed in a peripheral region of a cell and a distribution of Fab probes was visualized as such.

3. Experiment 3

Screening of Fab Probe
A library (1200 samples) of hybridoma was generated by using FLAG peptide (sequence number 2) as an antigen. After immunizing a mouse with an antigen, lymphocytes were collected from an iliac lymph node and were made to fuse with a mouse myeloma cell, and hybridoma was generated. The library of hybridoma was made through dilution culture. Culture supernatant was collected for each sample from the hybridoma library and was made to react with a 96 well glass bottom plate in which Protein G was solid phased and thereby an antibody in the culture supernatant was fixed to the surface of the bottom glass.

The 96 well glass bottom plate in which Protein G was solid phased and immobilization of the antibody were conducted in the following procedures. (3-aminopropyl) triethoxysilane was dissolved in a mixture of methanol and acetic acid (mixing ratio 100:5) and a 3% solution was produced. This solution was put in a 96 well multi-well plate having each of its wells made of glass, the solution was incubated for 30 minutes at an ambient temperature, and the glass surfaces of the well bottoms were coated. (3-aminopropyl) triethoxysilane that had made no reactions was washed a plurality of times with methanol so as to remove it and thereafter the plate was air dried so that (3-aminopropyl) triethoxysilane was made to remain on the glass surfaces. Next, a 0.1% glutaraldehyde solution was added to each well so as to cause reactions for 30 minutes at an ambient temperature and glutaraldehyde was made to bind to the glass surfaces. A 50 ng/µl Protein G (Thermo Scientific) solution was added to each well and was kept in contact with the glass surfaces to which glutaraldehyde bound, for 1 night at 4 degrees Celsius. Protein G causes covalent bonding with (3-aminopropyl) triethoxysilane via glutaraldehyde and is solid phased on the glass surfaces. Blocking was conducted on the glass surfaces on which Protein G was solid phased, with a 3% BSA solution for 1 night at 4 degrees Celsius. Thereafter, a hybridoma culture supernatant containing an antibody was added to each well and was left to stand for 1 night at 4 degrees Celsius. An antibody contained in the culture supernatant binds, specifically and strongly, to Protein G via the Fc domain thereof and is fixed to the glass surface. After removing the hybridoma culture supernatant, the glass surfaces were washed with a cell lysis buffer (10 mM Hepes pH 7.2, 3 mM MgCl2, 0.2% Triton X-100, 100 µM DTT), and received an observation step, which will be described later. In order to obtain a fused protein of FLAG peptide and FLAG peptide that becomes an antigen, an HEK-293F cell was transfected with a plasmid that encoded FLAG-EGFP. After culturing the transfected cell for 3 to 4 days, it was dissolved in a cell lysis buffer (10 mM Hepes pH 7.2, 3 mM MgCl2, 0.2% Triton X-100, 100 µM DTT) containing a protease inhibitor cocktail (Nacalai Tesque). After centrifugally separating the lysate, the supernatant liquid was collected. The FLAG-EGFP concentration contained in the supernatant liquid was estimated from the light emission intensity of EGFP, and a 50 nM FLAG-EGFP solution was prepared by diluting it with a cell lysis buffer.

Figure 18:
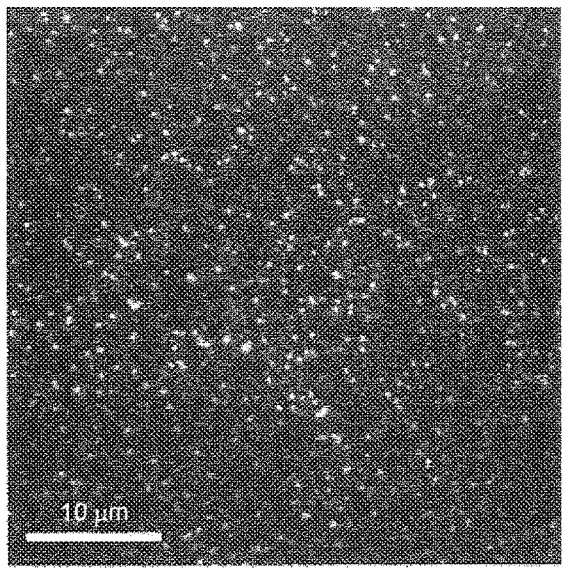
FIG. 18 show binding of FLAG-EGFP to a solid-phased antibody. An antibody contained in hybridoma culture supernatant was fixed to a glass surface and a FLAG-EGFP solution was added so as to observe it with a TIRF microscope. Each speckle is FLAG-EGFP that has bound to a solid-phased antibody.
Figure 18:
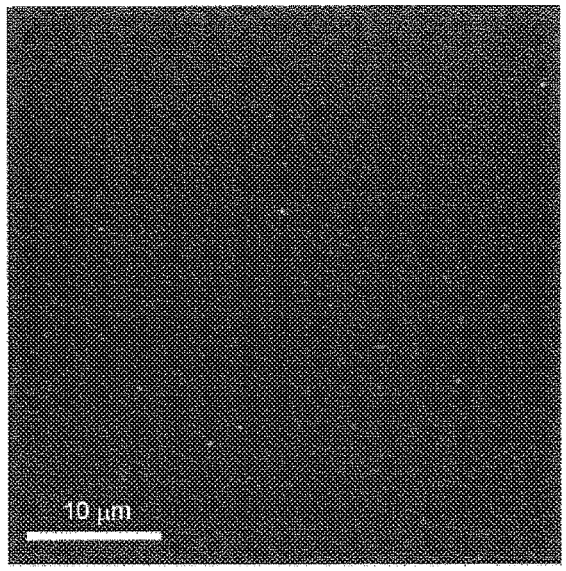

A 50 nM FLAG-EGFP solution was added to each well to which an antibody was fixed. By using a TIRF microscope, SiMS images (speckle images) of 500 frames were picked up with an exposure time of 50 ms for 1 frame and at a frame rate of 20 Hz (20 frames per second). As a result of observing 1200 wells, 10 to 300 speckles (0.006 to 0.178 speckles/µm2) were observed in the field of view of the microscope (41 µm×41 µm). Each speckle corresponds to EGFP of a single molecule. As examples of speckle images, FIG. 18A shows an image in which about 250 speckles were observed and FIG. 18B shows an image in which about 20 speckles were observed. In the case where 50 nM FLAG-EGFP solutions were added to wells in which antibodies had not been solid phased, the numbers of the speckles in the field of view were 10 to 20 (0.006 to 0.012/µm2). Then, the half-lives of binding between antibodies and FLAG-EGFP were measured by treating, as positive examples, a 26 well in which 40 (0.023/µm2) or more speckles had been observed in the field of view. Each of the wells had different half-lives. The half-life in the well shown in FIG. 18A was 55 ms.

From the 26 well in which 40 or more speckles had been observed in the field of view of the microscope as the positive examples, antibodies having half-lives of the probe-target complex that were equal to or more than 10 milliseconds and equal to or less than 3 seconds were selected. Hybridoma producing these antibodies was converted into monoclone and 2 ml to 10 ml of the culture supernatant was collected. 40 µl of a 50% slurry solution of Protein A beads (Protein A Sepharose CL-4B, GE) was added to the culture superresolution, and the antibodies were made to adsorb on the beads for 1 night at 4 degrees Celsius. After using PBS to wash and remove antibodies that had not adsorbed, the beads were suspended in 100 µl of PBS. To this suspension of beads, 16 µl of 0.5 µg/µl DyLight 488 NHS Ester (ThermoScientific) dissolved in DMSO was added, and the antibodies were fluorescence-labeled for 1 hour at an ambient temperature. DyLight 488 NHS Ester that had made no reactions was washed and removed with PBS and only beads were collected after centrifugation. In order to produce a Fab fragment from an antibody that bound to the beads, 20 µl of 0.01 mg/ml papain dissolved in Digestion Buffer (50 mM Tris-HCl pH8.0, 10 mM Cysteine-HCl, 2 mM EDTA) was added and reactions were caused for 1 hour at 37 degrees Celsius. After the centrifugation, supernatant containing a Fab fragment was collected and 2 µl of 0.01 mg/ml leupeptin was added in order to inhibit the activity of papain.

2.2. IRIS Super-Resolution Imaging of Actin

Preparation of a FLAG Tag Fused Actin Expression XTC Cell Sample

FLAG tag fused actin encoded by the base sequence described by sequence number 20 was expressed with an XTC cell.

Expression vector-(CLONETECH) encoding pEGFP-actin was cut with restriction enzyme Age-I, Bgl-II (NEB) to remove EGFP from the vector. Synthetic cDNA encoding FLAG peptide (DYKDDDDK) was inserted into the vector and an expression plasmid encoding an actin for which FLAG was tagged to an N terminus was constructed.

A *Xenopus laevis* XTC cell was transfected with the above expression plasmid in the following procedures. 3 µl of an expression plasmid of 1 µg/µ of FLAG fused actin was dissolved in 200 µl of a serum-free medium (70% dilution Leibovitz's L-15 medium) and 8µ of Polyethylenimine, linear, M.W. 25,000 (Polysciences) of 1 mg/ml was added and it was vortexed. After leaving it to stand for 30 minutes at an ambient temperature, a medium with serum of 1 ml (70% dilution Leibovitz's L-15 medium, 10% FCS supplement) was added. The solution containing this plasmid and the media of XTC cells spread in 6 wells were switched, and the cells were made to take in plasmids for 1 night.

3 to 4 days later than the transfecting, the cells were fixed and received the permeabilization process in the procedures described in detail in "procedures for imaging of multicolor super-resolution by IRIS" of experiment 1. After a blocking step with 4% bovine serum albumin for 30 minutes, the Fab probes were each brought into contact with the cells in an imaging solution comprising the HEPES-buffered solution (10 mM Hepes pH 7.2, 3 mM MgCl2, 100 µM DTT, 1 µg/ml leupeptin) supplemented with an oxygen-scavenging mix (200 µg/ml glucose oxidase, 35 µg/ml catalase, 4.5 mg/ml glucose, 0.5% 2-mercaptoethanol). The Fab probe concentration was 3 nM in the imaging solution.

Imaging and Image Reconstruction

Similarly to "procedures for imaging of multicolor super-resolution by IRIS" of experiment 1, SiMS images (speckle images) were obtained by using an inverted microscope (Olympus IX83-ZDC) equipped with an Olympus PlanApo 100×/1.45-numerical aperture (NA) objective lens, a 2×intermediate lens and an electron-multiplying EM-CCD camera (Evolve 512, Roper) and controlled by MetaMorph software (Molecular Device). The Fab probe fluorescence-labeled by being irradiated with a 488 nm laser beam (50 mW) was excited for TIRF observation. SiMS images (speckle images) of a total of 120,000 frames were picked up by conducting consecutive imaging of 500 frames for each under a condition such that the exposure time was 50 milliseconds for 1 frame and the frame rate (imaging speed) was 20 Hz (20 frames per second).

The procedures for image reconstruction from the above SiMS images of 120,000 frames are as described in detail in "procedures for image reconstruction in IRIS" of experiment 1.

2.4. Results

Figure 19:
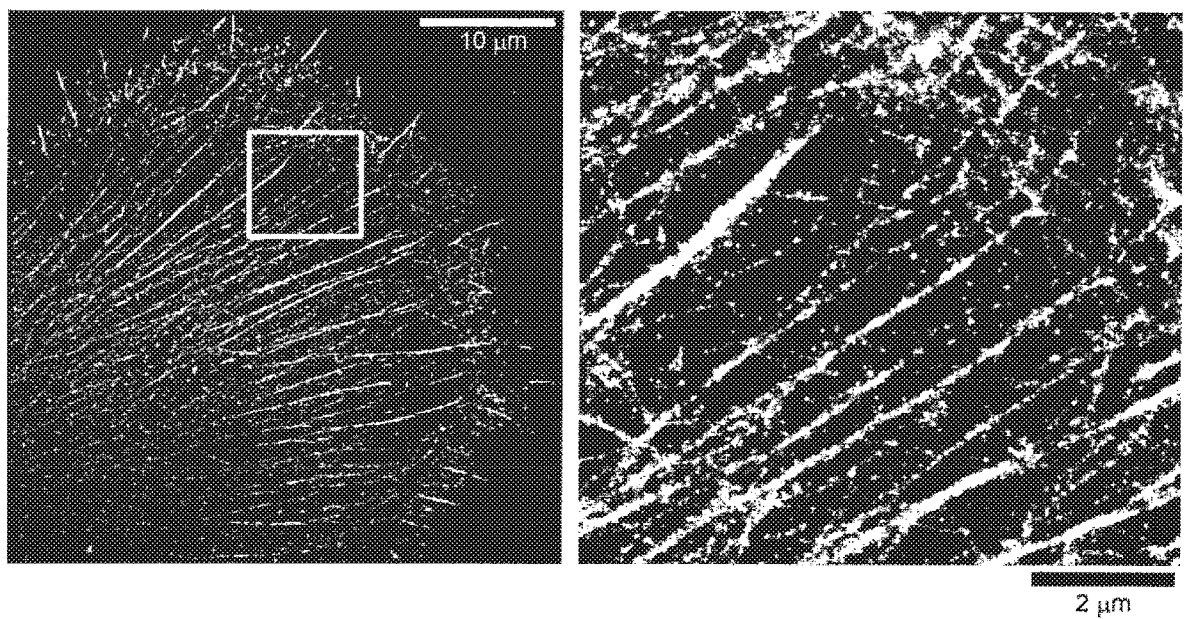
FIG. 19 shows super-resolution images of FLAG fused actins obtained by using a Fab probe derived from an anti-FLAG monoclonal antibody selected from a hybridoma library (203 milliseconds as the half-life of a probe-target complex). This cell has forcibly expressed a FLAG tag fused actin. The right image is an enlarged image of the region in the white frame in the left image.

FIG. 19 shows IRIS super-resolution images of FLAG fused actin by a Fab probe derived from an anti-FLAG monoclonal antibody selected by the above screening method. The half-life of a probe-target complex of a Fab probe and an FLAG fused actin used for the generation of these IRIS super-resolution images was 203 milliseconds.

The present screening method made it possible to select a Fab probe appropriate for IRIS super-resolution imaging.

4. Documents

The documents referred to herein are described below.
1. Fernandez-Suarez, M. & Ting, A. Y. Fluorescent probes for super-resolution imaging in living cells. Nat. Rev. Mol. Cell Biol. 9, 929-943, doi:10.1038/nrm2531 (2008).
2. Hell, S. W. Far-field optical nanoscopy. Science 316, 1153-1158, doi:10.1126/science.1137395 (2007).

3. Huang, B., Babcock, H. & Zhuang, X. Breaking the diffraction barrier: super-resolution imaging of cells. Cell 143, 1047-1058, doi:10.1016/j.cell.2010.12.002 (2010).
4. Huang, B., Bates, M. & Zhuang, X. Super-resolution fluorescence microscopy. Annu. Rev. Biochem. 78, 993-1016, doi:10.1146/annurev.biochem.77.061906.092014 (2009).
5. Sauer, M. Localization microscopy coming of age: from concepts to biological impact. J. Cell Sci. 126, 3505-3513, doi:10.1242/jcs.123612 (2013).
6. Shroff, H., Galbraith, C. G., Galbraith, J. A. & Betzig, E. Live-cell photoactivated localization microscopy of nanoscale adhesion dynamics. Nat. Methods 5, 417-423, doi:10.1038/nmeth.1202 (2008).
7. Kanchanawong, P. & Waterman, C. M. Localization-based super-resolution imaging of cellular structures. Methods Mol. Biol. 1046, 59-84, doi:10.1007/978-1-62703-538-5_4 (2013).
8. Betzig, E. et al. Imaging intracellular fluorescent proteins at nanometer resolution. Science 313, 1642-1645, doi: 10.1126/science.1127344 (2006).
9. Rust, M. J., Bates, M. & Zhuang, X. Sub-diffraction-limit imaging by stochastic optical reconstruction microscopy (STORM). Nat. Methods 3, 793-795, doi:10.1038/nmeth929 (2006).
10. Riedl, J. et al. Lifeact: a versatile marker to visualize F-actin. Nat. Methods 5, 605-607, doi:10.1038/nmeth.1220 (2008).
11. Watanabe, N. & Mitchison, T. J. Single-molecule speckle analysis of actin filament turnover in lamellipodia. Science 295, 1083-1086, doi:10.1126/science.1067470 (2002).
12. Higashida, C. et al. Actin polymerization-driven molecular movement of mDia1 in living cells. Science 303, 2007-2010, doi:10.1126/science.1093923 (2004).
13. Vale, R. D. Microscopes for fluorimeters: the era of single molecule measurements. Cell 135, 779-785, doi: 10.1016/j.cell.2008.11.009 (2008).
14. Holden, S. J., Uphoff, S. & Kapanidis, A. N. DAOSTORM: an algorithm for high-density super-resolution microscopy. Nat. Methods 8, 279-280, doi:10.1038/nmeth0411-279 (2011).
15. Perez, F., Diamantopoulos, G. S., Stalder, R. & Kreis, T. E. CLIP-170 highlights growing microtubule ends in vivo. Cell 96, 517-527 (1999).
16. Nikolic, B., Mac Nulty, E., Mir, B. & Wiche, G. Basic amino acid residue cluster within nuclear targeting sequence motif is essential for cytoplasmic plectin-vimentin network junctions. J. Cell Biol. 134, 1455-1467 (1996).
17. Di Paolo, G. et al. Recruitment and regulation of phosphatidylinositol phosphate kinase type 1 gamma by the FERM domain of talin. Nature 420, 85-89, doi: 10.1038/nature01147 (2002).
18. Gell, C., Berndt, M., Enderlein, J. & Diez, S. TIRF microscopy evanescent field calibration using tilted fluorescent microtubules. J. Microsc. 234, 38-46, doi:10.1111/j.1365-2818.2009.03147.x (2009).
19. Kanchanawong, P. et al. Nanoscale architecture of integrin-based cell adhesions. Nature 468, 580-584, doi: 10.1038/nature09621 (2010).
20. Sharonov, A. & Hochstrasser, R. M. Wide-field subdiffraction imaging by accumulated binding of diffusing probes. Proc. Natl. Acad. Sci. USA 103, 18911-18916, doi:10.1073/pnas.0609643104 (2006).
21. Bates, M., Huang, B., Dempsey, G. T. & Zhuang, X. Multicolor super-resolution imaging with photo-switchable fluorescent probes. Science 317, 1749-1753, doi: 10.1126/science.1146598 (2007).
22. Huang, B., Jones, S. A., Brandenburg, B. & Zhuang, X. Whole-cell 3D STORM reveals interactions between cellular structures with nanometer-scale resolution. Nat. Methods 5, 1047-1052, doi:10.1038/nmeth.1274 (2008).
23. Jungmann, R. et al. Multiplexed 3D cellular super-resolution imaging with DNA-PAINT and Exchange-PAINT. Nat. Methods 11, 313-318, doi:10.1038/nmeth.2835 (2014).
24. Shroff, H. et al. Dual-color superresolution imaging of genetically expressed probes within individual adhesion complexes. Proc. Natl. Acad. Sci. USA 104, 20308-20313, doi:10.1073/pnas.0710517105 (2007).
25. Liu, K. S. et al. RIM-binding protein, a central part of the active zone, is essential for neurotransmitter release. Science 334, 1565-1569, doi:10.1126/science.1212991 (2011).
26. Bieling, P. et al. CLIP-170 tracks growing microtubule ends by dynamically recognizing composite EB1/tubulin-binding sites. J. Cell Biol. 183, 1223-1233, doi:10.1083/jcb.200809190 (2008)
27. Kaverina, I., Krylyshkina, O. & Small, J. V. Microtubule targeting of substrate contacts promotes their relaxation and dissociation. J. Cell Biol. 146, 1033-1044 (1999).
28. Salmon, W. C., Adams, M. C. & Waterman-Storer, C. M. Dual-wavelength fluorescent speckle microscopy reveals coupling of microtubule and actin movements in migrating cells. J. Cell Biol. 158, 31-37, doi:10.1083/jcb.200203022 (2002).
29. Small, J. V. & Kaverina, I. Microtubules meet substrate adhesions to arrange cell polarity. Curr. Opin. Cell Biol. 15, 40-47, doi:10.1016/s0955-0674 (02)00008-x (2003).
30. Huda, S. et al. Microtubule guidance tested through controlled cell geometry. J. Cell Sci. 125, 5790-5799, doi:10.1242/jcs.110494 (2012).
31. Yamana, N. et al. The Rho-mDia1 pathway regulates cell polarity and focal adhesion turnover in migrating cells through mobilizing Apc and c-Src. Mol. Cell Biol. 26, 6844-6858, doi:10.1128/mcb.00283-06 (2006).
32. Tanji, M. et al. mDia1 targets v-Src to the cell periphery and facilitates cell transformation, tumorigenesis, and invasion. Mol. Cell Biol. 30, 4604-4615, doi:10.1128/mcb.00197-10 (2010).
33. Yamashiro, S. et al. New single-molecule speckle microscopy reveals modification of the retrograde actin flow by focal adhesions at nanometer scales. Mol. Biol. Cell 25, 1010-1024, doi:10.1091/mbc.E13-03-0162 (2014).
34. Desai, A., Verma, S., Mitchison, T. J. & Walczak, C. E. Kin I kinesins are microtubule-destabilizing enzymes. Cell 96, 69-78 (1999).
35. Mizuno, H. et al. Rotational movement of the formin mDia1 along the double helical strand of an actin filament. Science 331, 80-83, doi:10.1126/science.1197692 (2011).
36. Mizuno, H. & Watanabe, N. Rotational movement of formins evaluated by using single-molecule fluorescence polarization. Methods Enzymol. 540, 73-94, doi:10.1016/b978-0-12-397924-7.00005-4 (2014).
37. Smith, M. B. et al. Interactive, computer-assisted tracking of speckle trajectories in fluorescence microscopy: application to actin polymerization and membrane fusion. Biophys. J. 101, 1794-1804, doi:10.1016/j.bpj.2011.09.007 (2011).
38. Mimori-Kiyosue, Y. et al. CLASP1 and CLASP2 bind to EB1 and regulate microtubule plus-end dynamics at the cell cortex. The Journal of cell biology 168, 141-153, doi:10.1083/jcb.200405094 (2005).
39. Askham, J. M., Moncur, P., Markham, A. F. & Morrison, E. E. Regulation and function of the interaction between the APC tumour suppressor protein and EB1. Oncogene 19, 1950-1958, doi:10.1038/sj.onc.1203498 (2000).
40. Honnappa, S. et al. An EB1-binding motif acts as a microtubule tip localization signal. Cell 138, 366-376, doi:10.1016/j.cell.2009.04.065 (2009).
41. Okada, Y., Higuchi, H. & Hirokawa, N. Processivity of the single-headed kinesin KIF1A through biased binding to tubulin. Nature 424, 574-577, doi:10.1038/nature01804 (2003).
42. Cai, D., McEwen, D. P., Martens, J. R., Meyhofer, E. & Verhey, K. J. Single molecule imaging reveals differences in microtubule track selection between Kinesin motors. PLoS biology 7, e1000216, doi:10.1371/journal.pbio.1000216 (2009).
43. Olson, K. R., McIntosh, J. R. & Olmsted, J. B. Analysis of MAP 4 function in living cells using green fluorescent protein (GFP) chimeras. The Journal of cell biology 130, 639-650 (1995).
44. Lee, G. & Rook, S. L. Expression of tau protein in non-neuronal cells: microtubule binding and stabilization. Journal of cell science 102 (Pt 2), 227-237 (1992).
45. Yu, J. Z., Kuret, J. & Rasenick, M. M. Transient expression of fluorescent tau proteins promotes process formation in PC12 cells: contributions of the tau C-terminal minus to this process. Journal of neuroscience research 67, 625-633 (2002).46. Brown, M. C., Perrotta, J. A. & Turner, C. E. Identification of LIM3 as the principal determinant of paxillin focal adhesion localization and characterization of a novel motif on paxillin directing vinculin and focal adhesion kinase binding. The Journal of cell biology 135, 1109-1123 (1996).
47. Wood, C. K., Turner, C. E., Jackson, P. & Critchley, D. R. Characterization of the paxillin-binding site and the C-terminal focal adhesion targeting sequence in vinculin. Journal of cell science 107 (Pt 2), 709-717 (1994).
48. Humphries, J. D. et al. Vinculin controls focal adhesion formation by direct interactions with talin and actin. The Journal of cell biology 179, 1043-1057, doi:10.1083/jcb.200703036 (2007).
49. Nuckolls, G. H., Turner, C. E. & Burridge, K. Functional studies of the domains of talin. The Journal of cell biology 110, 1635-1644 (1990).
50. Calderwood, D. A. et al. The phosphotyrosine binding-like domain of talin activates integrins. The Journal of biological chemistry 277, 21749-21758, doi:10.1074/jbc.M111996200 (2002).
51. Tremuth, L. et al. A fluorescence cell biology approach to map the second integrin-binding site of talin to a 130-amino acid sequence within the rod domain. The Journal of biological chemistry 279, 22258-22266, doi:10.1074/jbc.M400947200 (2004).
52. Patel, B. et al. The activity of the vinculin binding sites in talin is influenced by the stability of the helical bundles that make up the talin rod. The Journal of biological chemistry 281, 7458-7467, doi:10.1074/jbc.M508058200 (2006).
53. Moes, M. et al. The integrin binding site 2 (IBS2) in the talin rod domain is essential for linking integrin beta subunits to the cytoskeleton. The Journal of biological chemistry 282, 17280-17288, doi:10.1074/jbc.M611846200 (2007).
54. Himmel, M. et al. Control of high affinity interactions in the talin C terminus: how talin domains coordinate protein dynamics in cell adhesions. The Journal of biological chemistry 284, 13832-13842, doi:10.1074/jbc.M900266200 (2009).
55. Kaplan, K. B. et al. Association of the amino-terminal half of c-Src with focal adhesions alters their properties and is regulated by phosphorylation of tyrosine 527. The EMBO journal 13, 4745-4756 (1994).
56. Hildebrand, J. D., Schaller, M. D. & Parsons, J. T. Identification of sequences required for the efficient localization of the focal adhesion kinase, pp125FAK, to cellular focal adhesions. The Journal of cell biology 123, 993-1005 (1993).
57. Cooley, M. A., Broome, J. M., Ohngemach, C., Romer, L. H. & Schaller, M. D. Paxillin binding is not the sole determinant of focal adhesion localization or dominant-negative activity of focal adhesion kinase/focal adhesion kinase-related nonkinase. Molecular biology of the cell 11, 3247-3263 (2000).
58. Lietha, D. et al. Structural basis for the autoinhibition of focal adhesion kinase. Cell 129, 1177-1187, doi:10.1016/j.cell.2007.05.041 (2007).

The present invention can provide a super-resolution microscope observation method that makes it possible to obtain, at a high density, position information of luminescent substances used for labeling and to generate a high resolution observation image exceeding the diffraction limit, and also it is made possible to clarify the formation process of a plurality of cytoskeleton structures that interact dynamically, by a combination between the present invention and a living-cell image technique, and thus the present invention has a high industrial applicability.

All publications, patents and patent applications referred to herein are incorporated herein in their entirety by reference.

What is claimed is:

1. A method of observing a sample containing a target substance, the method comprising:
an imaging step comprising obtaining a plurality of speckle images by performing, a plurality of different times, imaging to obtain a speckle image including, as a speckle, light emitted from a fluorescent substance under irradiation with excitation light in a state in which a medium is brought into contact with the sample, wherein the medium contains a probe that contains the fluorescent substance that emits light under the irradiation with the excitation light, and the probe repeatedly binds to and dissociates from the target substance directly and specifically; and
an observation image generation step comprising generating an observation image of the target substance in the sample from the plurality of speckle images,
wherein a half-life of a probe-target complex formed by binding between the probe and the target substance is equal to or more than 10 milliseconds and equal to or less than 3 seconds.

2. The method according to claim 1, wherein the observation image generation step comprises obtaining information of a position of a speckle included in each of the plurality of speckle images, and generating the observation image based on the information from the plurality of speckle images.

3. The method according to claim 1, wherein:
the sample includes two or more target substances,
the imaging step is sequentially performed on the sample by using different probes that are specific to each of the target substances, and
the observation image generation step comprises respectively generating observation images of the respective target substances in the sample from the plurality of speckle images obtained from the respective imaging steps.

4. The method according to claim 3, further comprising a multiple-observation image generation step comprising superposing observation images of the respective target substances in the sample generated in the observation image generation step so as to generate a multiple-observation image, which is an observation image of the two or more target substances in the sample.

5. The method according to claim 1, wherein a combination between the probe and the target substance is selected from a group of:
a combination wherein the probe is (a1) a polypeptide, linked to the fluorescent substance, which consists of an amino acid sequence of SEQ ID NO: 19, (a2) a polypeptide, linked to the fluorescent substance, which consists of the amino acid sequence described in (a1) where one or a plurality of amino acids have been substituted, deleted, inserted or added and for which a half-life of a probe-target complex formed by binding between the probe and the target substance is equal to or more than 10 milliseconds and equal to or less than 3 seconds, or (a3) a polypeptide, linked to the fluorescent substance, which consists of an amino acid sequence having at least a 70% identity with the amino acid sequence described in (a1) and for which a half-life of a probe-target complex formed by binding between the probe and the target substance is equal to or more than 10 milliseconds and equal to or less than 3 seconds, and the target substance is an actin polymer;
a combination wherein the probe is (b1) a polypeptide, linked to the fluorescent substance, which consists of an amino acid sequence that is a partial amino acid sequence of an amino acid sequence of SEQ ID NO: 12, that at least partially contains an amino acid sequence of residues 3-309 and that has 407 or fewer amino acids, an amino acid sequence that is a partial amino acid sequence of an amino acid sequence of SEQ ID NO: 14, that at least partially contains an amino acid sequence of residues 2536-2843 and that has 408 or fewer amino acids, an amino acid sequence that is a partial amino acid sequence of an amino acid sequence of SEQ ID NO: 14, that at least partially contains an amino acid sequence of residues 2781-2819 and that has 138 or fewer amino acids, an amino acid sequence that is a partial amino acid sequence of an amino acid sequence of SEQ ID NO: 4, that at least partially contains an amino acid sequence of residues 1-908 and that has 1008 or fewer amino acids, an amino acid sequence that is a partial amino acid sequence of an amino acid sequence of SEQ ID NO: 4, that at least partially contains an amino acid sequence of residues 659-908 and that has 394 or fewer amino acids, an amino acid sequence of SEQ ID NO: 5, or an amino acid sequence of SEQ ID NO: 6, (b2) a polypeptide, linked to the fluorescent substance, which consists of the amino acid sequence described in (b1) where one or a plurality of amino acids have been substituted, deleted, inserted or added and for which a half-life of a probe-target complex formed by binding between the probe and the target substance is equal to or more than 10 milliseconds and equal to or less than 3 seconds, or (b3) a polypeptide, linked to the fluorescent substance, which consists of an amino acid sequence having at least a 70% identity with the amino acid sequence described in (b1) and for which a half-life of a probe-target complex formed by binding between the probe and the target substance is equal to or more than 10 milliseconds and equal to or less than 3 seconds, and the target substance is a microtubule;
a combination wherein the probe is (c1) a polypeptide, linked to the fluorescent substance, which consists of an amino acid sequence that is a partial amino acid sequence of an amino acid sequence of SEQ ID NO: 8, that at least partially contains an amino acid sequence of residues 3777-4684 and that has 1008 or fewer amino acids, an amino acid sequence that is a partial amino acid sequence of an amino acid sequence of SEQ ID NO: 8, that at least partially contains an amino acid sequence of residues 3777-4364 and that has 688 or fewer amino acids, an amino acid sequence that is a partial amino acid sequence of an amino acid sequence of SEQ ID NO: 8, that at least partially contains an amino acid sequence of residues 3777-4313 and that has 637 or fewer amino acids, or an amino acid sequence that is a partial amino acid sequence of an amino acid sequence of SEQ ID NO: 8, that at least partially contains an amino acid sequence of residues 4022-4364 and that has 443 or fewer amino acids, (c2) a polypeptide, linked to the fluorescent substance, which consists of the amino acid sequence described in (c1) where one or a plurality of amino acids have been substituted, deleted, inserted or added and for which a half-life of a probe-target complex formed by binding between the probe and the target substance is equal to or more than 10 milliseconds and equal to or less than 3 seconds, or (c3) a polypeptide, linked to the fluorescent substance, which consists of an amino acid sequence having at least a 70% identity with the amino acid sequence described in (c1) and for which a half-life of a probe-target complex formed by binding between the probe and the target substance is equal to or more than 10 milliseconds and equal to or less than 3 seconds, and the target substance is an intermediate filament; and a combination wherein the probe is (d1) a polypeptide, linked to the fluorescent substance, which consists of an amino acid sequence of SEQ ID NO: 15, an amino acid sequence that is a partial amino acid sequence of an amino acid sequence of SEQ ID NO: 15, that at least partially contains an amino acid sequence of residues 54-557 and that has 556 or fewer amino acids, an amino acid sequence that is a partial amino acid sequence of an amino acid sequence of SEQ ID NO: 15, that at least partially contains an amino acid sequence of residues 54-498 and that has 545 or fewer amino acids, an amino acid sequence that is a partial amino acid sequence of an amino acid sequence of SEQ ID NO: 15, that at least partially contains an amino acid sequence of residues 167-557 and that has 491 or fewer amino acids, an amino acid sequence that is a partial amino acid sequence of an amino acid sequence of SEQ ID NO: 16, that at least partially contains an amino acid sequence of residues 1-251 and that has 351 or fewer amino acids, an amino acid sequence that is a partial amino acid sequence of an amino acid sequence of SEQ ID NO: 16, that at least partially contains an amino acid sequence of residues 3-251 and that has 349 or fewer amino acids or an amino acid sequence of SEQ ID NO: 18, (d2) a polypeptide, linked to the fluorescent substance, which consists of the amino acid sequence described in (d1) where one or a plurality of amino acids have been substituted, deleted, inserted or added and for which a half-life of a probe-target complex formed by binding between the probe and the target substance is equal to or more than 10 milliseconds and equal to or less than 3 seconds, or (d3) a polypeptide, linked to the fluorescent substance, which consists of an amino acid sequence having at least a 70% identity with the amino acid sequence described in (d1) and for which a half-life of a probe-target complex formed by binding between the probe and the target substance is equal to or more than 10 milliseconds and equal to or less than 3 seconds, and the target substance is a focal adhesion.

6. The method according to claim 1, wherein the probe contains an antibody or a fragment of an antibody, the antibody or the fragment being directed to the target substance and the antibody or the fragment being linked to the fluorescent substance.

7. The method according to claim 6, wherein the fragment of the antibody is a Fab fragment.

8. The method according to claim 1, wherein the target substance is an actin polymer, and the probe is a polypeptide, linked to the fluorescent substance, which consists of an amino acid sequence of SEQ ID NO: 19.

* * * * *